US008336705B2

(12) United States Patent
Okahisa

(10) Patent No.: US 8,336,705 B2
(45) Date of Patent: Dec. 25, 2012

(54) MULTI-CHAMBER CONTAINER

(75) Inventor: Toshiya Okahisa, Tokushima (JP)

(73) Assignee: Fuso Pharmaceuticals Industries, Ltd., Osaka (JP)

( * ) Notice: Subject to any disclaimer, the term of this patent is extended or adjusted under 35 U.S.C. 154(b) by 861 days.

(21) Appl. No.: 10/581,634

(22) PCT Filed: Dec. 1, 2004

(86) PCT No.: PCT/JP2004/017886

§ 371 (c)(1),
(2), (4) Date: Feb. 26, 2007

(87) PCT Pub. No.: WO2005/053598

PCT Pub. Date: Jun. 16, 2005

(65) Prior Publication Data

US 2007/0251838 A1 Nov. 1, 2007

(30) Foreign Application Priority Data

| | | |
|---|---|---|
| Dec. 2, 2003 | (JP) | 2003-403363 |
| Dec. 26, 2003 | (JP) | 2003-433415 |
| Mar. 31, 2004 | (JP) | 2004-104771 |
| Jul. 29, 2004 | (JP) | 2004-222084 |
| Jul. 29, 2004 | (JP) | 2004-222090 |
| Jul. 29, 2004 | (JP) | 2004-222095 |
| Aug. 4, 2004 | (JP) | 2004-227992 |
| Aug. 27, 2004 | (JP) | 2004-248361 |

(51) Int. Cl.
*B65D 25/08* (2006.01)
*A61B 19/00* (2006.01)

(52) U.S. Cl. ......................... 206/219; 206/221; 604/416

(58) Field of Classification Search .................. 206/219, 206/221, 568; 604/410, 416
See application file for complete search history.

(56) References Cited

U.S. PATENT DOCUMENTS

| | | | | | |
|---|---|---|---|---|---|
| 2,756,875 | A | * | 7/1956 | Yochim | 206/219 |
| 3,257,072 | A | * | 6/1966 | Reynolds | 494/10 |
| 3,950,158 | A | * | 4/1976 | Gossett | 62/4 |
| 3,983,994 | A | * | 10/1976 | Wyslotsky | 206/219 |
| 4,458,811 | A | * | 7/1984 | Wilkinson | 206/219 |
| 4,519,499 | A | * | 5/1985 | Stone et al. | 206/219 |
| 4,608,043 | A | * | 8/1986 | Larkin | 604/87 |

(Continued)

FOREIGN PATENT DOCUMENTS

DE 8914942 U1 2/1990

(Continued)

OTHER PUBLICATIONS

International Search Report for PCT/JP2004/017886, dated Mar. 2, 2005.

(Continued)

*Primary Examiner* — J. Gregory Pickett
*Assistant Examiner* — Kaushikkumar Desai
(74) *Attorney, Agent, or Firm* — Michaud-Kinney Group LLP

(57) ABSTRACT

The present invention provides causing a plurality of filling chambers to be opened and mixing agents inside the filling chambers using user's general operation between taking out a packed multi-chamber container and mounting the container on a device. The user's general operation includes operations for taking out a packed multi-chamber container and removing the package, for unfolding the multi-chamber container typically folded in two, for mounting i.e. hanging the unfolded multi-chamber container on the device, and the like.

4 Claims, 99 Drawing Sheets

U.S. PATENT DOCUMENTS

| | | | | | |
|---|---|---|---|---|---|
| 4,856,651 | A | * | 8/1989 | Francis, Jr. | 206/219 |
| 5,209,347 | A | * | 5/1993 | Fabisiewicz et al. | 206/219 |
| 5,353,927 | A | * | 10/1994 | Stupar et al. | 206/219 |
| 5,423,421 | A | * | 6/1995 | Inoue et al. | 206/219 |
| 5,492,219 | A | * | 2/1996 | Stupar | 206/219 |
| 5,494,190 | A | * | 2/1996 | Boettcher | 222/1 |
| 5,501,887 | A | * | 3/1996 | Tanaka et al. | 428/35.2 |
| 5,560,403 | A | * | 10/1996 | Balteau et al. | 141/9 |
| 5,577,369 | A | * | 11/1996 | Becker et al. | 53/474 |
| 5,610,170 | A | * | 3/1997 | Inoue et al. | 514/340 |
| 5,967,308 | A | * | 10/1999 | Bowen | 206/219 |
| 6,017,598 | A | * | 1/2000 | Kreischer et al. | 428/35.4 |
| 6,186,998 | B1 | * | 2/2001 | Inuzuka et al. | 604/410 |
| 6,245,176 | B1 | * | 6/2001 | Greenland | 156/182 |
| 6,286,670 | B1 | * | 9/2001 | Smith | 206/221 |
| 6,613,036 | B1 | * | 9/2003 | Farmer et al. | 604/408 |
| 2001/0000042 | A1 | * | 3/2001 | Inuzuka et al. | 604/410 |
| 2001/0030134 | A1 | * | 10/2001 | Goglio et al. | 206/221 |
| 2002/0029985 | A1 | * | 3/2002 | Stunnell | 206/221 |
| 2003/0047467 | A1 | * | 3/2003 | Smith et al. | 206/221 |
| 2004/0134802 | A1 | * | 7/2004 | Inoue et al. | 206/219 |
| 2007/0123836 | A1 | * | 5/2007 | Fukushima et al. | 604/410 |

FOREIGN PATENT DOCUMENTS

| | | | |
|---|---|---|---|
| EP | 0132632 | | 2/1985 |
| JP | 47-40972 | Y1 | 12/1972 |
| JP | 55-166752 | U | 12/1980 |
| JP | 03-099668 | | 4/1991 |
| JP | 6-81537 | | 11/1994 |
| JP | 7155362 | A | 6/1995 |
| JP | 10-005313 | | 1/1998 |
| JP | 11047235 | A | 2/1999 |
| JP | 2000-5275 | A | 1/2000 |
| JP | 3074885 | U | 1/2000 |
| JP | 2000-084042 | A | 3/2000 |
| JP | 2002-53140 | A | 2/2002 |
| JP | 2004141631 | | 5/2004 |
| JP | 2004-159778 | A | 6/2004 |
| JP | 2004-292041 | A | 10/2004 |
| JP | 2005-040415 | A | 2/2005 |

OTHER PUBLICATIONS

Supplementary EP Search Report, Application No. 04819872.5, date mailed Jun. 17, 2008.

Japanese Notice of Reasons for Rejection for Japanese Patent Application No. 2004-222095.

Japanese Notice of Reasons for Rejection of Japanese Patent Application No. 2004-222090.

Notice of Reasons for Rejection for Japanese Patent Application No. 2005-226130.

* cited by examiner

301

301

MULTI-CHAMBER CONTAINER

TECHNICAL FIELD

The present invention relates to a multi-chamber container, and more particularly, to a multi-chamber container which accommodates two or more kinds of liquids and the like such as agents, adhesives or the like to enable the agents to be mixed.

BACKGROUND ART

Conventionally, in the case of mixing two or more agents, in order to prevent the agents from deteriorating with time due to interaction, the agents have been mixed and adjusted immediately before administration in medical fields. However, such mixing of agents immediately before administration has defects such as contamination with microorganisms and/or intrusion of a foreign substance, incorrect mixing, inability to be administered promptly and the like. Therefore, such a multi-chamber container is currently being developed and is provided with dividing means such as a seal which can be peeled off by application of pressure, and that each of a plurality of chambers partitioned by the dividing means is filled with a respective unmixed agent. In this multi-chamber container, the dividing means is released immediately before administration to mix the agents.

As a method of releasing the dividing means to mix agents in such a multi-chamber container, there are a method of pressing a filling chamber by hand or the like to decrease the volume of the chamber, and thereby releasing the dividing means by pressure of the agent inside the chamber to mix the agents. There is also a method of providing an injection plug extending from a filling chamber to another filling chamber through the dividing means, and opening the injection plug to mix the agents, and the like.

In such mixing methods, an opening operation (pressing or opening of the plug) is necessary independently of the mounting operation in mounting the container to a predetermined device to administer. A problem arises in that it is possible to administer agents without performing the opening operation. Further, there is a type of container such that it is difficult to confirm that the dividing means is released and the agents are mixed, and it is often difficult to find that the opening operation is not performed.

It is an object of the present invention to provide a multi-chamber container that eliminates the possibility of forgetting to mix agents prior to administration.

DISCLOSURE OF INVENTION

The present invention is directed in one aspect to opening a plurality of filling chambers to mix agents inside the filling chambers, between taking out a packed container and mounting the container to a device.

A multi-chamber container of the present invention is a multi-chamber container that accommodates a plurality of agents, and has a plurality of filling chambers to fill agents, a communication portion is provided in at least one of the filling chambers to cause the filling chambers to be communicated with one another, and an opening preventing portion closes the communication portion in a carrying mode of the multi-chamber container, where the filling chambers are opened via the communication portion by user's operation in the carrying mode of the multi-chamber container to a use mode of the multi-chamber container.

Herein, as the user's general operation, i.e. as user's operations during a period from the carrying mode of the multi-chamber container to the use mode of the multi-chamber container, for example, there are an operation for taking out a packed multi-chamber container and removing the package, an operation for unfolding the multi-chamber container typically folded in two, and mounting the unfolded multi-chamber container on the device, i.e. hanging the container on the device. Accordingly, the present invention is directed to an aspect of opening a plurality of filling chambers using the operation for removing the package, another aspect of opening a plurality of filling chambers using the operation for unfolding a multi-chamber container folded in two, and still another aspect of opening a plurality of filling chambers using the operation for hanging the multi-chamber container in the device.

In other words, the multi-chamber container could be folded-in-two, the filling chambers opened in therebetween via the communication portion by expanding the multi-chamber container, and another aspect where in use, the multi-chamber container is hung so that the filling chambers open under their own weight as a result of hanging the multi-chamber container. In these cases, as opening preventing portions, there is a seal to peel off the communication portion, a folded tube having elasticity to recover by expanding, a clip to drop by expanding, a seal to peel off the communication portion by hanging, a clip to drop by hanging, a clogging member to be detached by hanging and the like.

Further, is an embodiment of the multi-chamber container of the present invention is a multi-chamber container that accommodates a plurality of agents, and has a plurality of filling chambers to fill agents, a communication portion that is provided in at least one of the filling chambers to cause the filling chambers to be communicated with one another, an opening preventing portion that closes the communication portion in a carrying mode of the multi-chamber container, and an opening portion that opens between the filling chambers via the communication portion by user's operation in the carrying mode of the multi-chamber container to a use mode of the multi-chamber container.

In such a configuration a plurality of filling chambers is opened using the user's general operation to mix agents inside the chambers, the multi-chamber container cannot be used unless the agents are mixed. Accordingly, the agents are always mixed when the user uses the multi-chamber container, and it is thereby possible to reliably prevent the occurrence of forgetting to mix the agents.

BEST MODE FOR CARRYING OUT THE INVENTION

Detailed Description of the Preferred Embodiments

Embodiments of the present invention will specifically be described below with reference to accompanying drawings.

First, Embodiments 1 to 12 described below explain an aspect where filling chambers are opened in therebetween by the operation for unfolding a multi-chamber container folded in two. In this aspect, a seal, tube, clip or the like is used as an opening preventing member, and a roller or the like is used as an opening member. Accordingly, before unfolding the multi-chamber container folded in two, filling chambers are not communicated with one another by the opening preventing member, and when the multi-chamber container is unfolded, due to the operation for unfolding the container, by the opening preventing member being detached, or by the opening member, the filling chambers are communicated with one another to be an open state. The Embodiments will be described below with reference to the drawings.

Embodiment 1

Embodiments 1 to 5 describe the case where the opening preventing member is a seal, the seal peels off by the operation for unfolding a multi-chamber container when the container is unfolded, and filling chambers are thereby communicated with each other to be an open state.

Figure 1A:
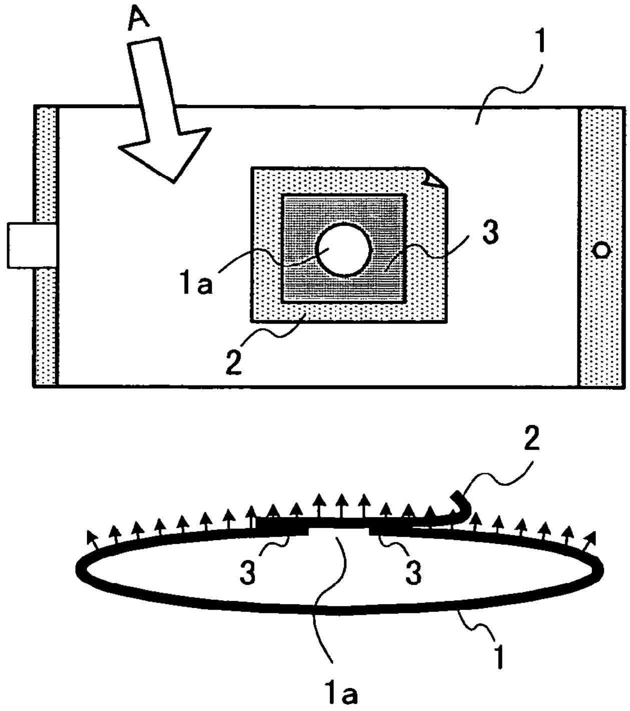
FIG. 1 shows a plan view and a cross-sectional view to explain a seal for use in a multi-chamber container according to Embodiment 1 of the present invention.
Figure 1B:
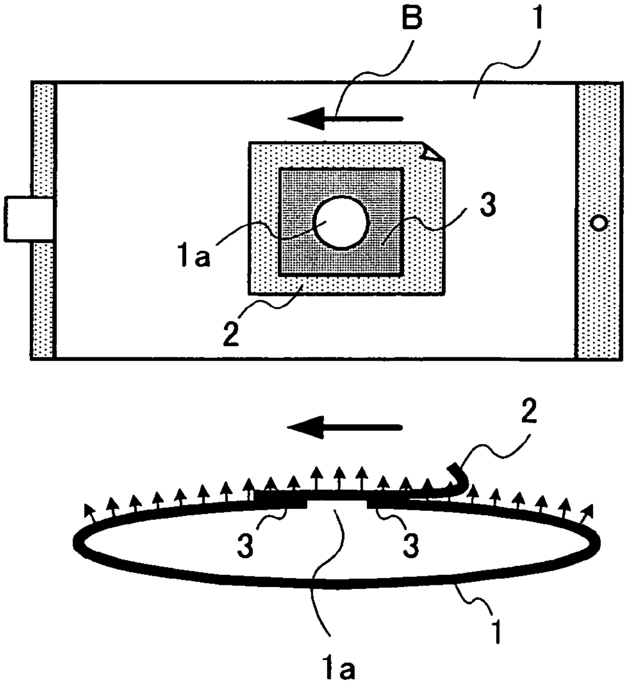

FIG. 1 shows a plan view and a cross-sectional view to explain the seal for use in the multi-chamber container according to Embodiment 1 of the invention. In FIG. 1, a hole 1*a* is formed in the center of a container 1. A seal 2 is bonded to the container 1 to cover the hole 1*a*. Between the container 1 and seal 2 are provided easy seal regions 3 where the seal 2 is adhered by adhesion to the extent such that the seal 2 can be easily peeled off. The seal 2 has sufficient resistance to pressure applied from above (the arrow A) as shown in FIG. 1(*a*). In other words, the pressure from above is dispersed over the entire container 1 and the seal 2 does not peel off. Further, as shown in FIG. 1(*b*), the seal 2 has the property of easily peeling off by the force from the lateral direction (the arrow B). By using such a seal as the opening preventing member, it is possible to cause the filling chambers to be opened in therebetween by the operation for unfolding the multi-chamber container.

Figure 2A:
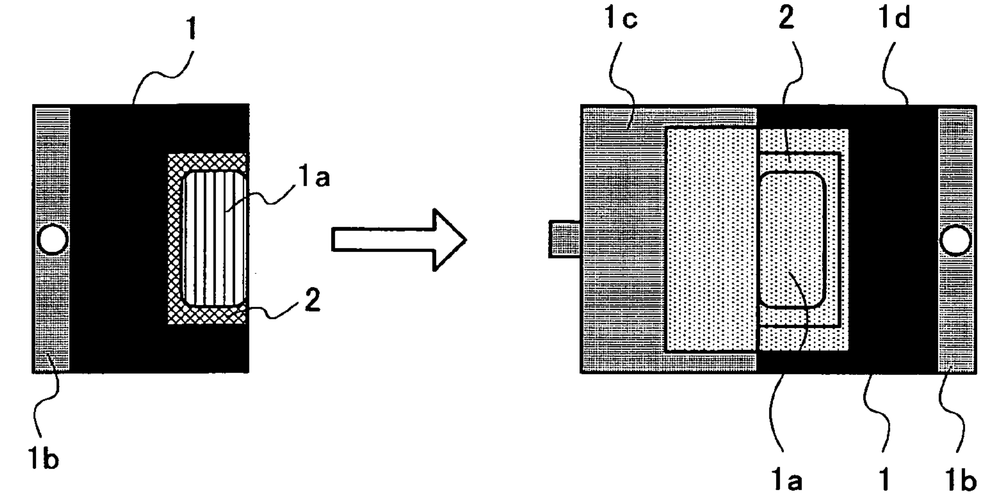
FIG. 2 shows a plan view and a side view showing the multi-chamber container using such a seal.
Figure 2B:
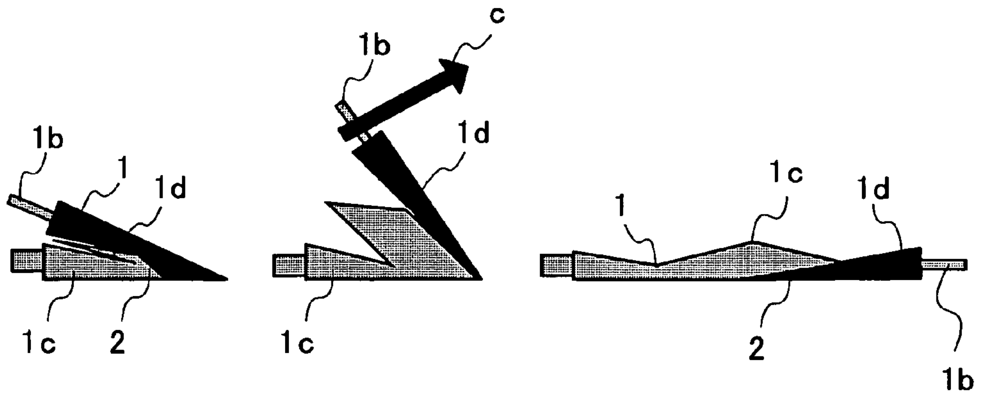

FIG. 2 shows a plan view and a side view showing the multi-chamber container using such a seal. The multi-chamber container 1 folded in two (right side of the sheet) is opened (left side of the sheet) as shown in FIG. 2(*a*), whereby the seal 2 peels off and the filling chambers 1*c* and 1*d* are opened and communicated. In other words, as shown in FIG. 2(*b*), by opening an end portion 1*b* in the direction of the arrow C, the seal 2 bonded between the filling chambers 1*c* and 1*d* is peeled off, the hole 1*a* closed by the seal 2 is opened, and an agent filled in the filling chamber 1*c* is mixed with another agent filled in the filling chamber 1*d*.

The multi-chamber container is generally transported with the container folded in two, and therefore, when using the container, the operation for unfolding the container as described above is always carried out. Accordingly, as described above, without performing the specific opening operation, only by unfolding the multi-chamber container, the seal peels off, the filling chambers are opened in therebetween, and therefore, when the user uses the container, the agents inside the respective filling chambers are mixed with reliability. As a result, it is possible to reliably avoid a situation that a user forgets to mix the agents. Further, only the action for unfolding the container is performed for the opening, and therefore, any foreign substances do not enter inside the filling chambers.

Figure 3A:
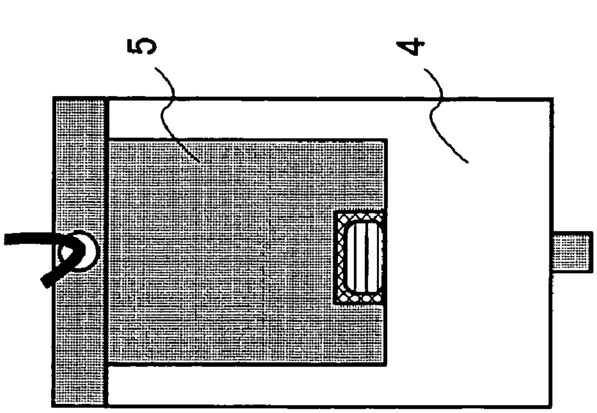
FIG. 3 is a view showing container placement of the multi-chamber container.
Figure 3B:
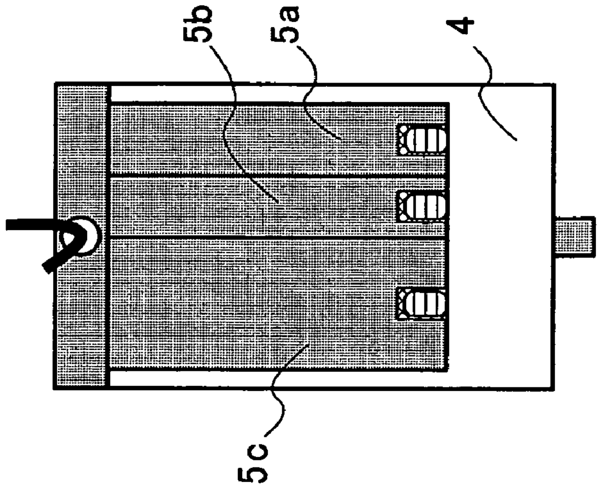
Figure 3C:
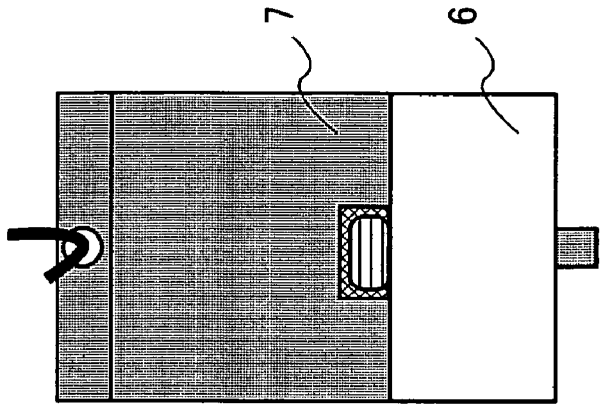

In this Embodiment, a form as shown in FIG. 3(*a*) may be provided that an inner filling chamber 5 is inserted into an outer filling chamber 4, and that a hole penetrating both the chambers is closed by the seal, another form as shown in FIG. 3(*b*) may be provided that a plurality of inner filling chambers 5*a* to 5*c* is inserted into an outer filling chamber 4, and that holes penetrating the outer filling chamber 4 and respective inner chambers 5*a* to 5*c* are closed by the seals, and still another form as shown in FIG. 3(*c*) may be provided that an upper filling chamber 7 is coupled to a lower filling chamber 6, and a hold penetrating both the chambers is closed by the seal. In addition, the number of filling chambers, and the arrangement form of the filling chambers are not limited particularly.

Embodiment 2

Figure 4:
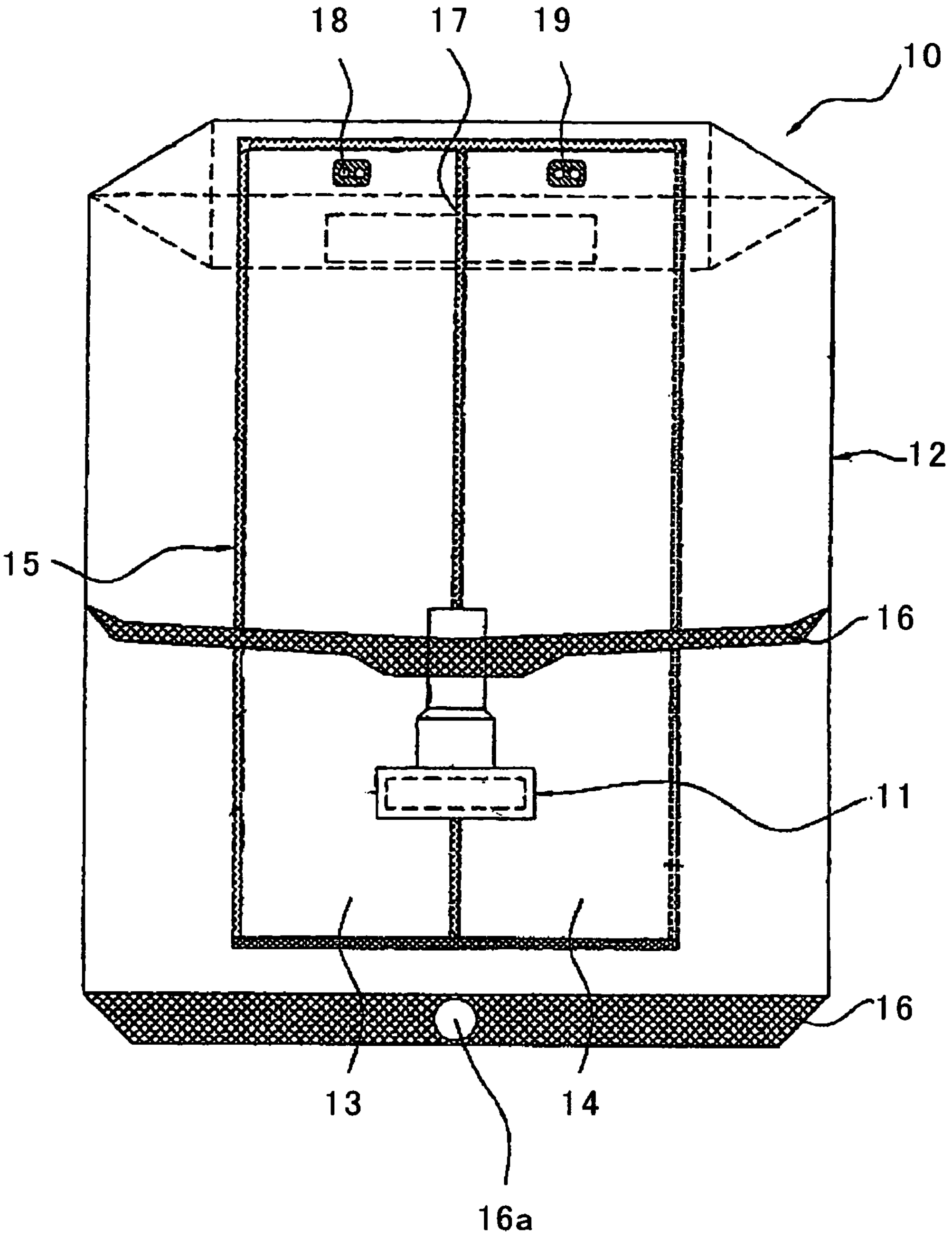
FIG. 4 is a view showing a multi-chamber container folded in two according to Embodiment 2 of the invention.
Figure 5:
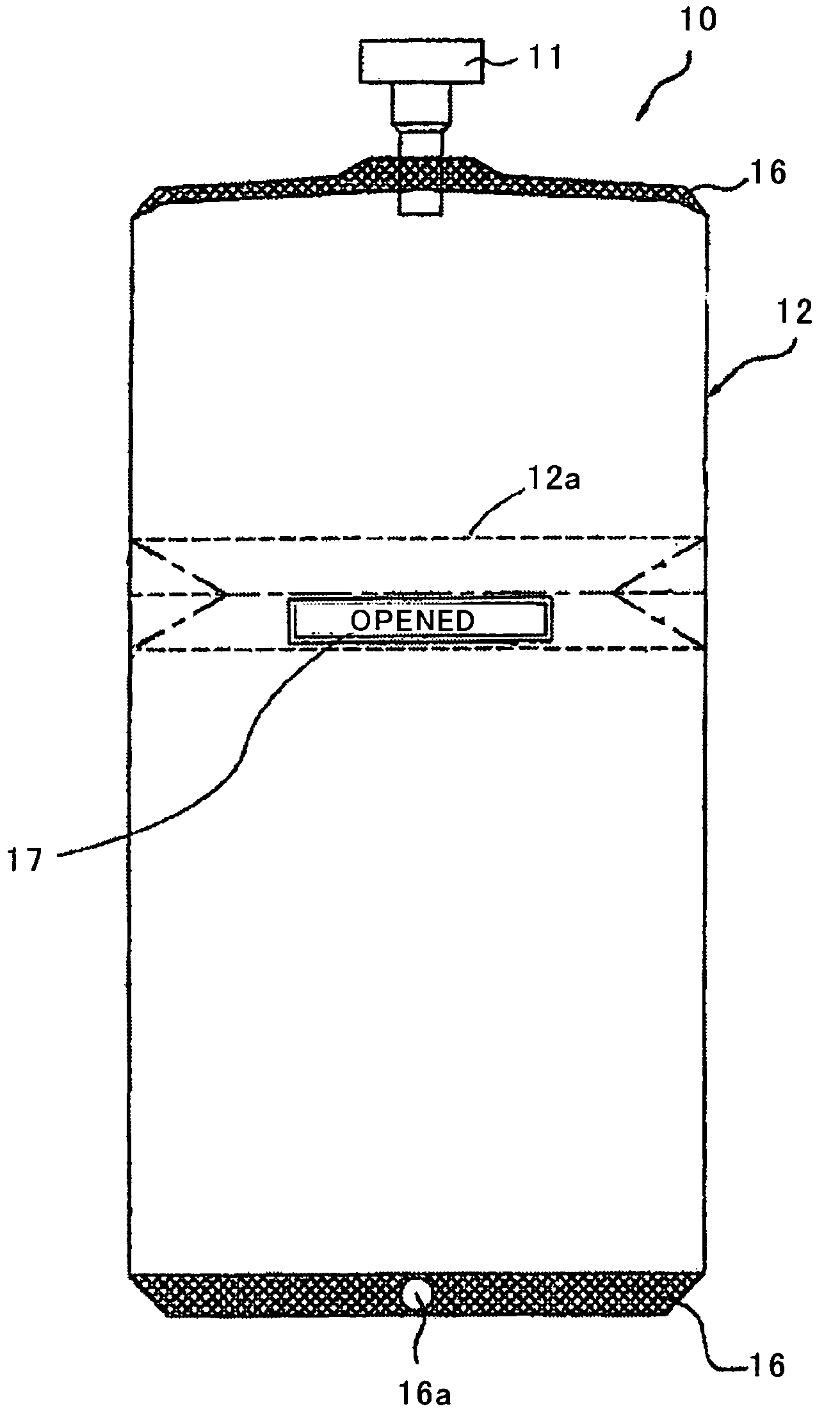
FIG. 5 is a view showing the expanded multi-chamber container according to Embodiment 2 of the invention.
Figure 6:
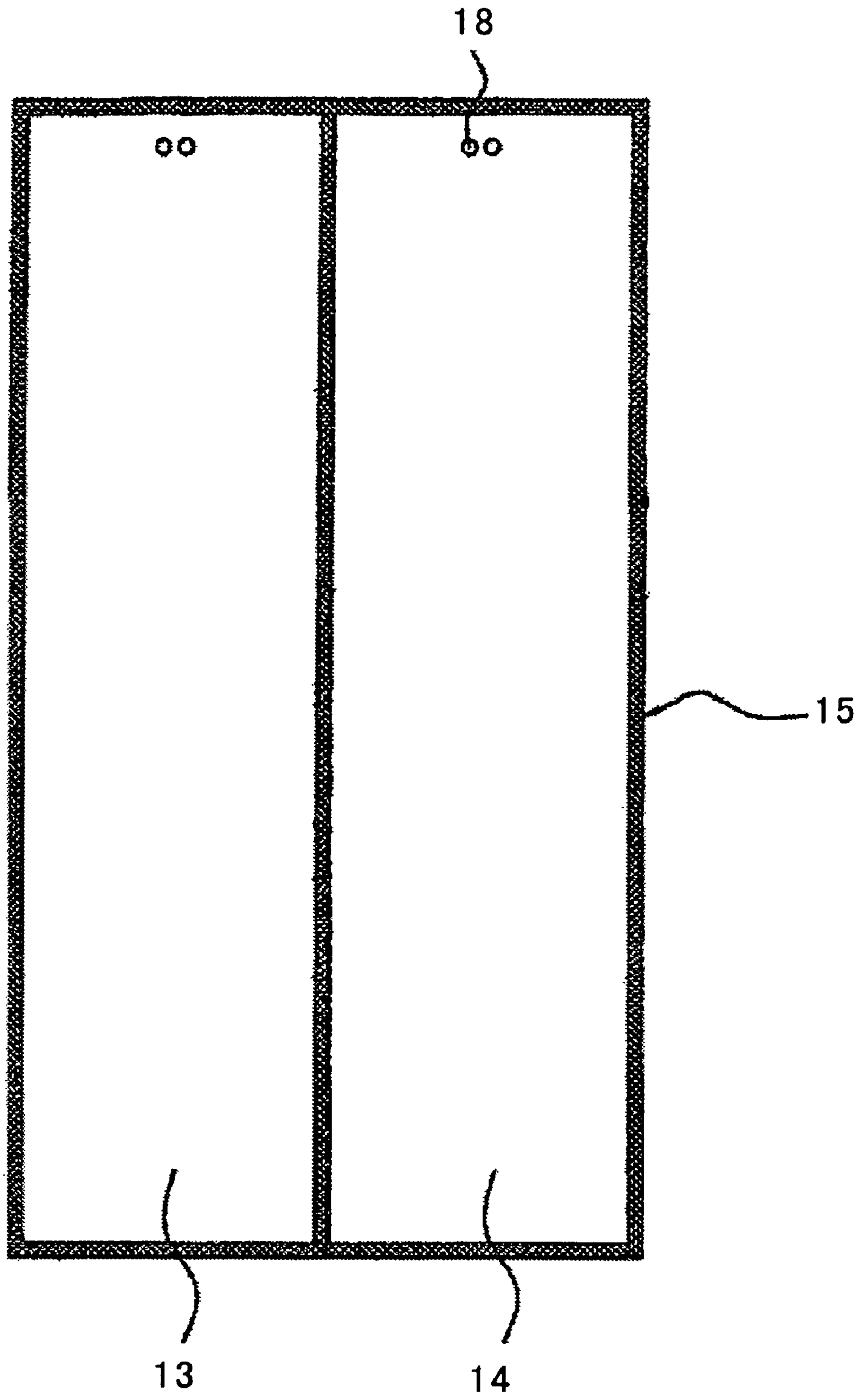
FIG. 6 is a front view of an internal container body of the multi-chamber container of FIG. 4.

FIG. 4 is a view showing a multi-chamber container folded in two according to Embodiment 2 of the invention. This multi-chamber container 10 is comprised of an outer container body 12 with a plug 11 as shown in FIG. 5, and an inner container body 15 provided with filling chambers 13 and 14 filled with unmixed agents as shown in FIG. 6.

The outer container body 12 is prepared by forming a transparent film sheet with flexibility into the shape of a tube, and fusing opened opposite end portions 16, and is thereby formed in the shape of a substantially rectangular bag. By folding the container along an interfold portion 12*a* of the outer container body 12, the multi-chamber container 10 as shown in FIG. 4 is obtained. The outer container body 12 has an indication label 17, bonded onto its outer surface, describing "opened" indicating the peeling of the seal described later.

The plug 11 is welded while being sandwiched by the film sheet of the outer container body 12, and attached to the upper end in the center of the outer container body 12. The plug 11 seals the inside of the outer container body 12 until a hollow needle is inserted therein in administering the agents.

The inner container body 15 is prepared by facing two transparent film sheets with flexibility opposite to each other and fusing the outer edge portion and center portion, and is thereby formed in the shape of a substantially rectangular bag. Two filling chambers 13 and 14 of the inner container body 15 are filled with different kinds of unmixed agents. In addition, substances filled in the filling chambers 13 and 14 are not limited to agents, and for example, adhesives and the like other than agents may be filled. In the inner container body 15, holes 18 are provided in the upper center of the filling chambers 13 and 14 to pass through the filled unmixed agents. The holes 18 are closed by seals 19. The seals 19 are configured to be able to peel off in synchronization with the operation for expanding the outer container body 12.

Figure 7:
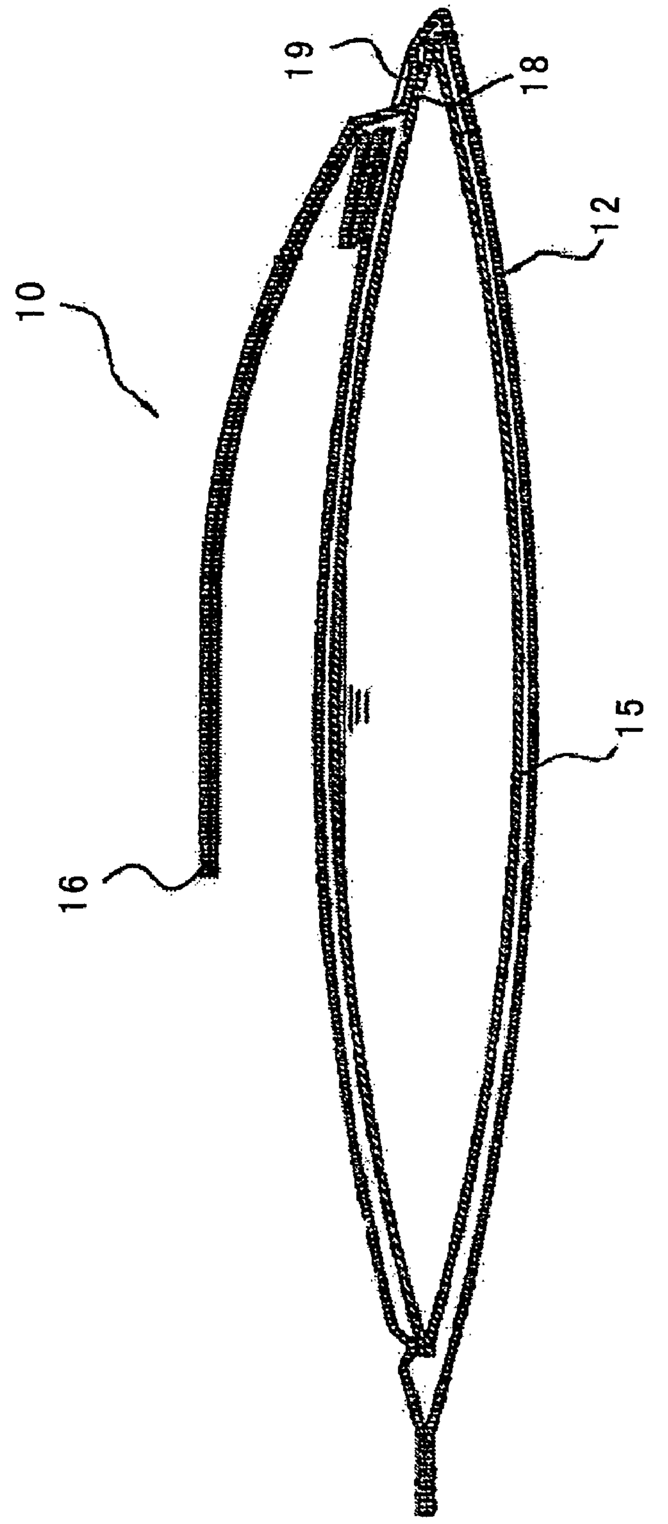
FIG. 7 is a cross-sectional view of the multi-chamber container of FIG. 4.
Figure 8:
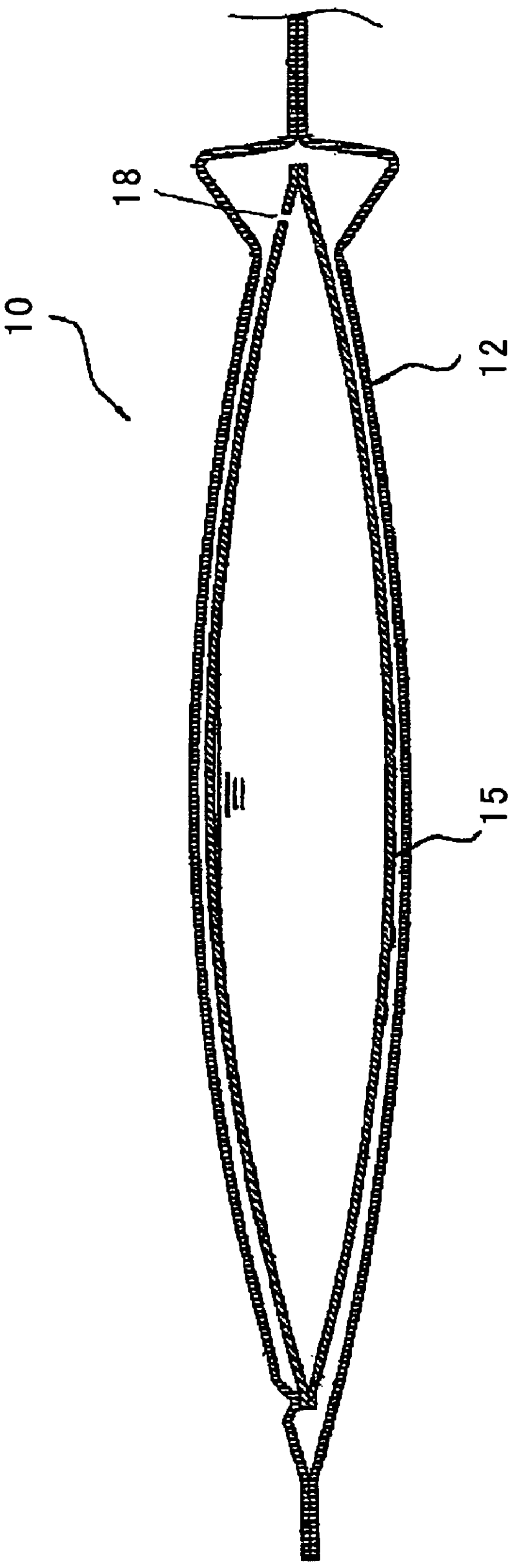
FIG. 8 is a cross-sectional view of the multi-chamber container of FIG. 5.

In the multi-chamber container 10 with the above-mentioned configuration, when the outer container body 12 is folded in two, as shown in FIG. 7, unmixed agents are completely sealed inside the filling chambers 13 and 14 by the seals 19 closing the holes 18 of the inner container body 15. When a user grasps the plug 11 and/or around the end portion 15 of the outer container body 12 and expands the outer container body 12, as shown in FIG. 8, the seals 19 closing the holes 18 peel off, and the outer container body 12 and filling chambers 13 and 14 of the inner container body 15 are communicated with one another through the holes 18. Then, a hook hole 16*a* provided in the outer container body 12 is put through a hook of a drip rack, the multi-chamber container 10 is thereby hung in the drip rack, a hollow needle is inserted into the plug 11, and the mixed agents are administered to a patient.

Further, since the form of the multi-chamber container 10 is different between before and after the peeling of the seals 19, the user is capable of recognizing that the seals 19 are not peeled off by the form of the appearance when the outer container body 12 is folded in two. Moreover, the indication label 17 is first faced outward by expanding the outer container body 12, and therefore, by checking the indication label 17, it is possible to recognize that the seals 19 have peeled off.

Also in this Embodiment, without performing the specific opening operation, only by unfolding the multi-chamber container, the seals peel off, the filling chambers are opened in therebetween, and therefore, the agents in the respective filling chambers are mixed with reliability when the user uses the container.

Embodiment 3

Figure 9:
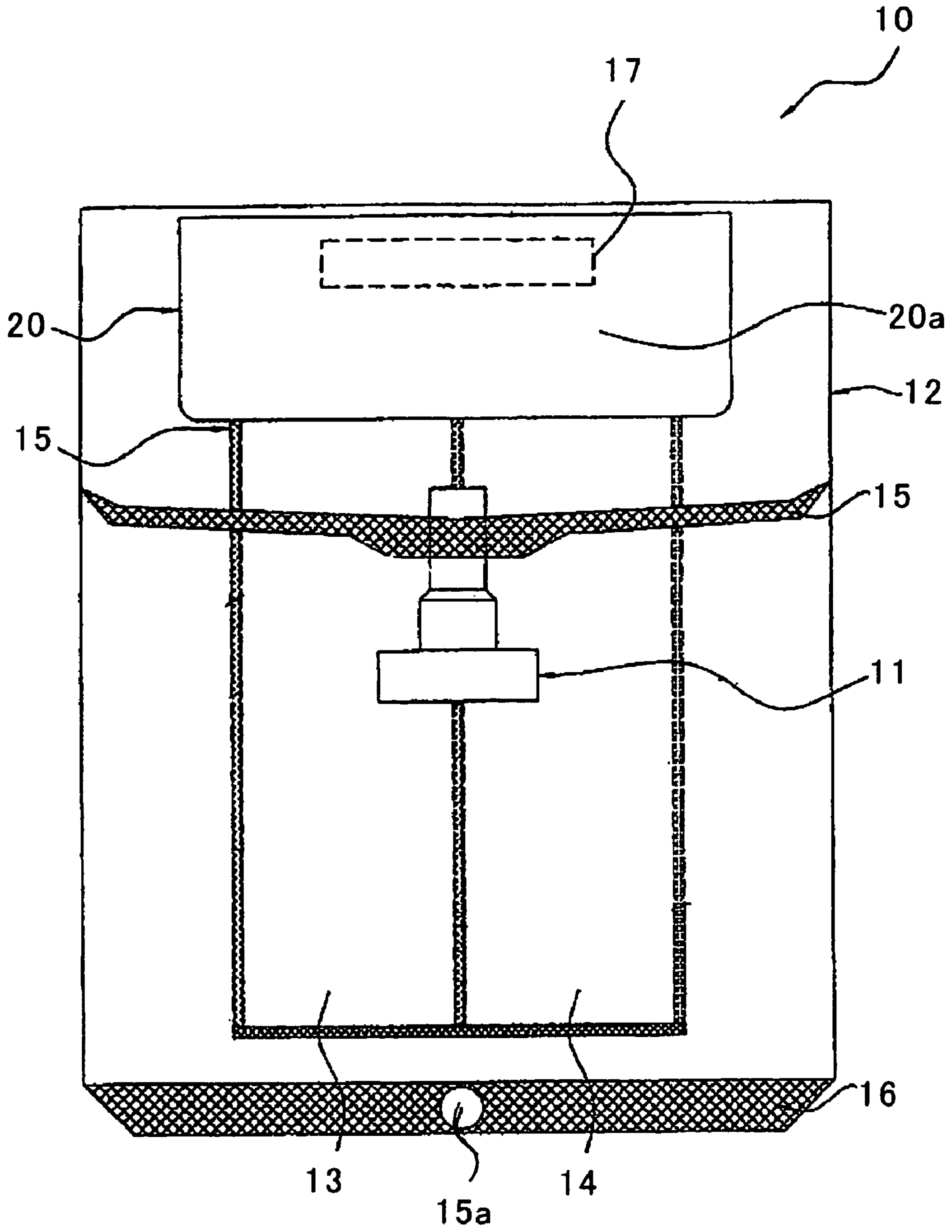
FIG. 9 is a view showing a multi-chamber container folded in two according to Embodiment 3 of the invention.

FIG. 9 is a view showing a multi-chamber container according to Embodiment 3 of the invention. In FIGS. 9 to 12, the same portions as in FIGS. 4 to 8 are assigned the same reference numerals as in FIGS. 4 to 8 to omit specific descriptions thereof.

Figure 10:
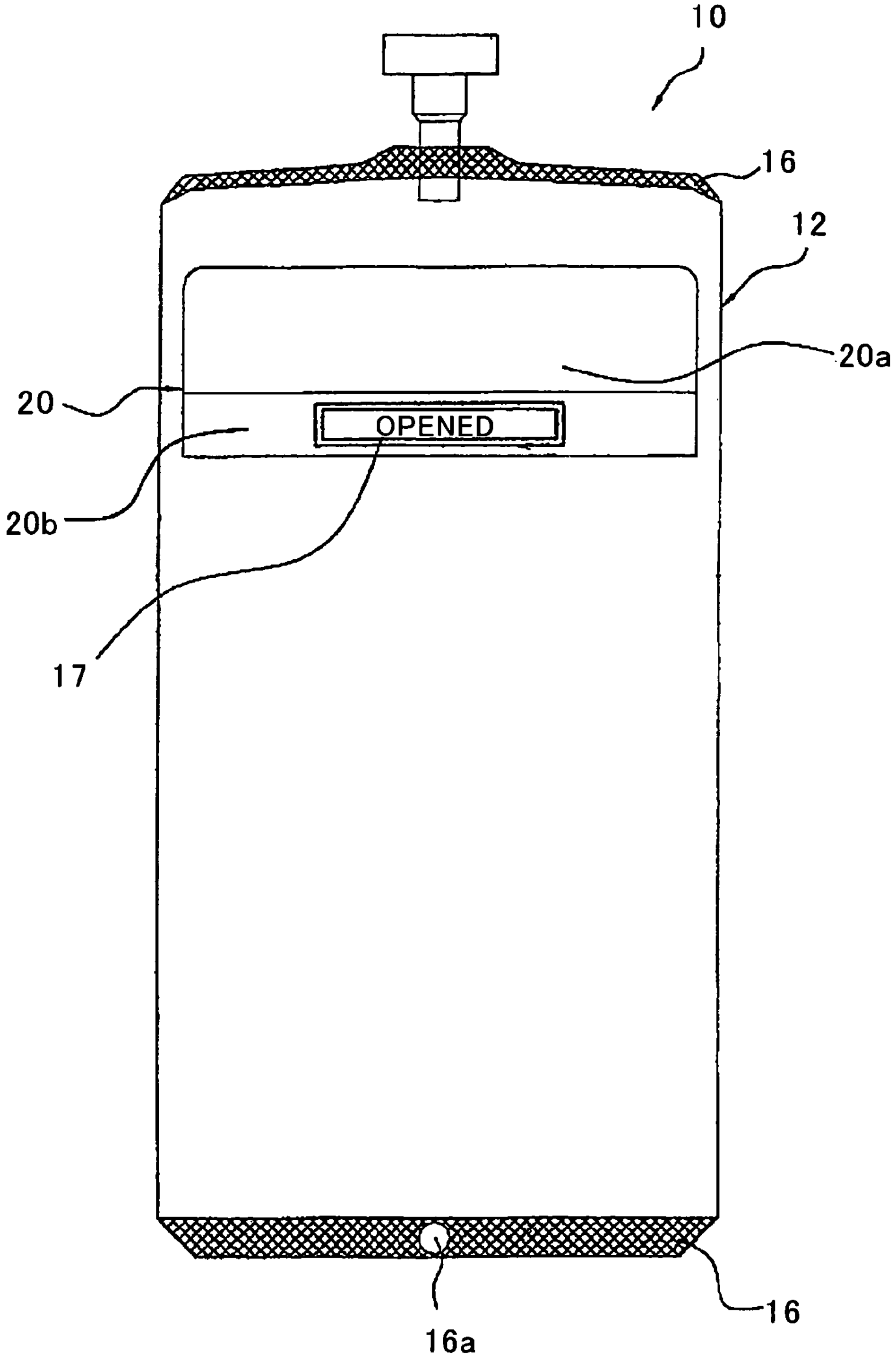
FIG. 10 is a view showing the expanded multi-chamber container according to Embodiment 3 of the invention.

As in the multi-chamber container 10 according to Embodiment 2, the multi-chamber container 10 according to this Embodiment is comprised of the outer container body 12 with the plug 11 attached thereto and the inner container body 15 provided with the filling chambers 13, 14 formed by dividing the inside. As shown in FIG. 10, to the outer container body 12 is attached a shape retaining member 20 in the interfold portion.

The shape retaining member 20 has a base portion 20*a* fixed to the inside of the outer container body 12, and a front end portion 20*b* toward which the base portion 20*a* is rounded and to which is bonded the label 17 describing "opened" indicating the peeling of the seals 19. As shown FIG. 11, the shape retaining member 20 has a cross section in the shape of a substantially hook. As shown in FIG. 10, the label 17 is bonded to the outer surface of the front end portion 20*b*, and can be visually identified when the multi-chamber container 10 is expanded. As shown in FIG. 12, the outer container body 12 is folded with the label 17 of the front end portion 20*b* of the shape retaining member 20 faced toward the filling chambers 13, 14 of the inner container body 15. At this point, the seals 19 provided on the outside of the front end portion 20*b* close the holes 18 of the inner container body 15.

Figure 11:
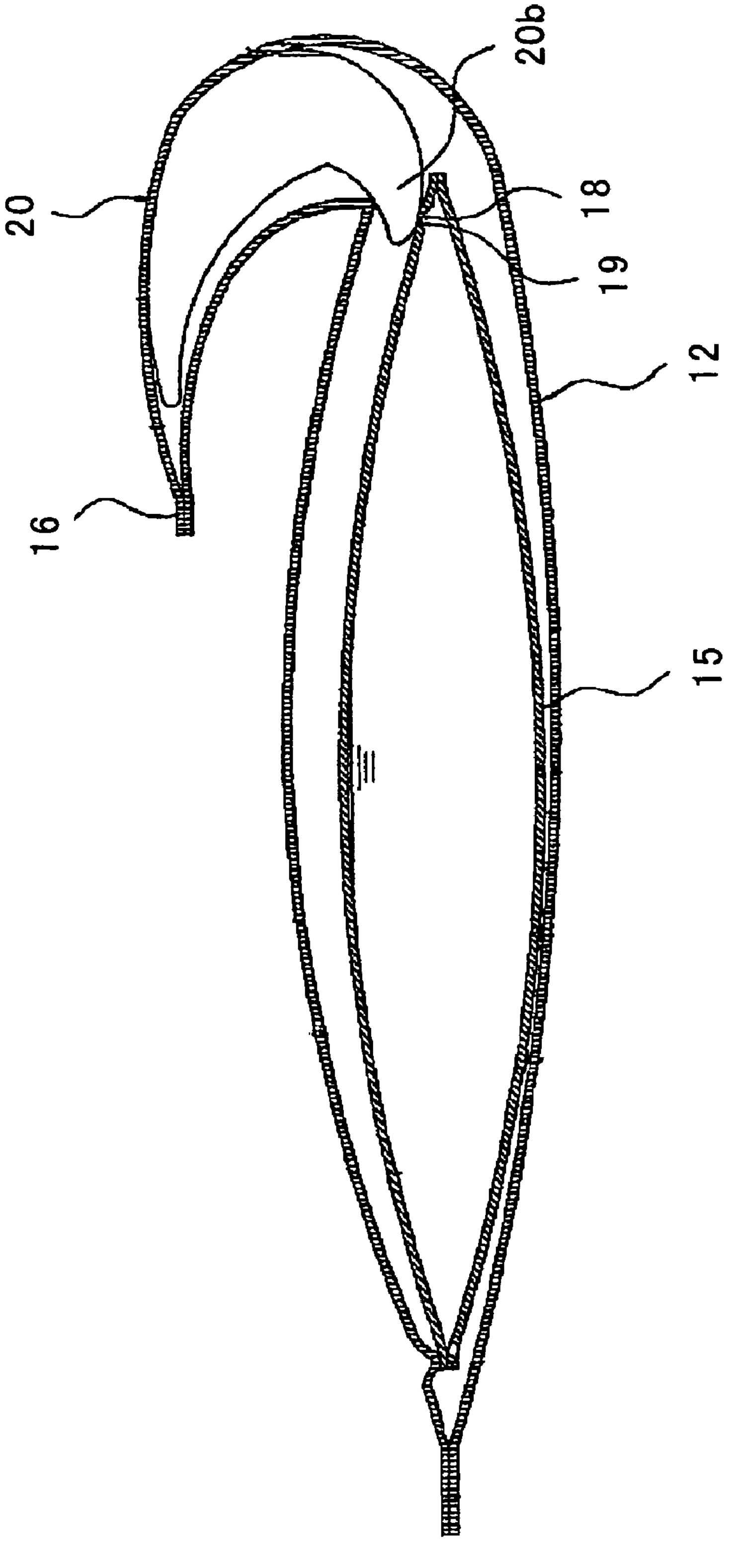
FIG. 11 is a cross-sectional view of the multi-chamber container of FIG. 9.
Figure 12:
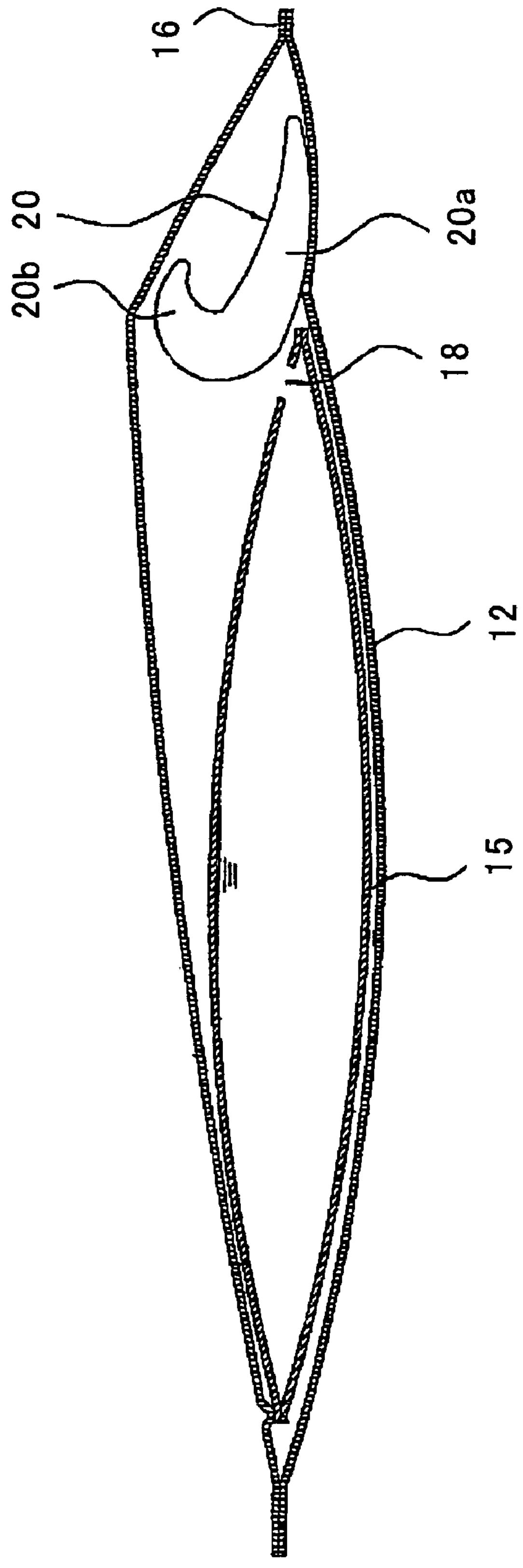
FIG. 12 is a cross-sectional view of the multi-chamber container of FIG. 10.

In the multi-chamber container 10 with the above-mentioned configuration, when the outer container body 12 is folded in two, as shown in FIG. 11, unmixed agents are completely sealed inside the filling chambers 13, 14 by the seals 19 closing the holes 18 of the inner container body 15. When a user grasps the plug 11 and/or around the end portion 16 of the outer container body 12 and expands the outer container body 12, as shown in FIG. 12, the base portion 20*a* fixed to the outer container body 12 is expanded, the seals 19 closing the holes 18 are thereby peeled off, and the outer container body 12 and filling chambers 13, 14 of the inner container body 15 are communicated with one another through the holes 18.

Also in this Embodiment, without performing the specific opening operation, only by unfolding the multi-chamber container, the seals peel off, the filling chambers are opened in therebetween, and therefore, the agents in the respective filling chambers are mixed with reliability when the user uses the container.

Embodiment 4

Figure 13:
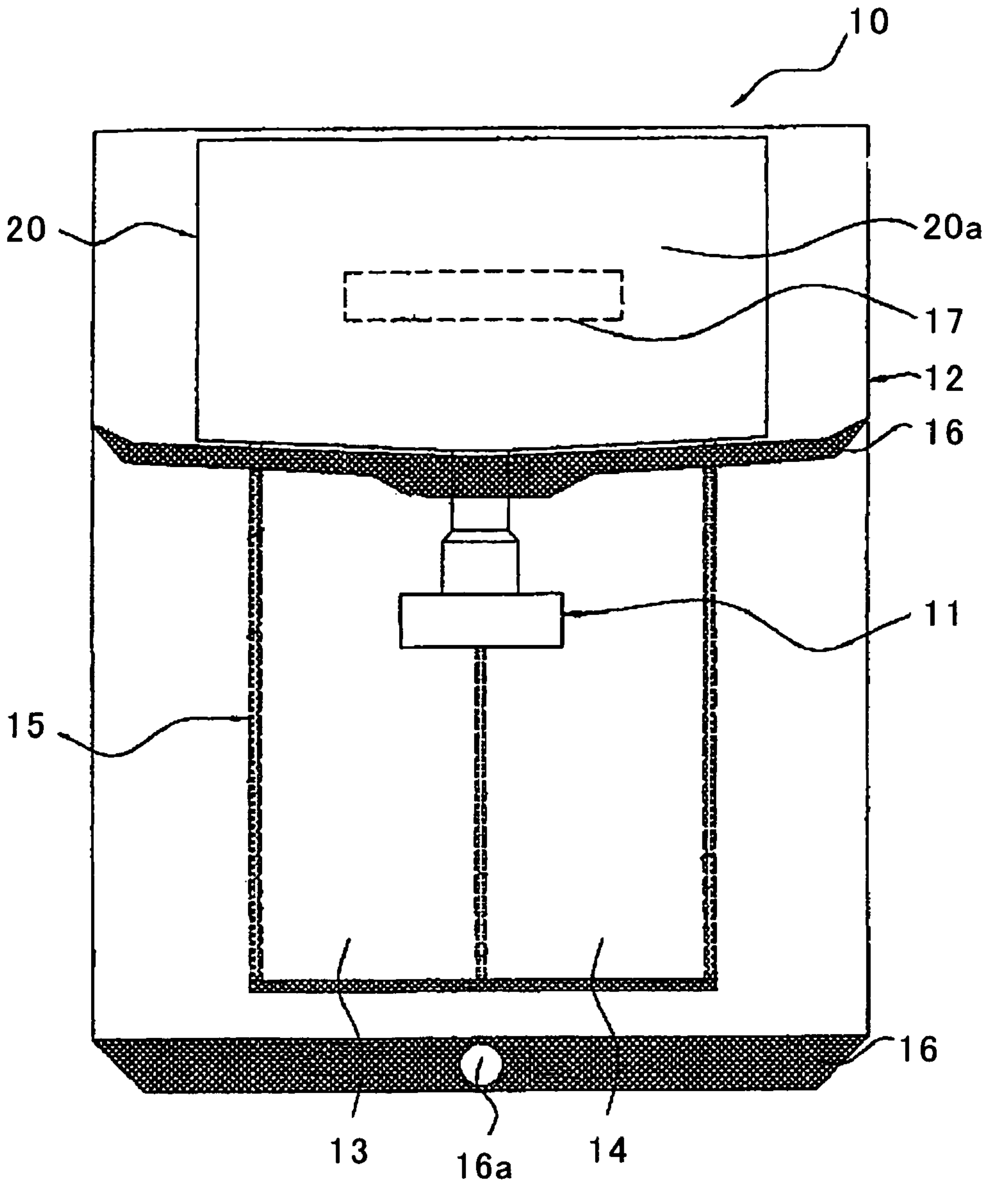
FIG. 13 is a view showing a multi-chamber container folded in two according to Embodiment 4 of the invention.

FIG. 13 is a view showing a multi-chamber container according to Embodiment 4 of the invention. In FIGS. 13 to 17, the same portions as in FIGS. 4 to 8 are assigned the same reference numerals as in FIGS. 4 to 8 to omit specific descriptions thereof.

Figure 14:
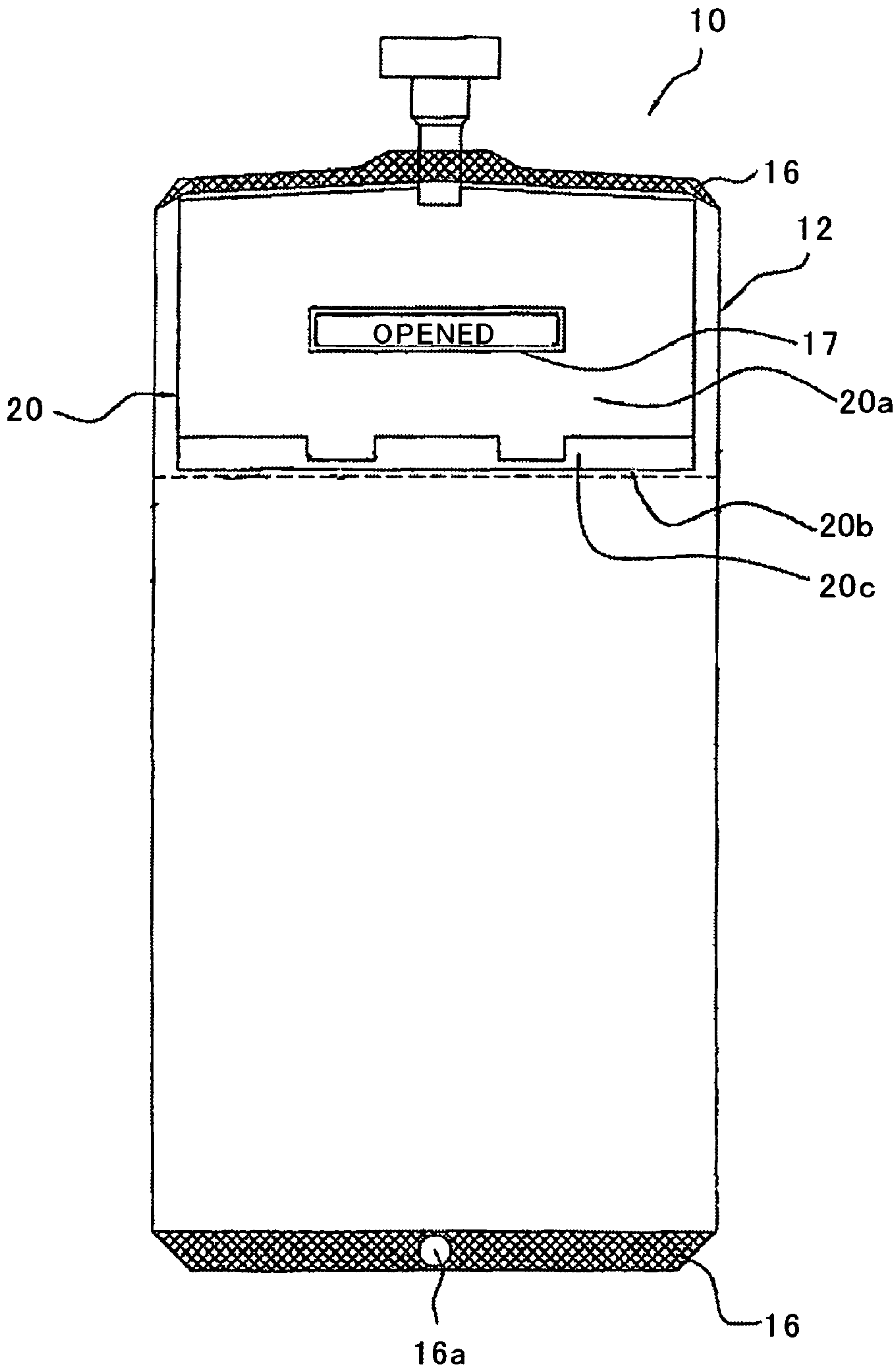
FIG. 14 is a view showing the expanded multi-chamber container according to Embodiment 4 of the invention.

As in the multi-chamber container 10 according to Embodiment 2, the multi-chamber container 10 according to this Embodiment is comprised of the outer container body 12 with the plug 11 attached thereto and the inner container body 15 provided with the filling chambers 13, 14 formed by dividing the inside. As shown in FIG. 14, to the outer container body 12 is attached a shape retaining member 20 in the interfold portion.

The shape retaining member 20 has the base portion 20*a* to which is bonded the label 17 describing "opened" indicating the peeling of the seals 19, and the front end portion 20*b* toward with the base portion 20*a* is rounded and which has claw portions 20*c*. As shown FIG. 16, the shape retaining member 20 has a cross section in the shape of a substantially hook. As shown in FIG. 14, the label 17 is bonded to the outer surface of the base portion 20*a*, and can be visually identified when the multi-chamber container 10 is expanded.

Figure 15:
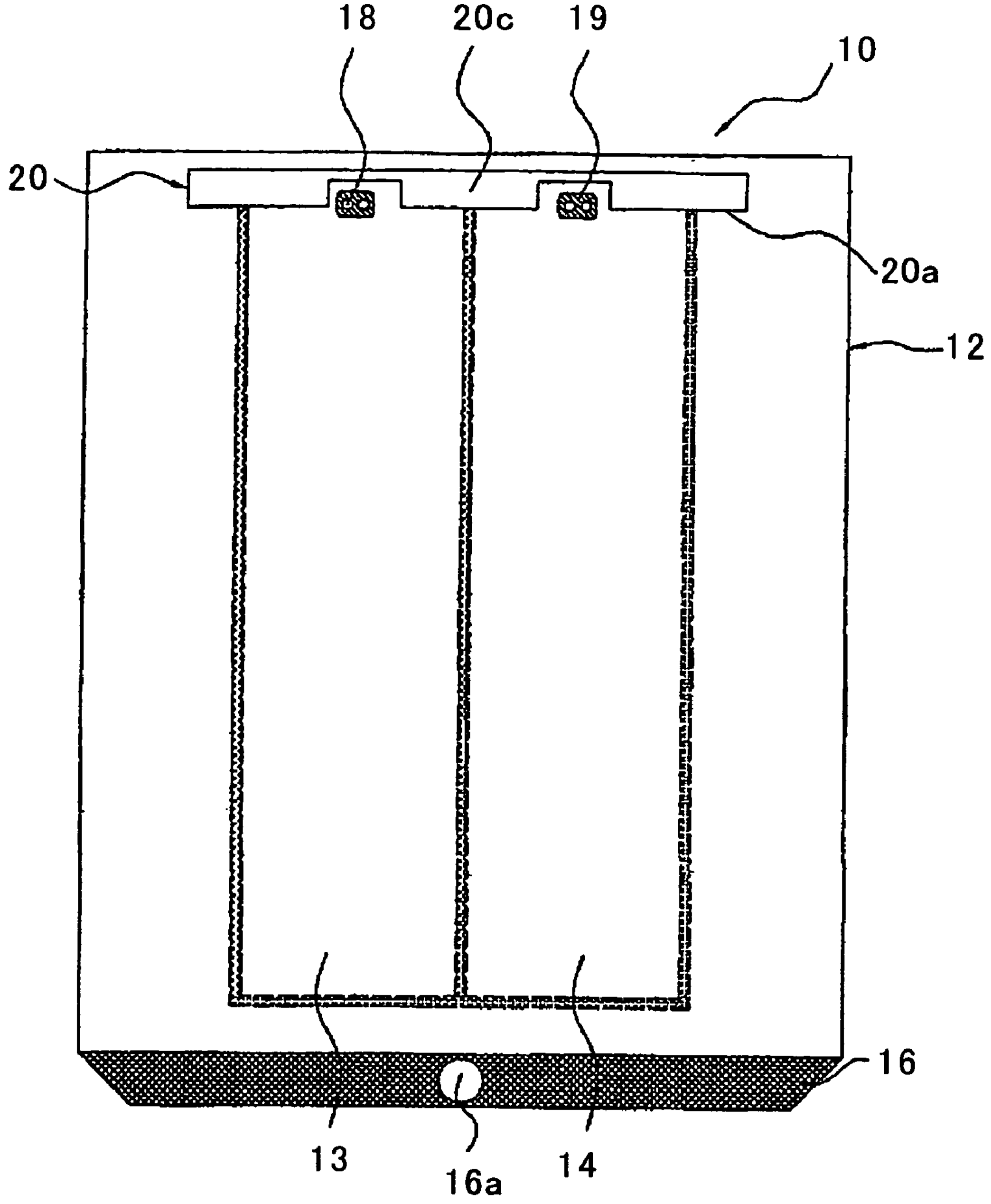
FIG. 15 is a rear view of the multi-chamber container of FIG. 14.
Figure 16:
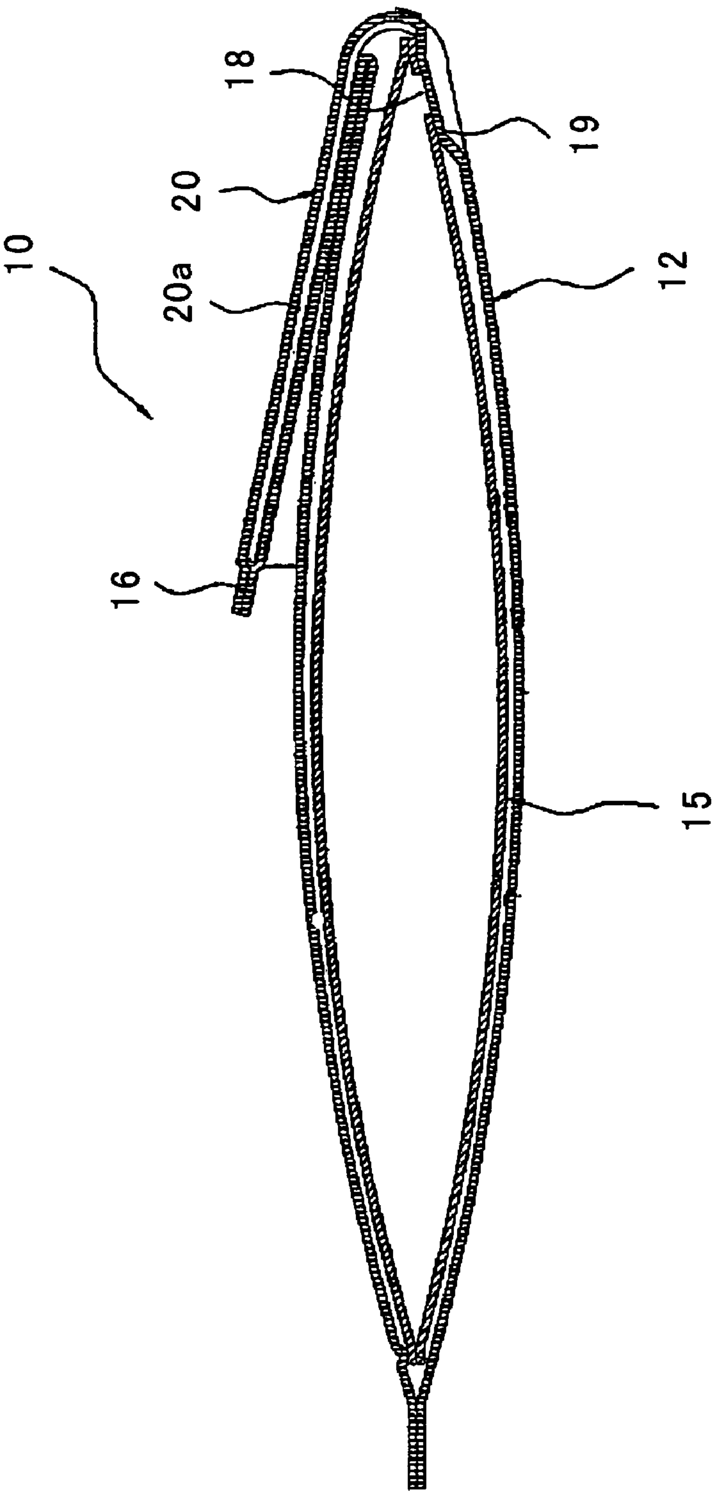
FIG. 16 is a cross-sectional view of the multi-chamber container of FIG. 13.

As shown in FIG. 15, in the inner container body 15, the holes 18 are respectively provided in the upper center of the filling chambers 13, 14 to eject filled unmixed agents. As shown in FIG. 16, the holes 18 are closed by the seals 19 when the outer container body 12 is folded with the label 17 of the base portion 20*a* of the shape retaining member 20 faced toward the filling chambers 13, 14 of the inner container body 15.

Figure 17:
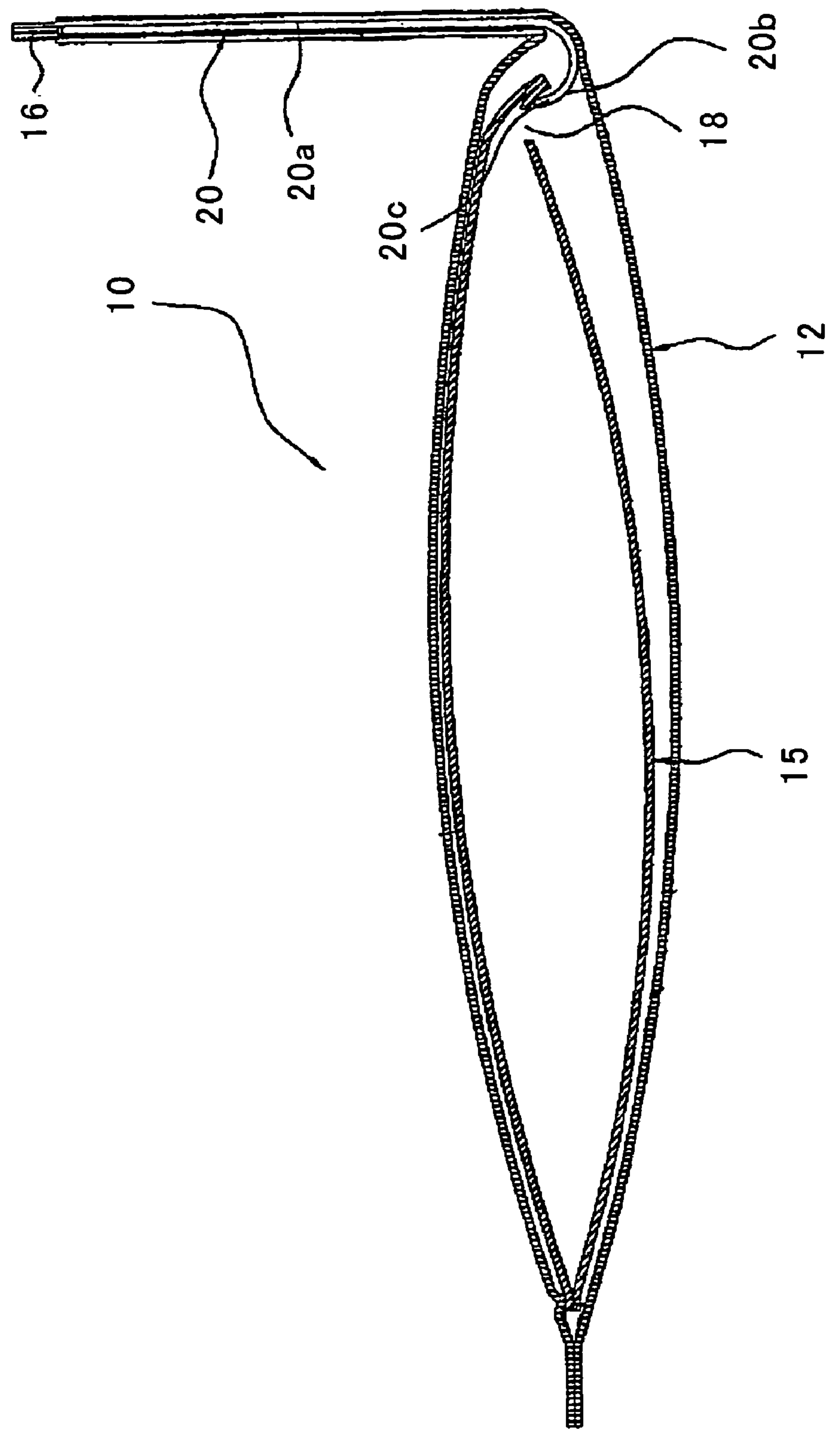
FIG. 17 is a cross-sectional view of the multi-chamber container of FIG. 14.

In the multi-chamber container 10 with the above-mentioned configuration, when the outer container body 12 is folded in two, as shown in FIG. 16, unmixed agents are completely sealed inside the filling chambers 13, 14 by the seals 19 closing the holes 18 of the inner container body 15. When a user grasps the plug 11 and/or around the end portion 16 of the outer container body 12 and expands the outer container body 12, as shown in FIG. 17, the base portion 20*a* fixed to the outer container body 12 is expanded, the seals 19 closing the holes 18 are thereby peeled off, and the outer container body 12 and filling chambers 13, 14 of the inner container body 15 are communicated with one another through the holes 18.

Also in this Embodiment, without performing the specific opening operation, only by unfolding the multi-chamber container, the seals are peeled off, the filling chambers are opened in therebetween, and therefore, the agents in the respective filling chambers are mixed with reliability when the user uses the container.

Embodiment 5

Figure 18:
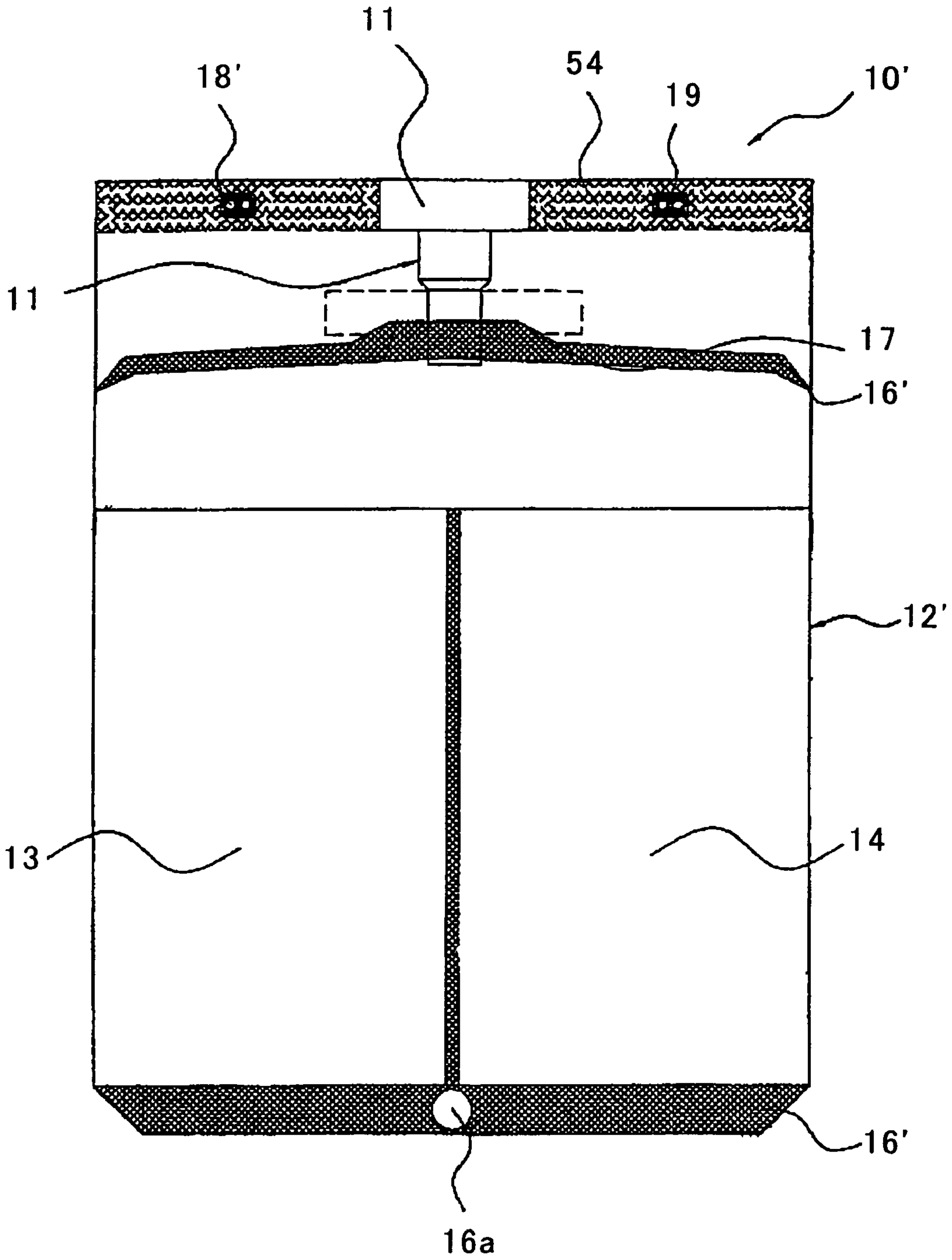
FIG. 18 is a view showing a multi-chamber container folded in two according to Embodiment 5 of the invention.
Figure 19:
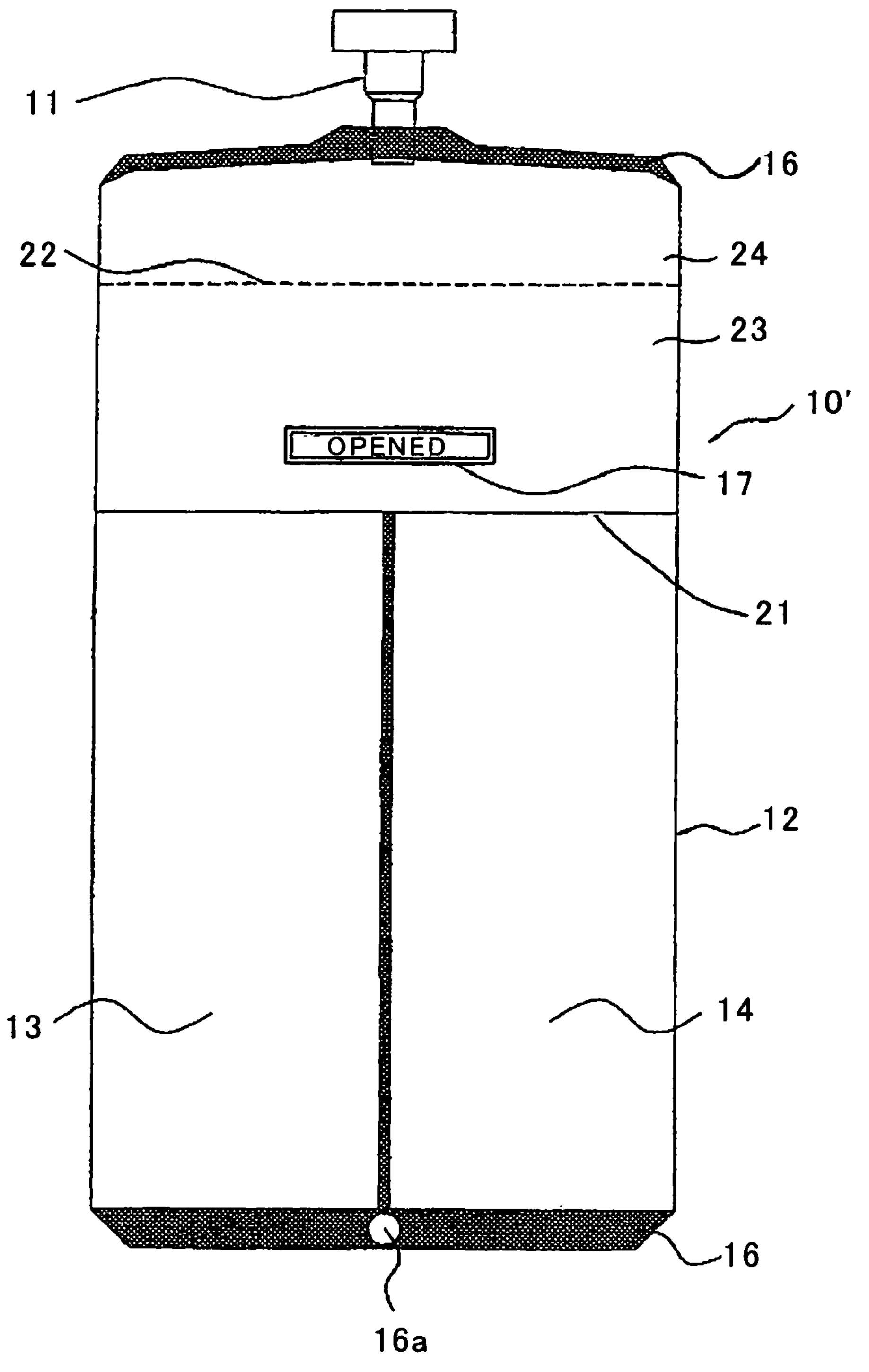
FIG. 19 is a view showing the expanded multi-chamber container according to Embodiment 5 of the invention.
Figure 20:
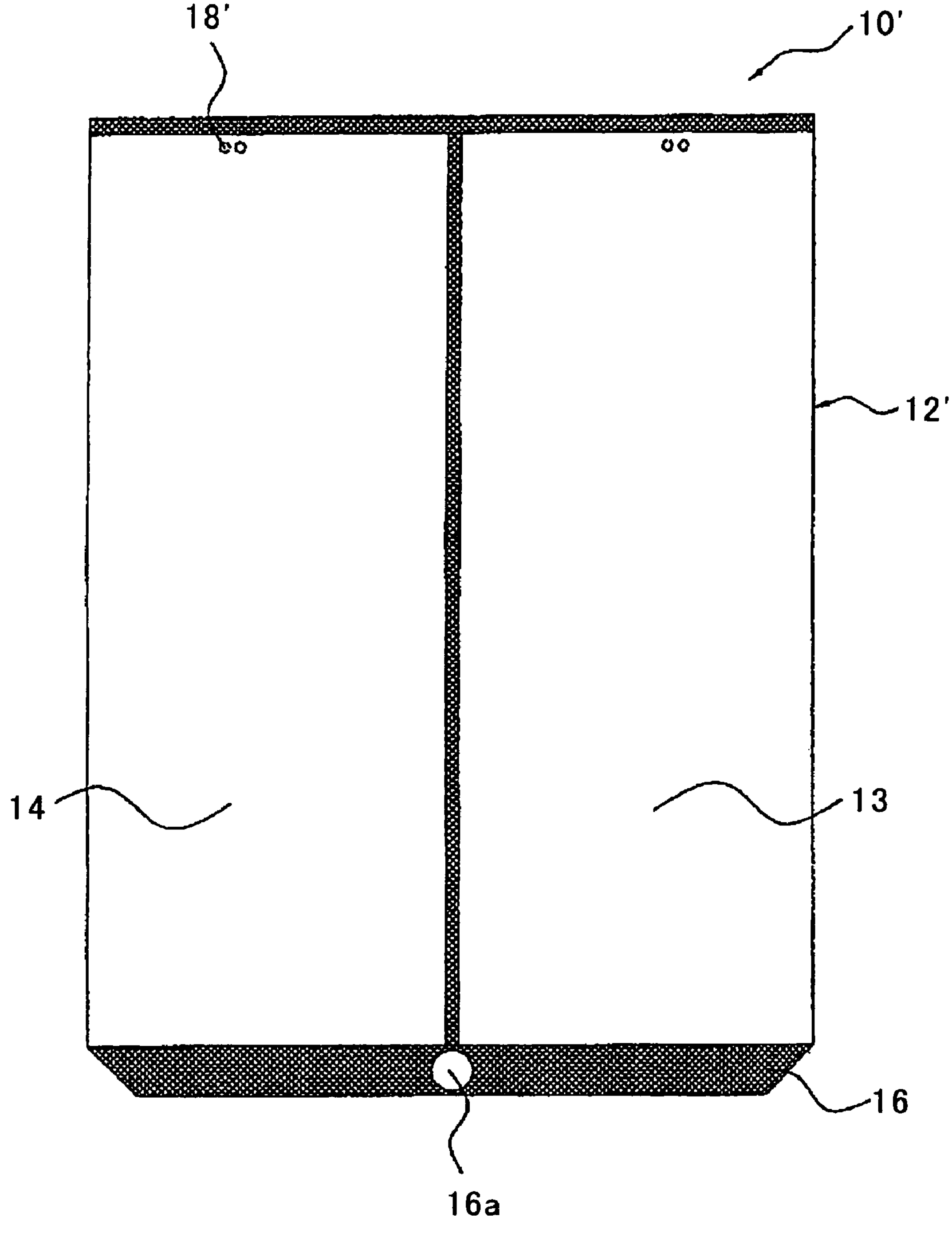
FIG. 20 is a rear view of the multi-chamber container of FIG. 19.

FIG. 18 is a view showing a multi-chamber container according to Embodiment 5 of the invention. As in the multi-chamber container 10 according to Embodiments 2 to 4, the multi-chamber container 10' according to this Embodiment is comprised of a container body 12' with a plug 11' attached thereto. The container body 12' has two divided filling chambers, 13' and 14'. As shown in FIG. 19, onto the surface of the container body 12' is bonded a substantially rectangular label 17' describing "opened" indicating the peeling of seals 19 described later. As shown in FIG. 20, the holes 18 are respectively provided in the upper center of the filling chambers 13', 14' on the side opposite to the label 17 of the container body 12'.

Figure 21:
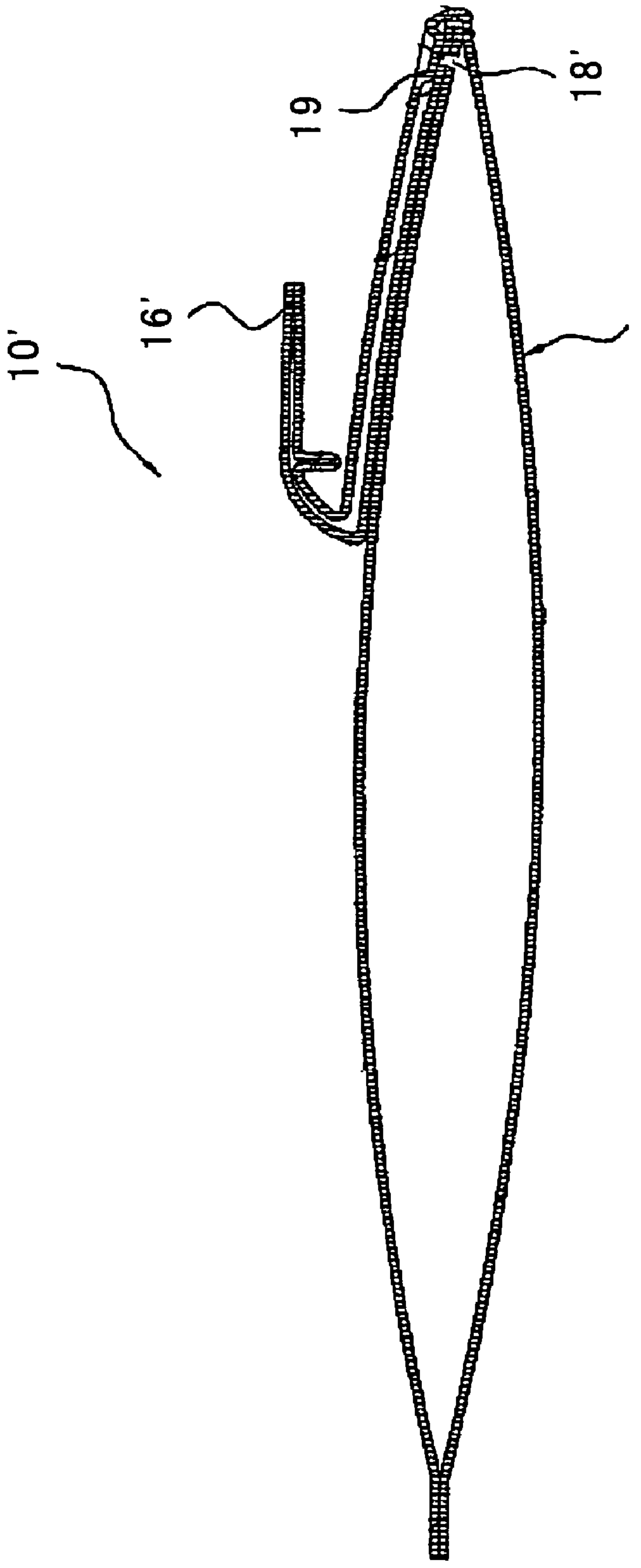
FIG. 21 is a cross-sectional view of the multi-chamber container of FIG. 18.

The multi-chamber container 10' as shown in FIG. 19 is valley-folded along the line 21, i.e. the filling chambers 13', 14' are made opposite to the label 17, and the container 10' is further mountain-folded along the line 22, whereby as shown in FIG. 21, the holes 18' are closed by the seals 19'. In other words, the multi-chamber container 10' is folded in three such that a label portion 23 is folded into a region of the filling chambers of the container body 12' and that the front end portion 24 is further folded from the label portion 23.

Figure 22:
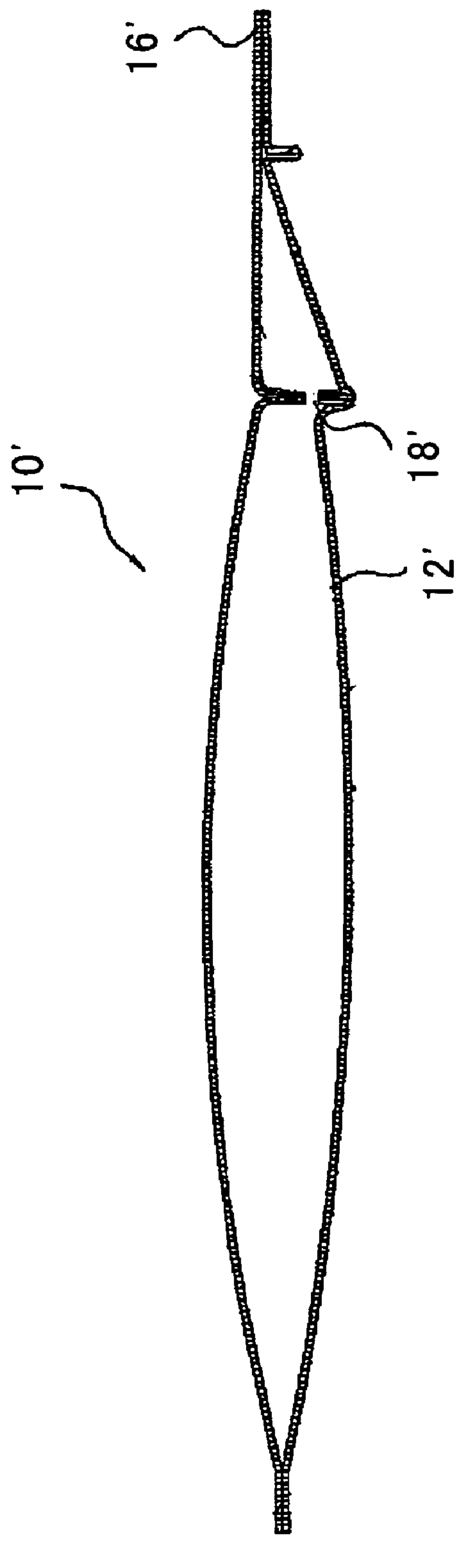
FIG. 22 is a cross-sectional view of the multi-chamber container of FIG. 19.

In the multi-chamber container 10' with the above-mentioned configuration, when the outer container body 12' is folded in three, as shown in FIG. 21, unmixed agents are completely sealed inside the filling chambers 13', 14' by the seals 19' closing the holes 18' of the container body 12'. When a user grasps the plug 11' and/or around an end portion 16' of the container body 12' and expands the container body 12', as shown in FIG. 22, the front portion 24 separates from the label portion 23, and the label portion 23 separates from the filling-chamber region. The seals 19' closing the holes 18' are thereby peeled off, and the filling chambers 13', 14' of the container body 12' are communicated with one another through the holes 18'.

Also in this Embodiment, without performing the specific opening operation, only by unfolding the multi-chamber container, the seals are peeled off, the filling chambers are opened in therebetween, and therefore, the agents inside the respective filling chambers are mixed with reliability when the user uses the container.

Embodiment 6

Embodiments 6 and 7 describe the case where an opening member is a roller, and when a multi-chamber container is unfolded, filling chambers are pressed by the operation for unfolding the container, and thereby communicated with each other to be an open state.

Figure 23:
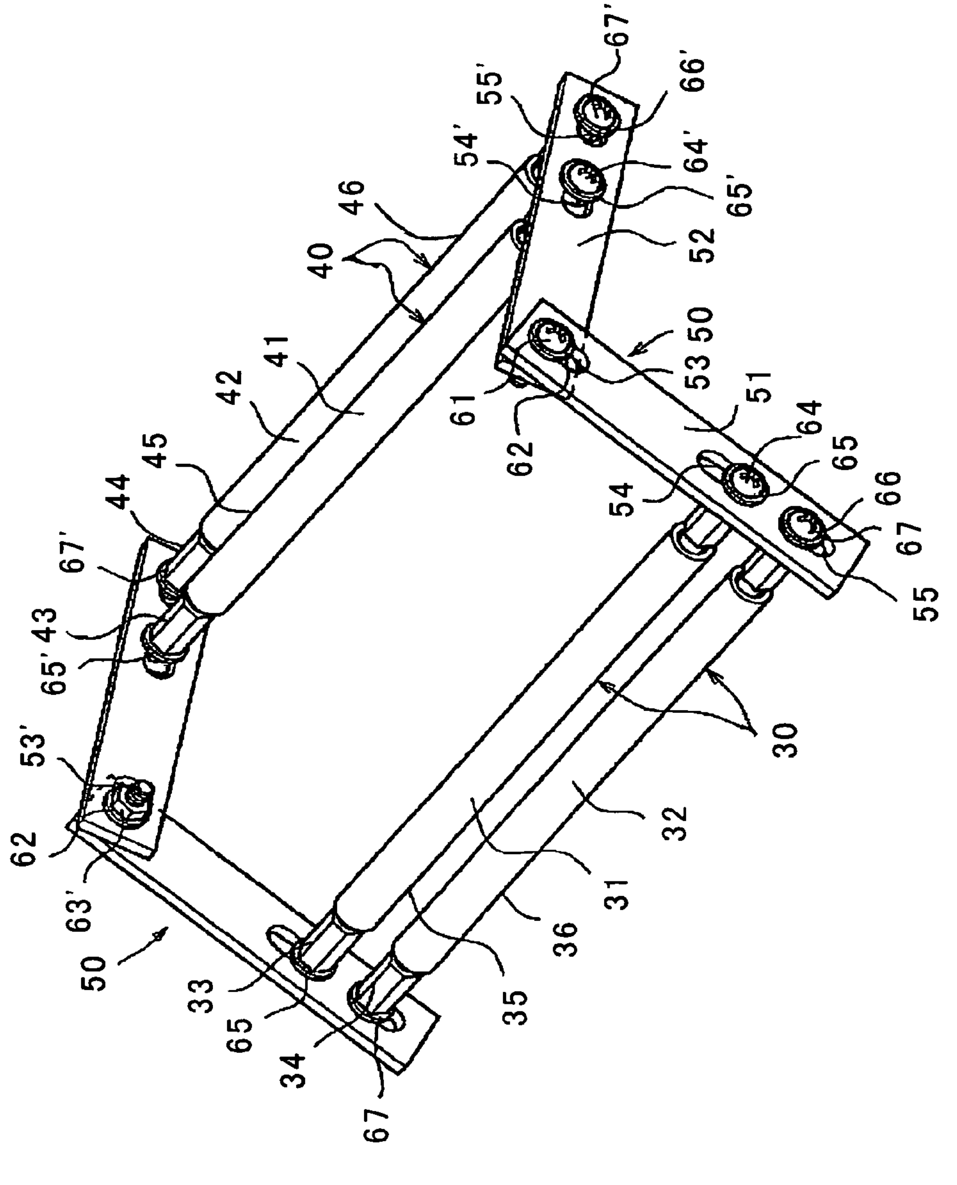
FIG. 23 is a perspective view showing an opening device of a multi-chamber container according to Embodiment 6 of the invention.

FIG. 23 is a perspective view showing an opening device of a multi-chamber container according to Embodiment 6 of the invention. The opening device is comprised of a pinching device 30 comprised of two rod-shaped members, 31 and 32, a holding device 40 comprised of two rod-shaped members, 41 and 42, and a pair of coupling devices 50, each comprised of a coupled rectangular first plate member 51 and second plate member 52, for fixing respective opposite ends of two rod-shaped members 31, 32 of the pinching device 30 and two rod-shaped members 41, 42 of the holding device 40.

The first plate member 51 is provided with an ellipse-shaped first screw hole 53 formed on one end side, an ellipse-shaped second screw hole 54 formed on the other end side slightly spaced from the center, and an ellipse-shaped third screw hole 55 formed on the other end side. As in the first plate member 51, the second plate member 52 is provided with an ellipse-shaped first screw hole 53' formed on one end side, an ellipse-shaped second screw hole 54' formed on the other end side slightly spaced from the center, and an ellipse-shaped third screw hole 55' formed on the other end side. The first plate member 51 and second plate member 52 overlap each other at a predetermined angle with part of the first screw hole 53 and first screw hole 53' matching each other. The first plate member 51 and second plate member 53 are coupled to each other by screwing a screw 61 inserted into the first screw holes 53 and 53' from the first plate member side 51 into a screw portion of a nut 63 with washers 62 on the head and opposite sides of the screw 61.

Figure 26:
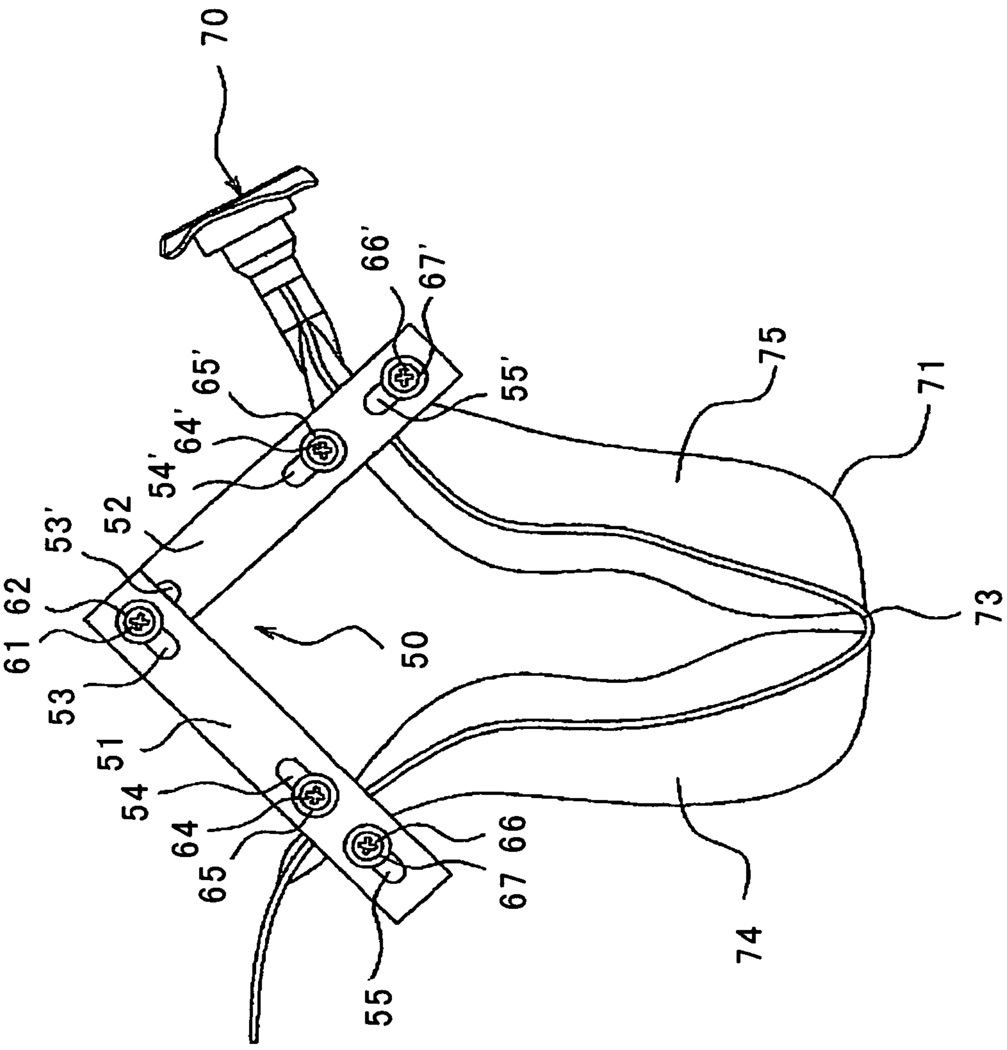
FIG. 26 is a front view showing the multi-chamber container inserted into the opening device of FIG. 23.
Figure 27:
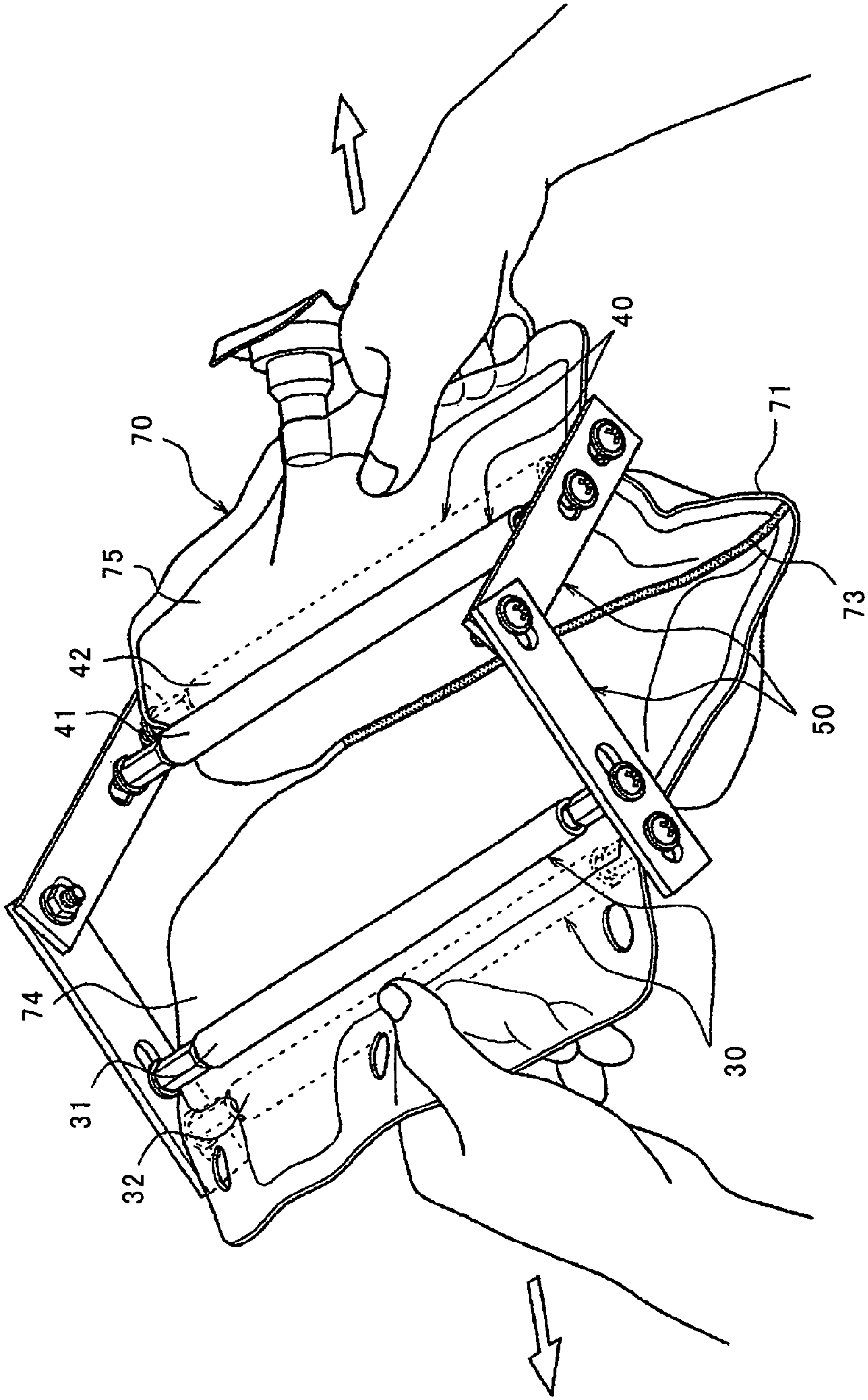
FIG. 27 a perspective view showing the multi-chamber container inserted into the opening device of FIG. 23.

One rod-shaped member 31 of the pinching device 30 is provided at opposite ends with hexagonal cylindrical screw cramp portions 33 each having a screw portion screwed with the screw. The one rod-shaped member 31 of the pinching device 30 is fixed to the first plate members 51 by screwing screws 64 inserted into the second screw holes 54 of a pair of the first plate members 51 into screw portions of screw cramp portions 33 at opposite ends with washers 65 on the head and opposite sides of the screws 64. The other rod-shaped member 32 of the pinching device 30 is provided at opposite ends with hexagonal cylindrical screw cramp portions 34 each having a screw portion screwed with the screw. The other rod-shaped member 32 of the pinching device 30 is fixed to the first plate members 51 by screwing screws 66 inserted into the third screw holes 55 of a pair of the first plate members 51 into screw portions of screw cramp portions 34 at opposite ends with washers 67 on the head and opposite sides of the screws 66. As shown in FIGS. 26 and 27, in the pinching device 30, an end portion on a first filling chamber 74 side of a multi-chamber container 70 folded in two is inserted into between two rod-shaped members 31, 32, and is pinched by two rod-shaped members 31, 32 each contacting a wall portion of the first filling chamber 74.

One rod-shaped member 41 of the holding device 40 is provided at opposite ends with hexagonal cylindrical screw cramp portions 43 each having a screw portion screwed with the screw. The one rod-shaped member 41 of the holding device 40 is fixed to the second plate members 52 by screwing screws 64' inserted into the second screw holes 54' of the second plate members 52 into screw portions of screw cramp portions 43 at opposite ends with washers 65' on the head and opposite sides of the screws 64'. The other rod-shaped member 42 of the holding device 40 is provided at opposite ends with hexagonal cylindrical screw cramp portions 44 each having a screw portion screwed with the screw. The other rod-shaped member 42 of the holding device 40 is fixed to the second plate members 52 by screwing screws 66' inserted into the third screw holes 55' of the second plate members 52 into screw portions of screw cramp portions 44 at opposite ends with washers 67' on the head and opposite sides of the screws 66'. In the holding device 40, an end portion on a plug 80 side of the multi-chamber container 70 folded in two is inserted into between two rod-shaped members 41,42, and a second filling chamber 75 is held by two rod-shaped members 41, 42 each contacting a wall portion of the second filling chamber 75.

Figure 25:
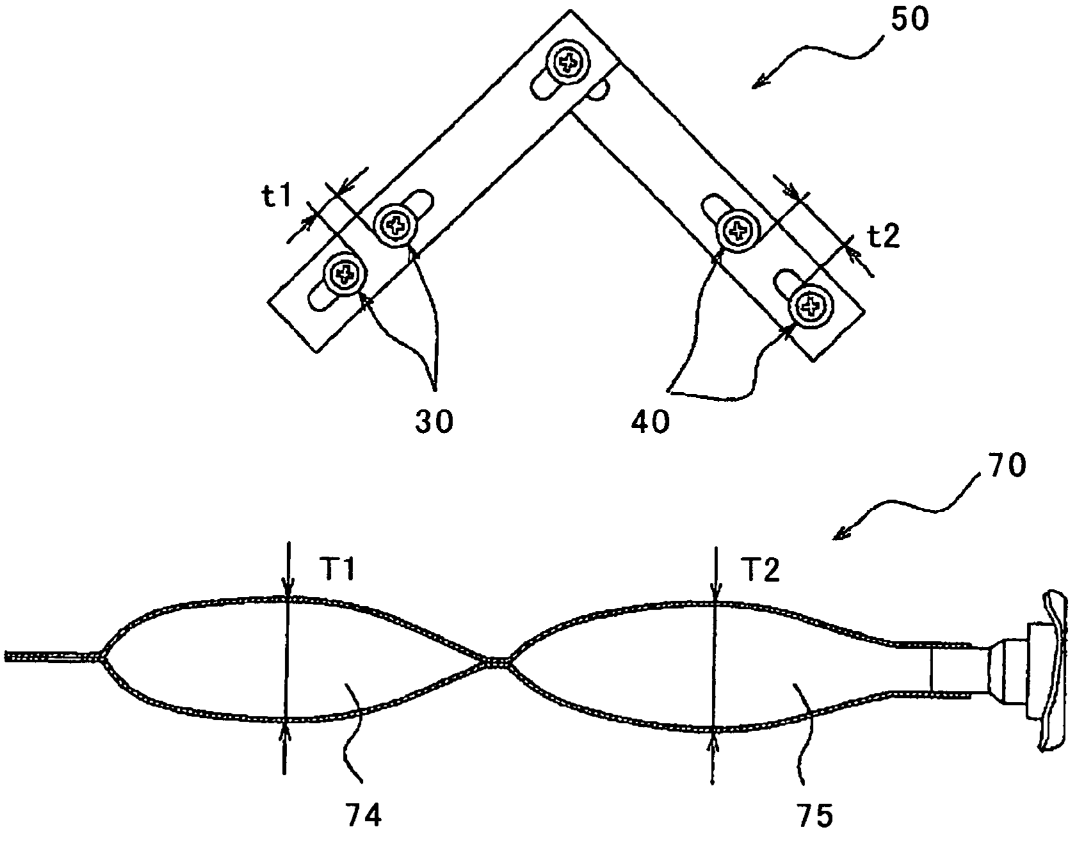
FIG. 25 is an explanatory view for comparisons among distances between two rod-shaped members of a pinching device and between two rod-shaped members of a holding device of the opening device of FIG. 23 and thicknesses of a first and second filling chambers of the multi-chamber container.

As shown in FIG. 25, two rod-shaped members 31,32 of the pinching device 30 form a predetermined distance t1 smaller than a thickness T1 of the first filling chamber 74. Two rod-shaped members 41, 42 of the holding device 40 are fixed to the second plate members 52 while being spaced a distance t2 wider than the distance t1 between two rod-shaped members 31, 32 of the pinching device 30 fixed to the first plate members 51, and thus form the predetermined distance t2 smaller than a thickness T2 of the second filling chamber 75.

Two rod-shaped members 31, 32 of the pinching device 30 are provided with roller portions 35, 36 between screw cramp portions 33 or 34, while two rod-shaped members 41, 42 of the holding device 40 are provided with roller portions 45, 46 between screw cramp portions 43 or 44, respectively. In addition, the roller portions aid the second filling chamber 75 of the multi-chamber container 70 to move outward by tensile force, and therefore, the roller portions 35, 36 may not be provided in two rod-shaped members 31, 32 of the pinching device 30 which does not need to move the first filling chamber 74 outward even by pulling the multi-chamber container 70 to omit the number of parts. In this case, two rod-shaped members 31, 32 of the pinching device 30 may be integrally secured to the multi-chamber container 70, and preferably, are secured to a seal portion 72 formed on an ejection tube 82 side of a plug 80 or at an end portion on the opposite side. Further, the roller portions 45, 46 do not need to necessarily be provided in two rod-shaped members 41, 42 of the holding device 40 which are capable of moving the second filling chamber 75 outward while pressing the wall portion of the second filling chamber 75, by pressing the end portion on the second filling chamber 75 side, even without having the roller portions 45, 46 provided between the screw cramp portions 43 or 44.

Figure 24:
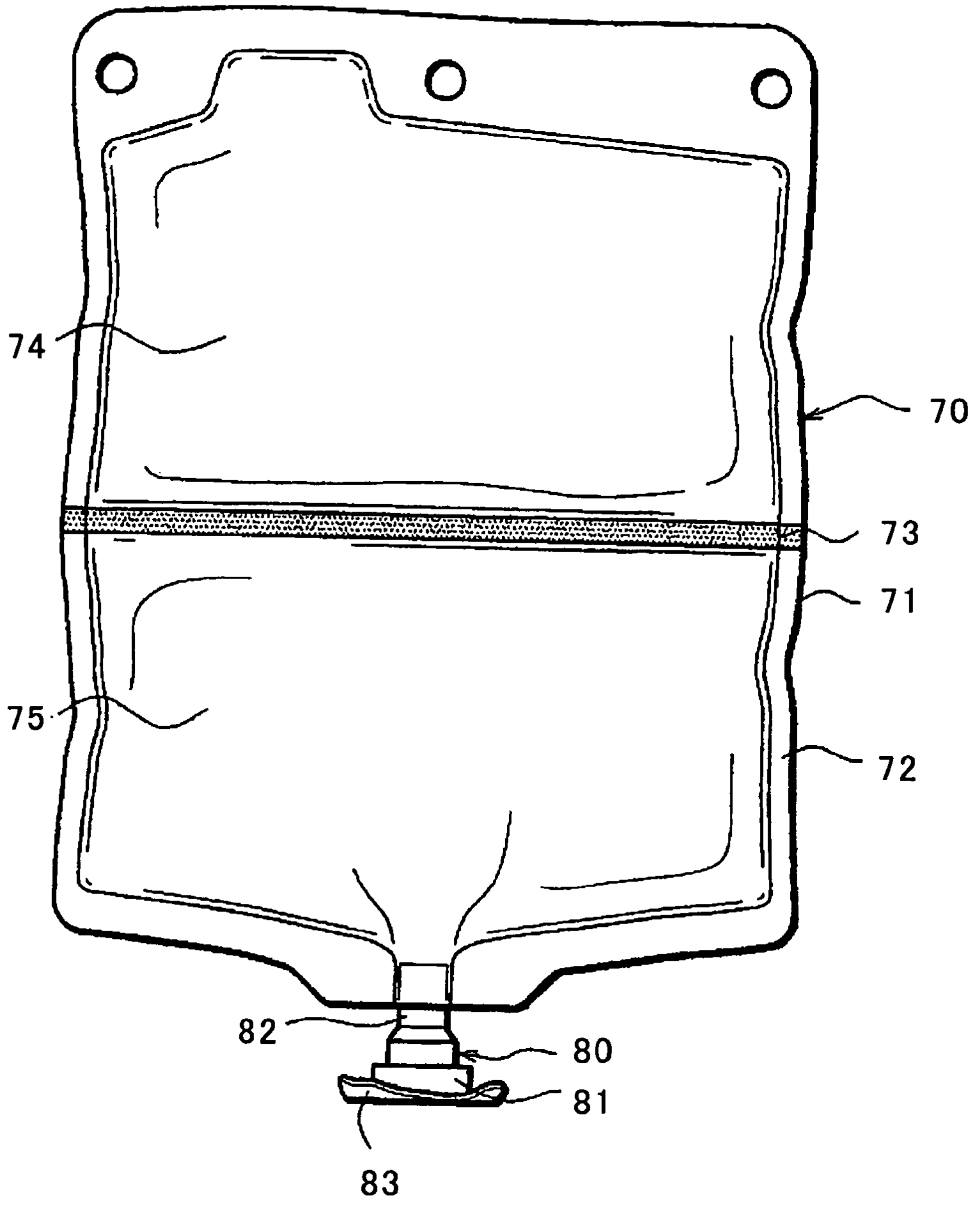
FIG. 24 is a view showing the multi-chamber container that is inserted into the opening device of FIG. 23.

As shown in FIG. 24, the multi-chamber container 70 is provided with a container body 71 and the ejection plug 80 attached to an opening of the container body 71. The multi-chamber container 70 is formed by heating and fusing peripheries of two opposite transparent film sheets with an ejection tube 82 held between inner walls of the sheets. In the multi-chamber container 70, an inner surface of one wall portion and an inner surface of the other opposite wall portion are, for example, bonded with mixed resin pieces, or the inner surfaces with mixed resin pieces held therebetween are heated and fused, and a seal portion 73 is thereby formed in the lateral direction close to the center of the container body 71. The seal portion 73 divides the inside of the container body 71 into the first and second filling chambers 74, 75, and is configured in strength that enables the portion 73 to peel off by pressing the wall portions of the first and second filling chambers 74, 75. A peripheral strong seal portion 72 is configured in strength that does not enable the portion 72 to peel off even by pressing the wall portions of the first and second filling chambers 74, 75. The plug 80 is in the shape of a tube, and comprised of an ejection outlet 81 and the ejection tube 82, and on the upper portion of the ejection outlet 81 is bonded a rectangular film sheet 83 describing a caution to urge to peel off the seal portion 73.

The action will be described below in using the opening device of the multi-chamber container configured as described above. In the opening device, the end portion on the first filling chamber 74 side is inserted into between two rod-shaped members 31, 32 of the pinching device 30 and thereby pinched therebetween, while the end portion on the second filling chamber 75 side is inserted into between two rod-shaped members 41, 42 of the holding device 40 and thereby held therebetween. Accordingly, the multi-chamber container 70 is kept folded in two until the seal portion 73 peels off, and it is thereby possible to confirm that the seal portion 73 is not peeled off from the form of the appearance.

Figure 28:
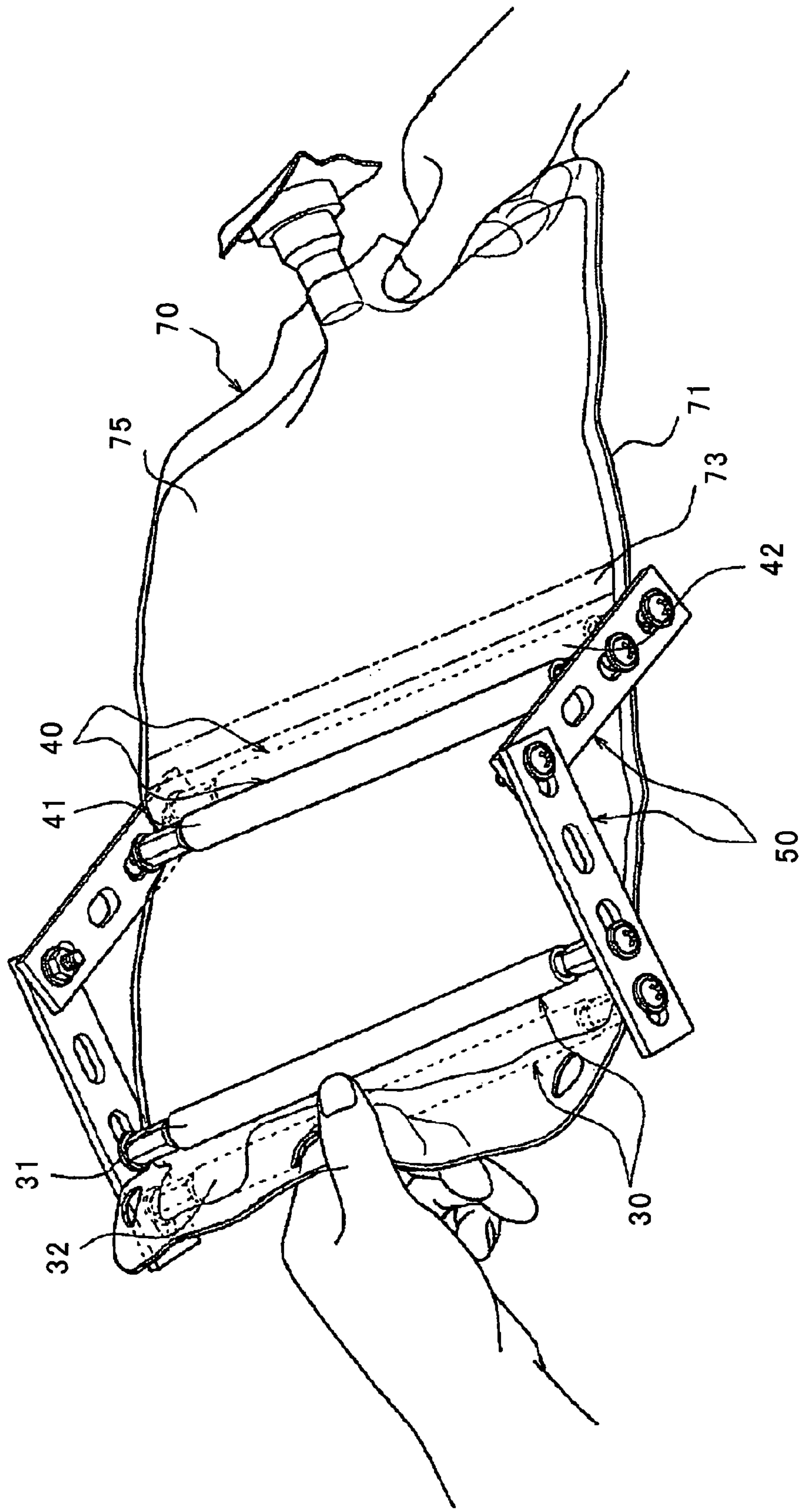
FIG. 28 is a perspective view showing a seal portion peeled off by pulling opposite ends of a container body of the multi-chamber container inserted into the opening device.

In peeling off the seal portion 73 of the multi-chamber container 70 to use, a user grasps appropriate portions at opposite ends of the container body 71, and pulls the opposite ends outward as shown by the arrow of FIG. 27. By this means, as shown in FIG. 28, without the first filling chamber 74 moves outward, the second filling chamber 75 moves outward while rotating the roller portions 45, 46 of two rod-shaped members 41,42 of the holding device 40. Two rod-shaped members 41, 42 of the holding member 40 press the wall portions of the second filling chamber 75 moving outward, and thereby generate the pressure inside the container body 71. The seal portion 73 is thereby peeled off and unmixed agents are mixed.

Also in this Embodiment, without performing the specific opening operation, only by unfolding the multi-chamber container, the seal peels off, the filling chambers are opened in therebetween, and therefore, the agents inside the respective filling chambers are mixed with reliability when the user uses the container.

Figure 29A:
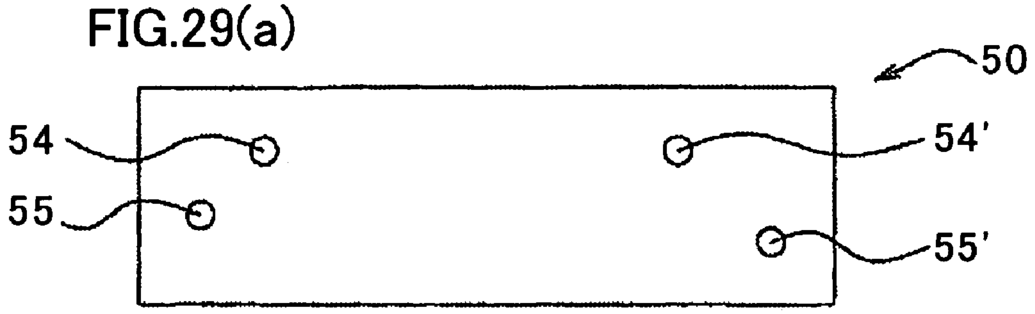
FIG. 29 is a front view showing other examples of a coupling device of the opening device of FIG. 23.
Figure 29B:
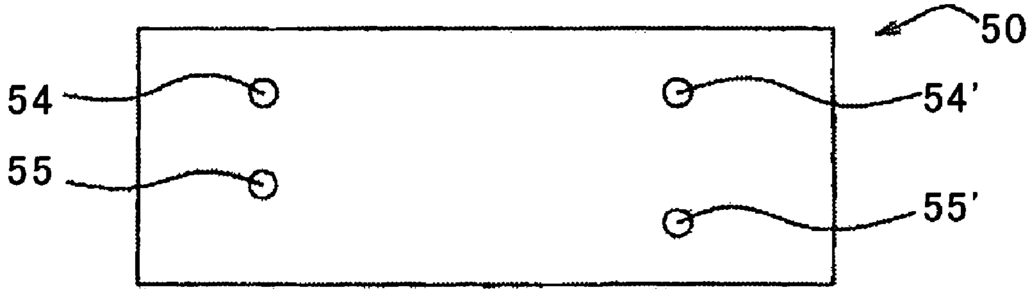
Figure 29C:
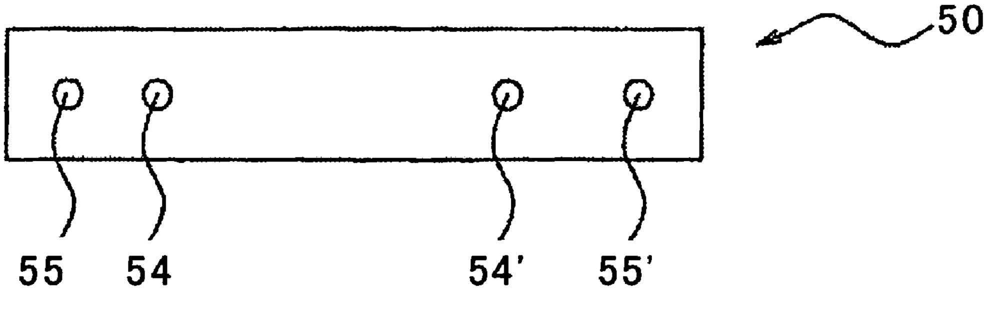

In addition, in the coupling device 50 as shown in FIG. 23, two rectangular plate members 51, 52 are coupled at a predetermined angle, and the major axis in the second screw hole 54 and third screw hole 55 of the first plate member 51 is configured to form a predetermined angle with the major axis in the second screw hole 54' and third screw hole 55' of the second plate member 52. Further, as shown in FIG. 29(*a*), four screw holes may be arranged at similar intervals in a single plate member. Furthermore, the major axis in the second screw hole 54 and third screw hole 55 of the first plate member 51 and the major axis in the second screw hole 54' and third screw hole 55' of the second plate member 52 do not need to be configured at a predetermined angle, and may be configured in parallel in the vertical direction as shown in FIG. 29(*b*), or configured in a lateral line as shown in FIG. 29(*c*).

Embodiment 7

Figure 30:
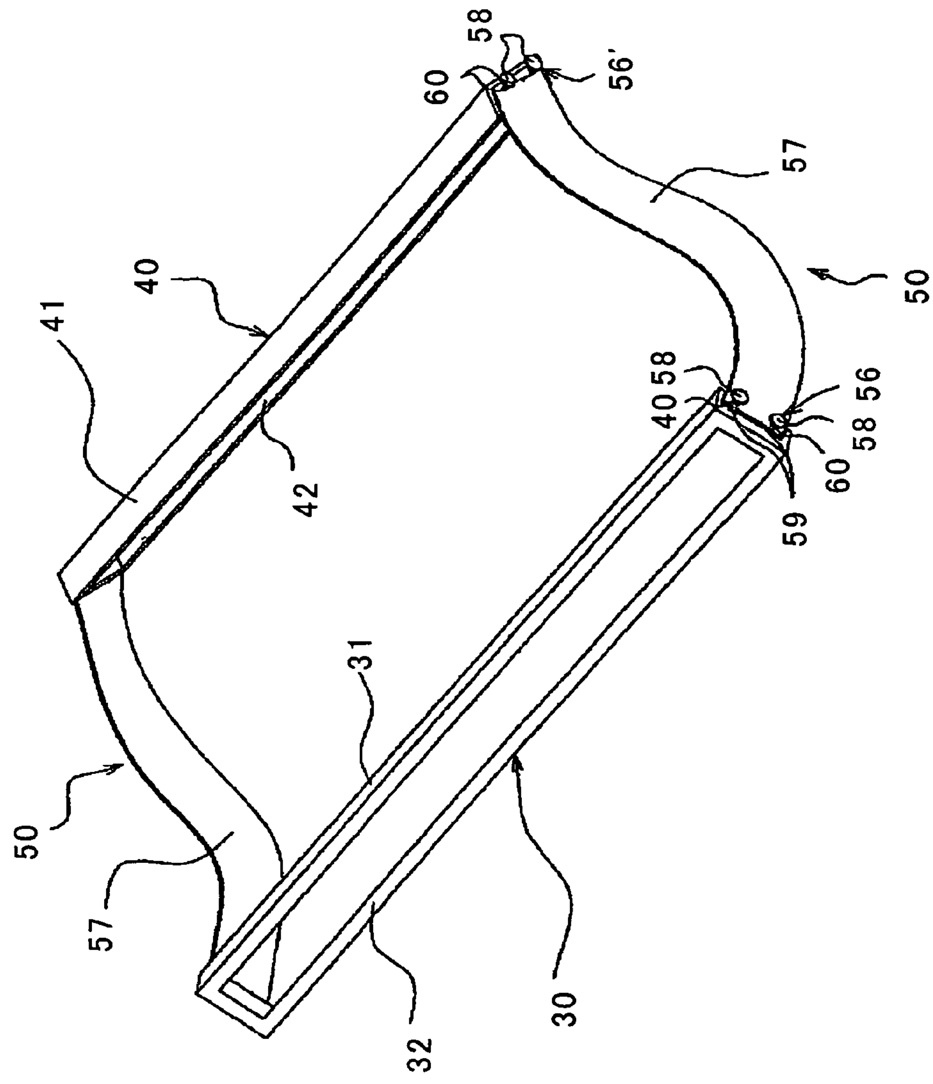
FIG. 30 is a perspective view showing an opening device of a multi-chamber container according to Embodiment 7 of the invention.

FIG. 30 shows an opening device of a multi-chamber container according to Embodiment 7 of the invention. The opening device is comprised of a pinching device comprised of two rod-shaped members, 31 and 32, a holding device 40 comprised of two rod-shaped members, 41 and 42, and a pair of coupling devices 50 each comprised of end members 56 and 56' and a flexible member 57 that couples the end members 56 and 56'.

The end members 56 of the coupling devices 50 are integrally formed with the two rod-shaped members 31, 32 of the pinching device 30, and fix respective opposite ends of two rod-shaped members 31, 32. The end members 56' of the coupling devices 50 are integrally formed with the two rod-shaped members 41, 42 of the holding device 40, and fix respective opposite ends of two rod-shaped members 41, 42. Each of the end members 56, 56' of the coupling device 50 is provided with two fasteners 58 with the disk-shaped upper portion and two fastener securing holes 59 into which the fasteners 58 are inserted. The flexible member 57 is formed in the shape of a band, and provided at opposite ends with two fastener insertion holes 60 into which are inserted the fasteners 58 of the end members 56, 56'. The flexible member 57 is configured in dimensions such that the upper portion is shorter than the lower portion. By thus configuring the dimensions such that the upper portion of the flexible member 57 is shorter than the lower portion, the end members 56, 56' are coupled at a predetermined angle. However, the dimension of the upper portion of the flexible member 57 may be made the same as the length of the lower portion to configure and couple the end members 56, 56' in parallel in the vertical direction, or in a lateral line.

In the pinching device 30, an end portion on the first filling chamber 74 side of the multi-chamber container 70 folded in two is inserted into between two rod-shaped members 31, 32, and is pinched by two rod-shaped members 31, 32 each contacting a wall portion of the first filling chamber 74.

In the holding device 40, an end portion on the second filling chamber 75 side of the multi-chamber container 70 folded in two is inserted into between two rod-shaped members 41, 42, and is held by two rod-shaped members 41, 42 each contacting a wall portion of the second filling chamber 75. In addition, a plug passing hole curving larger than outer dimensions of the plug 80 may be formed in the center portion of one of two rod-shaped members of the pinching device 30 or holding device 40 to facilitate passage of the plug 80.

As in Embodiment 6, two rod-shaped members 31, 32 of the pinching device 30 form a predetermined distance smaller than the thickness of the first filling chamber 74. Two rod-shaped members 41, 42 of the holding device 40 are fixed to the end member 56' while being spaced a distance wider than the distance between two rod-shaped members 31, 32 of the pinching device 30, and thus form a predetermined distance smaller than the thickness of the second filling chamber 75.

Also in the opening device according to Embodiment 7, as in Embodiment 6, when the filling chambers 74, 75 of the multi-chamber container 70 are respectively held by two rod-shaped members 31, 32 of the pinching device 30 and two rod-shaped members 41, 42 of the holding device 40, the container 70 is kept folded in two until the seal portion 73 peels off. Further, when a user grasps opposite ends of the multi-chamber container 70 and pulls respectively outward, without the first filling chamber 74 of the multi-chamber container 70 moves outward, the second filling chamber 75 of the multi-chamber container 70 moves outward. Two rod-shaped members 41, 42 of the holding member 40 press both wall portions of the second filling chamber 75 moving outward, and thereby generate the pressure inside the container body 71. The seal portion 73 is thereby peeled off and unmixed agents are mixed.

Also in this Embodiment, without performing the specific opening operation, only by unfolding the multi-chamber container, the seal peels off, the filling chambers are opened in therebetween, and therefore, the agents inside the respective filling chambers are mixed with reliability when the user uses the container.

Embodiment 8

Embodiments 8 and 9 describe the case where an opening preventing member is a folded tube, the tube is released by the operation for unfolding a multi-chamber container when the container is unfolded, and filling chambers are thereby communicated with each other to be an open state.

Figure 31A:
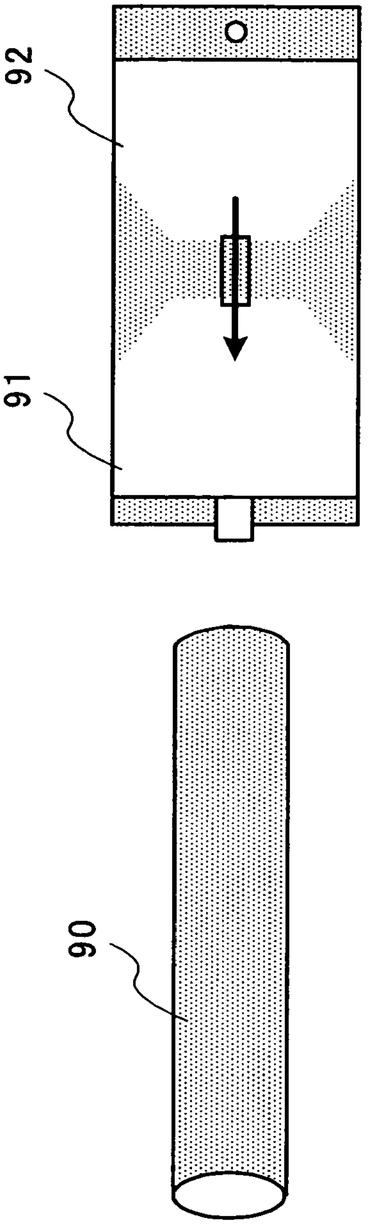
FIG. 31 is view to explain a tube for use in a multi-chamber container of Embodiments 8 and 9 of the invention.
Figure 31B:
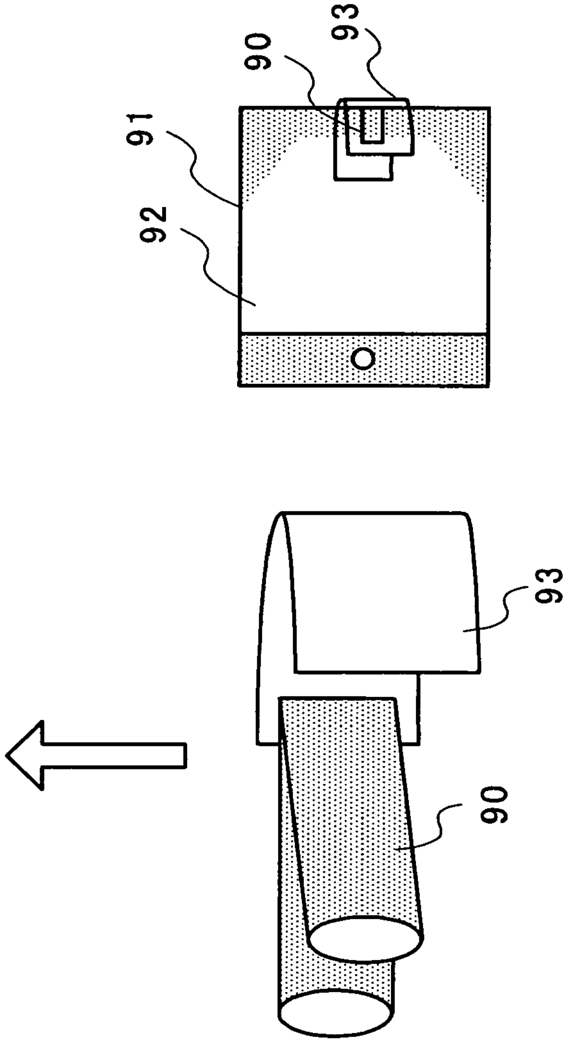

FIG. 31 is a view to explain the tube for use in this Embodiment. As shown in FIG. 31(*a*), the tube 90 is provided in the almost center and attached to cause filling chambers 91 and 92 to be communicated. After filling the filling chambers 91, 92 with agents and the like, the multi-chamber container is folded in two in the tube portion and covered with a protection material 93. The tube thereby functions as the opening preventing member. In addition, available as the tube 90 are flexible tubes and the like such as silicon tubes, Teflon (Registered Trademark) tubes and the like.

Figure 32:
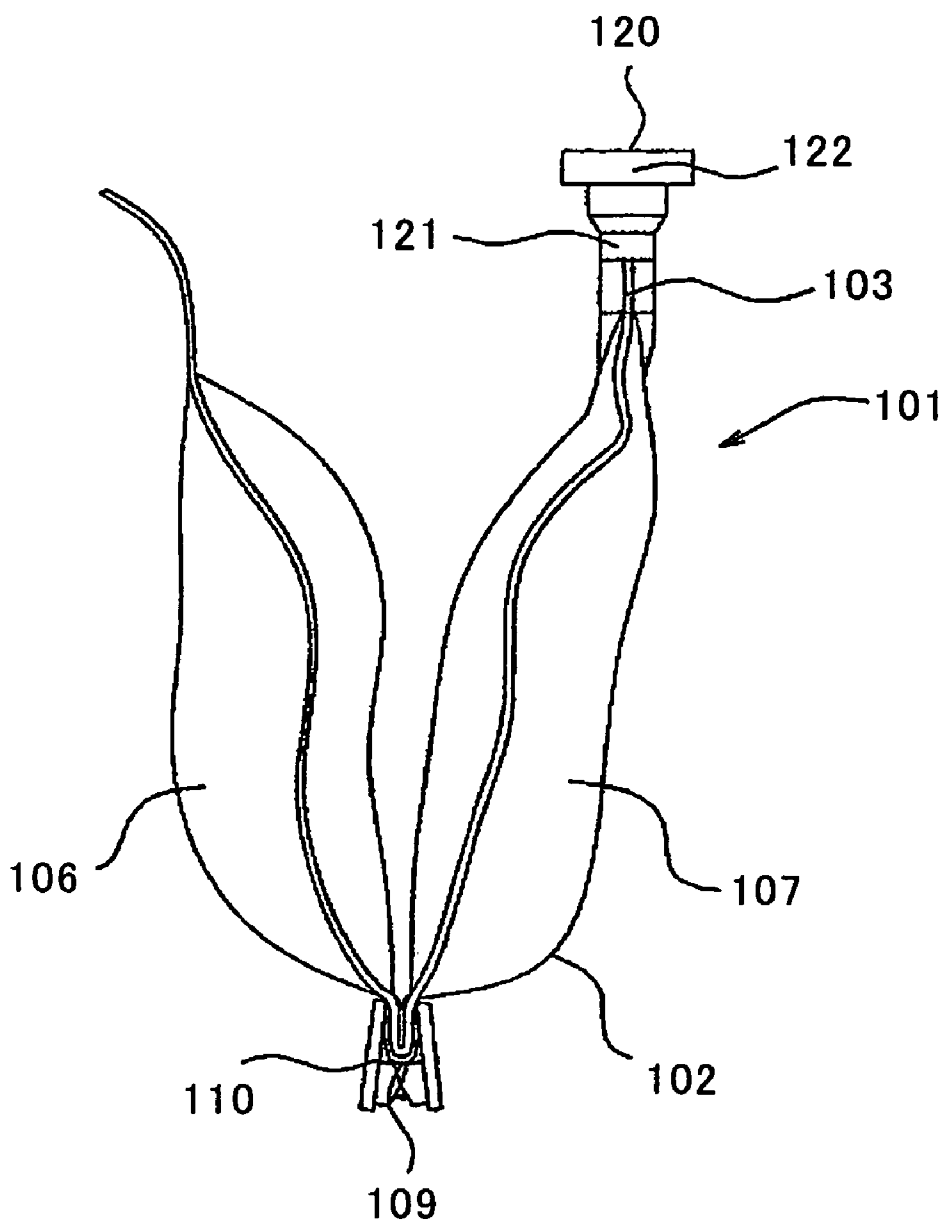
FIG. 32 is a side view showing the multi-chamber container according to Embodiment 8 of the invention.
Figure 33:
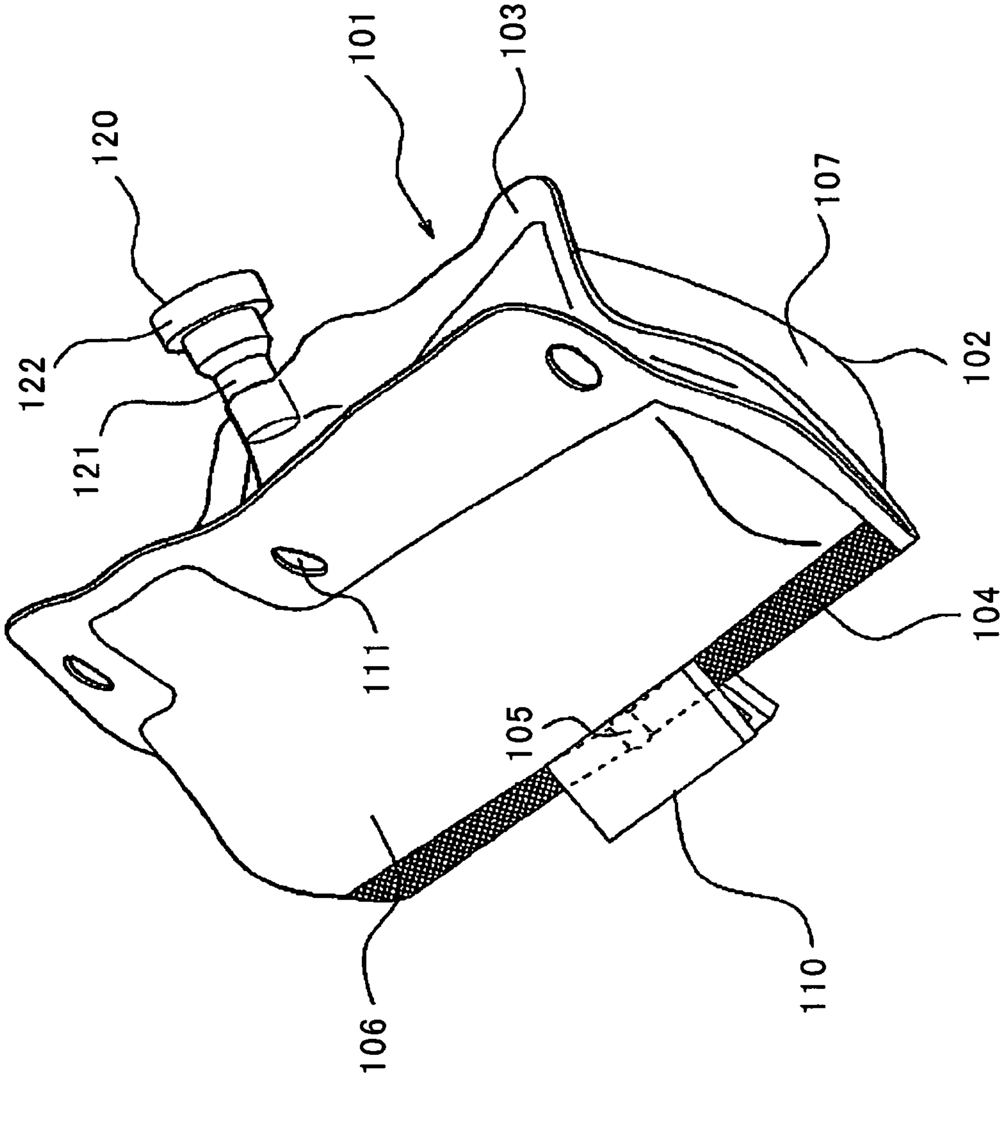
FIG. 33 is a perspective view showing the multi-chamber container according to Embodiment 8 of the invention.
Figure 34:
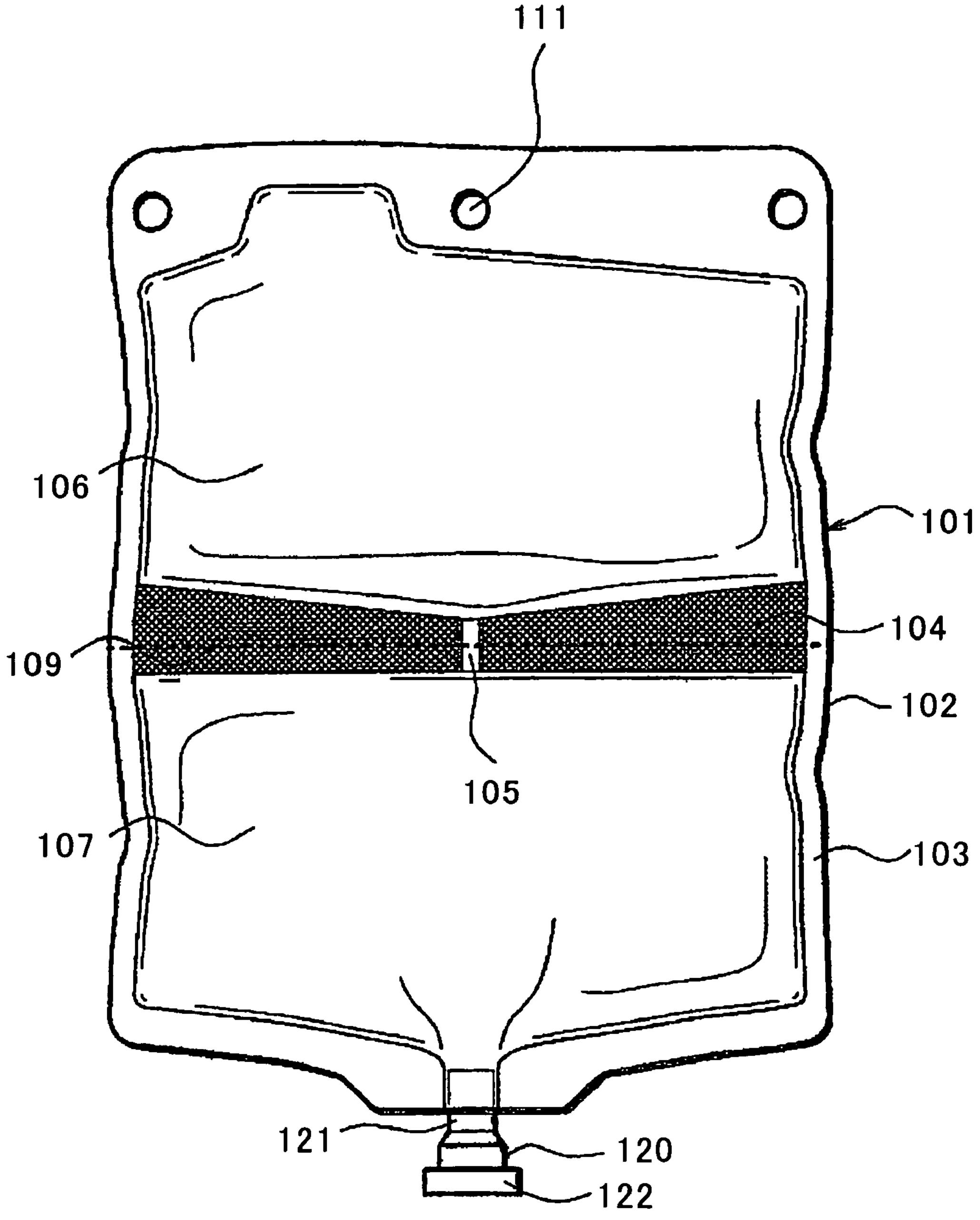
FIG. 34 is a front view showing the multi-chamber container with the container body expanded.

FIG. 32 shows a multi-chamber container 101 according to Embodiment 8 of the invention. As shown in FIGS. 32 to 34, the multi-chamber container 101 is comprised of a container body 102 comprised of two opposite transparent film sheets and an ejection plug 120 attached to an opening of the container body 102.

As shown in FIG. 34, the multi-chamber container 101 is provided with a seal portion 103 formed on the periphery of the container body 102. The seal portion 103 is formed by heating and fusing the inner surfaces on the peripheries of the two film sheets constituting the container body 102 with the ejection tube 121 of the plug 120 held therebetween. The plug 120 is in the shape of a tube, and comprised of the ejection tube 121 and an ejection outlet 122 sealed by a rubber stopper until a hollow needle is inserted.

As shown in FIGS. 33 and 34, the multi-chamber container 101 is provided with a seal portion 104 formed in the lateral direction near the center of the container body 102. The seal portion 104 is formed by heating and fusing inner surfaces near the center of the two film sheets constituting the container body 102 with the flexible tube 106 held therebetween, and thereby divides the inside of the container body 102 into a first and second filling chambers 106 and 107. As shown in FIG. 34, the lower portion of the filling chamber 106 is inclined downward toward a flow inlet of the flexible tube 105 from the seal portion 104 side at opposite ends. The flexible tube 105 may be cut such that the opposite ends are perpendicular to the axis direction, and preferably, as shown in FIGS. 35 (*a*) to (*c*), is cut in a slanting direction to facilitate the holding by a clip member 110 described later.

Figure 35B:
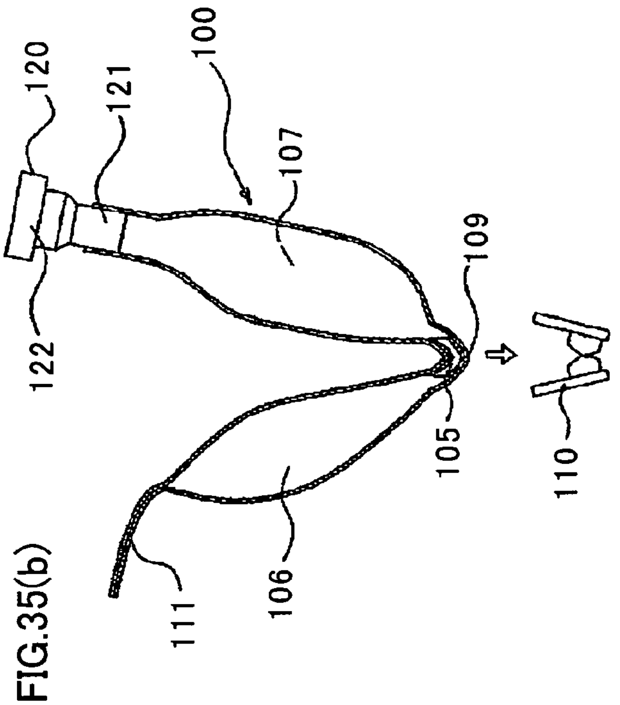
FIG. 35 is a view to explain a state up to expansion of the container body folded in two.
Figure 35A:
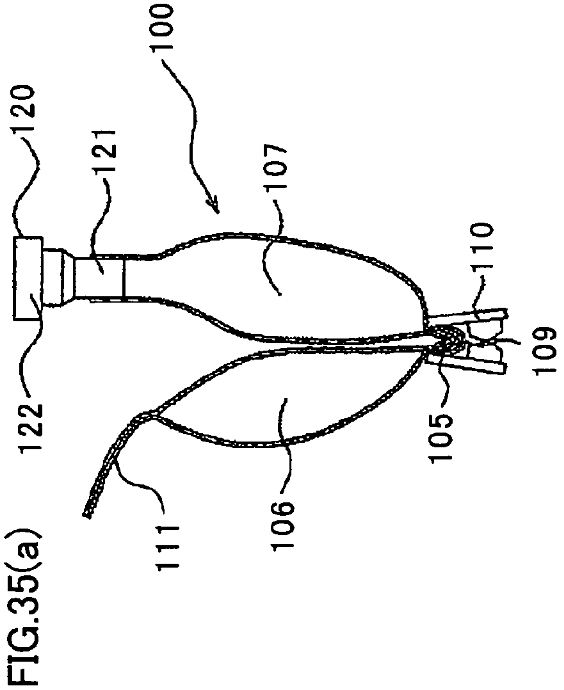
Figure 35C:
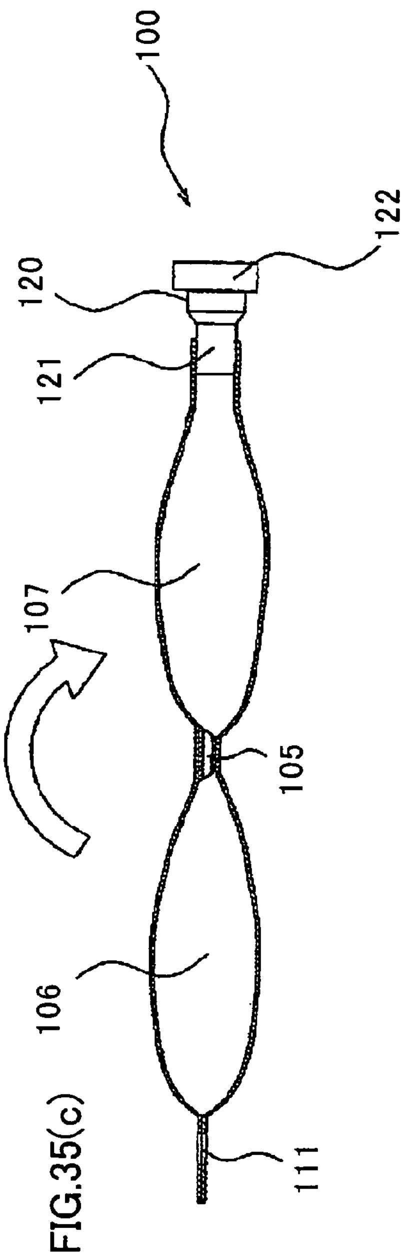

As shown in FIGS. 34 and 35(*a*), the multi-chamber container 101 has a fold line 109 to fold the container body 102 in two with the inside of the flexible tube 105 clogged. The fold line 109 is formed in the lateral direction of the container body 102 in which the seal portion 104 is formed.

As shown in FIGS. 32, 33 and 35(*a*), the multi-chamber container 101 has the clip member 110 that is a retaining member to maintain the folded state of the container body 102. The clip member 110 is attached to the outer surface of the container body 102 around which the flexible tube 105 is fused, with the container body 102 folded, and pinches the container body 102 and flexible tube 105.

In the multi-chamber container 101 with the above-mentioned configuration, as shown in FIG. 35(*c*), since the container body 102 is kept folded and the flexible tube 105 is clogged with reliability by the clip member 110, it does not happen that the container body 102 expands spontaneously, and that the first and second filling chambers 106, 107 are communicated with each other via the flexible tube 105. By this means, a user is capable of recognizing that the operation for mixing unmixed agents is not performed from the form of the appearance of the multi-chamber container 101. Further, the unmixed agents can be stored inside the first and second filling chambers 106, 107 until the multi-chamber container 101 is used.

In performing the operation for mixing the agents, a user removes the clip member 110 as shown in FIG. 35(*b*), and expands the container body 102 as shown in FIG. 35(*c*). The flexible tube 105 thereby restores to the shape of a tube by elasticity, the first and second filling chambers 106, 107 are communicated with each other via the flexible tube 105, and unmixed agents filled in the first and second filling chambers 106, 107 are mixed. At this point, as shown in FIG. 34, since the lower portion of the first filling chamber 106 is formed to incline downward toward the flexible tube 105 from the seal portion 104 side at opposite ends, the unmixed agent filled in the first filling chamber 106 is easy to flow into the flexible tube 105 provided in the seal portion 104.

Figure 36:
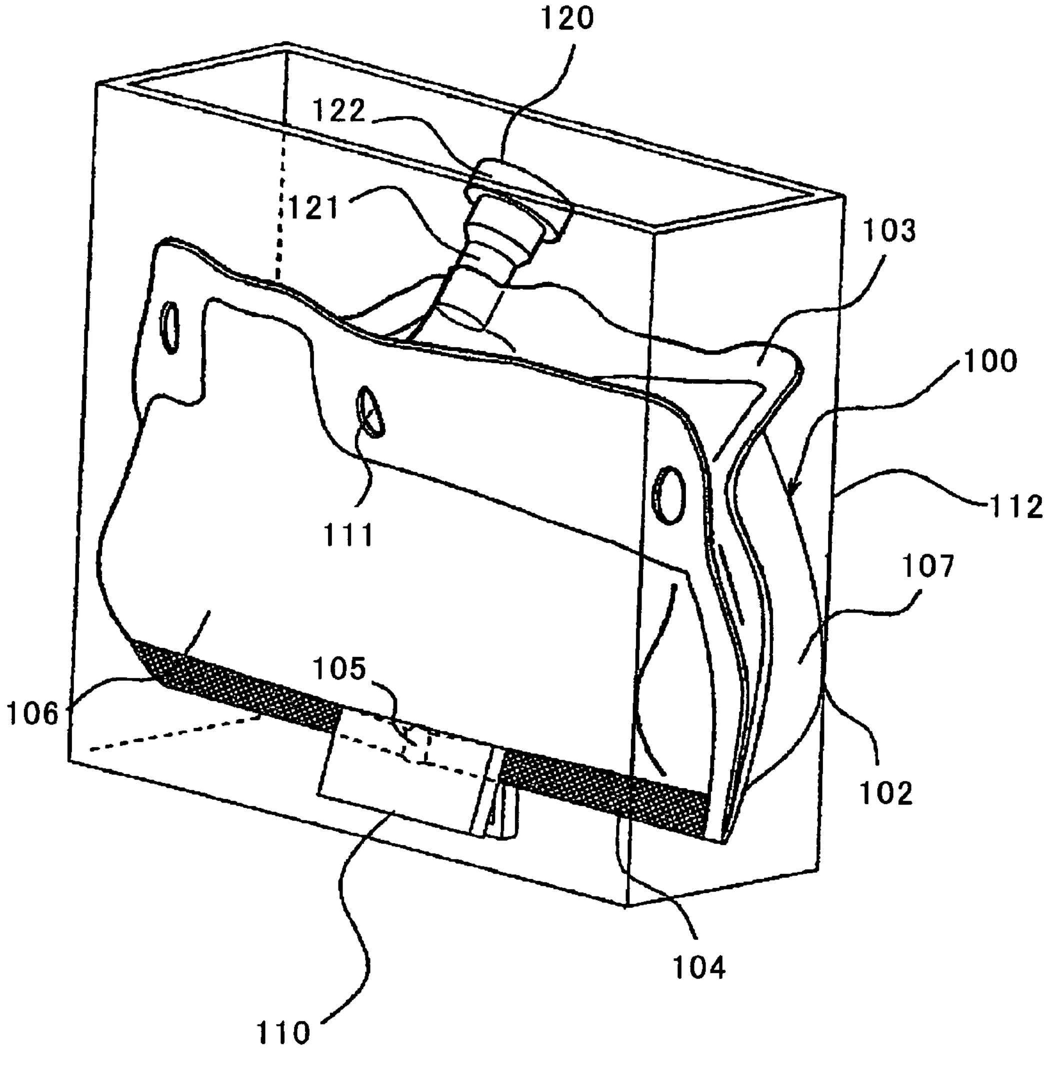
FIG. 36 is a perspective view of the multi-chamber container stored in a package container (secondary container) with an integrally formed clip member.
Figure 37:
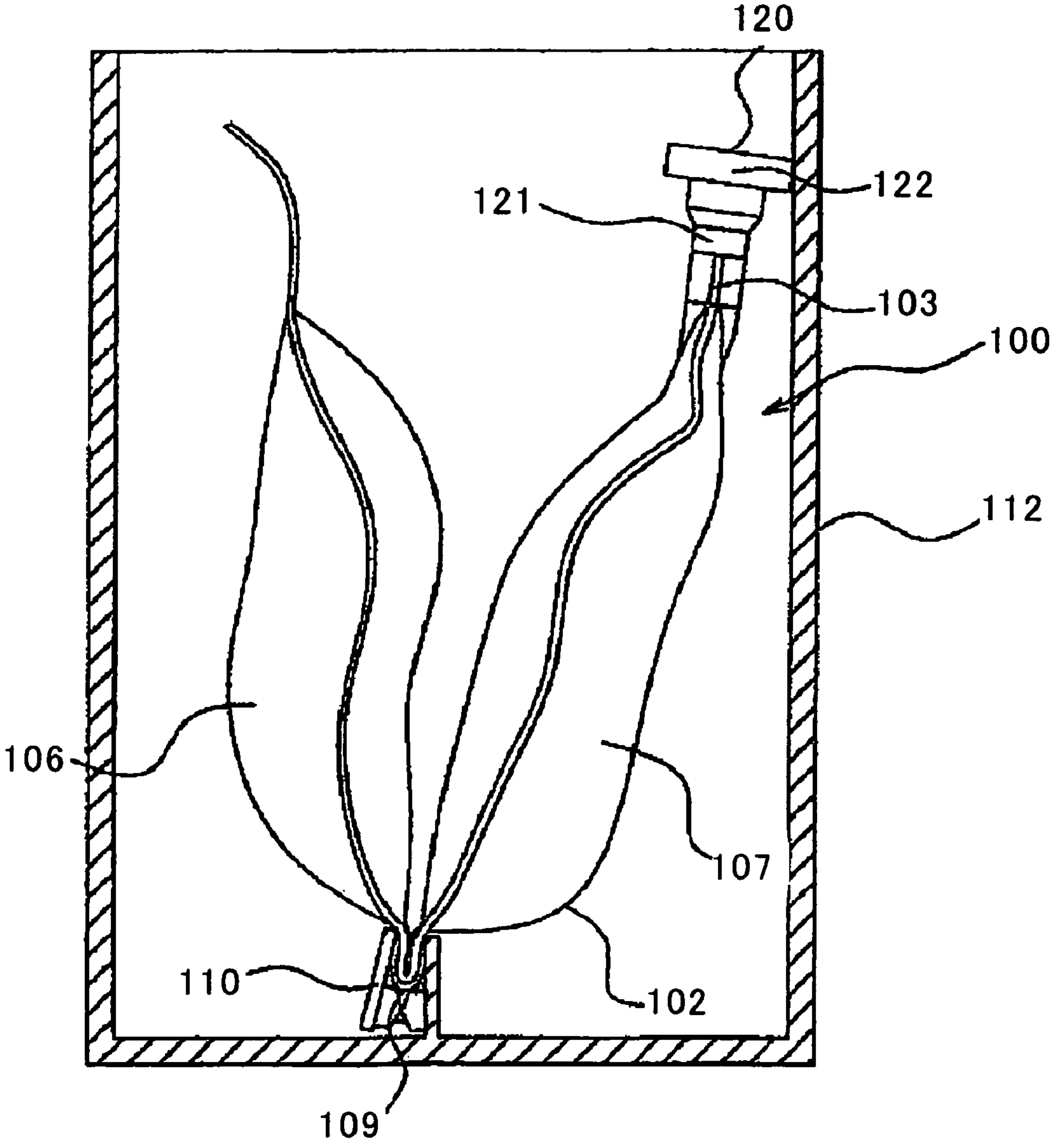
FIG. 37 is a side view showing the multi-chamber container of FIG. 36.

In addition, as shown in FIGS. 36 and 37, one of pinching portions of the clip member 110 may be formed integrally with the bottom of an outer container 112 (secondary container) that stores the multi-chamber container 101, or secured by screw in the bottom of the outer container 112 (secondary container) to be integrated. In the case where one of pinching portions of the clip 110 is thus integrated with the bottom of the outer container 112 (secondary container), the pinching portions of the clip member 110 are preferably configured in pinching force such that the container body 102 and flexible tube 105 can be released when the multi-chamber container 101 is pulled out to the ejection'outlet side of the outer container 112 (secondary container). By this means, the user does not need to grasp the clip member 110 provided in the outer container 112 (secondary container) to release, and is only required to take out the multi-chamber container 101 of the outer container 112 (secondary container) and expand the container body 102.

Also in this Embodiment, without performing the specific opening operation, only by unfolding the multi-chamber container, the folded tube recovers, the filling chambers are opened in therebetween, and the agents inside the filling chambers are reliably mixed when the user uses the container.

Embodiment 9

Figure 38:
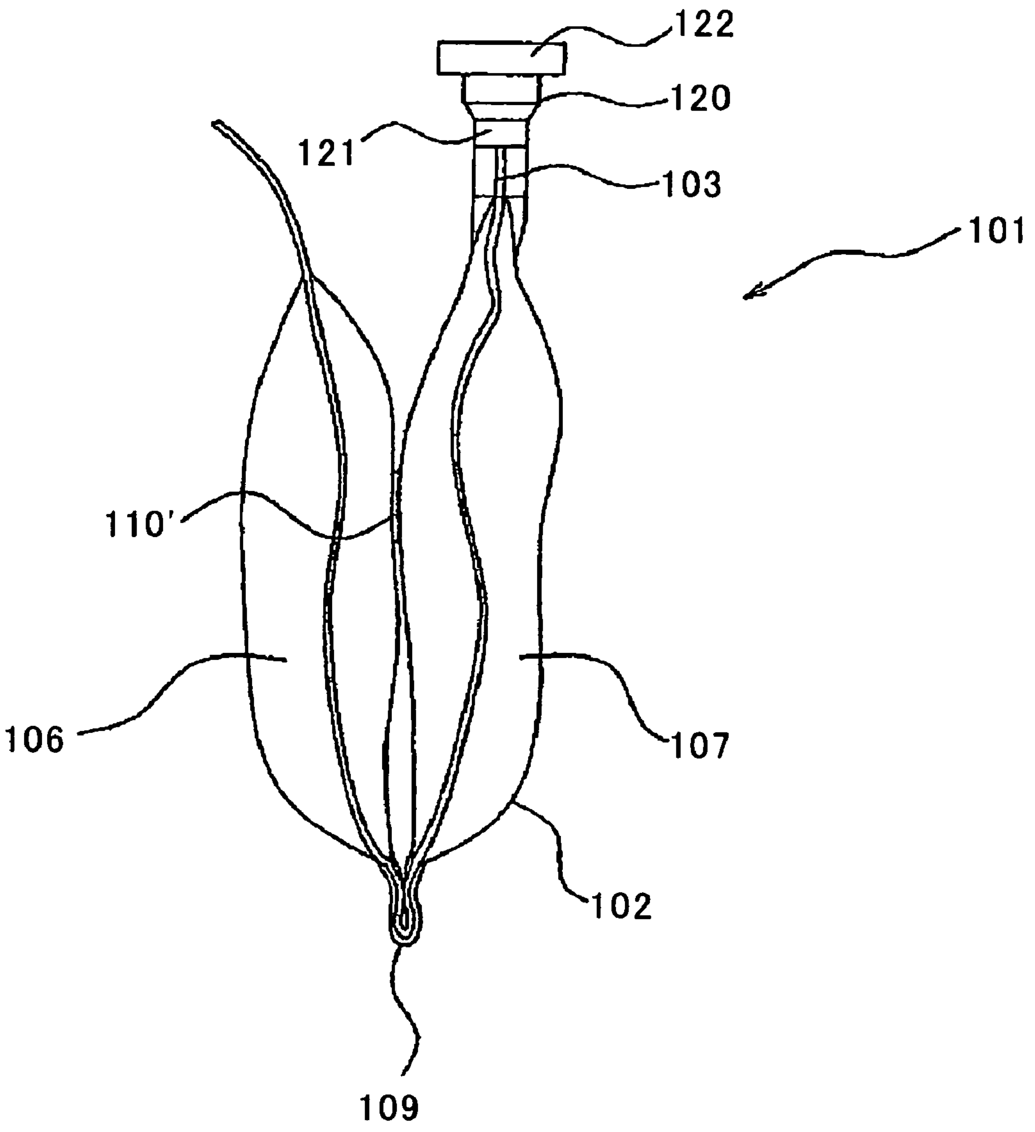
FIG. 38 is a side view showing a multi-chamber container according to Embodiment 9 of the invention.

FIG. 38 shows a multi-chamber container 101 according to Embodiment 9 of the invention. As in Embodiment 8, the multi-chamber container 101 is comprised of the container body 101 with the seal portions 103, 104 formed therein, and the ejection plug 120 attached to the opening of the container body 102.

As in Embodiment 8, the fold line 109 is formed in the seal portion 104. The container body 102 is folded in two along the fold line 109 with the inside of flexible tube 105 provided in the seal portion 104 clogged.

Figure 39:
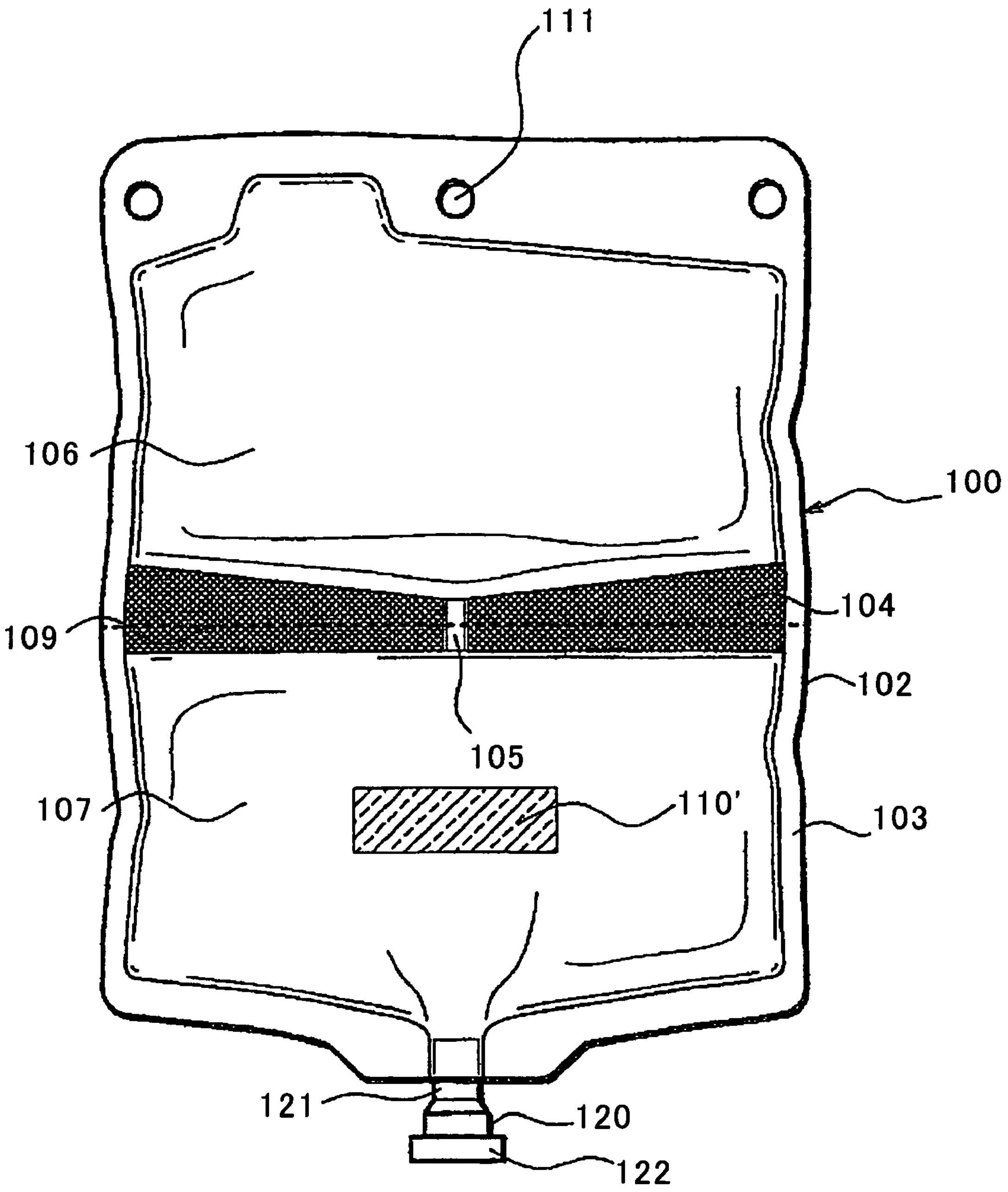
FIG. 39 is a front view showing the multi-chamber container of FIG. 38 with the container body expanded.

As shown in FIGS. 38 and 39, the multi-chamber container 101 is provided with a two-sided tape 110' that maintains the folded state of the container body 102. As shown in FIG. 38, the two-sided tape 110' is bonded to opposite outer surfaces of wall portions of the first and second filling chambers 106, 107 folded in the fold line 109.

Also in the multi-chamber container 101 according to Embodiment 9, with the multi-chamber container 101 hung on a hook of a stand (not shown) through which a hang hole 111 is passed, when a user peels off the adhesion surface of the two-sided tape 110' bonded to one of the first and second filling chambers 106, 107, the container body 102 expands spontaneously by the weight of an unmixed agent filled in the second filling chamber 107. The flexible tube 105 thereby restores to the shape of a tube by elasticity, the first and second filling chambers 106, 107 are communicated with each other via the flexible tube 105, and unmixed agents filled in the first and second filling chambers 106, 107 are mixed.

Figure 40:
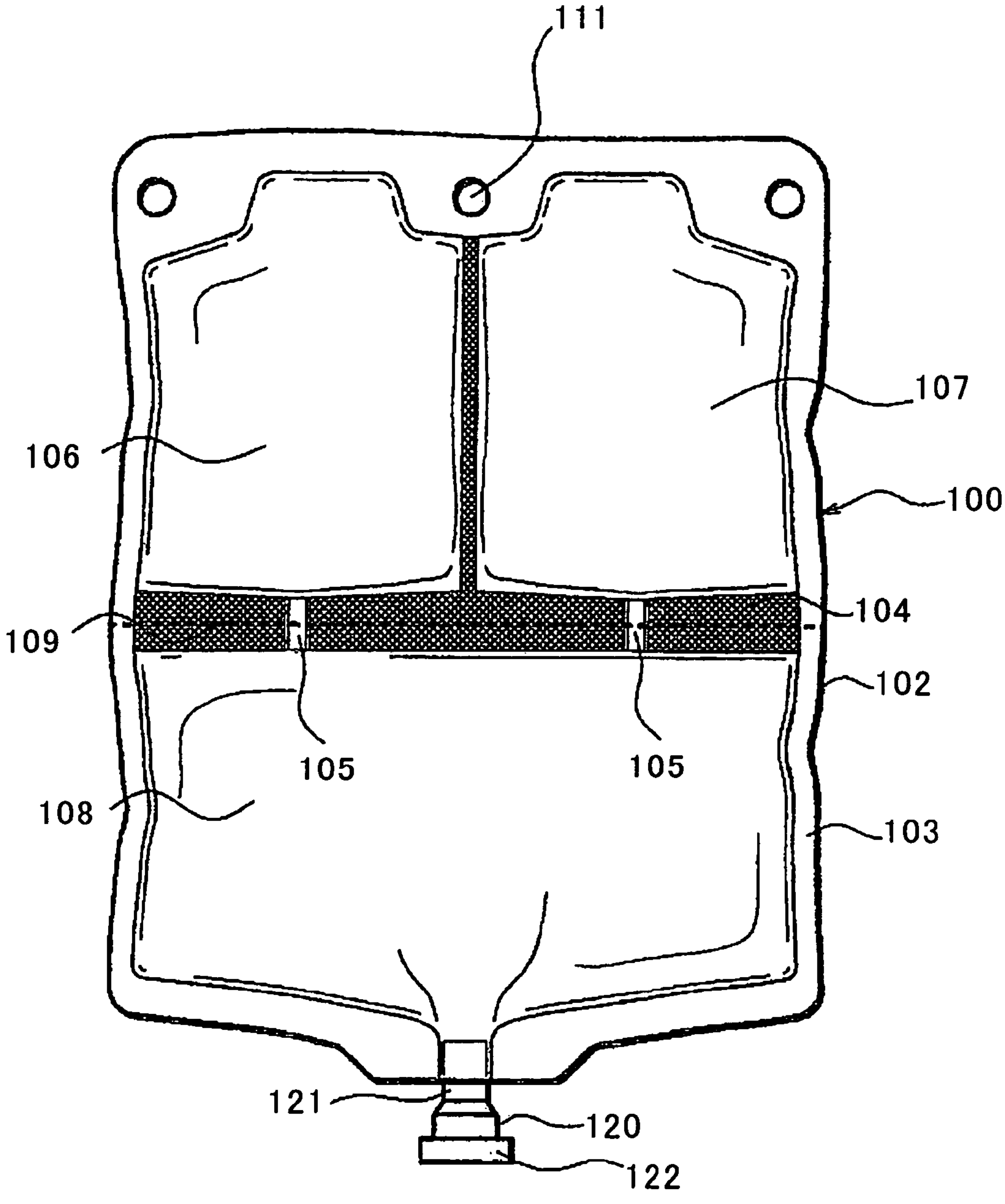
FIG. 40 is a front view showing a multi-chamber container according to the invention provided with three filling chambers.

In addition, in Embodiments 8 and 9, in the multi-chamber container 101, the first and second filling chambers 106, 107 are formed by dividing the inside of the container body 102 into two portions by the seal portion 104, but the inside of the container body 102 may be divided into three or more portions by the seal portion 104 to form three or more filling chambers. For example, as shown in FIG. 40, the seal portion 104 is formed in T-shape by heating and fusing opposite inner surfaces of two film sheets constituting the container body 102 to divide the filling chamber into three chambers. In this case, not-mixed agents can be mixed when each of the first and second filling chambers 106, 107 communicates with a third filling chamber 108, and therefore, flexible tubes 105 are respectively provided in the seal portion 104 positioned between the first filling chamber 106 and third filling chamber 108, and between the second filling chamber 107 and third filling chamber 108.

Figure 41:
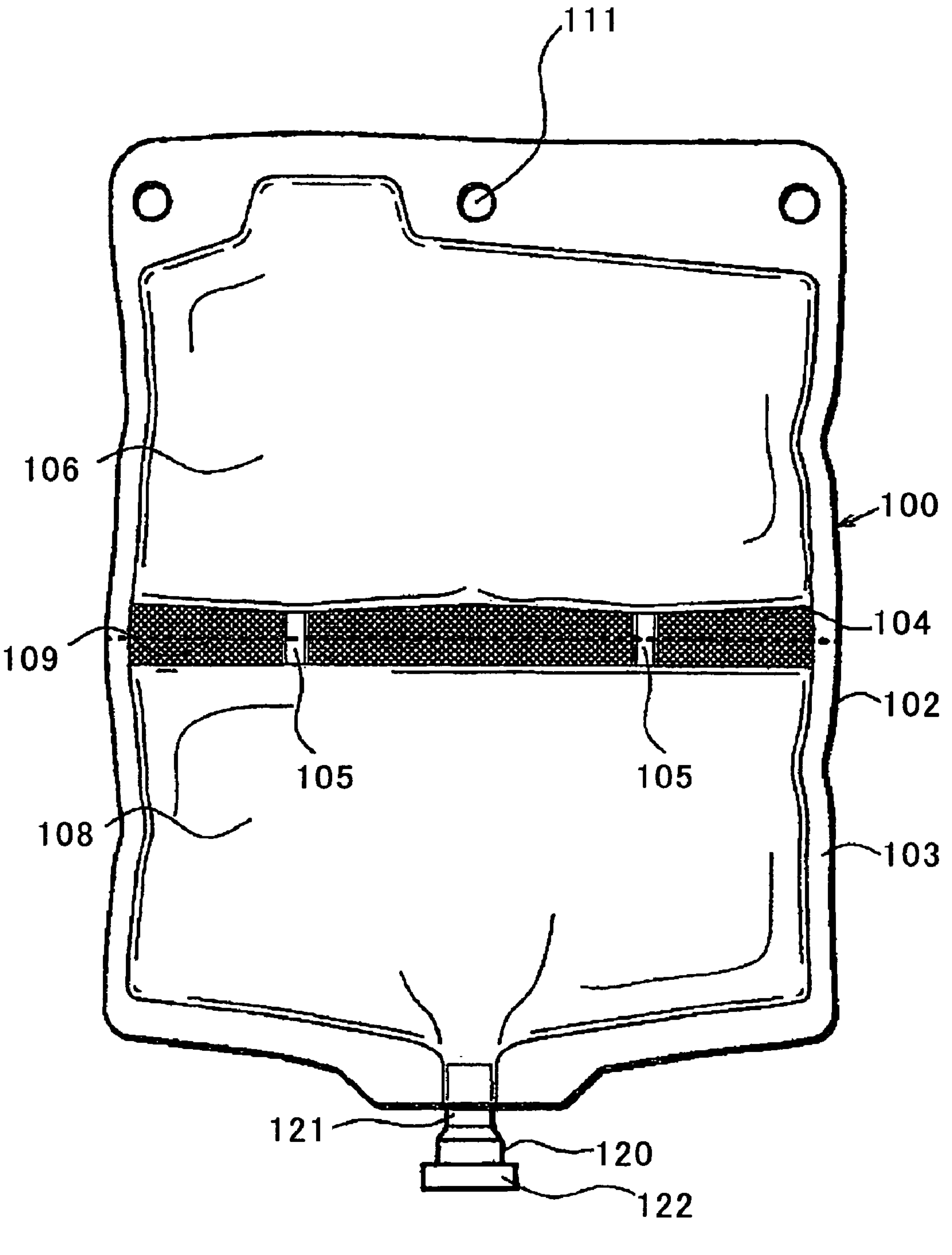
FIG. 41 is a front view showing a multi-chamber container according to the invention provided with two flexible tubes.

Further, in Embodiments 8 and 9, in the multi-chamber container 101, a plurality of flexible tubes 105 to cause the first and second filling chambers 106, 107 to be communicated may be provided in the seal portion 104, and for example, as shown in FIG. 41, two flexible tubes 105 are provided in the seal portion 104 to facilitate the mixing of unmixed agents.

Also in this Embodiment, without performing the specific opening operation, only by unfolding the multi-chamber container, the folded tube recovers, the filling chambers are opened in therebetween, and therefore, the agents inside the respective filling chambers are reliably mixed when the user uses the container.

In addition, above-mentioned Embodiments 8 and 9 describe the type such that the tube is embedded in the filling chamber, but in the present invention, such a configuration may be provided that an elastic material is coated from the outside of the filling chamber in which a tube is not embedded, or an elastic member, for example, a tube cut in half is attached. According to such a configuration, the processing is made easy, resulting in cost down, and further, it is possible to maintain the inside of the filling chamber clean.

Embodiment 10

Embodiments 10 to 12 describe the case where an opening preventing member is a folded clip, the clip is detached by the operation for unfolding a multi-chamber container when the container is unfolded, and filling chambers are thereby communicated with each other to be an open state.

Figure 42:
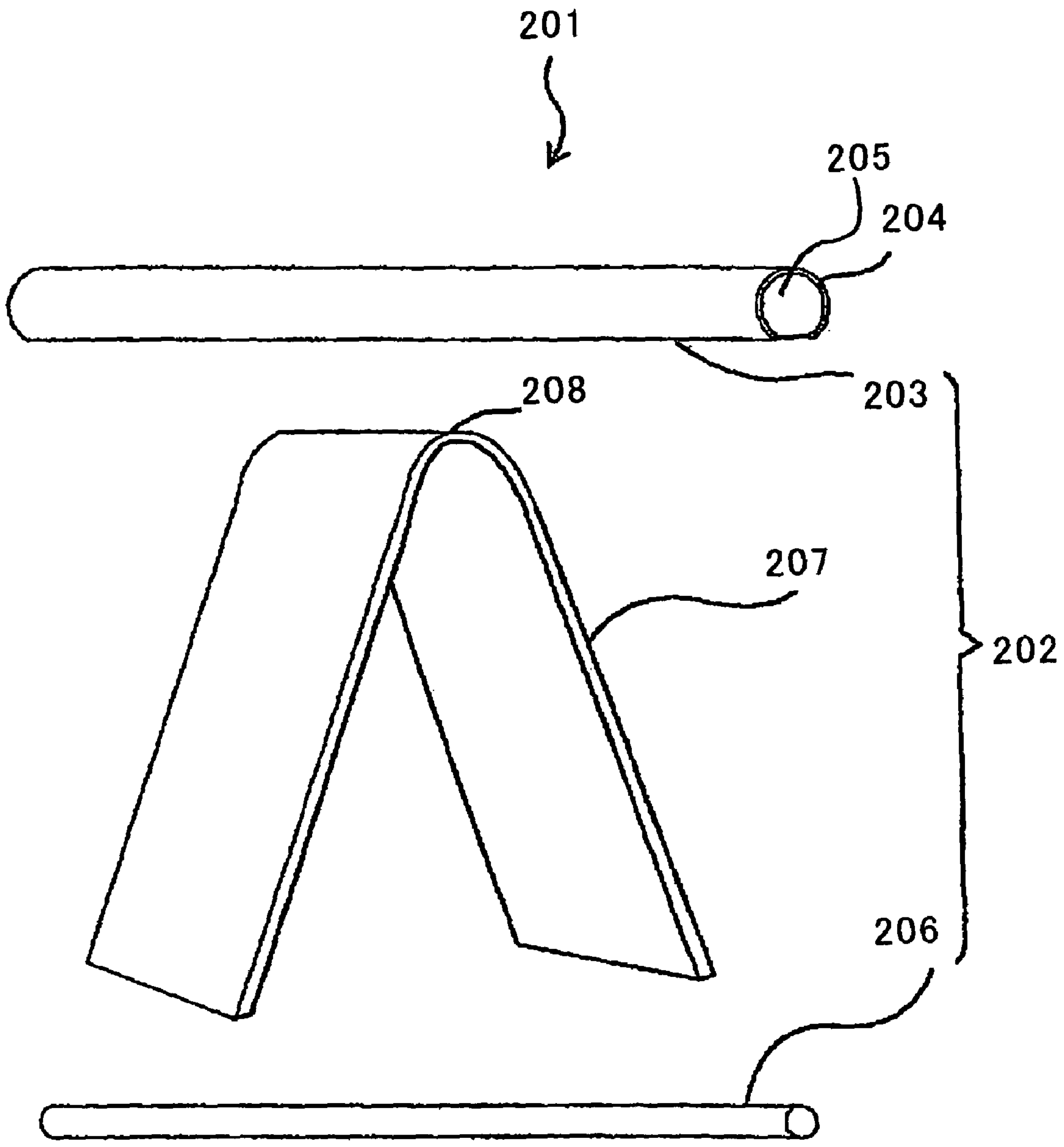
FIG. 42 is a perspective view showing a dividing unit according to Embodiment 10 of the invention.

FIG. 42 is a view showing a dividing unit including the clip that is the opening preventing member according to Embodiment 10 of the invention. The unit 201 is comprised of dividing means 202 and a straddling plate 107 formed of rigid material.

The dividing means 202 is comprised of a clip 203 and a rod-shape aid 206. The clip 203 is formed of rigid material with elasticity, and pinches the rod-shaped aid 206 in contact with one wall portion 222 of a container body 221 from the other wall portion 223 to clog the inside of the container body 221 of a multi-chamber container 220. The clip 203 has a cross section in the shape of a substantially circle with part of the circle lacked, and is comprised of a pinch portion 204 and pinch space 205 formed inside the pinch portion 204. The clip 203 may be formed of metal such as iron having the elasticity, but in consideration of safety, is preferably formed of elastic plastic material.

Figure 43:
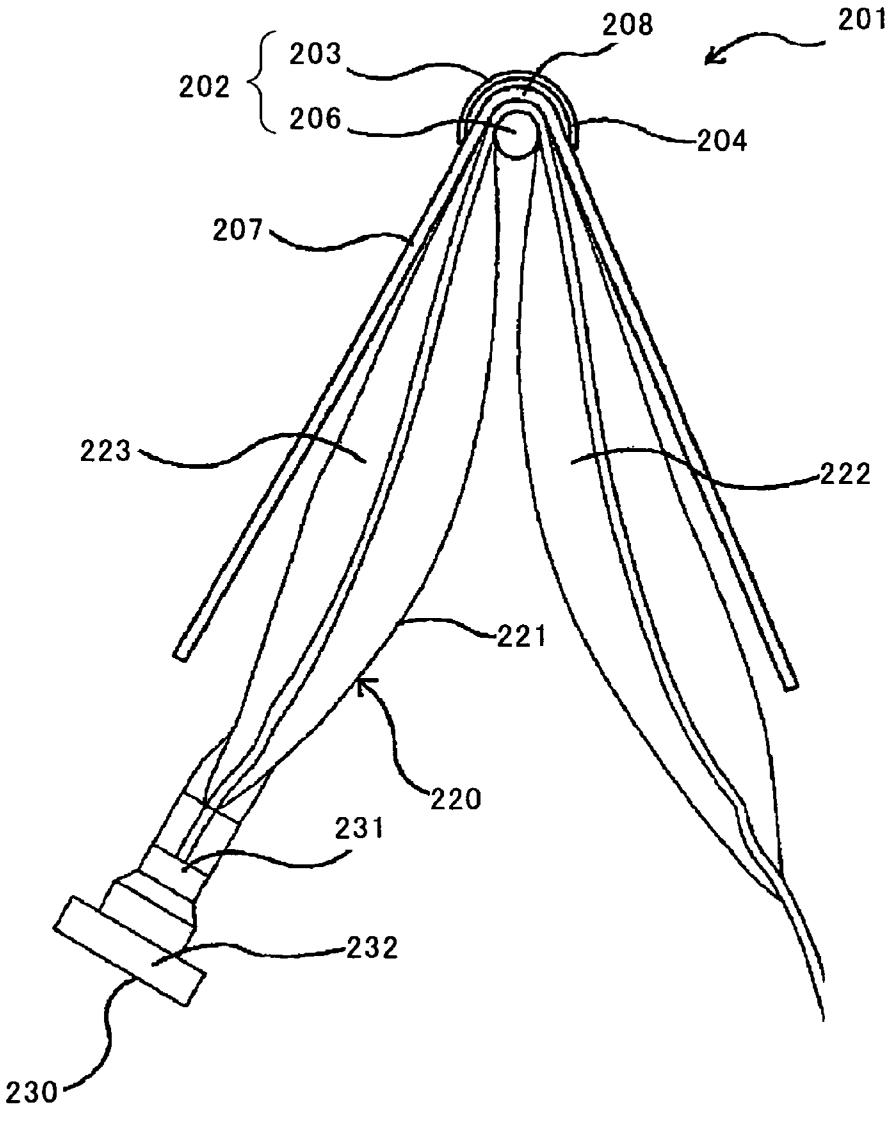
FIG. 43 is a side view showing the dividing unit of FIG. 42 attached to a multi-chamber container.
Figure 44:
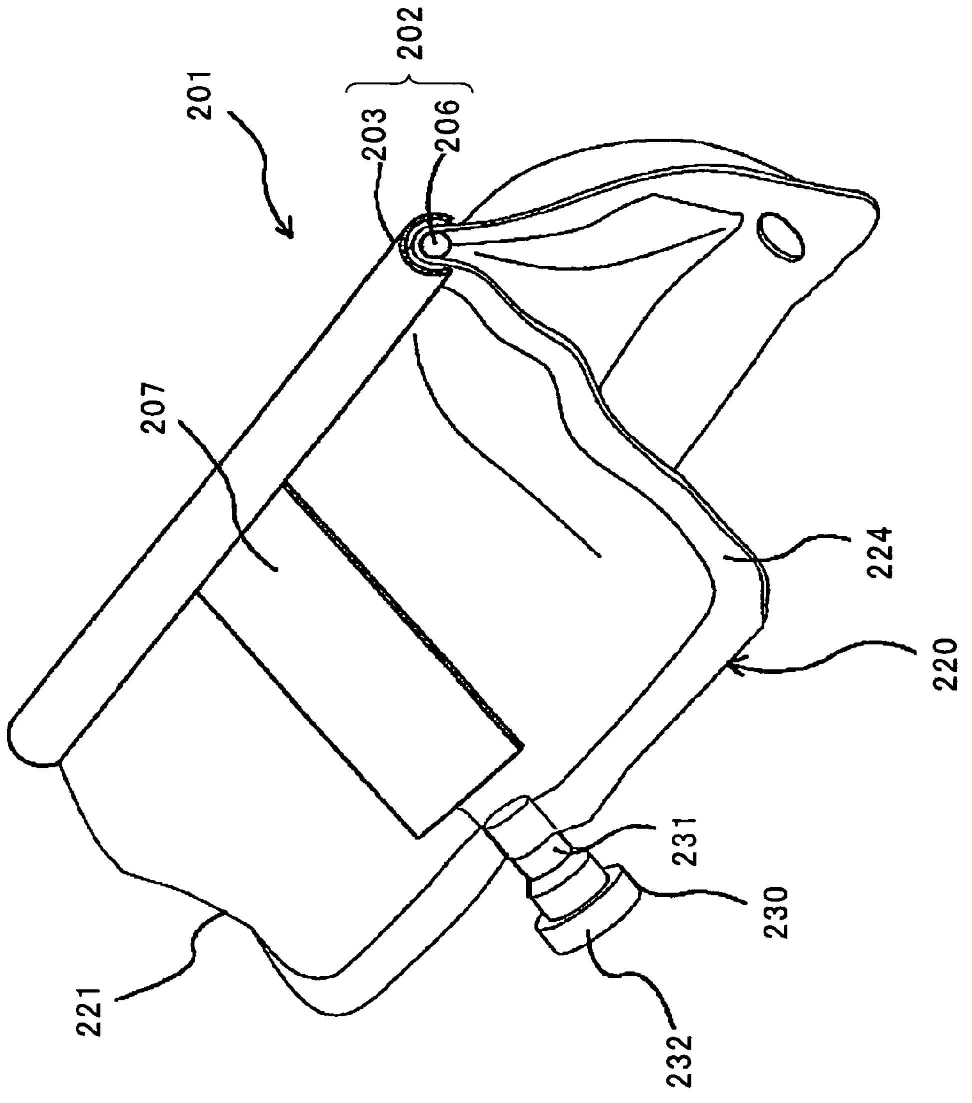
FIG. 44 is a perspective view showing the dividing unit of FIG. 42 attached to the multi-chamber container.

The aid 206 is formed of synthesized resin of substantially circular cross section. As shown in FIG. 43, the aid 206 is pinched by the pinch portion 204 of the clip 203 while being brought into contact with one wall portion 222 of the container body 221 of the multi-chamber container 220 described later. The aid 206 may be secured integrally to one wall portion 222 of the container body 221 by adhesive or the like.

The straddling plate 207 is formed by curving the rigid material formed in the shape of a long band. As shown in FIG. 43, the straddling plate 207 is pinched by the pinch portion 204 of the clip 203 while being brought into contact with the other wall portion 223 on the side opposite to one wall portion 222 with which the aid 206 is in contact. The straddling plate 207 may be formed of metal such as iron being hard, but in consideration of safety, is preferably formed of plastic material.

Figure 45:
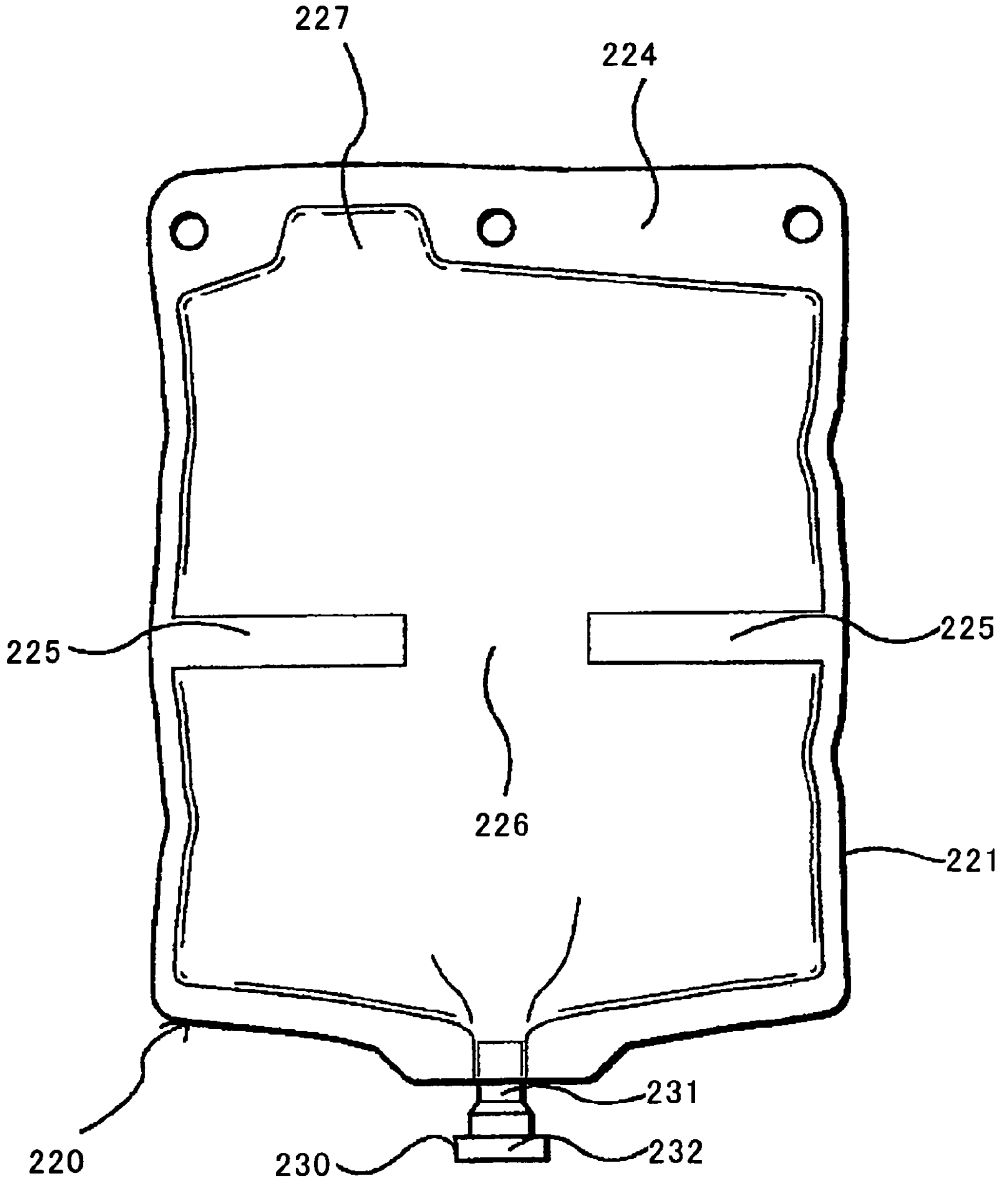
FIG. 45 is a front view showing a multi-chamber container.

As shown in FIG. 45, the multi-chamber container 220 is provided with a seal portion 224 formed on the periphery of the container body 221. The seal portion 224 is formed by heating and fusing inner surfaces on the peripheries of two film sheets constituting the container body 221 with an ejection tube 231 of a plug 230 held therebetween. The plug 230 is in the shape of a tube, and comprised of the ejection tube 231 and an ejection outlet 232 sealed by a rubber stopper until a hollow needle is inserted. The multi-chamber container 220 is provided with seal portions 225 spaced a predetermined distance from the center to the right and left, and a communication portion 226 formed between the seal portions 225. The seal portions 225 are formed by heating and fusing inner surfaces of the two film sheets, constituting the container body 221, spaced the predetermined distance from the center to the right and left. The opening width of the communication portion 226 is configured to be narrower than the width of the straddling plate 207.

When the inside of the container body 221 is divided using the unit 201 with the above-mentioned configuration, first, the aid 206 is brought into contact with one wall portion 222 of the container body 221 along the seal portions 225 and communication portion 226. Next, in the contact position of the aid 206, the container body 221 is folded in two such that one wall portion 222 is inside. Then, the straddling plate 207 is brought into contact with the other wall portion 223 such that the curving portion 208 of the straddling plate 207 is positioned in the communication portion 226. In the position where the aid 206 and the curving portion 208 of the straddling plate 207 contact the container, the container body 221 of the multi-chamber container 220 is inserted into the pinch space 205 of the clip 203, and thereby pinched by the pinch portion 204 of the clip 203.

After attaching the unit 201 to the multi-chamber container 220 and dividing the inside of the container body 221, unmixed agents are respectively filled from the ejection outlet 232 of the plug 230 and from a filling inlet 227 formed at an end portion on the side opposite to the plug 230. Then, the ejection outlet 232 is sealed by a rubber stopper material, and the filling inlet 227 is fused and sealed to seal each unmixed agent.

Figure 46B:
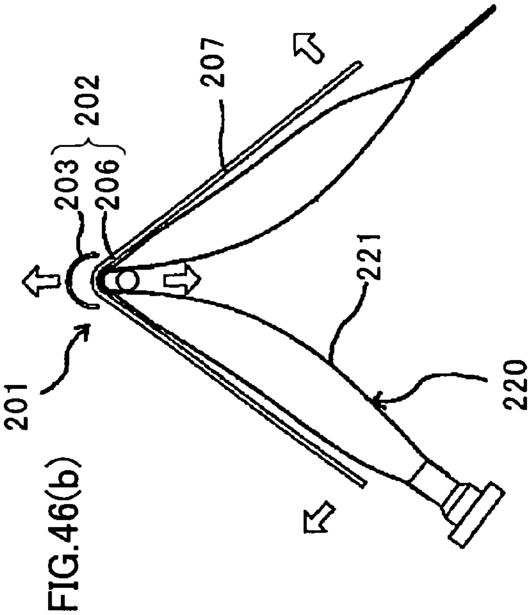
FIG. 46 is a view to explain a state up to expansion of a container body folded in two.
Figure 46A:
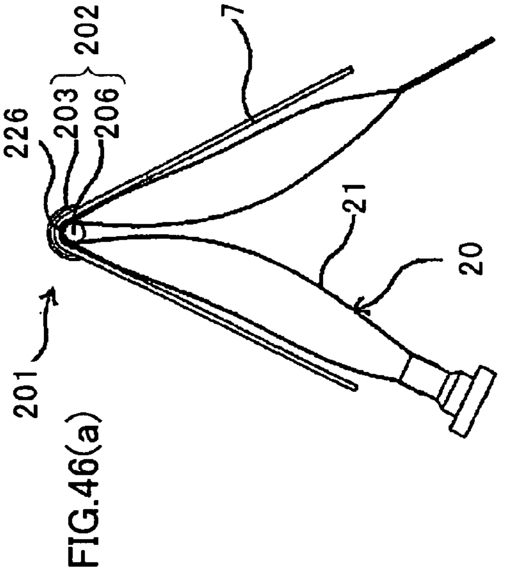
Figure 46C:
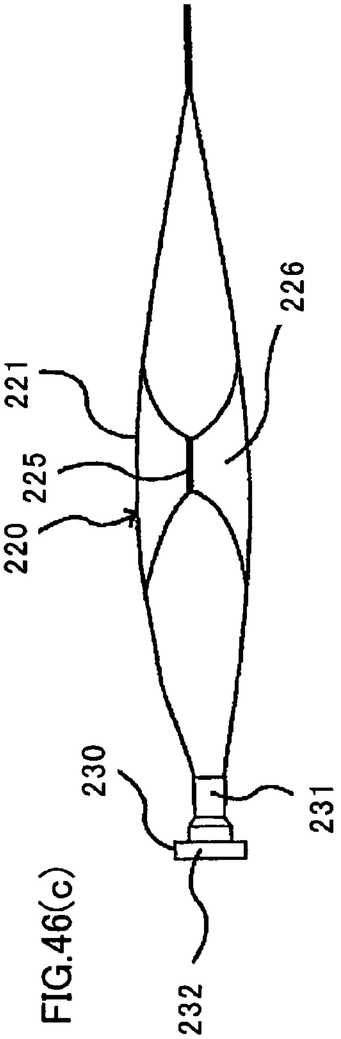

When the unit 201 is attached to the multi-chamber container 220, as shown in FIG. 46(*a*), the communication portion 226 of the multi-chamber container 220 which the aid 206 and the curving portion 208 of the straddling plate 207 contact is pinched by the clip 203 and thus clogged, while in a portion where the straddling plate 207 does not contact, the inside of the container body 221 is clogged by the seal portions 225, and it is thereby possible to partition the inside of the container body 221 of the multi-chamber container 220 into two portions to completely divide. Further, the unit 201 is capable of keeping the multi-chamber container 220 folded in two by the straddling plate 207, and the multi-chamber container 220 can be identified, from the appearance, as being not allowed to administer agents even when hung on a hook.

In removing the unit 201 from the multi-chamber container 220, by grasping near opposite ends of the straddling plate 207 and extending the straddling plate 207 outward as shown in FIG. 46(*b*), the pinch portion 204 of the clip 203 is broadened to release the pinching of the clip with ease. The partition by the unit 201 is thereby released, and as shown in FIG. 46(*c*), it is possible to expand the container body 221 of the multi-chamber container 220 and mix unmixed agents.

Figure 47:
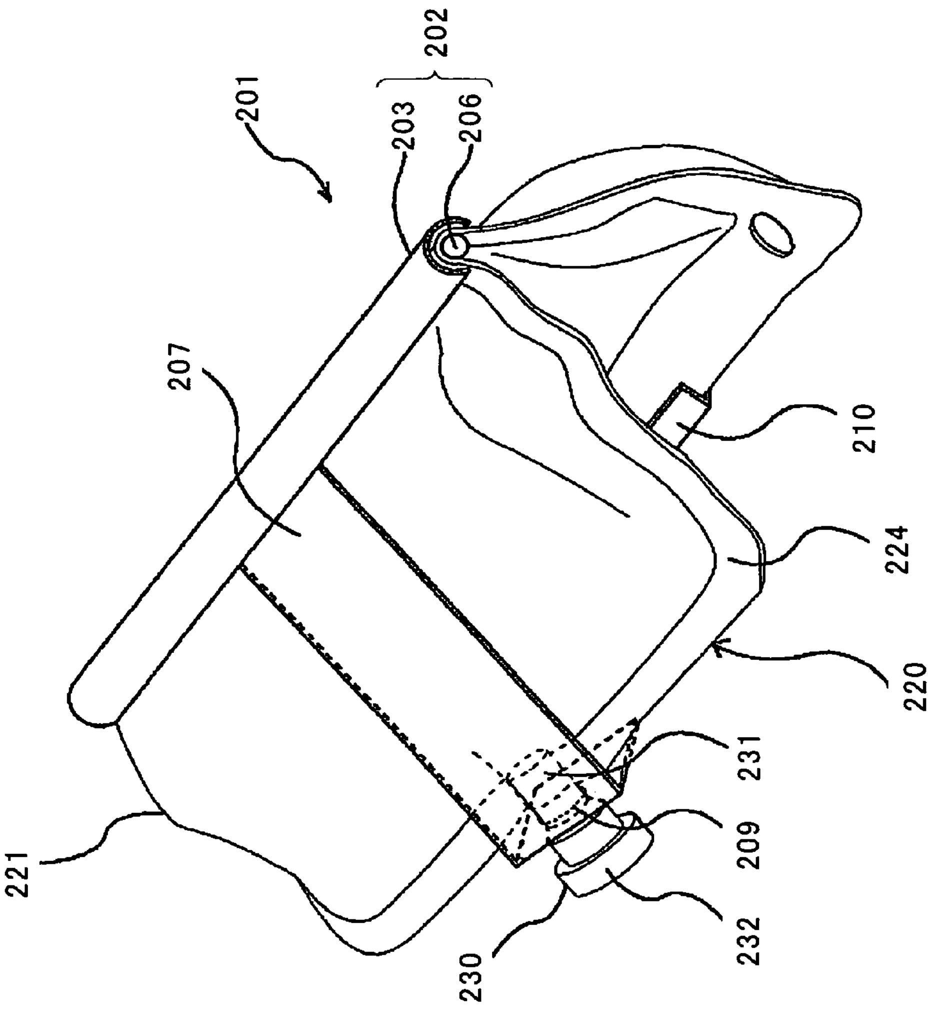
FIG. 47 is a perspective view showing the dividing unit according to Embodiment 10 attached to the multi-chamber container using another example of a straddling plate.

In addition, as shown in FIG. 47, the straddling plate 207 may be provided at one end with an insertion hole 209 to insert the plug 230 of the multi-chamber container 220, and further at the other end with a fastening portion 210 that holds an end portion of the container body 221 on the side opposite to the plug 230. The straddling plate 207 is thereby capable of keeping the container body 221 of the multi-chamber container 220 folded in two in a certain position.

Also in this Embodiment, without performing the specific opening operation, only by unfolding the multi-chamber container, the clip is detached, the filling chambers are opened in therebetween, and therefore, the agents inside the respective filling chambers are reliably mixed when the user uses the container.

Embodiment 11

Figure 48:
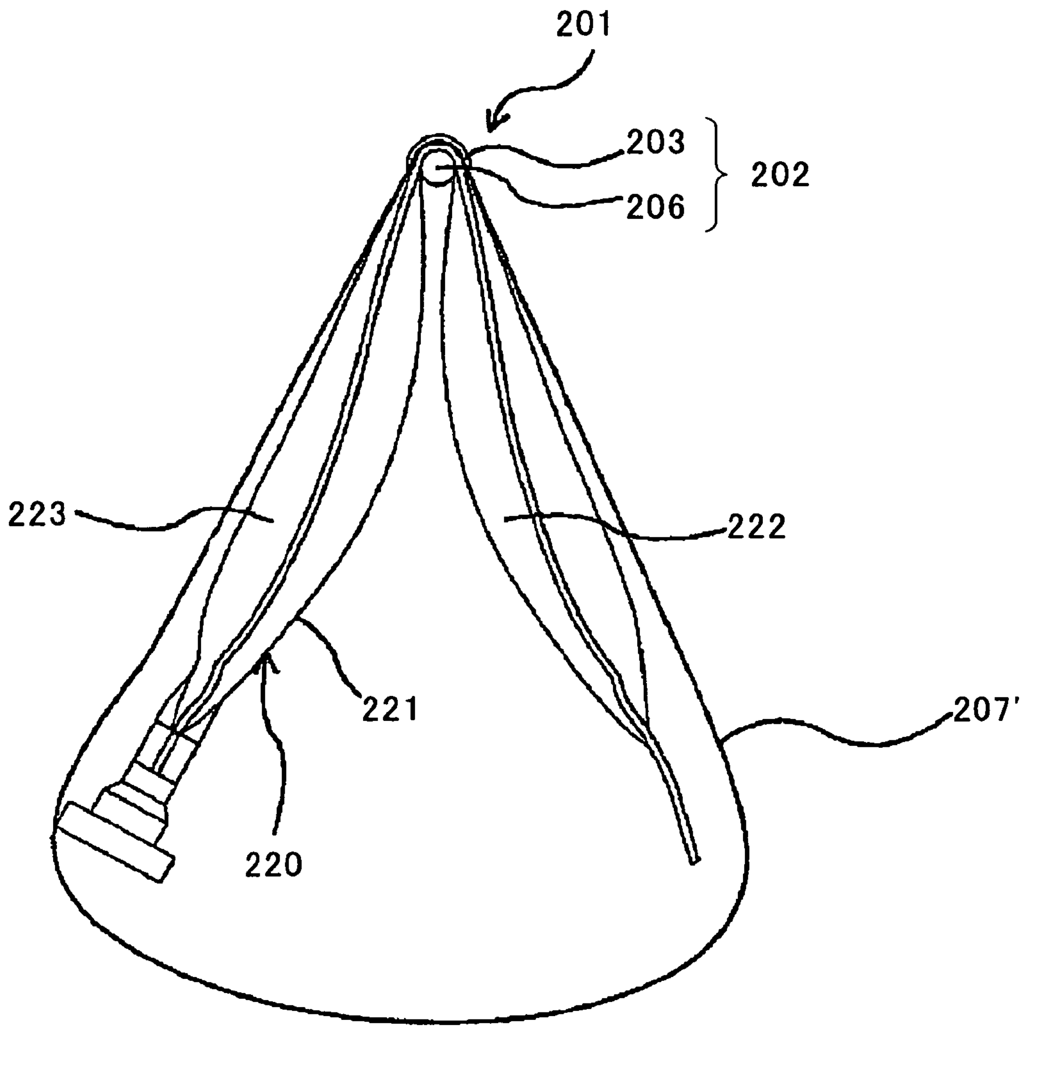
FIG. 48 is a side view showing a dividing unit according to Embodiment 11 of the invention attached to a multi-chamber container.

FIG. 48 is a view showing a dividing unit according to Embodiment 11 of the invention attached to a multi-chamber container. The unit 201 is comprised of the dividing means 202 configured as in Embodiment 10 and a straddling device 207' formed of flexible material such as a cloth or the like.

Figure 49:
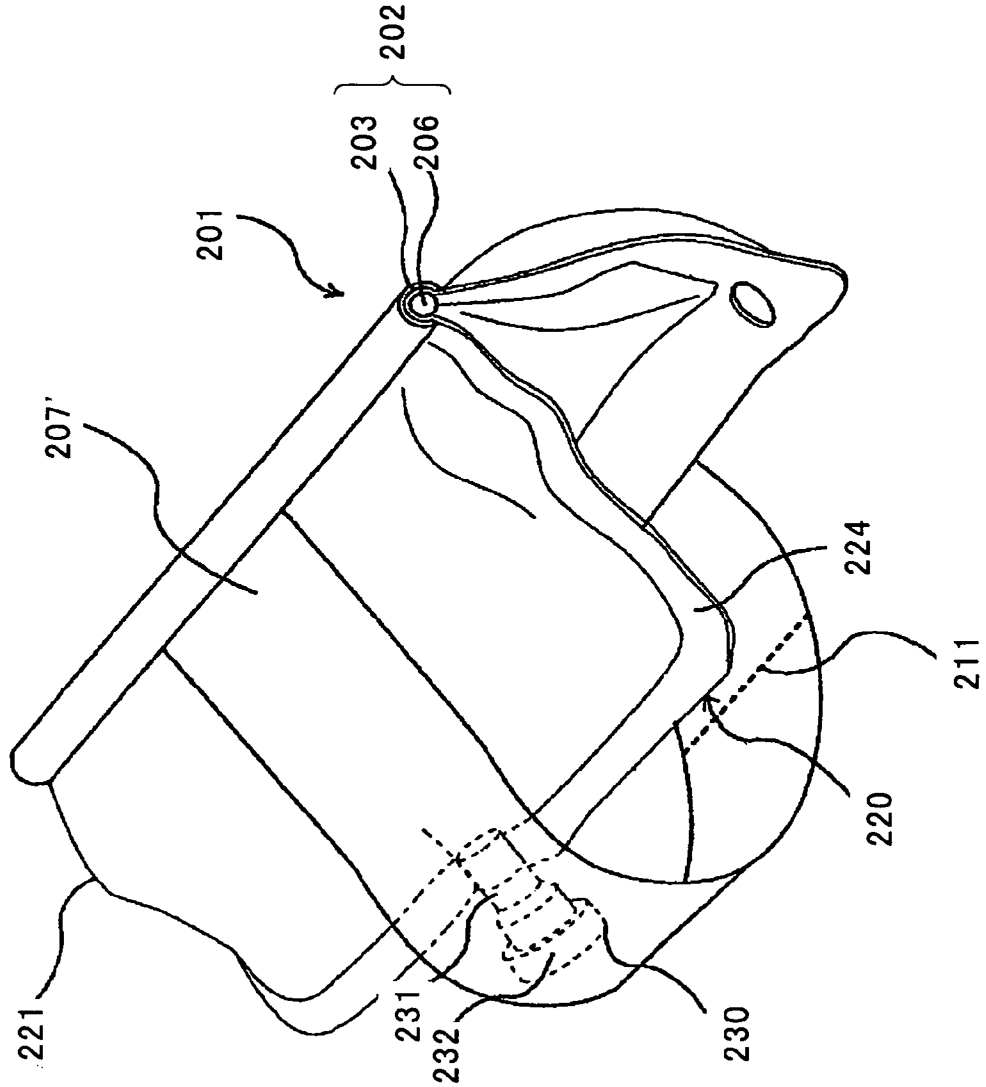
FIG. 49 is a perspective view showing the dividing unit according to Embodiment 11 of the invention attached to the multi-chamber container.

As shown in FIG. 48, the straddling device 207' is formed in the shape of a ring. As shown in FIG. 49, the straddling device 207' has a rupture portion 211 to release the container body 221 of the multi-chamber container 220 folded in two.

In partitioning the container body 221 of the multi-chamber container 220 using the dividing unit 201 with the above-mentioned configuration, first, with the aid 206 brought into contact with one wall portion 222 of the container body 221 along the seal portions 225 and communication portion 226, the container body 221 is folded in two such that one wall portion 22 is inside. Then, the straddling device 207' is wound around the other wall portion 223 of the container body 221 such that the straddling device 207' is positioned in the communication portion 226, and that the rupture portion 211 is positioned on the side opposite to the communication portion 226. Then, in the position where the aid 206 contacts the container, the container body 221 of the multi-chamber container 220 is inserted into the pinch space 205 of the clip 203, and thereby pinched by the pinch portion 204 of the clip 203. Subsequently, in the same method as in Embodiment 10, each unmixed agent is filled inside the container body 221 of the multi-chamber container 220 partitioned by the unit 201.

In the dividing unit 201 according to Embodiment 11, as in Embodiment 10, the communication portion 226 of the multi-chamber container 220 which the aid 206 and the straddling device 207' contact is pinched by the clip 203 and thus clogged, while in a portion where the straddling device 207' does not contact, the inside of the container body 221 is clogged by the seal portions 225, and it is thereby possible to partition the inside of the container body 221 of the multi-chamber container 220 into two portions to completely divide. Further, as shown in FIGS. 48 and 49, since the rupture portion 211 of the straddling device 207' is not broken, the unit 201 is capable of keeping the multi-chamber container 220 folded in two, and the multi-chamber container 220 can be identified, from the appearance, as being not allowed to administer agents even when hung on a hook.

In removing the unit 201 from the multi-chamber container 220, by grasping separate portions formed by rupturing the rupture portion 211 to extend outward, the pinch portion 204 of the clip 203 is broadened, and the clip 203 can be released. The partition by the unit 201 is thereby released, and it is possible to expand the container body 221 of the multi-chamber container 220 and mix unmixed agents. In addition, the clip 203 may be released by rupturing the clip 203, and in this case, to facilitate the rupture of the clip 203, a notch for rupture is preferably provided in the center portion of the clip 203.

Also in this Embodiment, without performing the specific opening operation, only by unfolding the multi-chamber container, the clip is detached, the filling chambers are opened in therebetween, and therefore, the agents inside the respective filling chambers are reliably mixed when the user uses the container.

Embodiment 12

Figure 50:
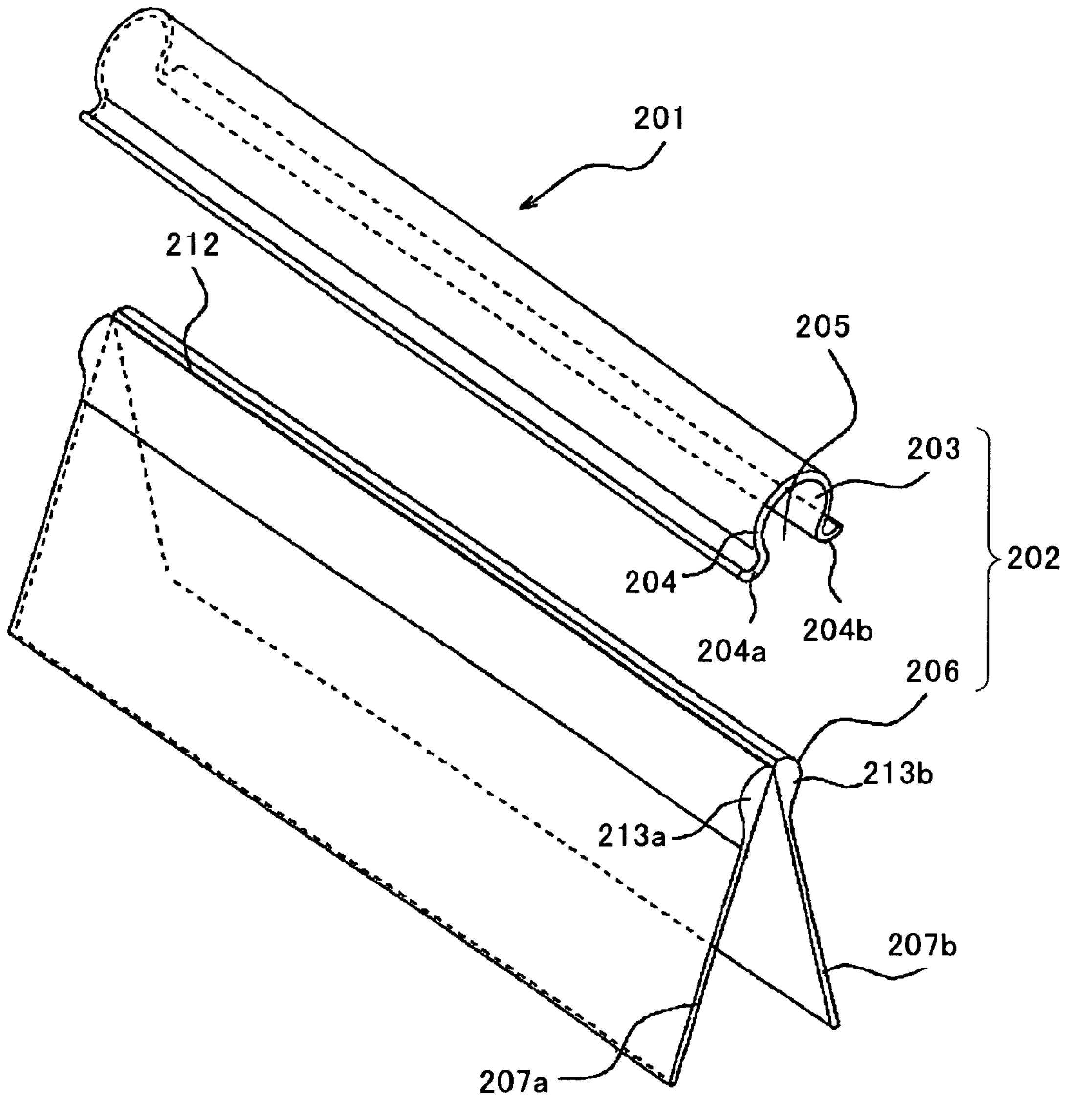
FIG. 50 is a perspective view showing a dividing unit according to Embodiment 12 of the invention.
Figure 51:
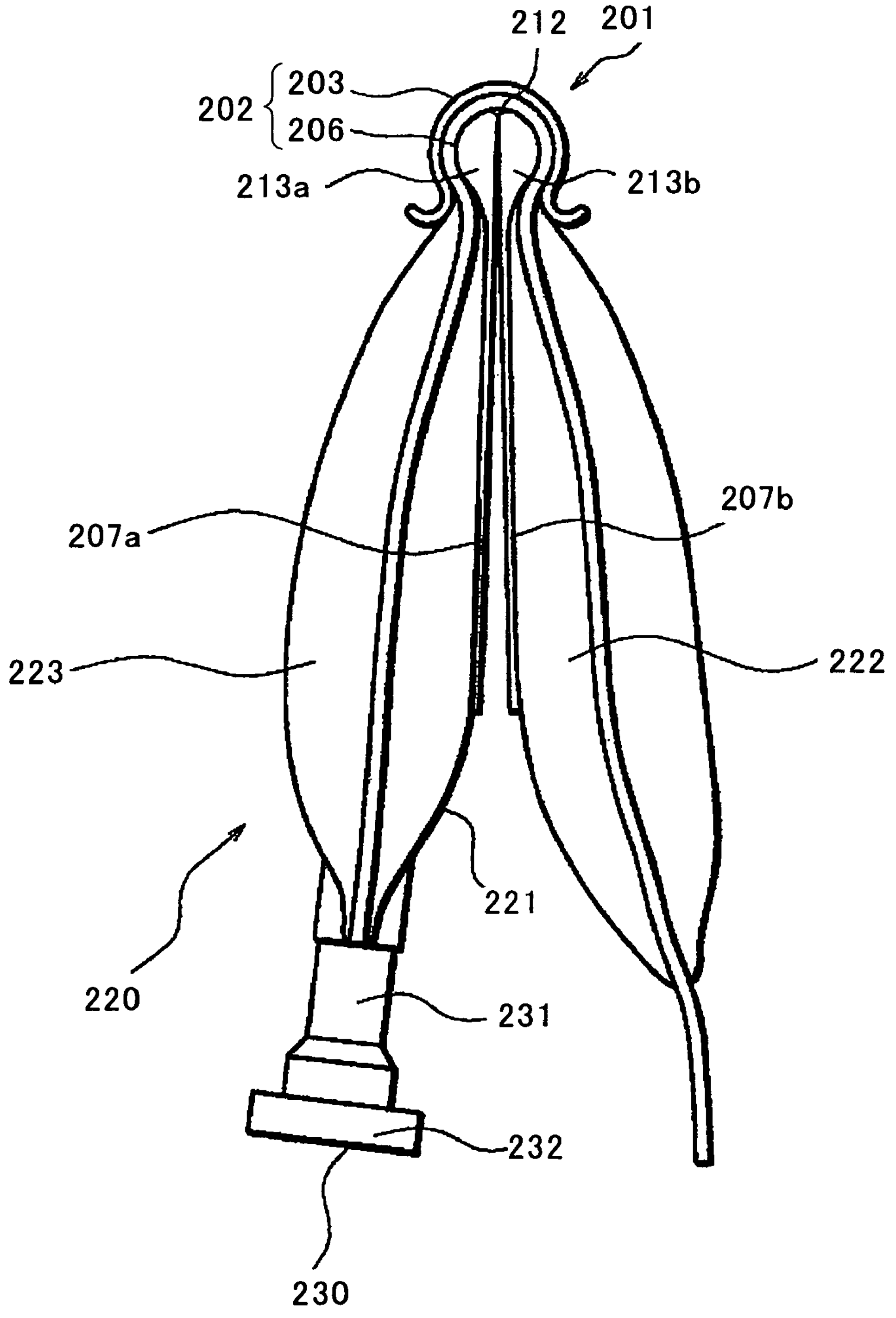
FIG. 51 is a side view showing the dividing unit of FIG. 50 attached to a multi-chamber container.
Figure 52:
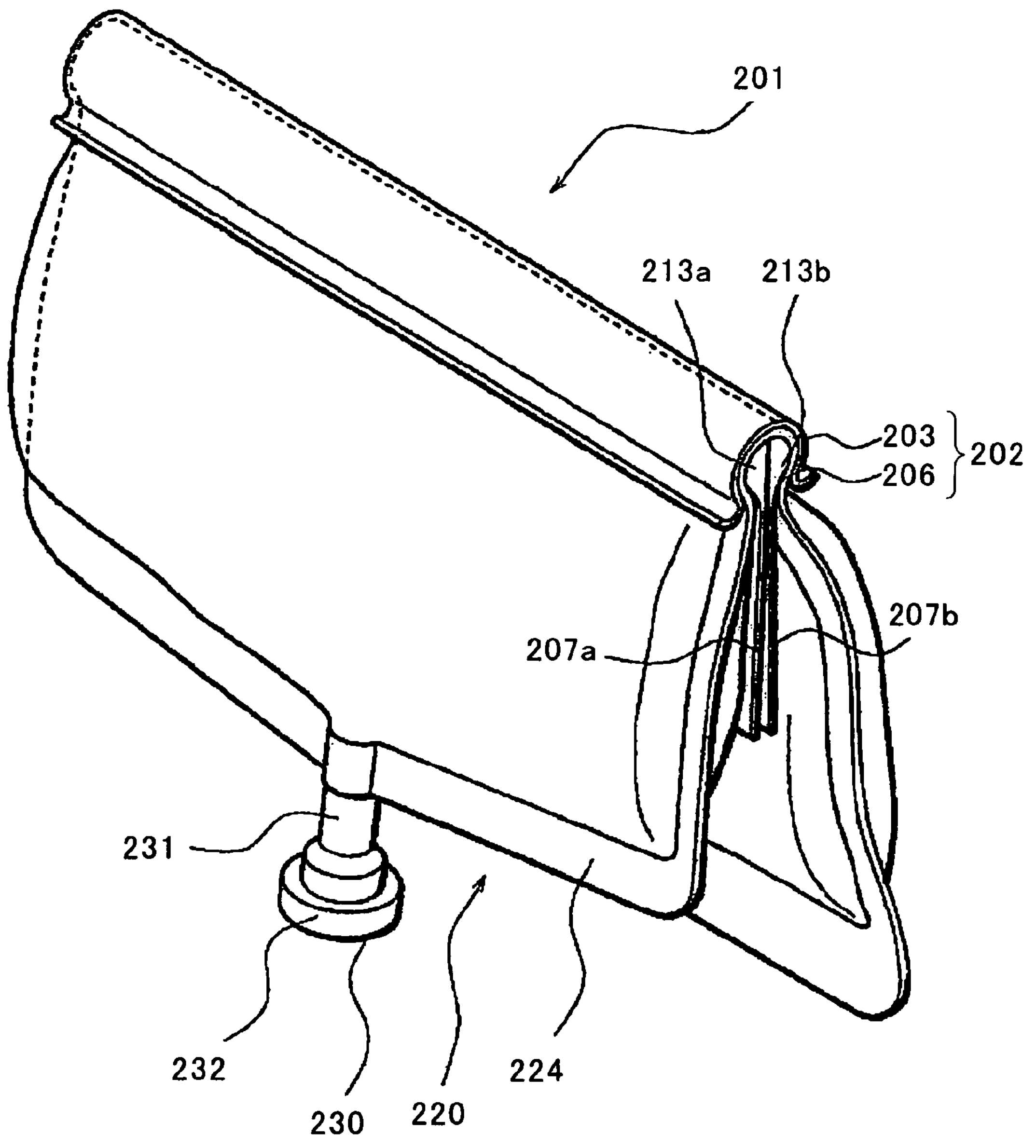
FIG. 52 is a perspective view showing the dividing unit of FIG. 50 attached to the multi-chamber container.

FIG. 50 is a view showing a dividing unit according to Embodiment 12 of the invention. The unit 201 is comprised of the dividing means 202 and straddling plates **207*a* and 207*b*** formed of a pair of hard rigid materials.

The unit 202 includes the clip 203 and aid 206. The clip 203 further has curving portions **204*a* and 204*b* extending outward provided in the pinch portion 204 of the clip 203** of Embodiments 10 and 11.

The aid 206 is formed of the hard rigid material. As shown in FIG. 50, the aid 206 is comprised of half-cut rod-shaped members **213*a* and 213*b* coupled to each other to be able to be folded in a thin portion 212. The aid 206 is pinched by the pinch portion 204 of the clip 203 while closing the half-cut rod-shaped members 213*a*, 213*b* in contact with one wall portion 222 of the container body 221**.

The pair of straddling plates **207*a*, 207*b* are each comprised of long-band-shaped hard rigid material, and formed integrally with opposite ends of the aid 206. The aid and pair of straddling plates 207*a*, 207*b*** may be formed of metal such as iron being hard, but in consideration of safety, are preferably formed of plastic materials.

In partitioning the container body 221 of the multi-chamber container 220 using the dividing unit 201 with the above-mentioned configuration, first, the pair of half-cut rod-shaped members **213*a*, 213*b* of the aid 206 are brought into contact with one wall portion 222 along the seal portions 225 and communication portion 226, and then, the pair of straddling plates 207*a*, 207*b* are fixed to the multi-chamber container 220 with two-sided tapes or the like bonded to the other ends of the pair of straddling plates 207*a*, 207*b*. Next, in the position where the thin portion 212 of the aid 206 is disposed, the container body 221 is folded in two such that one wall portion 22 is inside. Then, in the position where the half-cut rod-shaped members 213*a*, 213*b* of the aid 206 contact the container, the container body 221 of the multi-chamber container 220 is inserted into the pinch space 205 of the clip 203, and thereby pinched by the pinch portion 204 of the clip 203. This state is as shown in FIG. 56**(*a*). Then, as shown in FIG. 56(*b*), agents are filled inside the container body 221. Subsequently, as shown in FIG. 56(*c*), the multi-chamber container is sterilized and checked, and then, as shown in FIG. 56(*d*), the straddling plates **207*a*, 207*b* are adhered to wall portions 222 of the container body 221. In this way, each unmixed agent is filled into the container body 221 of the multi-chamber container 220 partitioned by the unit 201**.

In the dividing unit 201 according to Embodiment 12, as in Embodiment 10, the communication portion 226 of the multi-chamber container 220 which the half-cut rod-shaped members **213*a*, 213*b* of the aid 206 contact is pinched by the clip 203 and thus clogged, while the inside of the container body 221 is clogged by the seal portions 225, and it is thereby possible to partition the inside of the container body 221 of the multi-chamber container 220** into two portions to completely divide.

Figures 53A, 53B, 53C:
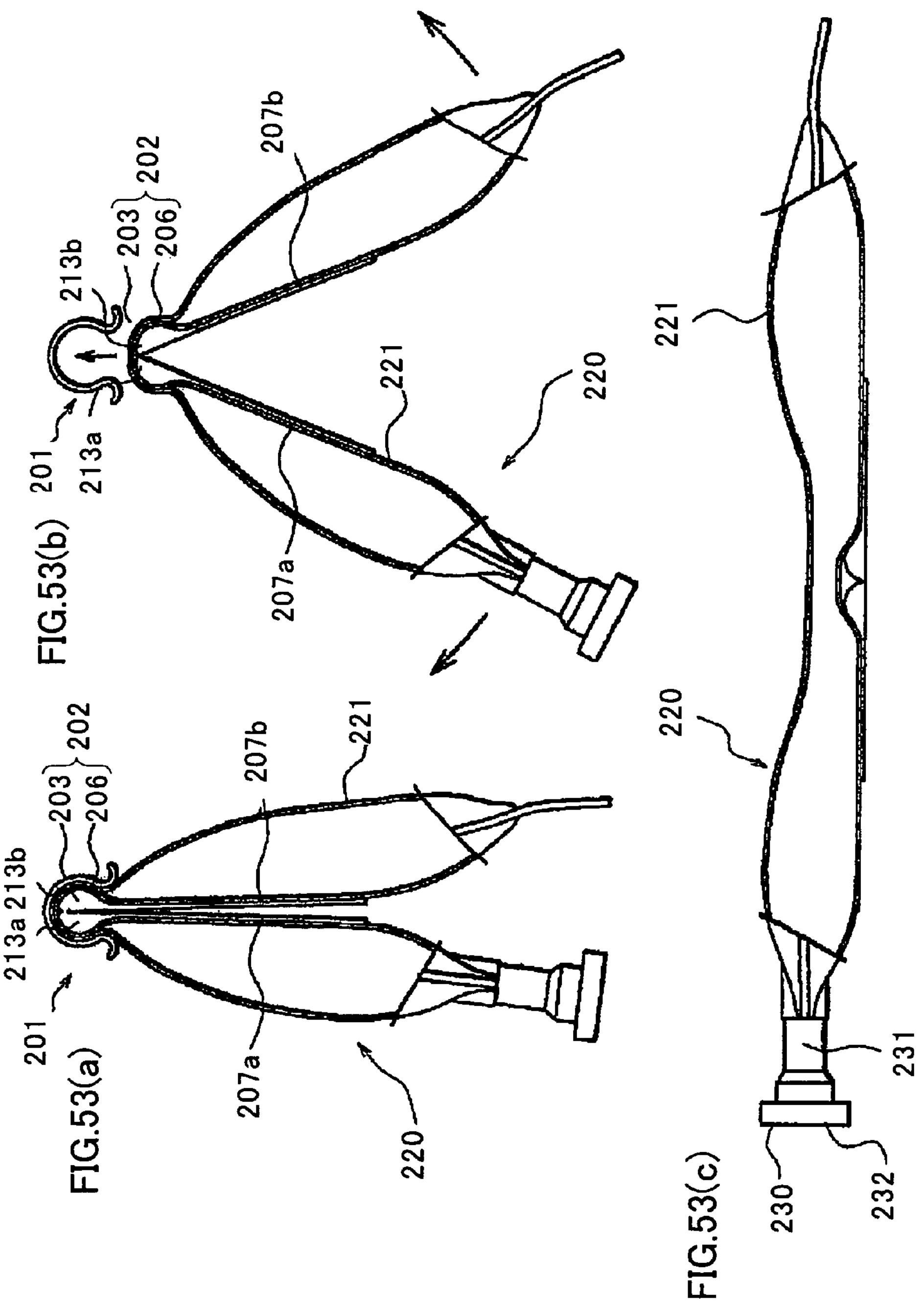
FIG. 53 is a view to explain a state up to expansion of a container body folded in two.

In removing the unit 201 from the multi-chamber container 220, by grasping near the other ends of the pair of straddling plates **207*a*, 207*b*, and as shown in FIG. 53**(*b*), extending the straddling plates **207*a*, 207*b* outward, the pinch portion 204 of the clip 203 is broadened, and the clip 203 can be released. The partition by the unit 201 is thereby released, and it is possible to expand the container body 221 of the multi-chamber container 220 and mix unmixed agents, as shown in FIG. 53**(*c*).

Figure 54:
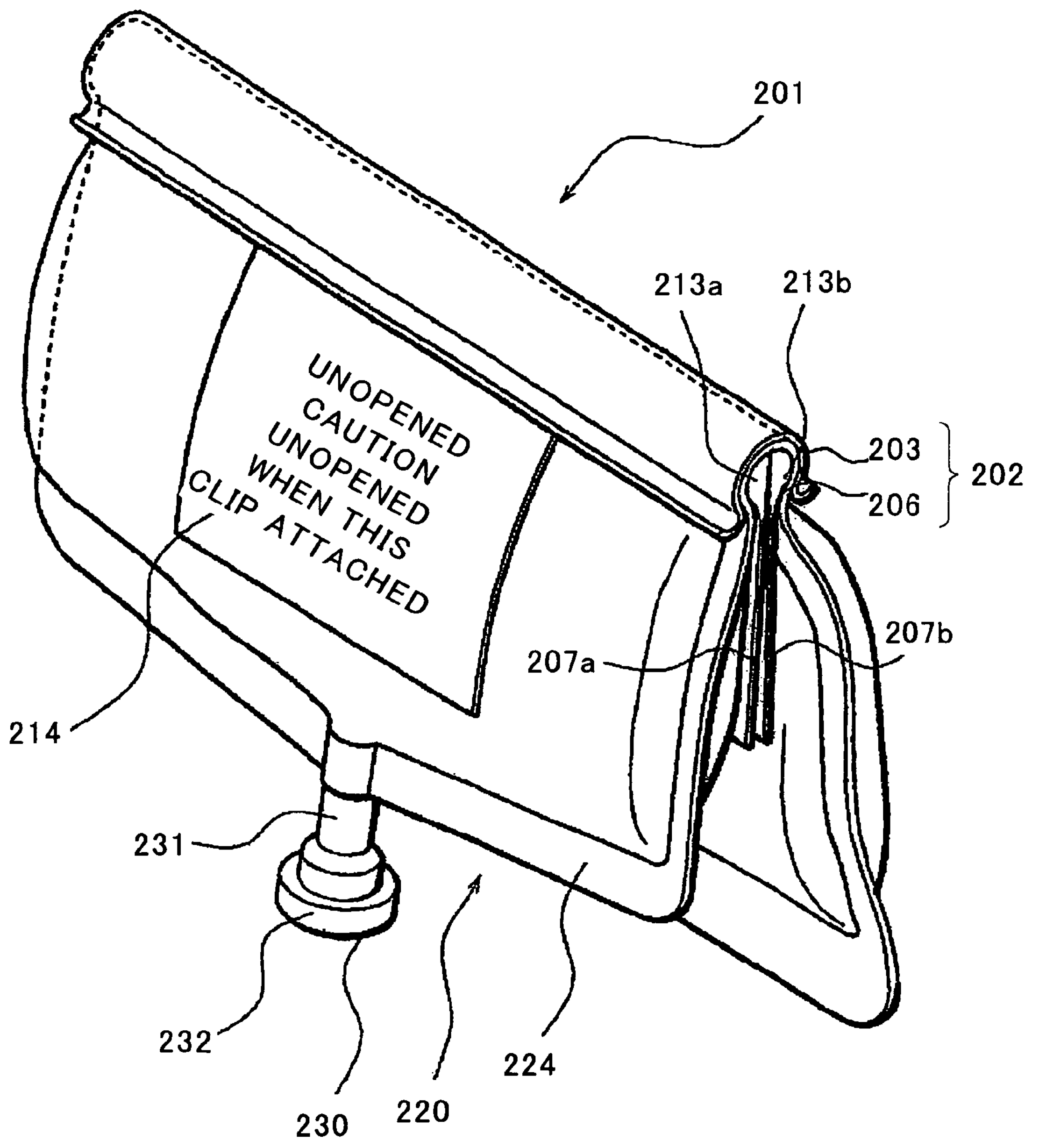
FIG. 54 is a perspective view showing the diving unit of FIG. 50 attached to the multi-chamber container.
Figure 55:
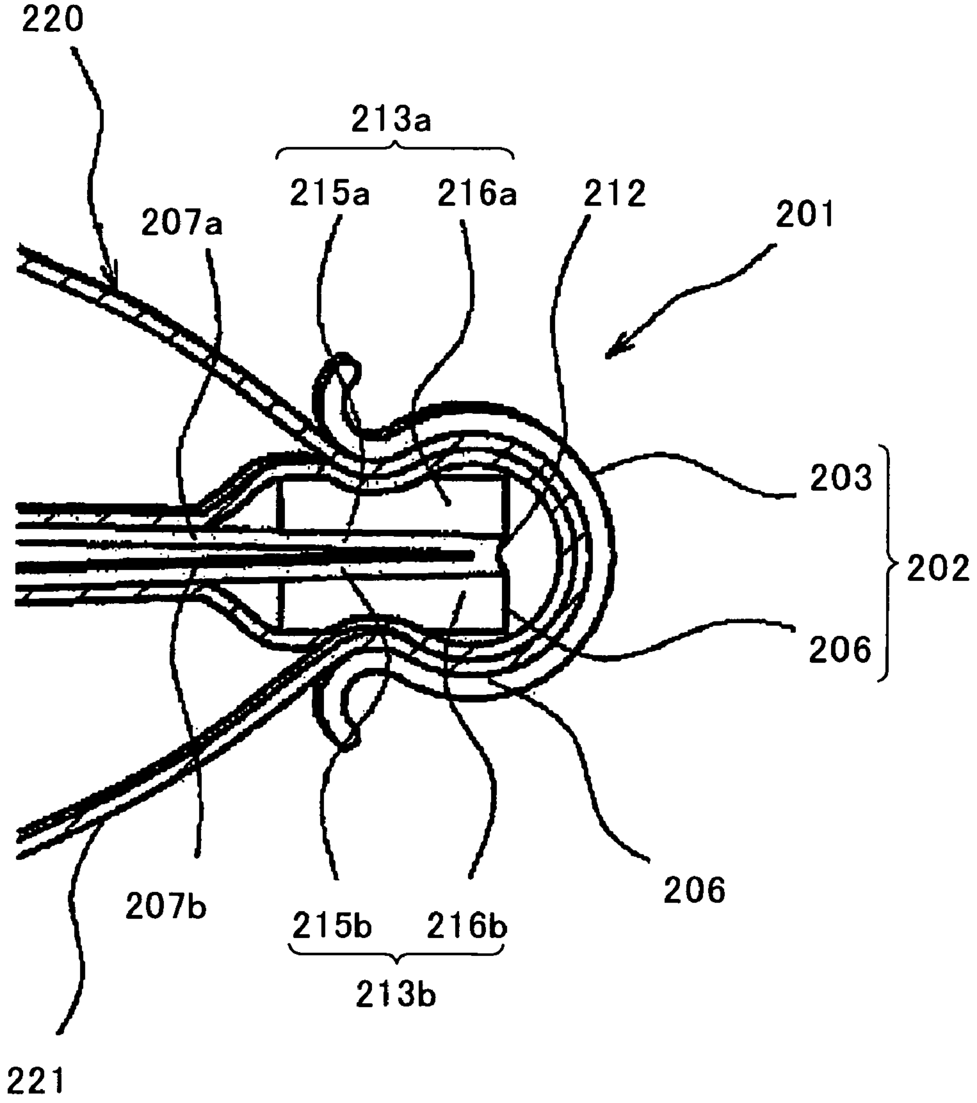
FIG. 55 is a partial expanded cross-sectional view showing the multi-chamber container with the aid of FIG. 50 pinched by a clip.
Figure 56A:
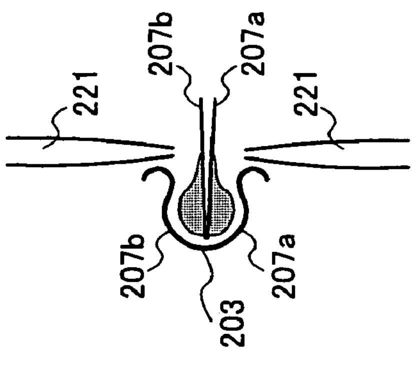
FIG. 56 is a view to explain a method of filling agents into the multi-chamber container as described in Embodiment 12.
Figure 56B:
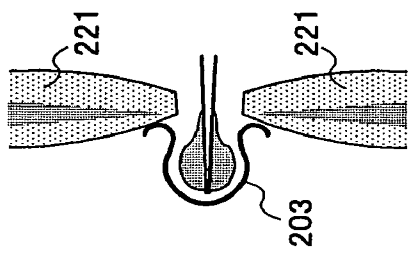
Figure 56C:
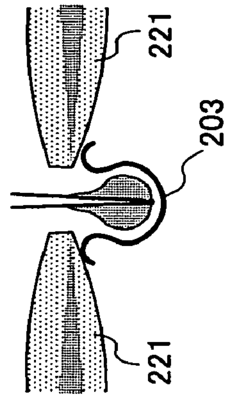
Figure 56D:
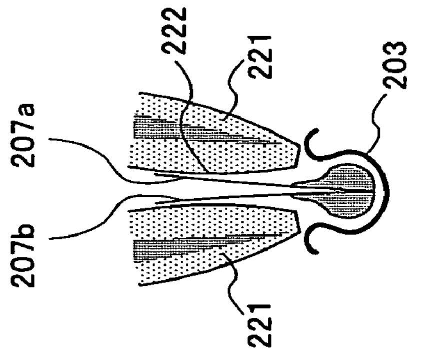

In addition, as shown in FIG. 54, a caution sheet 214 may be bonded to the pinch portion 204 of the clip 203. If the caution sheet 214 is bonded, even when the multi-chamber container 220 is hung on a hook, a user is capable of recognizing that the inside of the container body 221 is not opened. Further, the half-cut rod-shaped members **213*a*, 213*b* constituting the aid 206 may be comprised of a pair of plate portions 215***a*, 215*b* which are formed of hard rigid material, coupled at one ends to be openable/closable in the thin portion 212, and formed at the other ends integrally with the straddling plates 207*a*, 207*b*, and a pair of elastic pieces 216*a*, 216*b* which are formed of elastic material such as rubber, and respectively secured integrally to the pair of plate portions 215*a*, 215*b*. Using the elastic pieces 216*a*, 216*b* of the half-cut rod-shaped members 213*a*, 213*b*, as shown in FIG. 55, with the half-cut rod-shaped members 213*a*, 213*b* held and pinched near the opposite ends of the pinch portion 204 of the clip 203, the inside of the container body 221 can be clogged.

Also in this Embodiment, without performing the specific opening operation, only by unfolding the multi-chamber container, the clip is detached, the filling chambers are opened in therebetween, and therefore, the agents inside the respective filling chambers are reliably mixed when the user uses the container.

Figure 57A:
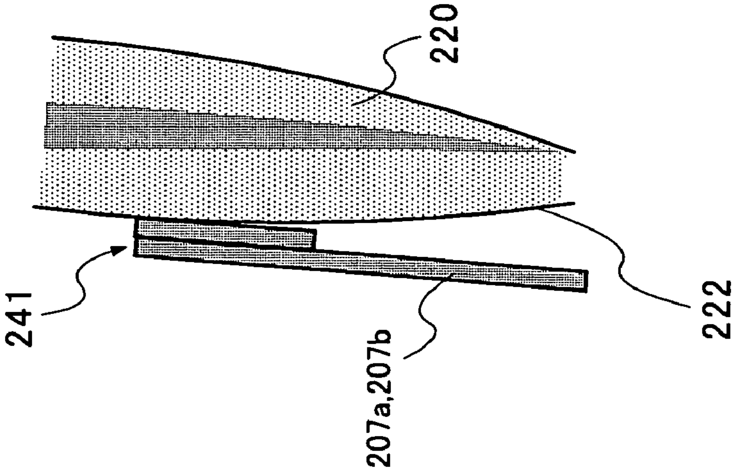
FIG. 57 is a view to explain a method of attaching a straddling plate to the container body in Embodiment 12.
Figure 57B:
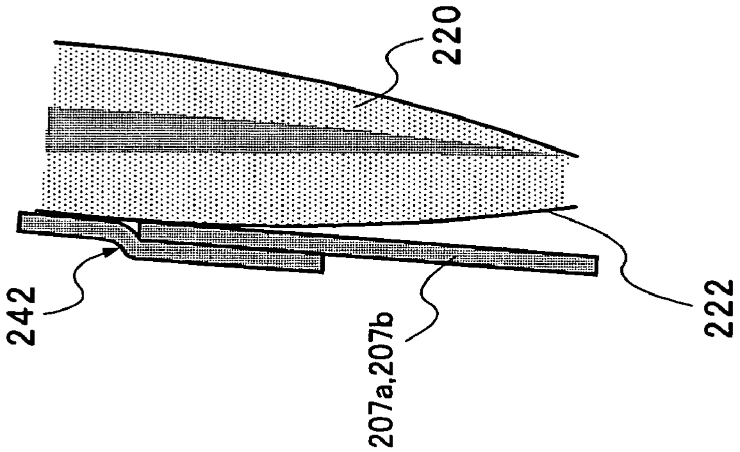
Figure 57C:
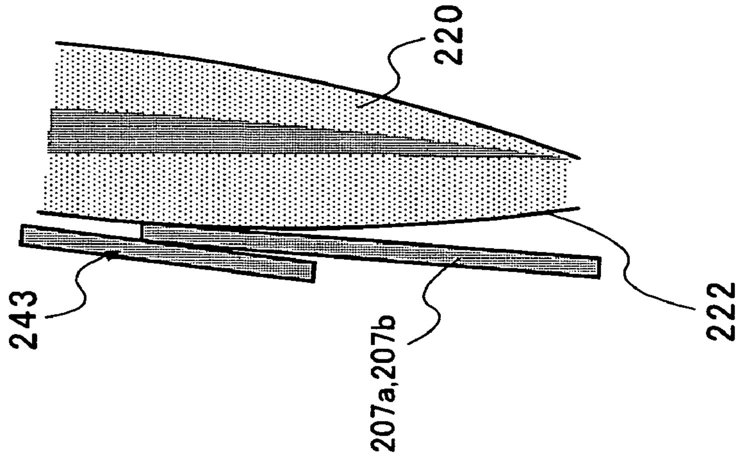

Herein, as a method of fixing the straddling plates 207*a*, 207*b* to the wall portions 222 of the container body 220, there are methods of providing two-sided tapes 241 between the straddling plates 207*a*, 207*b* and the wall portions 222 as shown in FIG. 57(*a*), of aligning the straddling plates 207*a*, 207*b* along the container body 220 and fixing the straddling plates 207*a*, 207*b* and the wall portions 222 by one-sided tapes 242 as shown in FIG. 57(*b*), of aligning the straddling plates 207*a*, 207*b* along the container body 220 and fixing from above the straddling plates 207*a*, 207*b* by one-sided adhesive plates 243 as shown in FIG. 57(*c*), and the like.

Figure 58C:
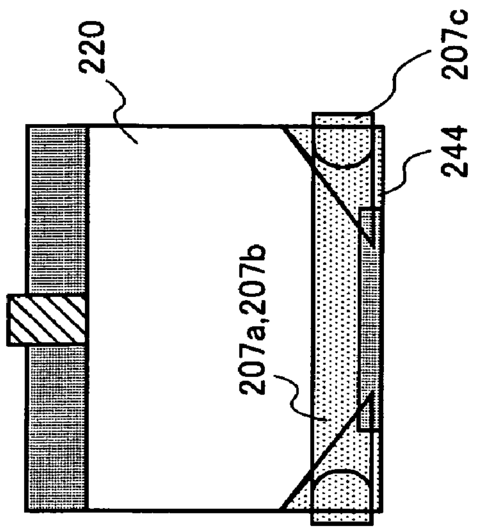
FIG. 58 is a view to explain a method of fixing the straddling plate to the container body in Embodiment 12.
Figure 58B:
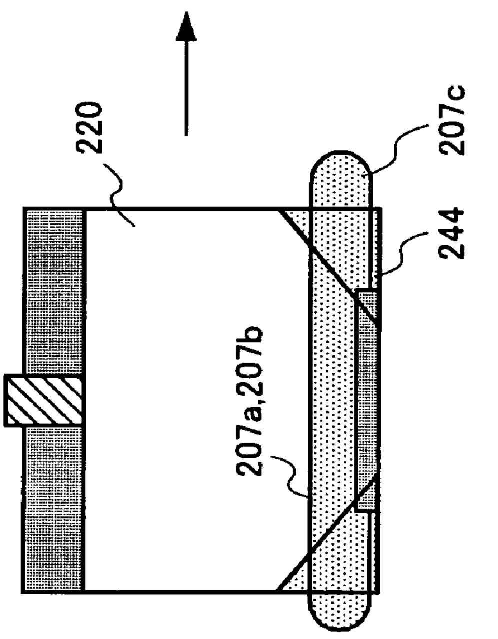
Figure 58A:
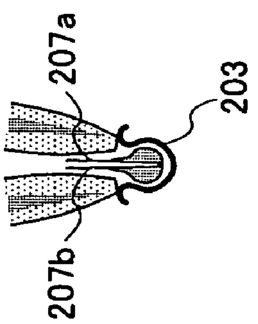
Figure 59B:
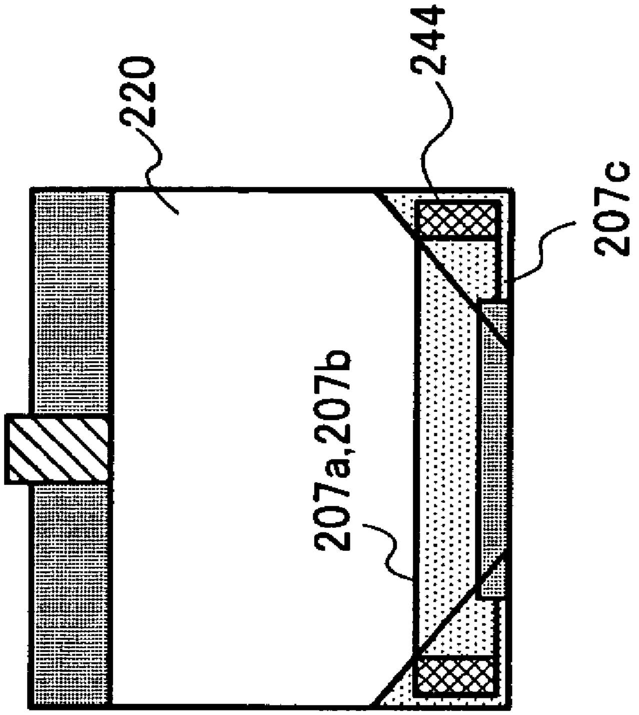
FIG. 59 is another view to explain the method of fixing the straddling plate to the container body in Embodiment 12.
Figure 59A:
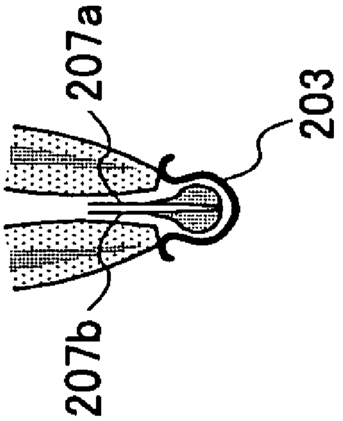

Further, as another method of fixing the straddling plates 207*a*, 207*b* to the wall portions 222 of the multi-chamber container 220, as shown in FIGS. 58(*a*) to 58(*c*), the length of each of the straddling plates 207*a*, 207*b* is set to be longer than the width of the container body 220, and each portion 207*c* extending from the container body 220 is bent to pinch the seal portion 244. At this point, bending of the straddling plates 207*a*, 207*b* is performed by bending processing while heating. The heating is only performed on the bending portions of the straddling plates 207*a*, 207*b*, and the effect of the heating is reduced on the container body 220. Furthermore, as shown in FIGS. 59(*a*) and 59(*b*), the straddling plates 207*a*, 207*b* may be fixed to the seal portion 244 of the container body 220 by sealing.

Figure 60B:
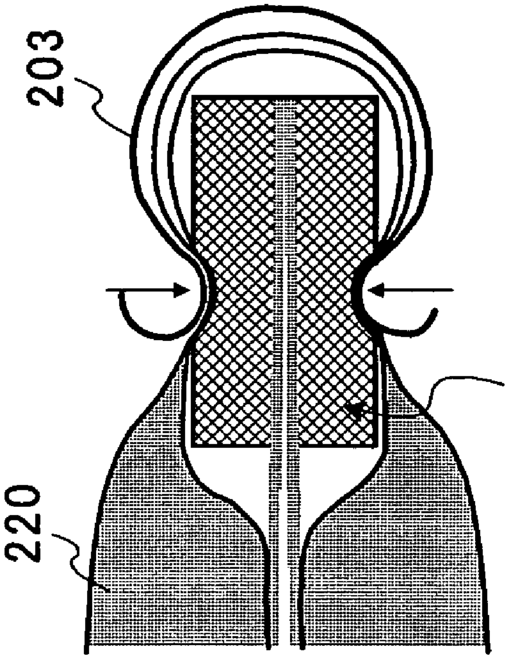
FIG. 60 is a view showing another example of the dividing unit.
Figure 60A:
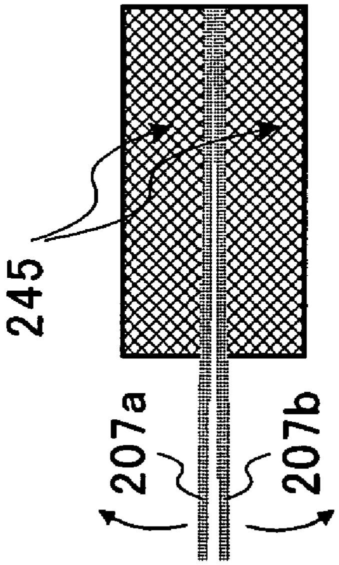

Moreover, as shown in FIG. 60(*a*), elastic members 245 each with a predetermined thickness are attached to the outside of the straddling, plates 207*a*, 207*b*, and as shown in FIG. 60(*b*), the clip 203 is attached to pinch the elastic members 245 in attaching the dividing unit to the container body 220. By providing such a configuration, it is possible to enhance the sealing property between the filling chambers.

Figure 61A:
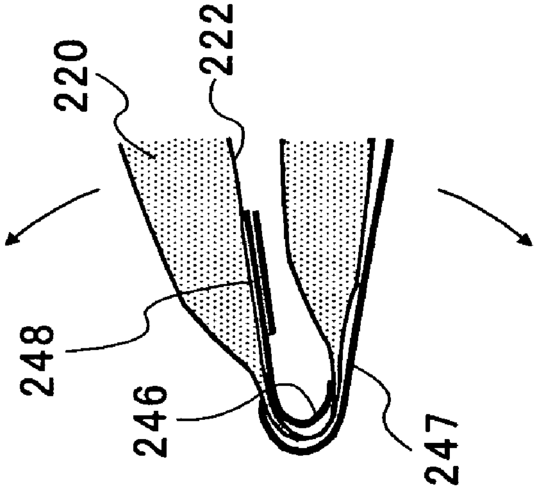
FIG. 61 is a view showing another example of the dividing unit.
Figure 61B:
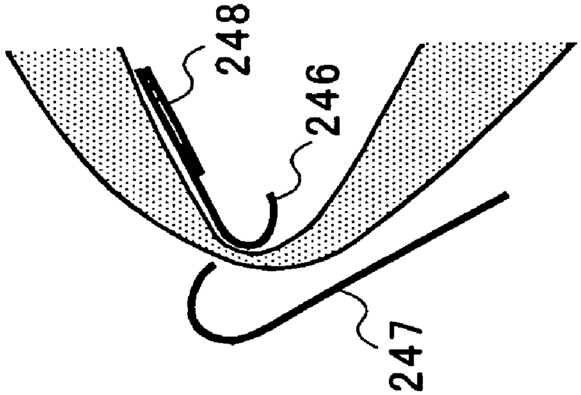

The present invention is not limited to the dividing units as described in above-mentioned Embodiments 10 to 12, and allows use of dividing units with other configurations. For example, as shown in FIG. 61(*a*), the dividing unit may be comprised of a pair of clips 246, 247 of substantially J-shaped cross section. Each of the clips 246, 247 has such a shape that the front end is curved, and the curvature of the curved portion of the outer clip 247 is set to be slightly larger than the curvature of the inner clip 246. Accordingly, the clip 247 can be covered and engaged over the clip 246. The inner clip 246 is adhered to the wall portion 222 of the container body 220, and the outer clip 247 is mounted onto the inner clip 246 with the container body 220 folded in two. By this means, the filling chambers of the container body 220 are divided. In this state, by unfolding the container body 220 in the direction of the arrows as shown in FIG. 61(*a*), the outer clip 247 is detached as shown in FIG. 61(*b*), the filling chambers are communicated with each other, and the agents are mixed.

Embodiment 13

Embodiments 13 to 18 described below explain an aspect for opening a plurality of filling chambers using the operation for hanging a multi-chamber container in a device.

Figure 62:
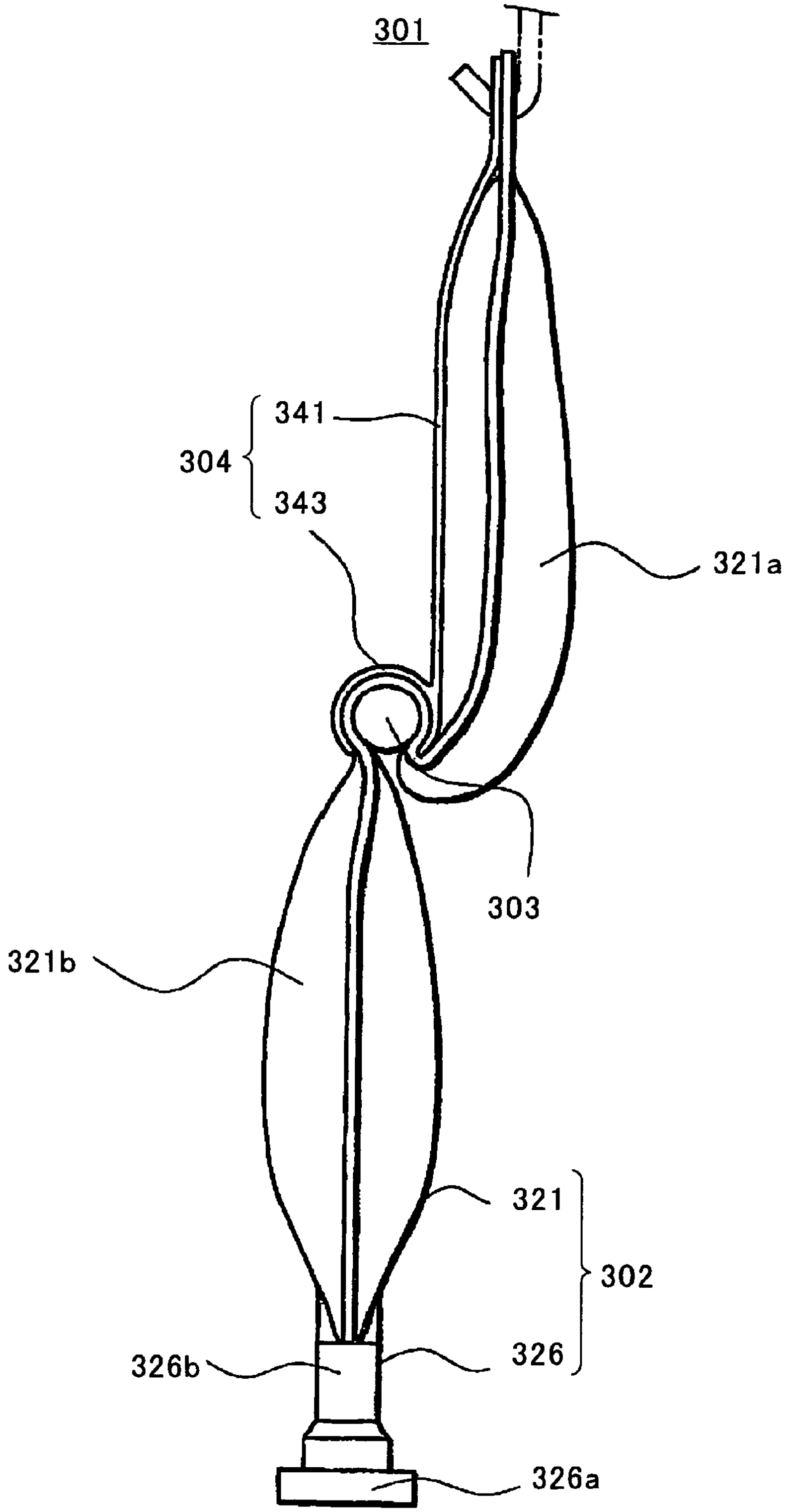
FIG. 62 is a side view showing a multi-chamber container according to Embodiment 13 of the invention.
Figure 63:
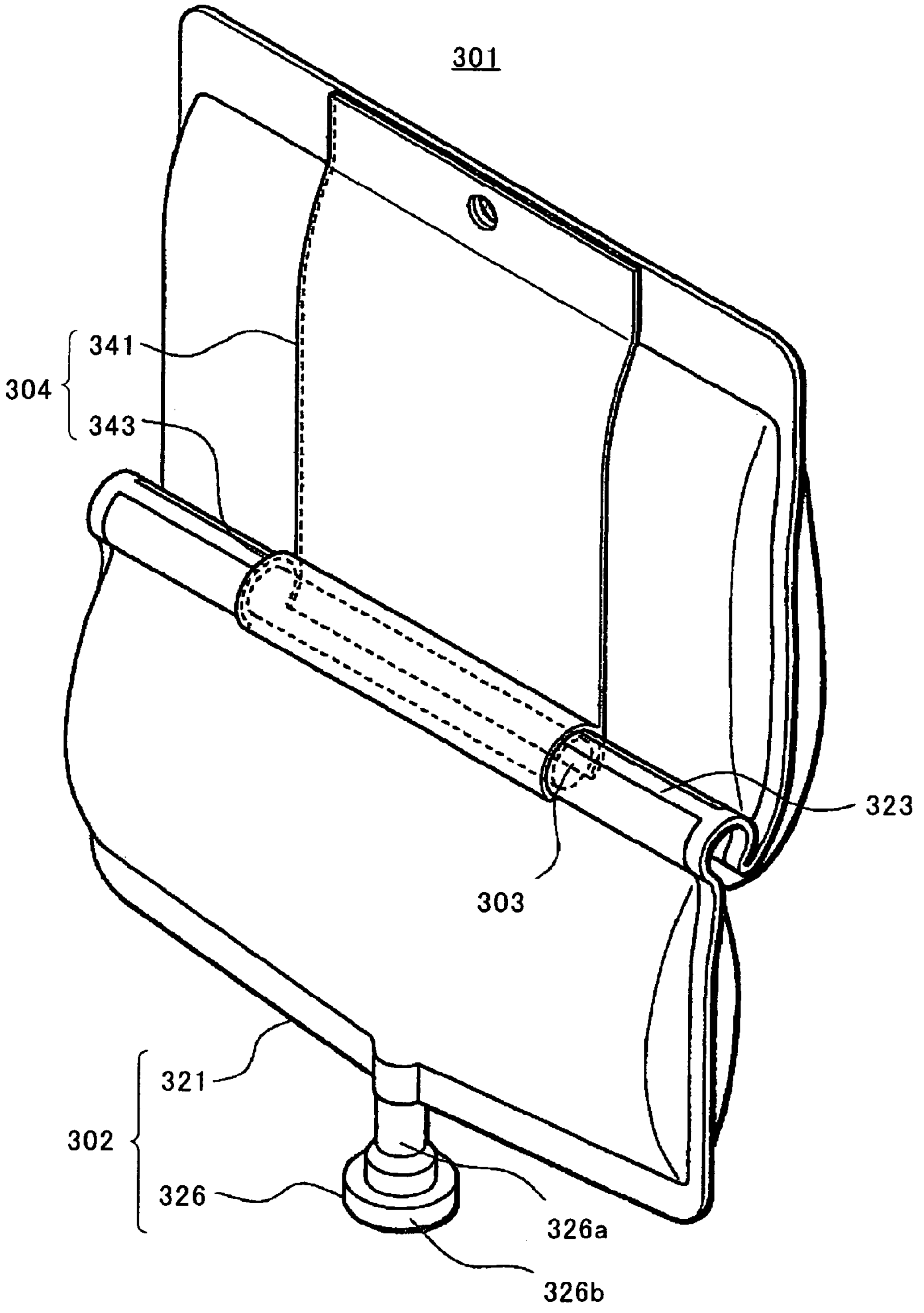
FIG. 63 is a perspective view showing the multi-chamber container of FIG. 62.
Figure 64:
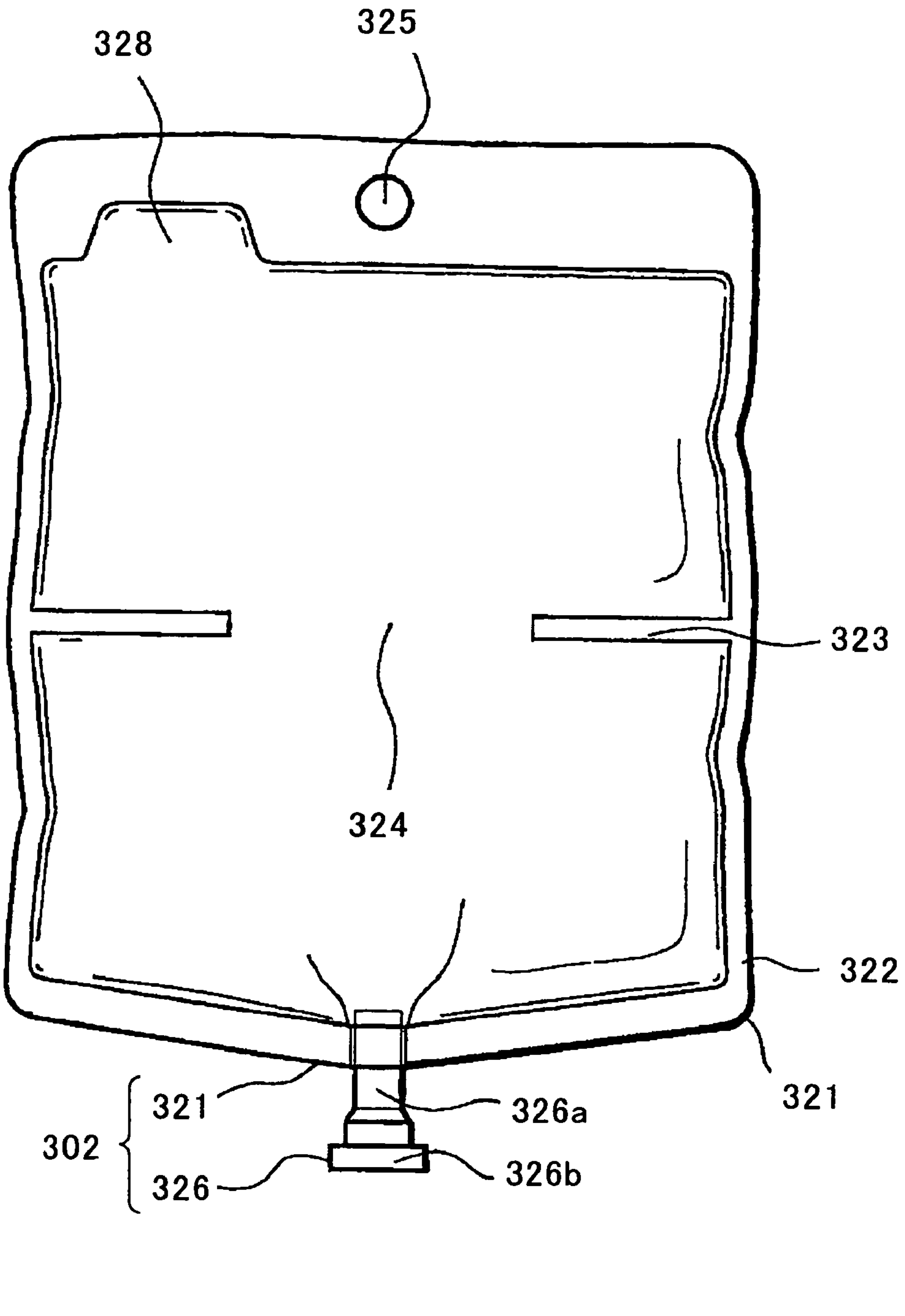
FIG. 64 is a front view showing a container body of the multi-chamber container of FIG. 62.

FIGS. 62 and 63 are views showing a multi-chamber container according to Embodiment 13 of the invention. The multi-chamber container 301 has a container body 302. As shown in FIG. 64, the container body 302 has a bag member 321. The bag member 321 has a seal portion 322 formed on its periphery. The seal portion 322 is formed by heating and fusing inner surfaces on the peripheries of two rectangular film sheets with an ejection tube 326*a* of a plug 326 described later pinched therebetween, and configured in strength such that the seal portion cannot peel off even by pressing the bag member 321 by hand or the like. The container body 302 is provided with seal portions 323 spaced a predetermined distance from the center to the right and left, and an opening 324 formed between the seal portions 323. The seal portions 323 are formed by heating and fusing inner surfaces of the bag member 321 spaced the predetermined distance from the center to the right and left, and configured in strength such that the seal portions cannot peel off even by pressing the bag member 321 by hand or the like. The opening width of the opening 324 is configured to be narrower than the width of the clip 304 and rod-shaped member 303 described later. The bag member 321 has a hanging hole 325 formed at its upper end. The container body 302 has the plug 326 attached to the opening of the bag member 321. The plug 326 is in the shape of a tube, and comprised of an ejection tube 326*a* and an ejection outlet 326*b* sealed with a rubber stopper until a hollow needle is inserted therein.

Figure 65:
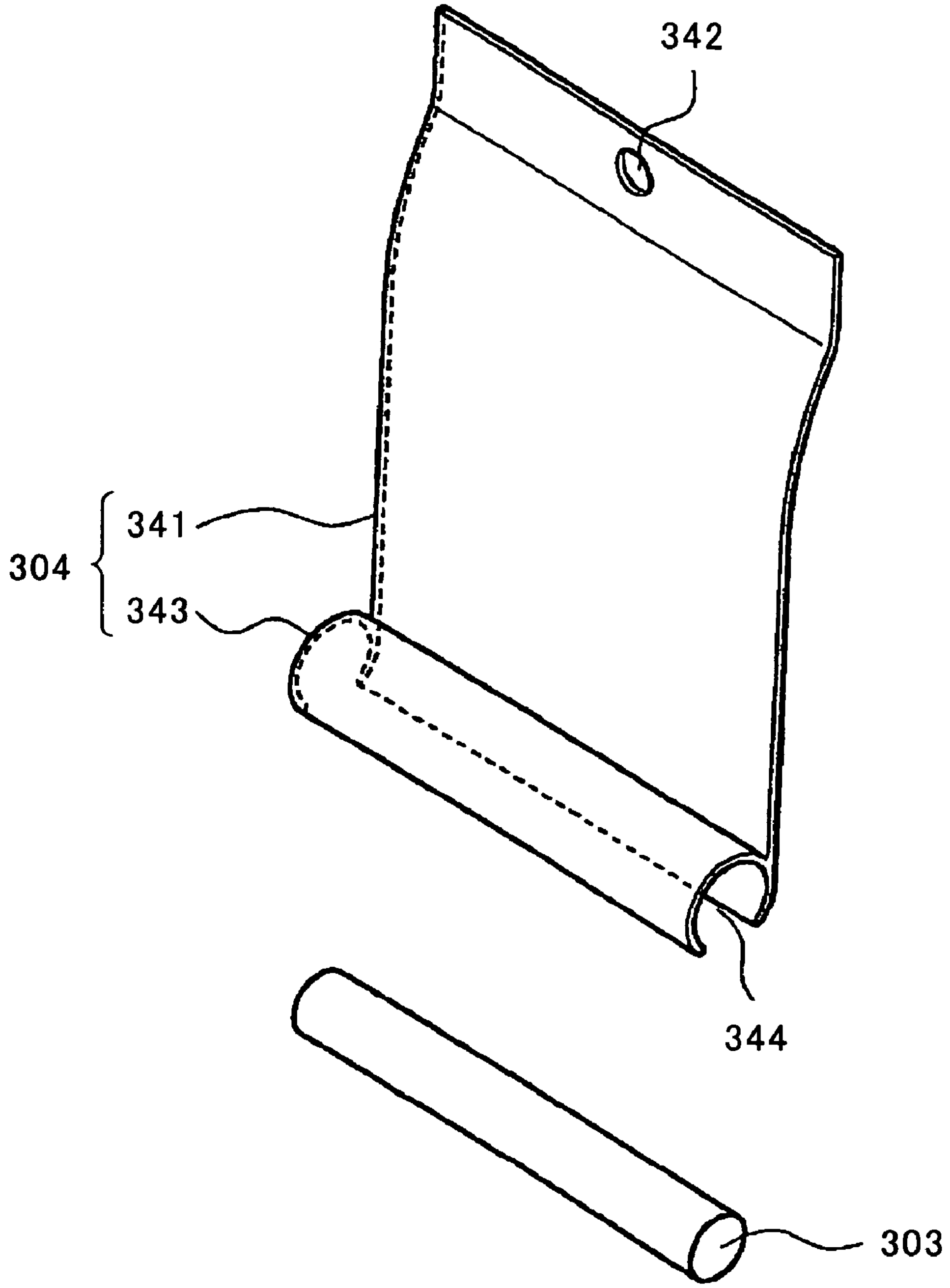
FIG. 65 is a perspective view showing a clip of FIG. 62.

The multi-chamber container 301 has the clip 304. The clip member 304 is comprised of a hang plate 341 and a pinch portion 343 as shown in FIG. 65. The hang plate 341 is configured in rectangle-shape, and has a hang hole 342 formed in the center at the upper end. The clip 304 is secured to the one wall portion 321*a* side of the bag member 321 by heating and fusing the upper end of the hang plate 341 and the other end of the bag member 321 with a hole 342 of the hang plate 341 and a hole 325 of the bag member 321 mutually matched. The lower end of the hang plate 341 is coupled integrally to the pinch portion 343. The pinch portion 343 is formed in the shape of a substantially inverse V in lateral cross section, and pinch space 344 is formed inside the pinch portion 343. The pinch portion 343 is coupled integrally to the lower end of the hang plate 341 with the front end faced toward the plug 326 side, and is positioned above the seal portions 323 and opening 324 of the bag member 321. The pinch portion 343 pinches the bag member 321 folded with the other wall portion 321*b* faced inside in the seal portions 323 and opening 324 from one wall portion 321*a*, clogs the inside of the bag member 321, and partitions the inside of the bag member 321 to a first and second filling chambers 327*a* and 327*b*. The pinch portion 343 has the pinch force configured to be able to be released by the weight of the container body 302 with unmixed agents filled inside the bag member 321. The clip 304 is formed of rigid material having elastic force such as plastic, and may be formed of metal such as iron having the elastic force. In consideration of safety, the clip 304 is preferably formed of elastic plastic material.

In the multi-chamber container 301 with the above-mentioned configuration, in dividing the inside of the bag member 321 to the first and second filling chambers 327*a* and 327*b*, the bag member 321 is folded with the other wall portion 321*b* faced inside in the seal portions 323 and opening 324, inserted into the pinch space 344 of the pinch portion 343 from the bending portion of the bag member 321, and pinched by the pinch portion 343 of the clip 304.

After dividing the inside of the bag member 321 into the first and second filling chambers 327*a*, 327*b* by the pinch portion 343 of the clip 304, unmixed agents are respectively filled from the ejection outlet 326*b* of the plug 326 and from a filling inlet 328 formed at the other end portion of the bag member 321. Then, the ejection outlet 326*b* is sealed by a rubber stopper material, and the filling inlet 328 is fused and sealed to seal each unmixed agent.

Figures 66A, 66B, 66C:
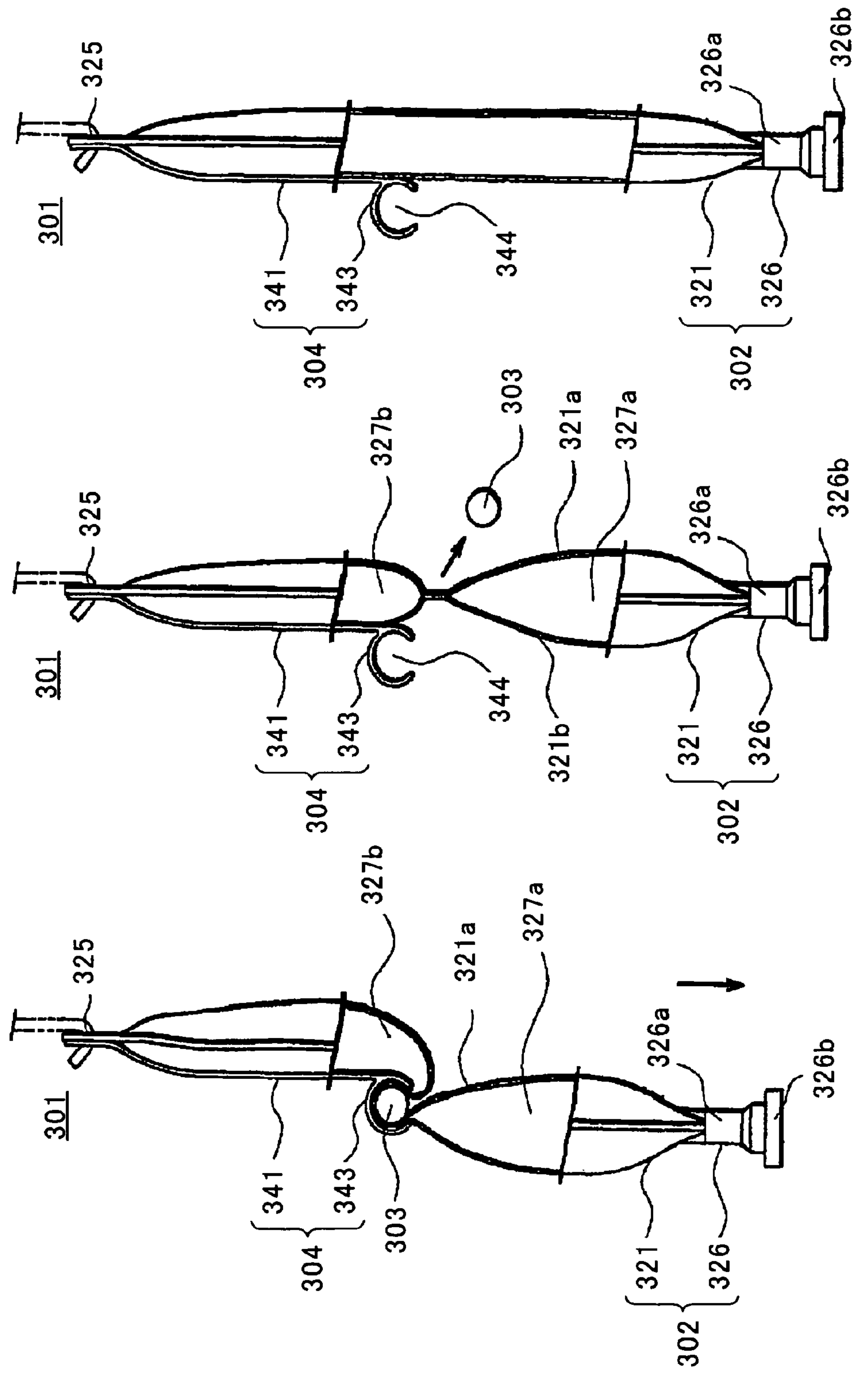
FIG. 66 is a view to explain a state where the clip is detached from the container body with the clip attached thereto of FIG. 62.

Then, as shown in FIG. 66(*a*), when the multi-chamber container 301 according to Embodiment 13 of the invention is hung with the hang hole 325 passed through a hook, since the pinch force of the pinch portion 343 is configured to be able to be released by the weight of the container body 302 with the unmixed agents filled inside the bag member 321, the clogged portion of the bag member 321 pinched by the clip 304 moves downward to be out of the clip 304 as shown in FIG. 66(*b*). By this means, the partition inside the bag member 321 by the clip 304 is released, and as shown in FIG. 66(*c*), the unmixed agents filled inside the bag member 321 are spontaneously mixed.

Also in this Embodiment, without performing the specific opening operation, only by hanging the multi-chamber container, due to the weight of the container body, the filling chambers are opened in therebetween, and therefore, the agents inside the respective filling chambers are mixed with reliability when the user uses the container.

Embodiment 14

Figure 67:
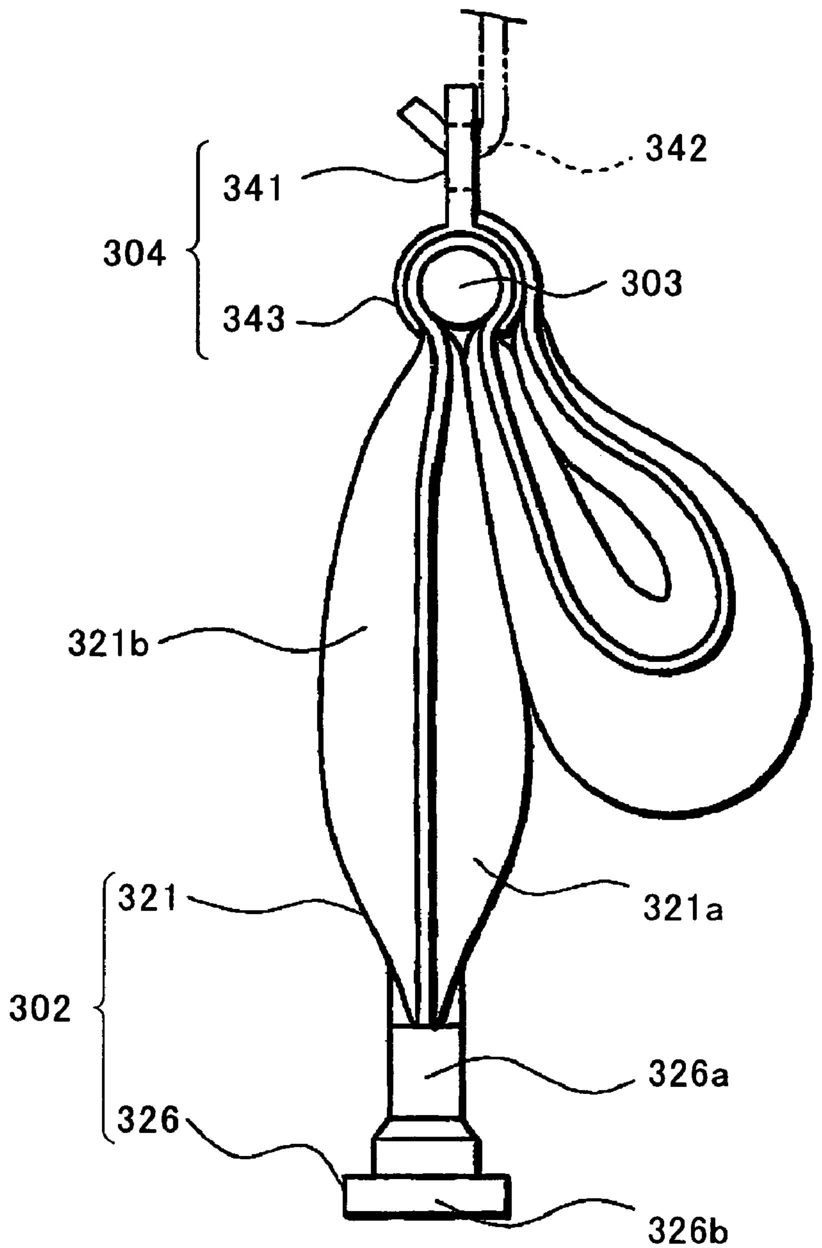
FIG. 67 is a side view showing a multi-chamber container according to Embodiment 14 of the invention.
Figure 69:
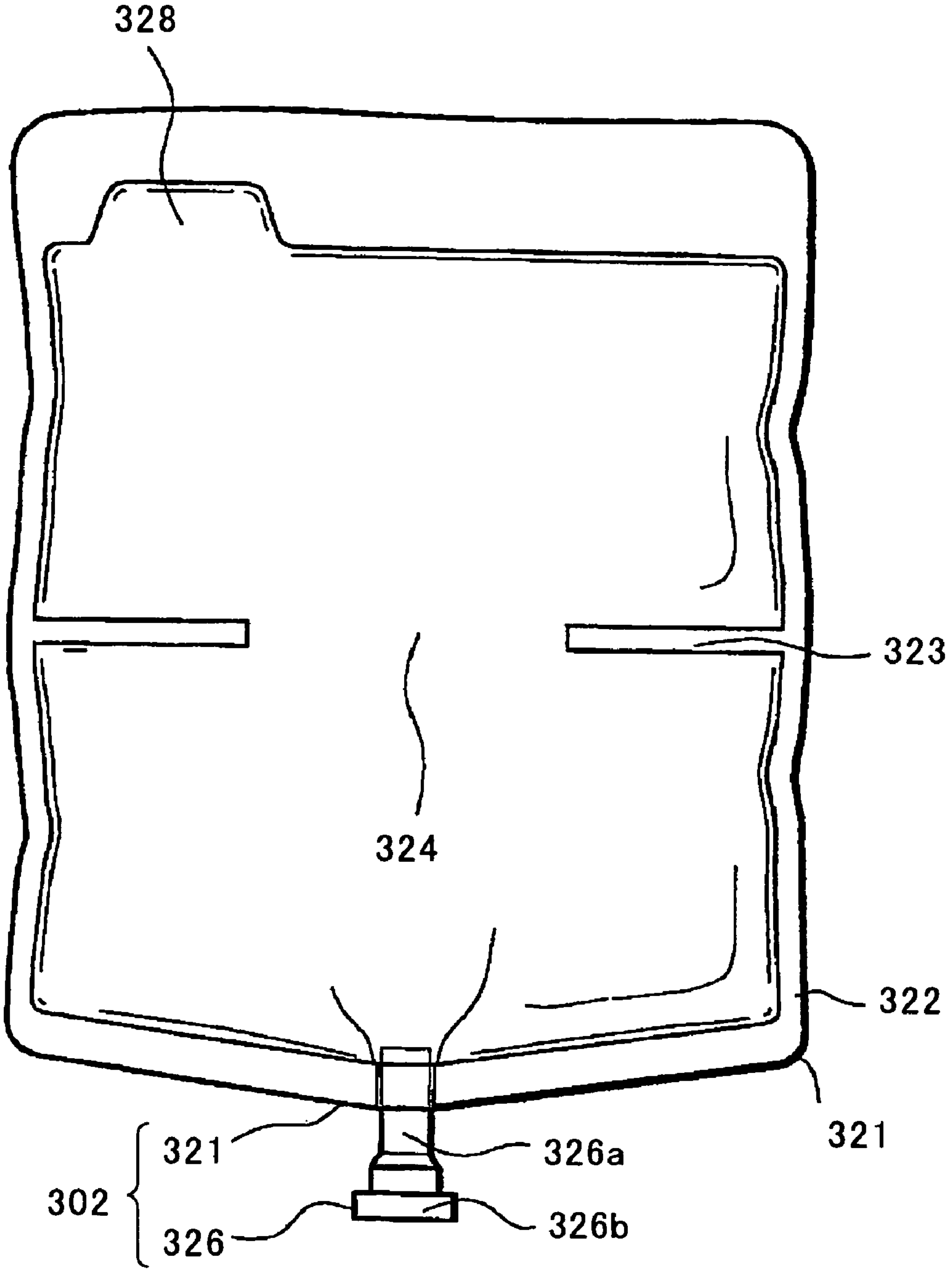
FIG. 69 is a front view showing a container body of the multi-chamber container of FIG. 67.

FIGS. 67 and 69 are views showing a multi-chamber container 301 according to Embodiment 14 of the invention. The multi-chamber container 301 has a container body 302. The container body 302 is the same as the container body 302 of Embodiment 13 except that the bag member 321 does not have a hang hole, and therefore, the same reference numerals are assigned to corresponding portions to omit descriptions thereof.

Figure 70:
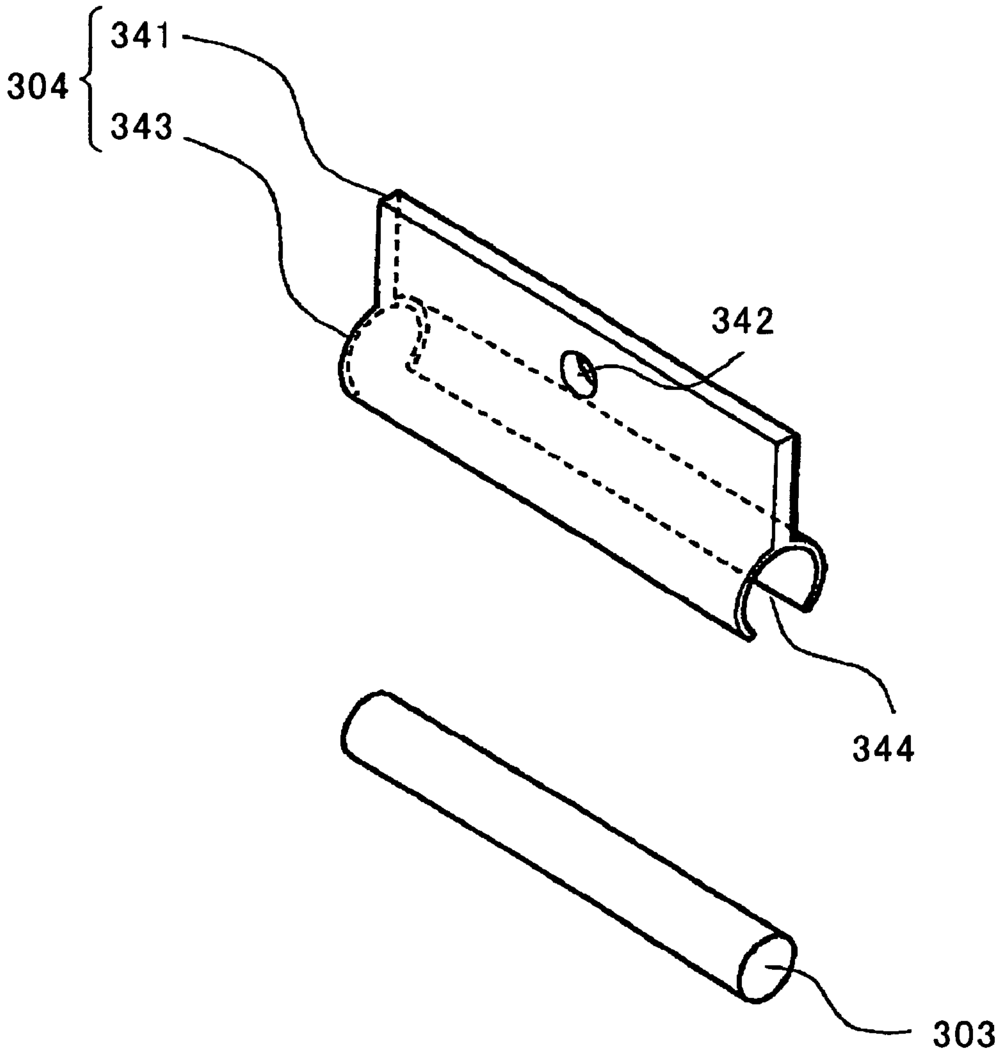
FIG. 70 is a perspective view showing a clip and a rod-shaped member of FIG. 67.

The multi-chamber container 301 has a clip 304 and rod-shaped member 303. As shown in FIG. 70, the clip 304 is comprised of a hang plate 341 and a pinch portion 343. The clip member 304 is secured on the one wall portion 321*a* side of the bag member 321 by heating and fusing the outside of the pinch portion 343 and the other end of the bag member 321, or the like. As shown in FIG. 70, the clip 304 is comprised of the hang plate 341 and pinch portion 343. The hang plate 341 is configured in rectangle-shape, and has a hang hole 342 formed in the upper center. The lower end of the hang plate 341 is coupled integrally to the pinch portion 343. The pinch portion 343 is formed in the shape of a substantially C in lateral cross section, and pinch space 344 is formed inside the pinch portion 343. The pinch portion 343 is coupled integrally to the lower end of the hang plate 341 with the front end faced toward the plug 326 side, and is positioned above seal portions 323 and opening 324 of the bag member 321 with which the rod-shaped member 303 described later comes into contact. The pinch portion 343 pinches the rod-shaped member 303 in contact with the other side wall portion 321*b* of the bag member 321 from one wall portion 321*a*, clogs the inside of the bag member 321, and partitions the inside of the bag member 321 to the first and second filling chambers 327*a* and 327*b*. The pinch portion 343 has the pinch force that is configured to be able to be released by the weight of the container body 302 with unmixed agents filled inside the bag member 321. The clip 304 is formed of rigid material having elastic force such as plastic, and may be formed of metal such as iron having the elastic force. In consideration of safety, the clip 304 is preferably formed of elastic plastic material.

Figure 68:
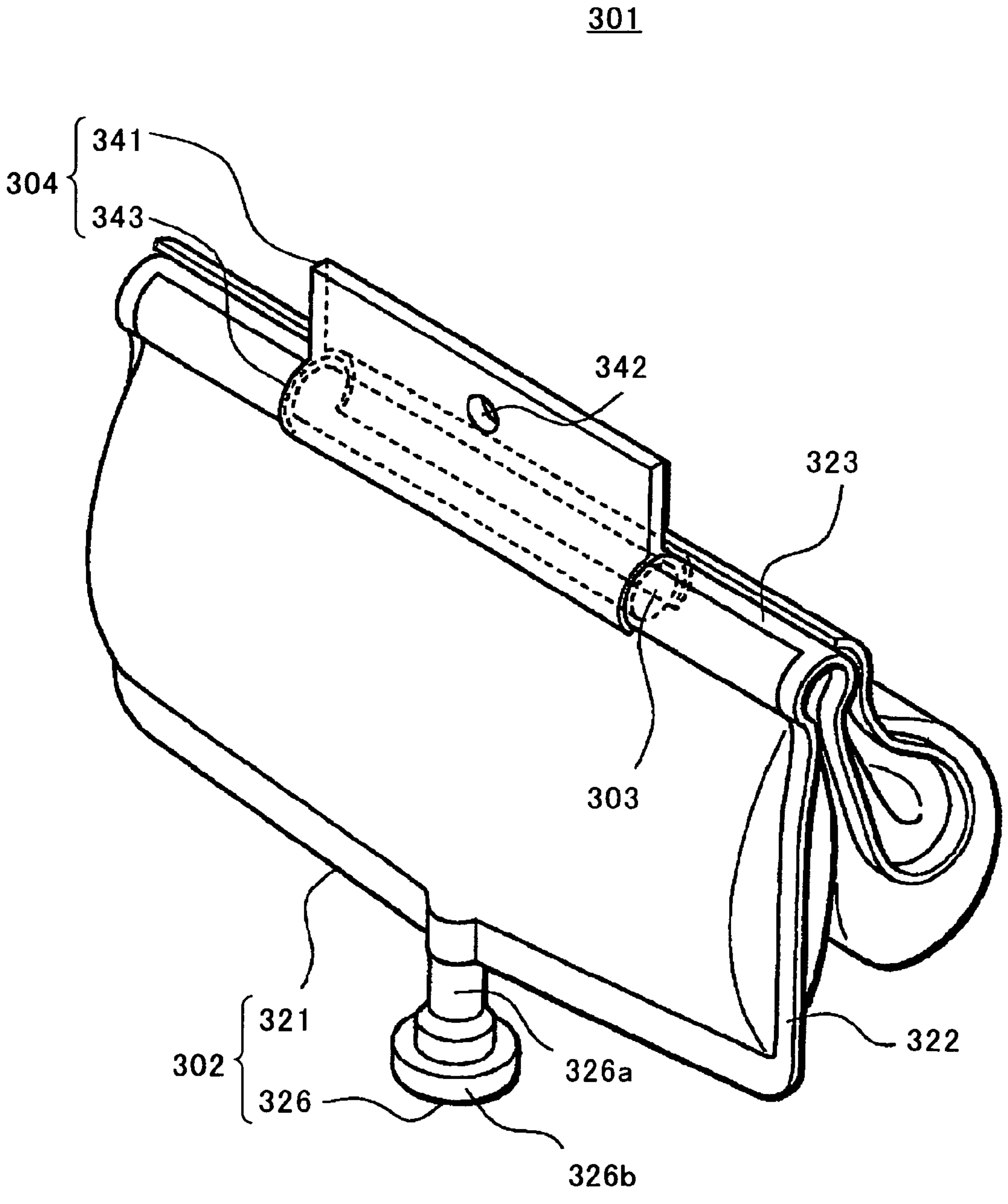
FIG. 68 is a perspective view showing the multi-chamber container of FIG. 67.

The rod-shaped member 303 is formed of synthesized resin of circular lateral cross section. As shown in FIGS. 67 and 68, the rod-shaped member 303 is pinched by the pinch portion 343 of the clip 304 while being brought into contact with the other wall portion 321*b* of the bag member 321 of the container body 302. The rod-shaped member 303 may be secured integrally to the other wall portion 321*b* of the bag member 321 of the container body 302 by adhesive or the like.

In the multi-chamber container 301 with the above-mentioned configuration, in dividing the inside of the bag member 321 of the container body 302, with the rod-shaped member 303 in contact with the other wall portion 321*b* of the bag member 321 along the seal portions 323 and opening 324, the bag member 321 is inserted into the pinch space 344 of the pinch portion 343 and pinched by the clip 304. Subsequently, in the same method as in Embodiment 13, each unmixed agent is filled into the bag member 321.

Figures 71A, 71B, 71C:
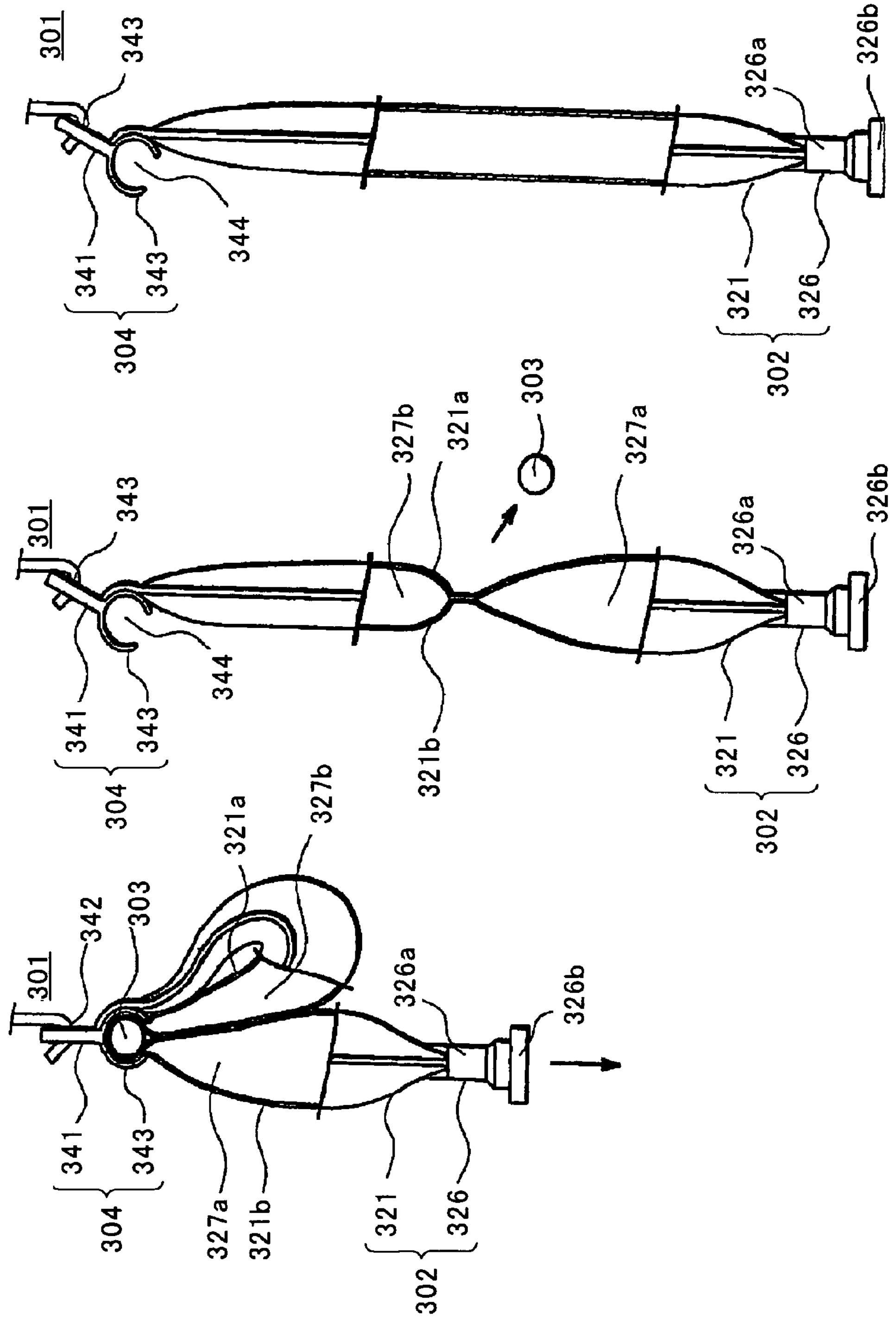
FIG. 71 is a view to explain a state where the clip is detached from the container body with the clip attached thereto of FIG. 67.

Then, as shown in FIG. 71(*a*), when the multi-chamber container 301 according to Embodiment 14 of the invention is hung with a hang hole 342 passed through a hook, since the pinch force of the pinch portion 343 is configured to be able to be released by the weight of the container body 302 with unmixed agents filled inside the bag member 321, the rod-shaped portion 303 expands the pinch portion 343 while moving downward, and is detached from the clip 304 as shown in FIG. 71(*b*). By this means, the partition inside the bag member 321 by the clip 304 and rod-shaped member 303 is released, and as shown in FIG. 71(*c*), the unmixed agents filled inside the bag member 321 are spontaneously mixed.

Also in this Embodiment, without performing the specific opening operation, only by hanging the multi-chamber container, due to the weight of the container body, the filling chambers are opened in therebetween, and therefore, the agents inside the respective filling chambers are mixed with reliability when the user uses the container.

Embodiment 15

Figures 72A, 72B, 72C:
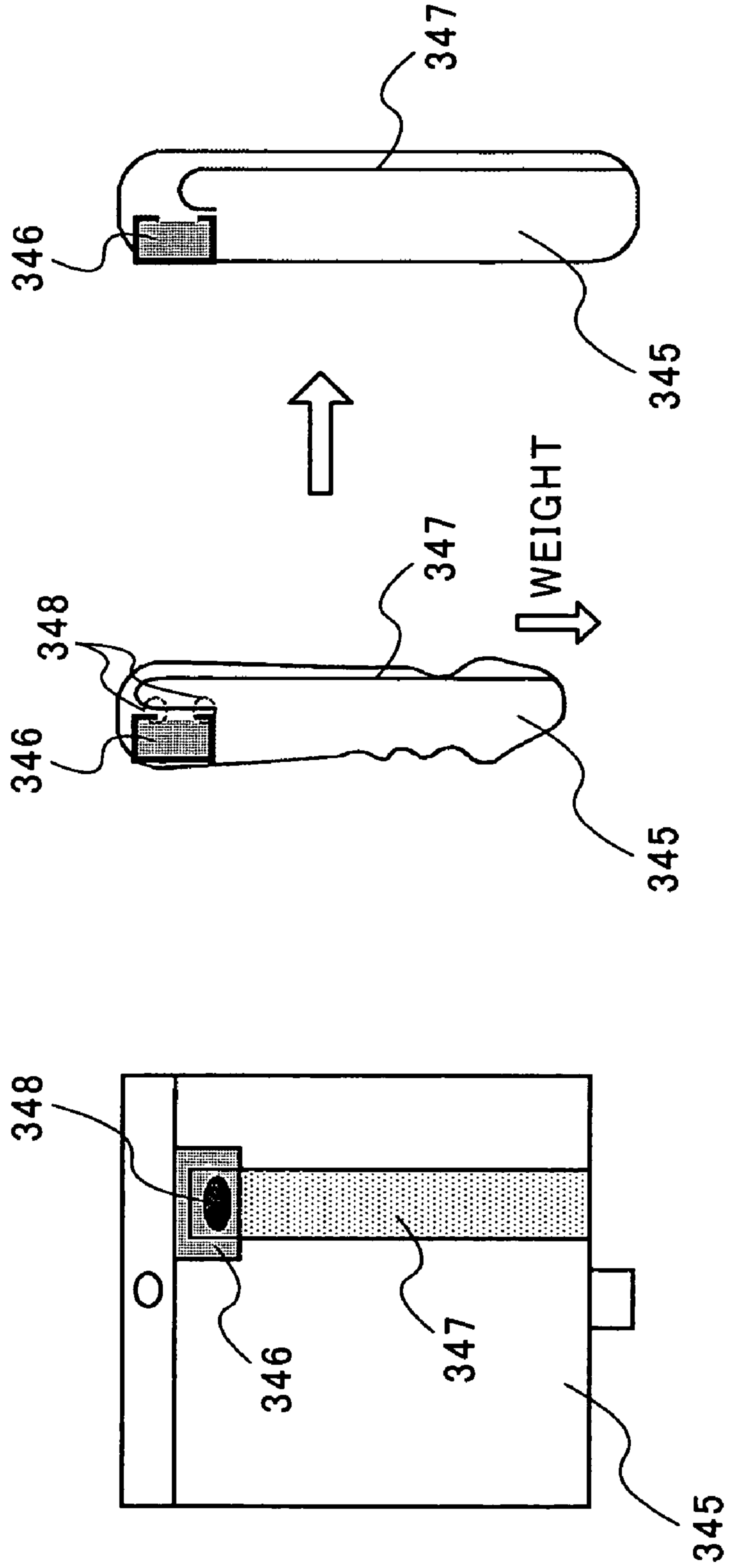
FIG. 72 is a view to explain an aspect of a multi-chamber container according to Embodiment 15 of the invention.

This Embodiment describes an aspect where a second container is packed inside a first container, a seal is adhered to an opening of the second container and peels off by the weight of the container, and an agent in the second container is mixed with another agent in the first container. FIG. 72 is a view to explain the aspect of this Embodiment. As shown in FIG. 72(*a*), an upper chamber 346 that is the second container is packed inside a lower chamber 345 that is the first container. As shown in FIG. 72(*b*), an opening of the upper chamber 346 is sealed by one end portion of a band 347. The band 347 is fixed at the other end to the bottom of the lower chamber 345. In such a multi-chamber container, the lower chamber 345 extends by its weight, as shown in FIG. 72(*c*), the band 347 is pulled by the lower chamber 345, the seal peels off, and the agent in the upper chamber 346 is mixed with the agent in the lower chamber 345.

Figure 73:
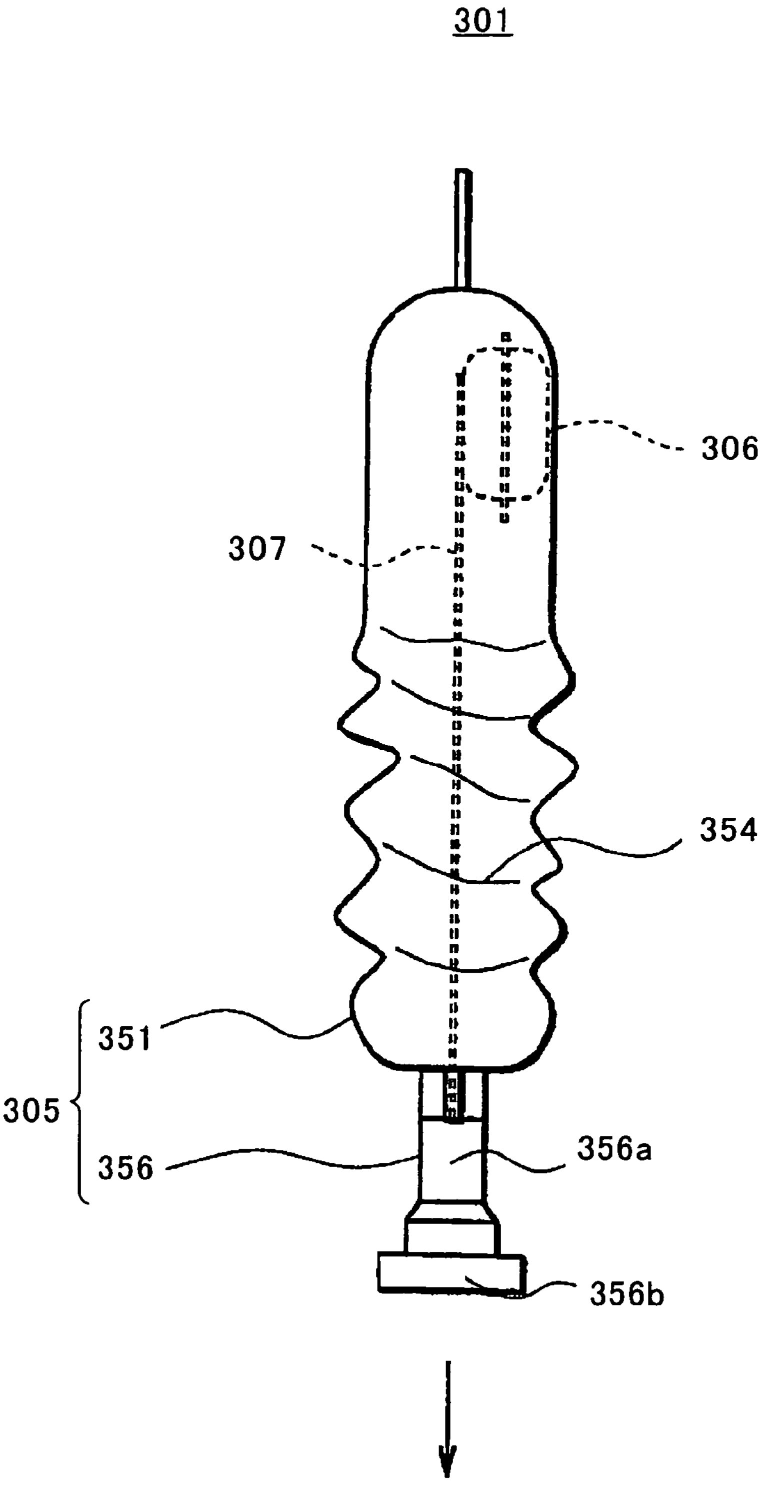
FIG. 73 is a side view showing the multi-chamber container according to Embodiment 15 of the invention.
Figure 74:
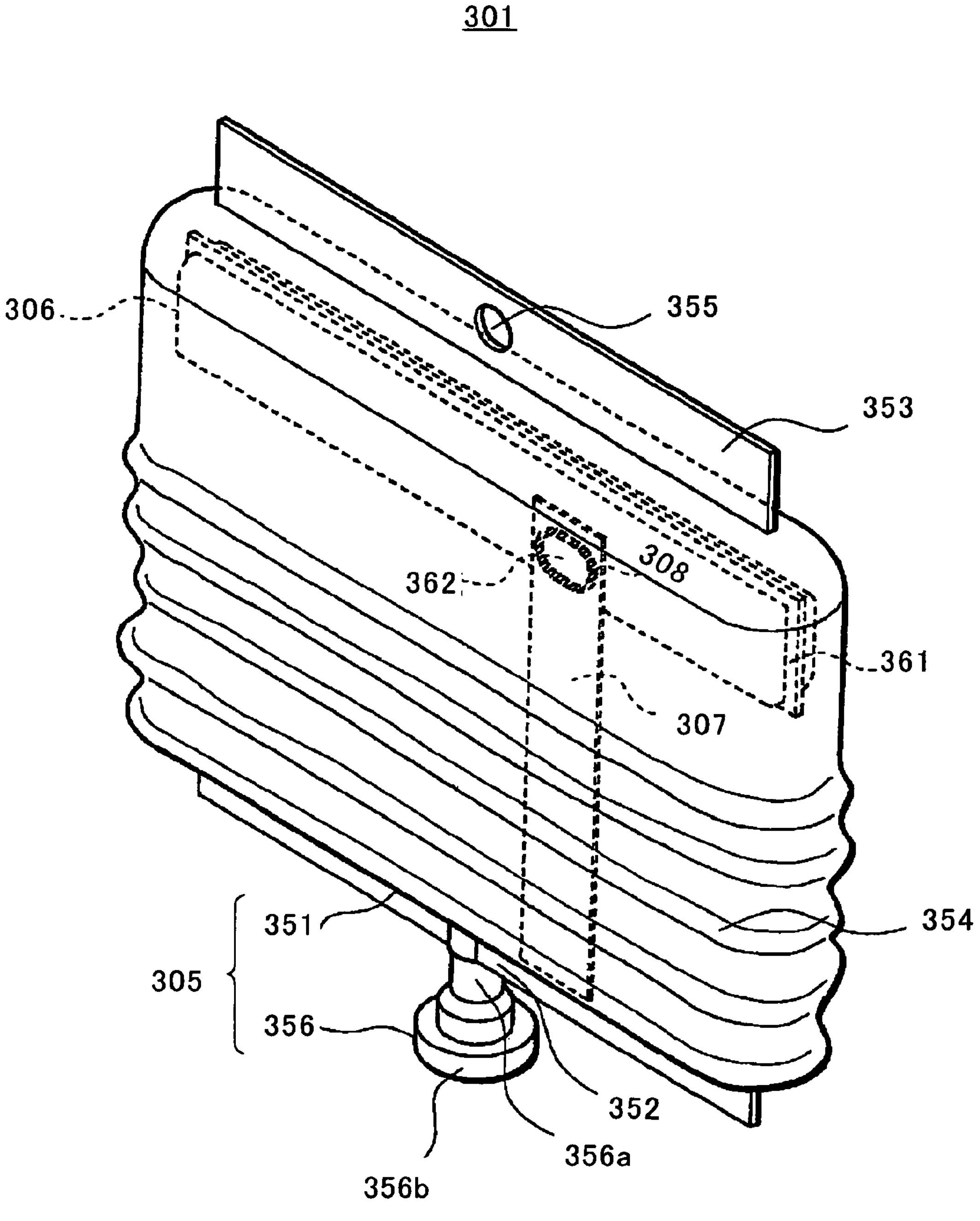
FIG. 74 is a perspective view showing the multi-chamber container of FIG. 72.

FIGS. 73 and 74 are views showing the multi-chamber container according to Embodiment 15 of the invention. The multi-chamber container 301 has a first container 305 and a second container 306 secured to the inside of the first container 305.

The first container 305 has a bag member 351. The bag member 351 has a plug-side seal portion 352 and hang-side seal portion 353 formed respectively at opposite lower and upper ends. The plug-side seal portion 352 and hang-side seal portion 353 are formed by heating and fusing the inner surface at lower and upper opposite ends of a tube-shaped film sheet with an ejection tube 356*a* of a plug 356 and one end of a clogging device 307 described later held between the inner surface, and configured in strength such that the seal portions do not peel off even by pressing the bag member 351 by hand or the like. The bag member 351 has a bellows portion 354 formed from near the center to the plug-side seal portion 352 to be extendable. The first container 305 has a hang hole 355 formed in the center of the hang-side seal portion 353. The first container 305 further has the plug 356 attached to the opening of the bag member 351. The plug 356 is in the shape of a tube, and comprised of an ejection tube 356*a* and an ejection outlet 356*b* sealed by a rubber stopper until a hollow needle is inserted.

The second container 306 is secured to the inner surface of the bag member 351 close to the hang-side seal portion 353 of the first container 305. The second container 306 has a seal portion 361. The seal portion 361 is formed by heating and fusing inner surfaces on the peripheries of two rectangular film sheets. The second container 306 has an opening 362 communicated with the inside of the first container 305.

The multi-chamber container 301 has a clogging device 307. The clogging device 307 is configured in band-shape with a flexible film sheet or the like, and formed in the shape of a substantially inverse J. The clogging device 307 is heated and fused with its one, end held between the inner surface of the film sheet constituting the plug-side seal portion 352, thereby secured at one end to the lower end of the first container 305, further secured at the other end to the periphery of the opening 362 of the second container 306 by the seal portion 308, and maintains the bellows portion 354 of the first container 305 shrunk. The seal portion 308 is formed by bonding the other end of the clogging device 307 and the periphery of the opening 362 of the second container 206 with mixed resin pieces, for example, or by heating and fusing them with mixed resin pieces held therebetween. The seal portion 308 is configured to be able to peel off by the weight of the first container 305 with an unmixed agent filled inside the bag member 321. The clogging member 307 clogs the opening 362 of the second container 306.

Figure 75A:
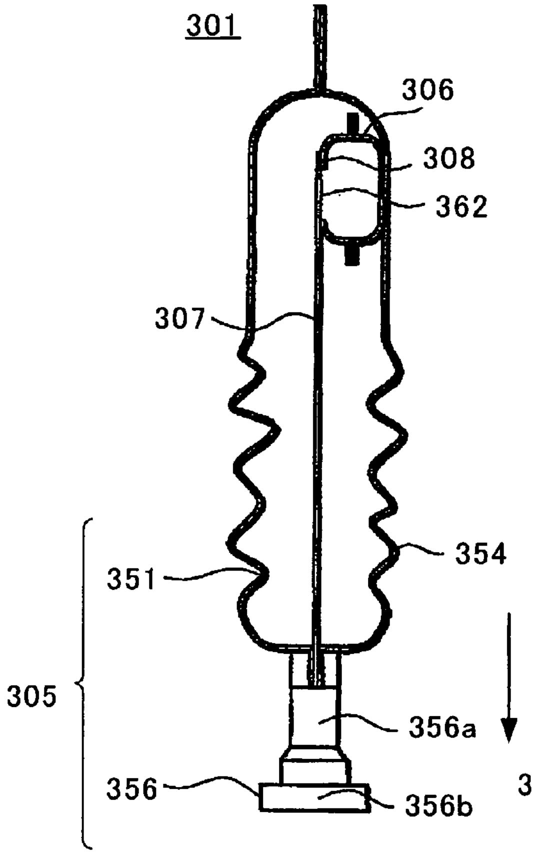
FIG. 75 is a view to explain a state where a clogging device is detached from a container body with the clogging device attached thereto of FIG. 72.
Figure 75B:
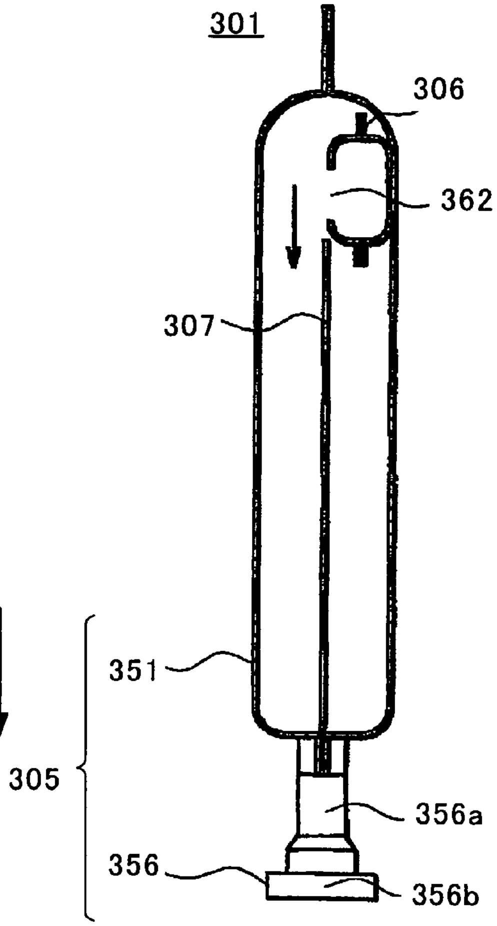

As shown in FIG. 75(*a*), when the multi-chamber container 301 according to Embodiment 15 of the invention is hung with the hang hole 355 passed through a hook, since the weight of the first container 305 is applied in the direction of the plug 356, as shown in FIG. 75(*b*), the clogging device 307 moves downward in synchronization with extension of the bellow portion 354, and the seal portion 308 spontaneously peels off. By this means, the first container 305 is communicated with the inside of the second container 306 via the opening 362, and unmixed agents filled in the respective chambers are spontaneously mixed.

Also in this Embodiment, without performing the specific opening operation, only by hanging the multi-chamber container, due to the weight of the container body, the filling chambers are opened in therebetween, and therefore, the agents inside the respective filling chambers are mixed with reliability when the user uses the container.

Embodiment 16

Figure 76:
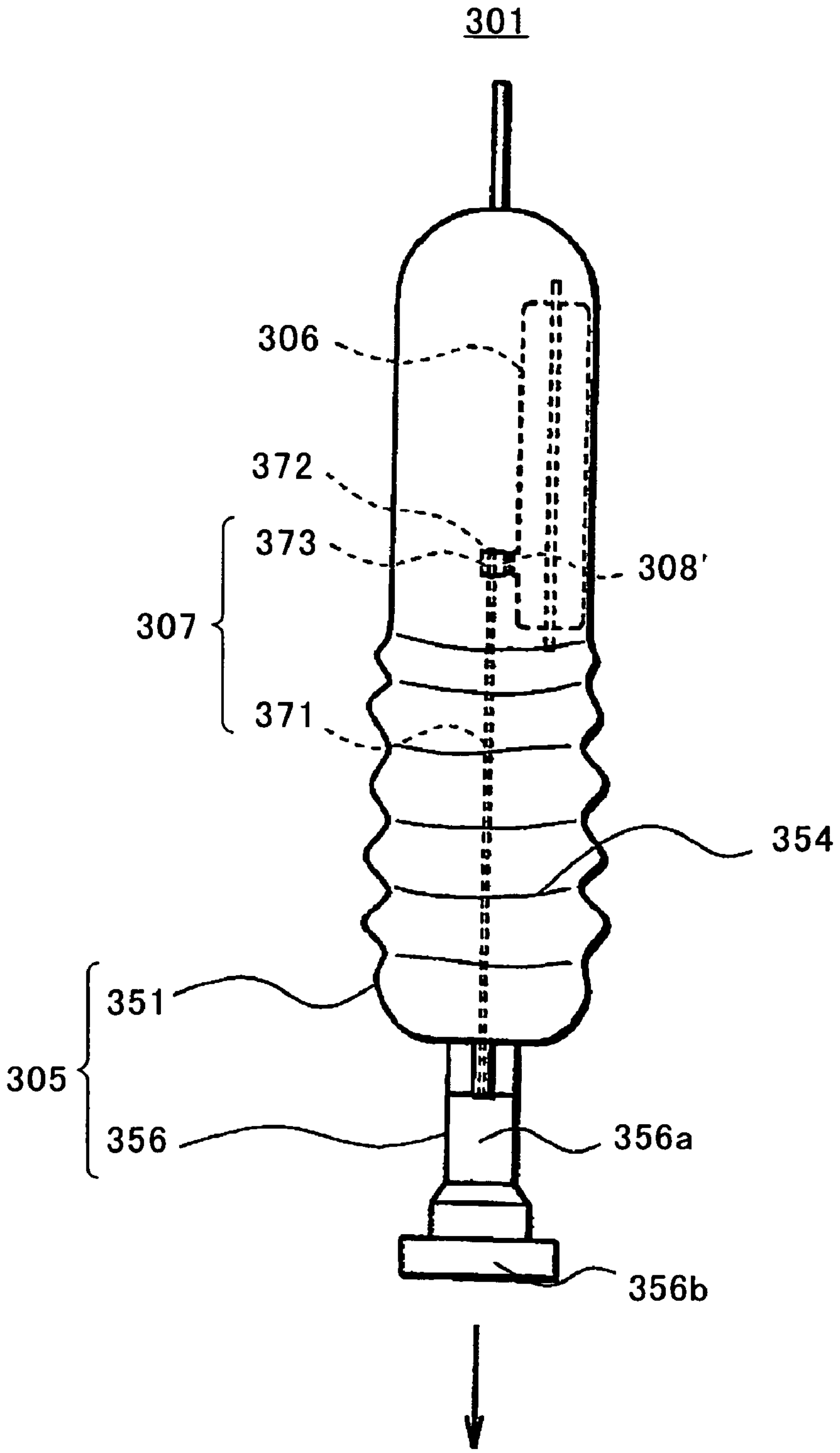
FIG. 76 is a side view showing the multi-chamber container according to Embodiment 15 of the invention.
Figure 77:
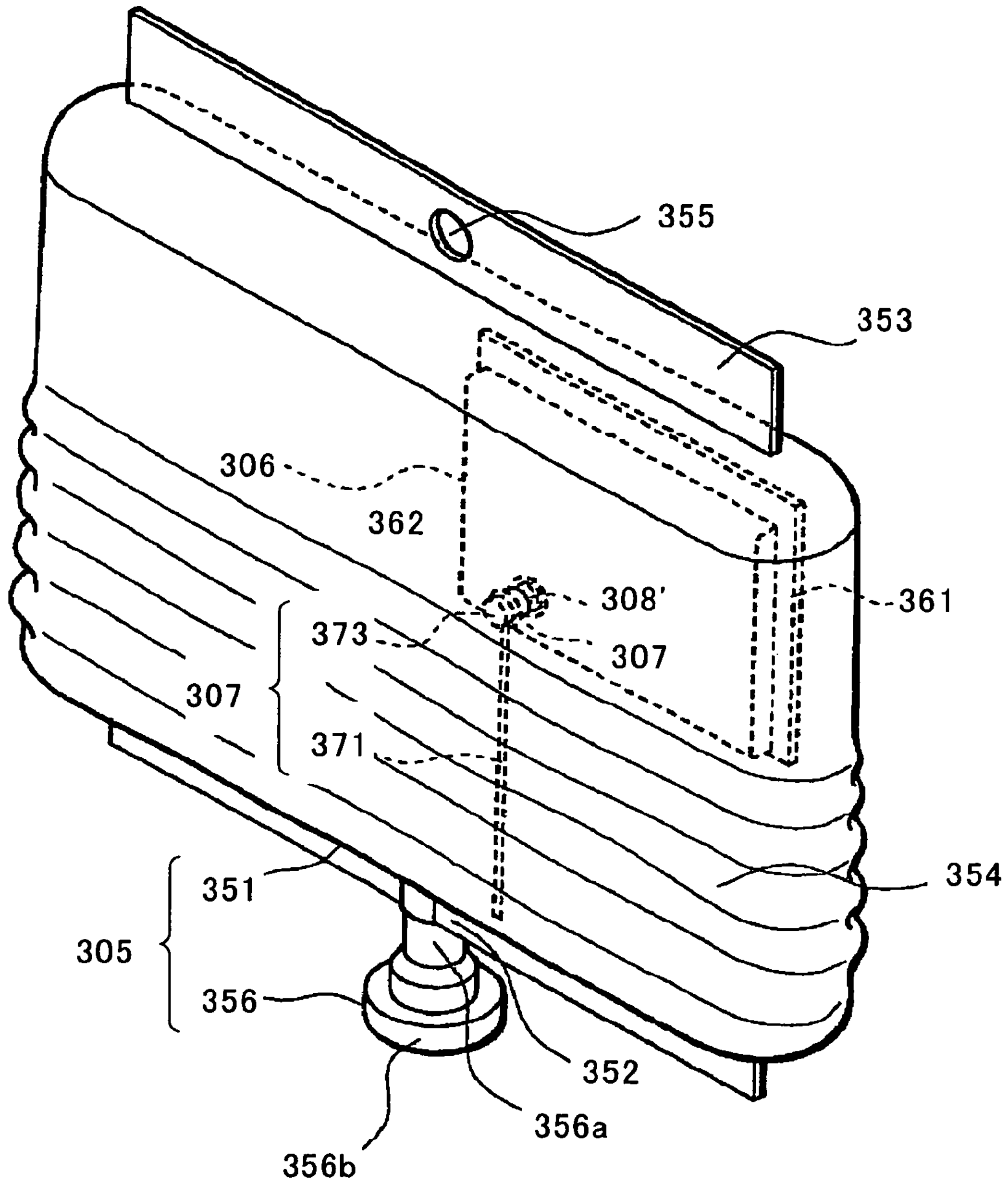
FIG. 77 is a perspective view showing the multi-chamber container of FIG. 76.

FIGS. 76 and 77 are views showing a multi-chamber container according to Embodiment 16 of the invention. The multi-chamber container 301 has a first container 305 and a second container 306 secured to the inside of the first container 305. In addition, the first container 305 is the same as the first container 305 according to Embodiment 15, and the same reference numerals are assigned to corresponding portions to omit descriptions thereof. Further, the second container 306 is the same as the second container 306 of Embodiment 15 except that the size of the container 306 and the size of the opening 362 are configured to be smaller than those in the second container 306 of Embodiment 15, and the same reference numerals are assigned to corresponding portions to omit descriptions thereof.

The multi-chamber container 301 has a clogging device 307. The clogging device 307 is comprised of a rod member 371 and a sealing portion 373. The rod member 371 is comprised of rigid material such as plastic, and secured to the lower end of the first container 305 with its one end held between the inner surface of the film sheet constituting the plug-side seal portion 352. The rod member 371 has an engagement portion 372 formed at the other end. The rod member 371 is coupled integrally to the sealing portion 373 with the engagement portion 372 engaged in the outer circumference surface of the sealing portion 373 described later. The sealing portion 373 is formed of rigid material such as plastic, and formed in the shape of a cylinder with the bottom. The sealing portion 373 has a flange portion 373*a* formed at the end portion on the outer circumference surface on the side opposite to the bottom. The sealing portion 373 is attached by heating and fusing the flange portion 373*a* and the inner surface around the opening 362 of the second container 306, and thus clogs the opening 362. The sealing portion 373 has a weak portion 308' formed on the outer circumference surface. The weak portion 308' is configured to be able to rupture by the weight of the first container 305 with an unmixed agent filled inside the bag member 351.

Figure 78A:
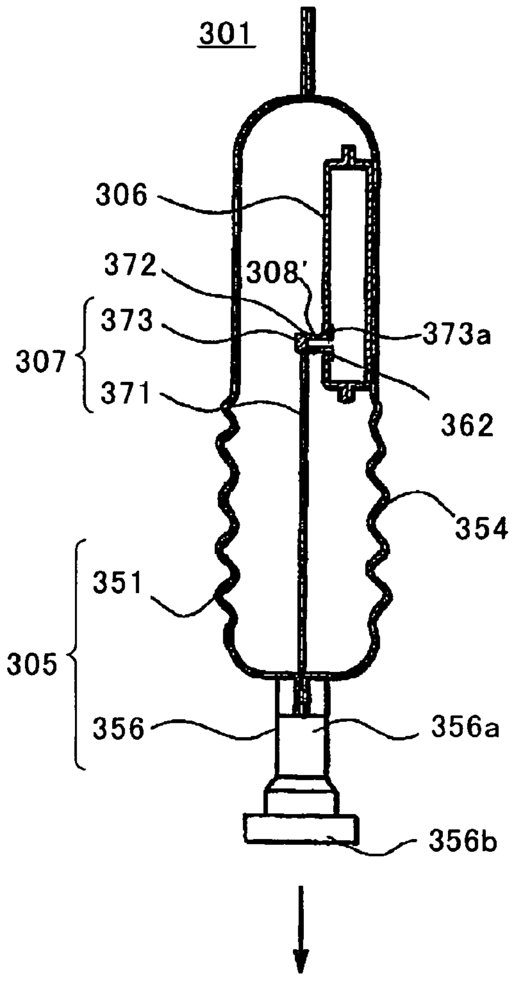
FIG. 78 is a view to explain a state where a clogging device is detached from a container body with the clogging device attached thereto of FIG. 76.
Figure 78B:
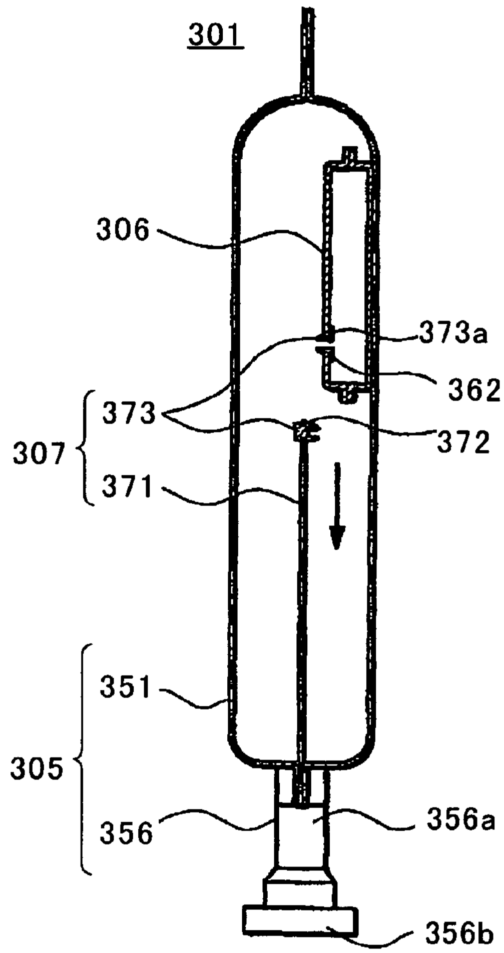

As shown in FIG. 78(*a*), when the multi-chamber container 301 according to Embodiment 16 of the invention is hung with the hang hole 355 passed through a hook, since the weight of the first container 305 is applied in the direction of the plug 356, as shown in FIG. 78(*b*), the clogging device 307 moves downward in synchronization with extension of the bellow portion 354, and the weak portion 308' ruptures. By this means, the clogging device 307 is detached, the first container 305 is communicated with the inside of the second container 306 via the opening 362, and unmixed agents filled in the respective chambers are spontaneously mixed.

Also in this Embodiment, without performing the specific opening operation, only by hanging the multi-chamber container, due to the weight of the container body, the filling chambers are opened in therebetween, and therefore, the agents inside the respective filling chambers are mixed with reliability when the user uses the container.

Embodiment 17

Figure 79:
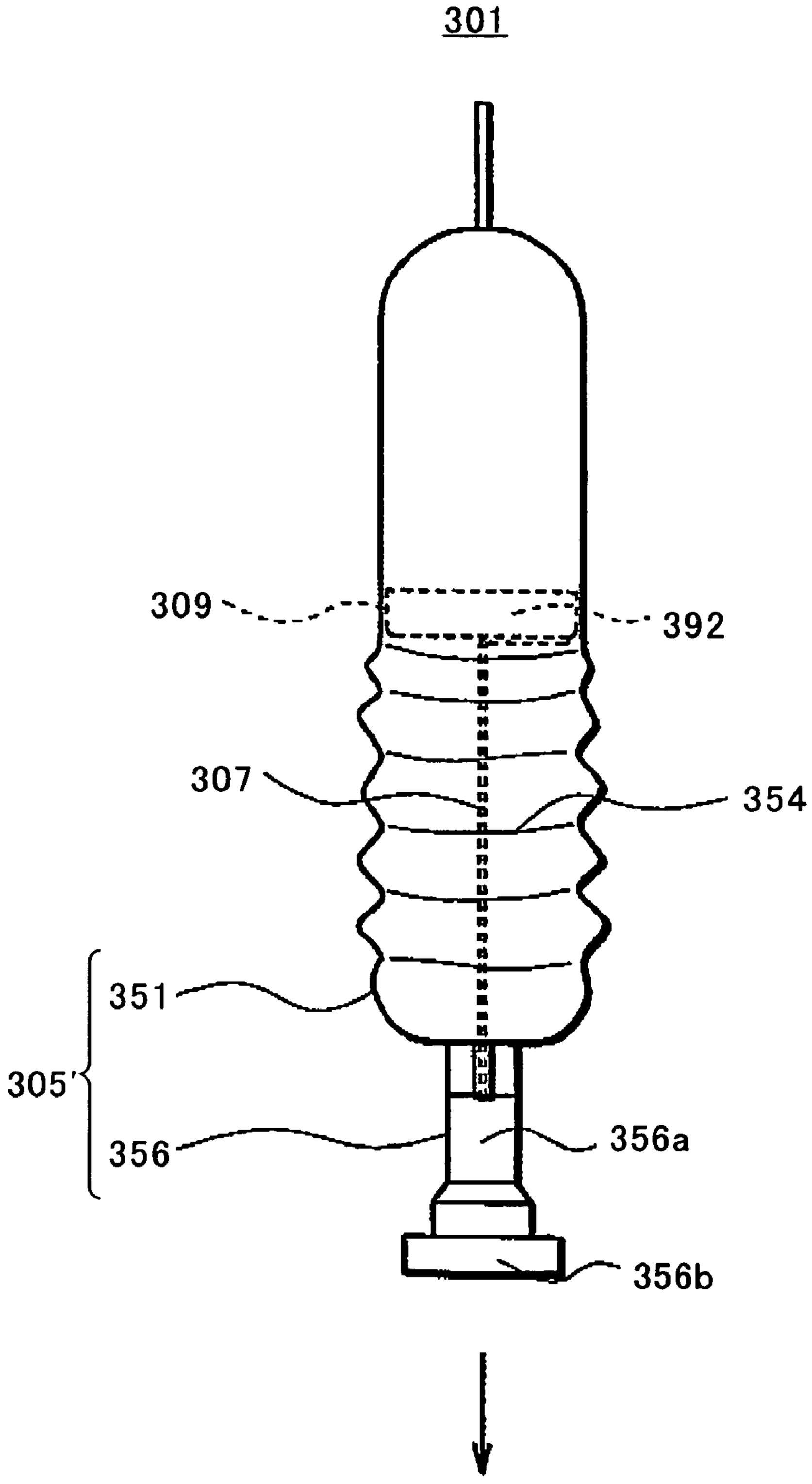
FIG. 79 is a side view showing a multi-chamber container according to Embodiment 17 of the invention.
Figure 80:
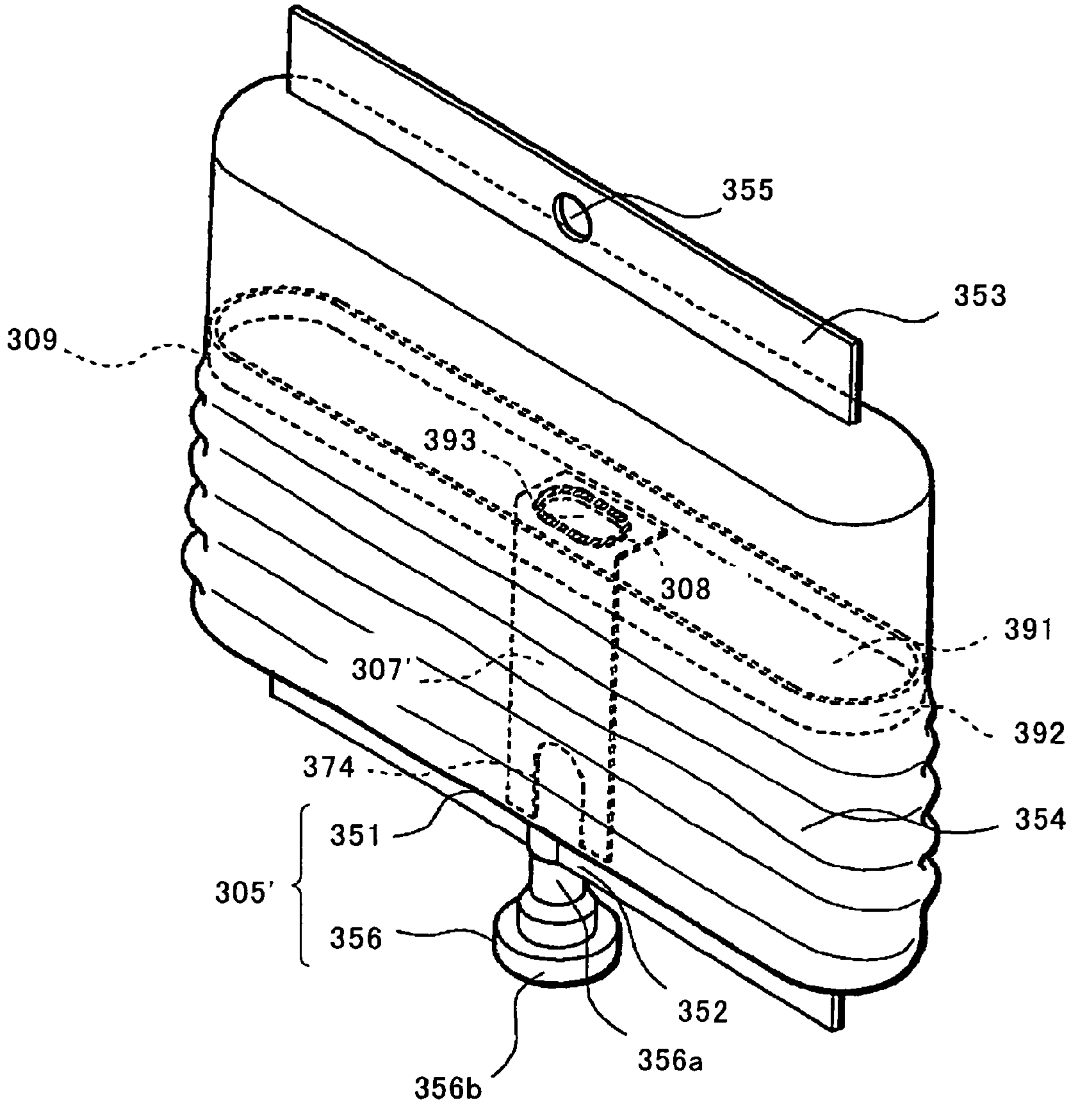
FIG. 80 is a perspective view showing the multi-chamber container of FIG. 79

FIGS. 79 and 80 are views showing a multi-chamber container 301 according to Embodiment 17 of the invention. The multi-chamber container 301 has a container body 305'. In addition, the container body 305' is substantially the same as the first container 305 according to Embodiment 15 except that the second container is not secured to its inside, and the same reference numerals are assigned to corresponding portions to omit descriptions thereof.

The multi-chamber container 301 has a partition portion 309. The partition portion 309 is configured of rigid material such as plastic, and comprised of a bottom plate 391 and outer wall 392. The partition portion 309 is secured to the inner surface of the bag member 351 by heating and fusing the outer wall 392 along the inner surface in the center of the bag member 351. The partition portion 309 has an opening 393 formed in the bottom plate 391.

The multi-chamber container 301 has a clogging device 307'. The clogging device 307' is configured in band-shape with a flexible film sheet or the like, and formed in the shape of a substantially inverse L. The clogging device 307' has a concave portion 374 formed on one end side. The clogging device 307' is secured at one end to the lower end of the bag member 351 by heating and fusing one end held between the inner surface of the film sheet constituting the plug-side seal portion 352 with the ejection tube 356*a* of the plug 356 positioned in the concave portion 374, further secured at the other end to the periphery of the opening 393 of the partition portion 309 by the seal portion 308, and maintains the bellows portion 354 of the bag member 351 shrunk. The clogging device 307' clogs the opening 393 of the partition portion 309. The seal portion 308 is formed by bonding the other end of the clogging device 307' and the periphery of the opening 393 of the partition portion 309 with mixed resin pieces, for example, or by heating and fusing them with mixed resin pieces held therebetween. The seal portion 308 is configured to be able to peel off by the weight of the bag member 351 filled with unmixed agents.

Figure 81A:
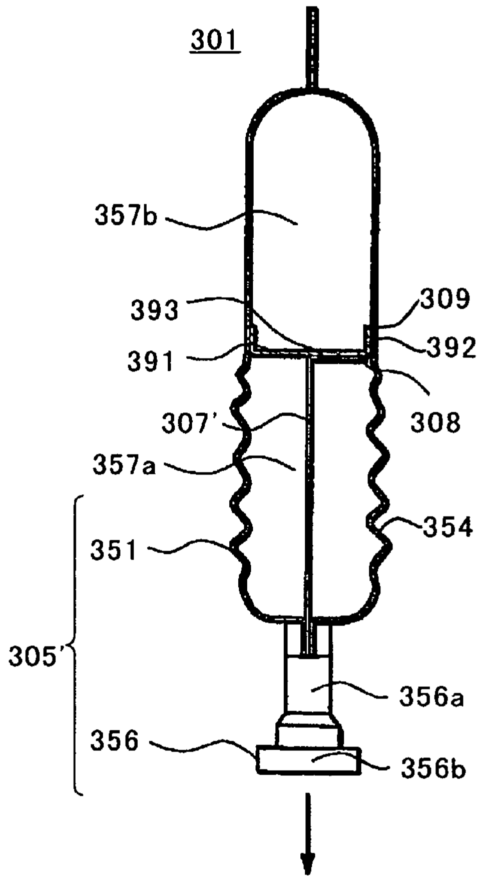
FIG. 81 is a view to explain a state where a partition portion is detached from a container body with the partition portion attached thereto of FIG. 79
Figure 81B:
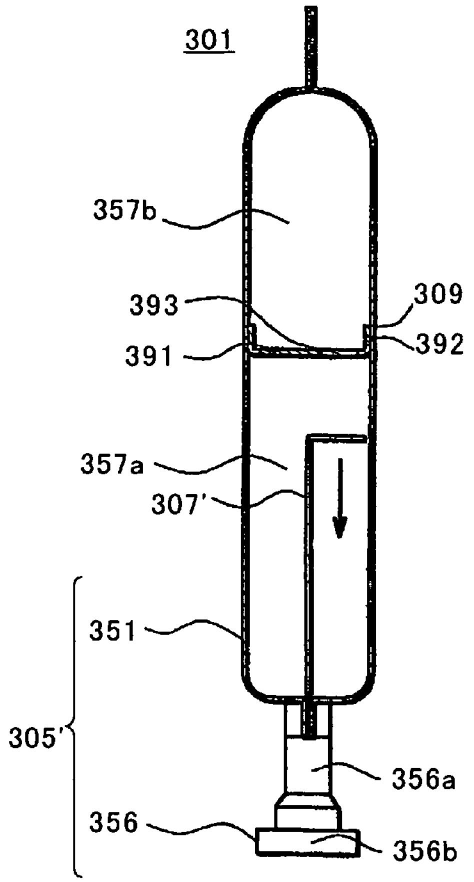

The multi-chamber container 301 has a first and second filling chambers 357*a* and 357*b* obtained by dividing the inside of the bag member 351 by the partition portion 309 and clogging device 307'. As shown in FIG. 81(*a*), when the multi-chamber container 301 according to Embodiment 17 of the invention is hung with the hang hole 355 passed through a hook, since the weight of the multi-chamber container 301 is applied in the direction of the plug 356, as shown in FIG. 81(*b*), the clogging device 307' moves downward in synchronization with extension of the bellow portion 354, and the seal portion 308 spontaneously peels off. By this means, the first and second filling chambers 357*a*, 357*b* inside the bag member 351 are communicated with each other via the opening 393 of the partition portion 309, and the unmixed agents filled inside the bag member 351 are spontaneously mixed.

Also in this Embodiment, without performing the specific opening operation, only by hanging the multi-chamber container, due to the weight of the container body, the filling chambers are opened in therebetween, and therefore, the agents inside the respective filling chambers are mixed with reliability when the user uses the container.

Embodiment 18

Figure 82:
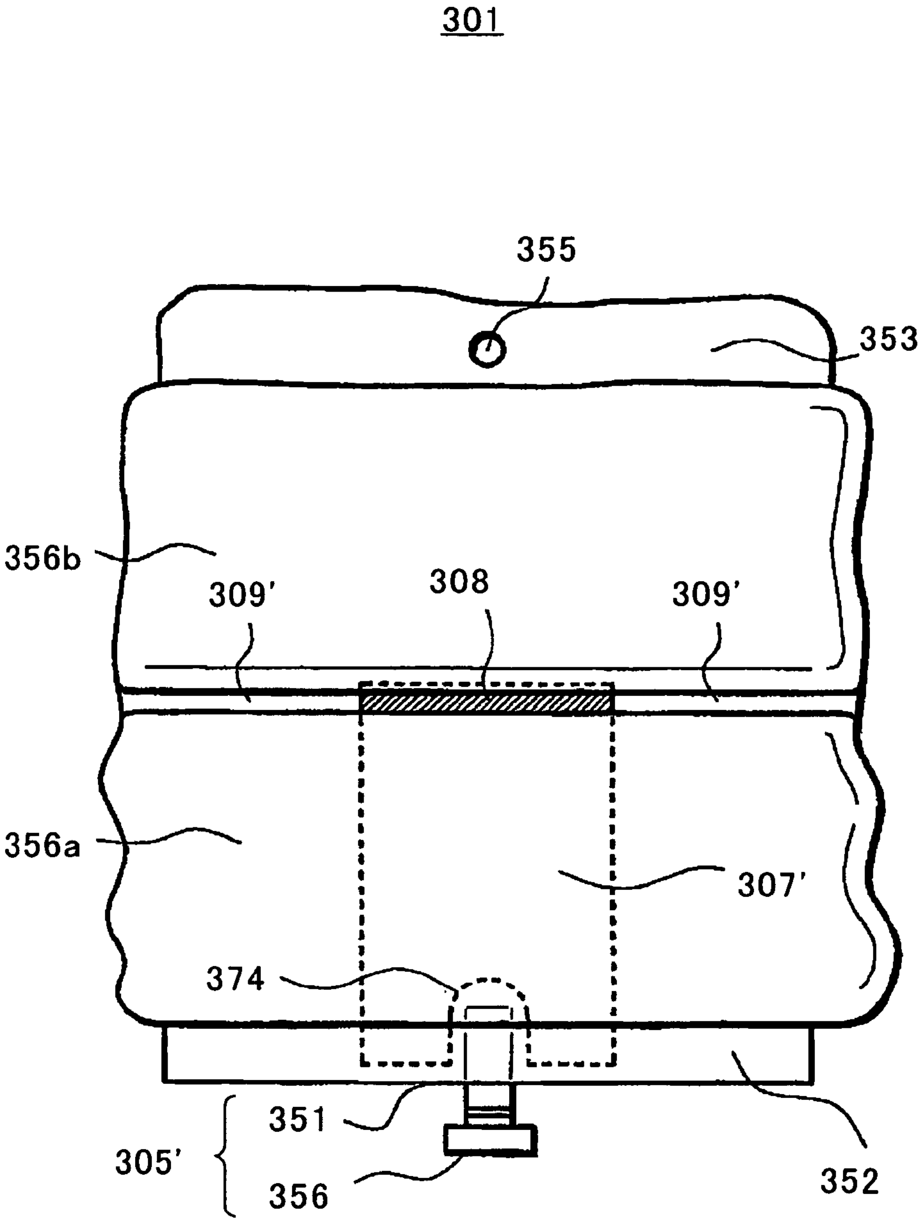
FIG. 82 is a front view showing a multi-chamber container according to Embodiment 18 of the invention

FIG. 82 is a view showing a multi-chamber container 301 according to Embodiment 18 of the invention. The multi-chamber container 301 has a container body 305'. The container body 305' has a bag member 335. The bag member 351 has seal portions 309' spaced a predetermined distance from the center to the right and left, and an opening 399 formed between the seal portions 309'. The seal portions 309' are formed by heating and fusing inner surfaces of the bag member 321 spaced the predetermined distance from the center to the right and left, and configured in strength such that the seal portion cannot peel off even by pressing by hand or the like. The container body 305' is substantially the same as the first container 305 according to Embodiment 15 except the above-mentioned respect and the second container 306 not being secured inside, and the same reference numerals are assigned to corresponding portions to omit descriptions thereof.

The multi-chamber container 301 has a clogging device 307'. The clogging device 307' is secured at one end to the lower end of the bag member 351 by heating and fusing one end held between the inner surface of the film sheet constituting the plug-side seal portion 352 with the ejection tube 356*a* of the plug 356 positioned in the concave portion 374, further secured at the other end to the opposite inner surface in the center of the bag member 351 by the seal portion 308, and maintains the bellows portion 354 of the bag member 351 shrunk. The clogging device 307' clogs the opening 393 of the bag member 351. The seal portion 308 is formed by bonding opposite inner surfaces of the opening 393 of the bag member 351 with the clogging device 307' inserted into the opening 393 of the bag member 351 with mixed resin pieces, for example, or by heating and fusing them with mixed resin pieces held therebetween. The seal portion 308 is configured to be able to peel off by the weight of the container body 305' with unmixed agents filled inside the bag member 351.

The multi-chamber container 301 has the first and second filling chambers 357*a* and 357*b* obtained by dividing the inside of the bag member 351 by the clogging device 307' and seal portion 309'.

Figure 83:
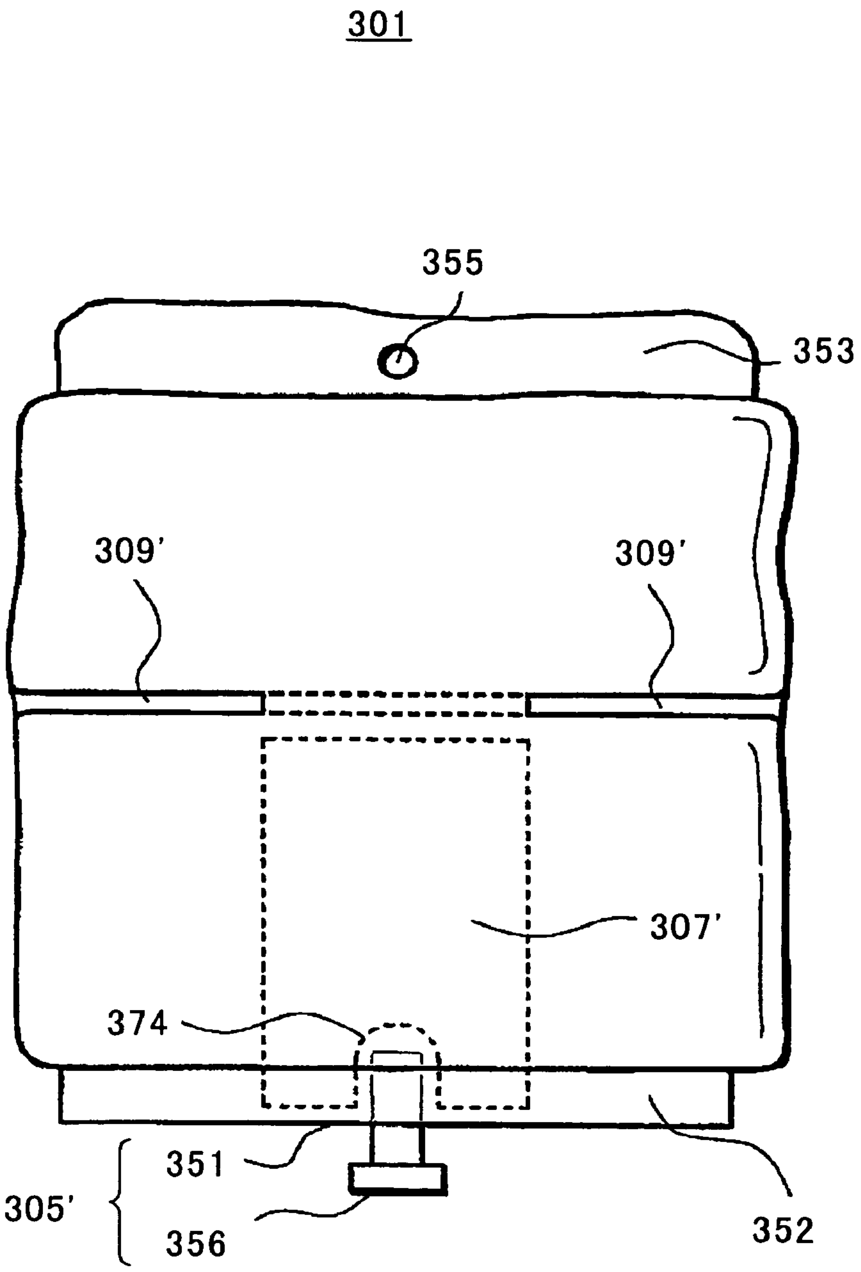
FIG. 83 is a view to explain a state where a clogging device is detached from a container body with the clogging device attached thereto of FIG. 82

When the multi-chamber container 301 according to Embodiment 18 of the invention is hung with the hang hole 355 passed through a hook, since the weight of the multi-chamber container 301 is applied in the direction of the plug 356, as shown in FIG. 83, the clogging device 307' moves downward in synchronization with extension of the bellow portion 354, and the seal portion 308 spontaneously peels off. By this means, the first and second filling chambers 357*a*, 357*b* inside the bag member 351 are communicated with each other via the opening 393, and the unmixed agents filled in the first and second filling chambers 357*a*, 357*b* are spontaneously mixed.

Also in this Embodiment, without performing the specific opening operation, only by hanging the multi-chamber container, due to the weight of the container body, the filling chambers are opened in therebetween, and therefore, the agents inside the respective filling chambers are mixed with reliability when the user uses the container.

Embodiment 19

Embodiments 19 and 20 describe an aspect that a plurality of filling chambers is opened using the operation for removing a package of a multi-chamber container.

Figure 84:
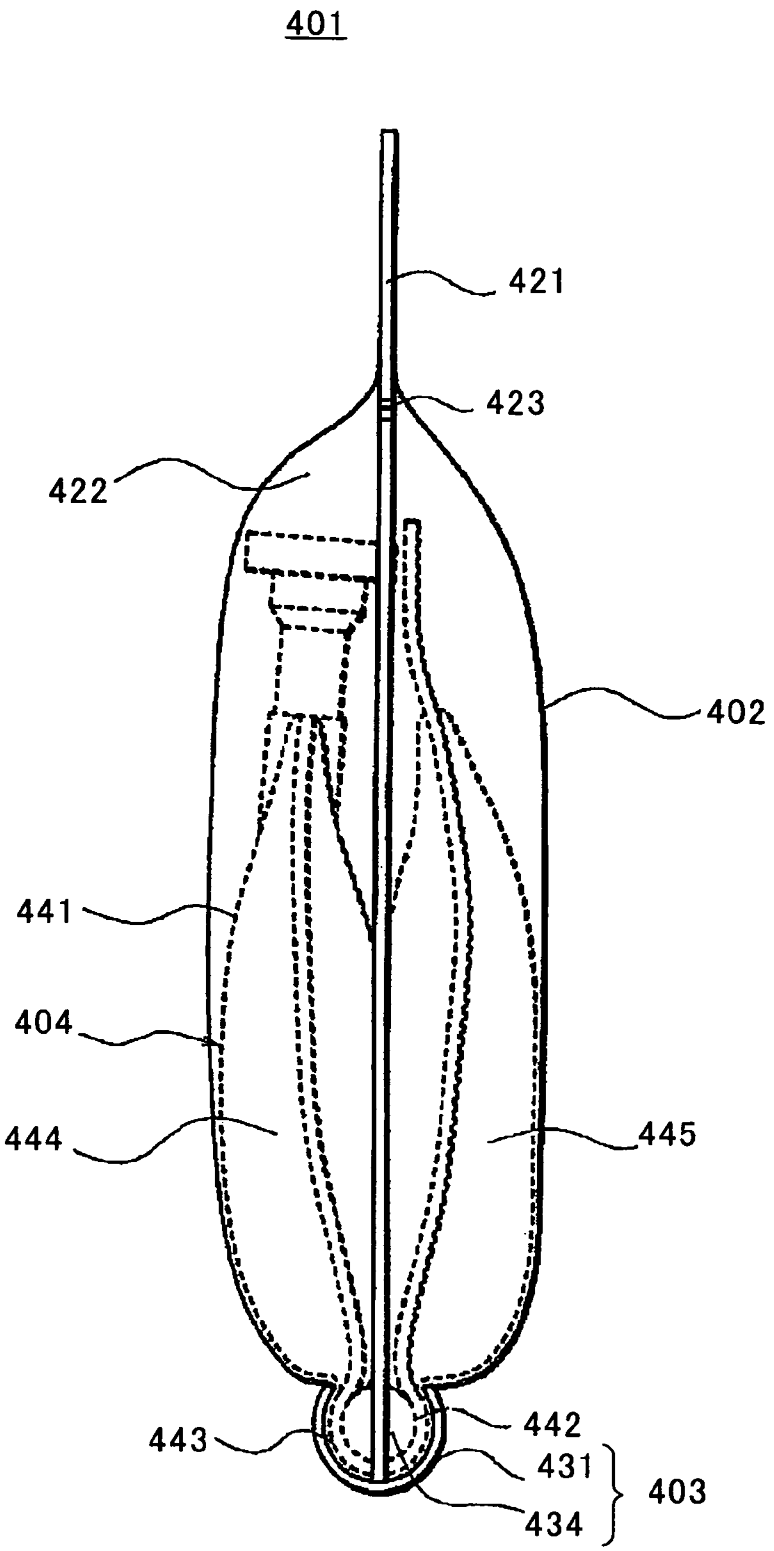
FIG. 84 is a side view showing a storage member according to Embodiment 19 in which a multi-chamber container is stored
Figure 85:
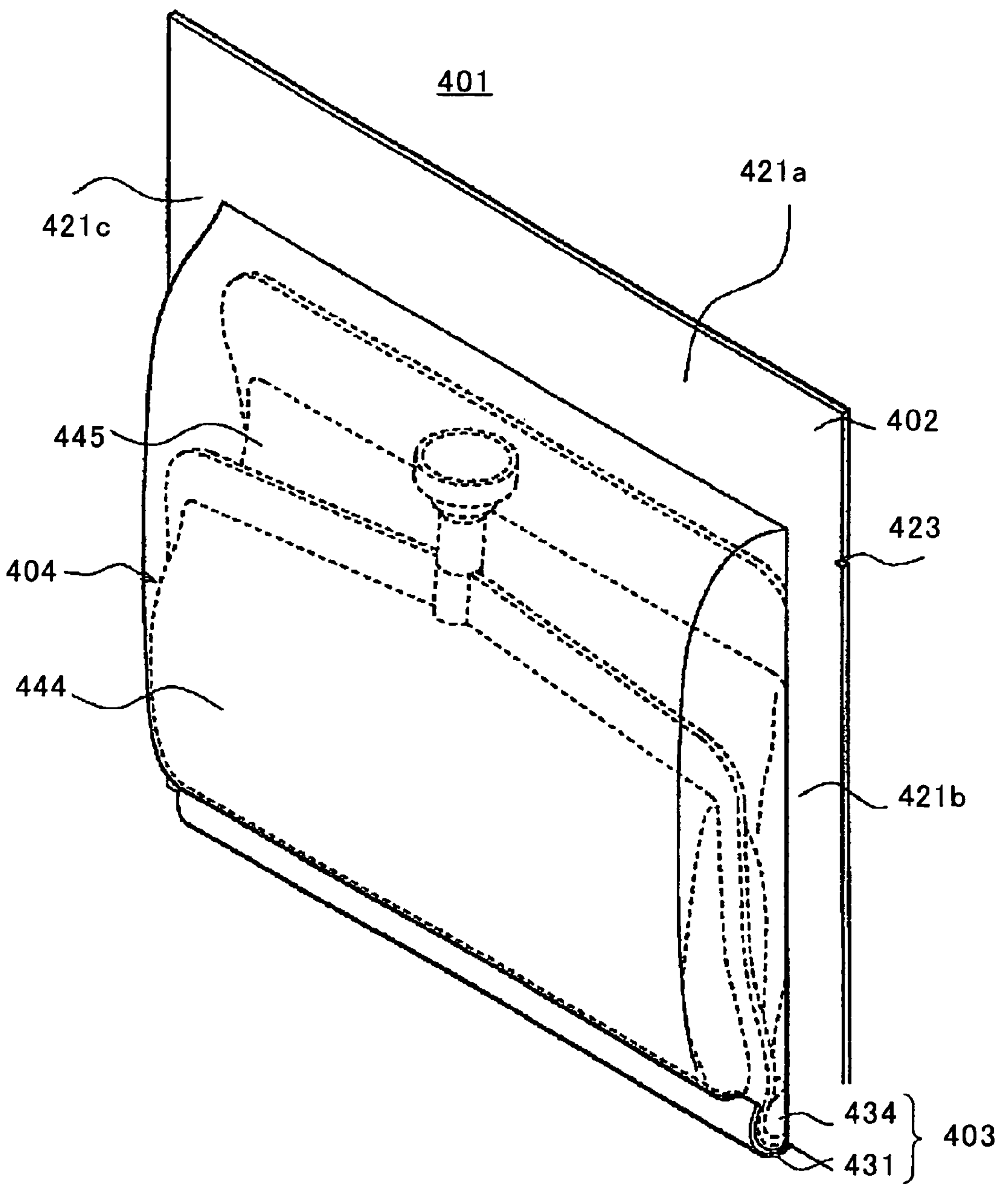
FIG. 85 is a perspective view showing the storage member of FIG. 84

FIGS. 84 and 85 are views showing a storage member according to Embodiment 19 in which a multi-chamber container is stored. The storage member 401 is comprised of a storage member body 402 and dividing means 403.

The storage member body 402 is comprised of a sealing portion 421 and multi-chamber container storage portion 442. The sealing portion 421 is formed by heating and fusing the inner surface on the periphery in the shape of a substantially inverse U with one rectangular film sheet folded in two. The multi-chamber container storage portion 422 is formed inside the sealing portion in the shape of a substantially inverse U, and stores the multi-chamber container 404 folded in two with one wall portion 442 of the container body 441 being inward. The sealing portion 421 has a notch portion 423 to cut the upper portion of the storage member body 402. The notch portion 423 is formed in one sealing portion 421*b* on the side positioned under an upper sealing portion 421*a*.

Figure 86:
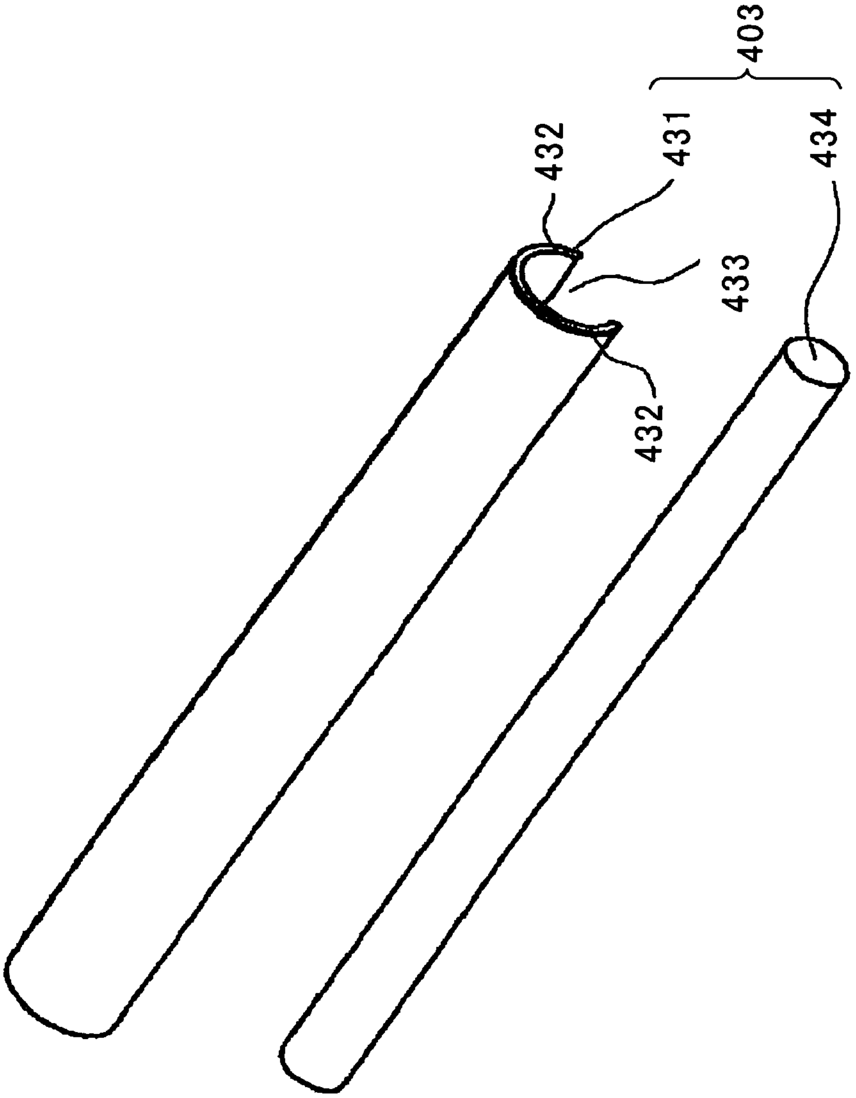
FIG. 86 is a perspective view showing dividing means attached to a storage member body of the storage member of FIG. 84

As shown in FIG. 86, the dividing means 403 includes a clip 403 and a rod-shape member 434. The clip 431 is formed of rigid material with elasticity, pinches the rod-shaped member 434 described below in contact with one wall portion 442 of the multi-chamber container 404 from the outside of the bottom of the storage member body 402 to clog the inside of the container body 441 of the multi-chamber container 404, and divides the inside of the container body 441 into a first and second filling chambers 444 and 445. The clip 431 has a lateral cross section formed in the shape of a substantially C, and is comprised of a pinch portion 432 and pinch space 433 formed inside the pinch portion 432. The clip 432 may be formed of metal such as iron having elastic force, but in consideration of safety, is preferably formed of elastic plastic material.

The rod-shaped member 434 is configured of synthesized resin with the lateral cross section formed in the shape of a circle. As shown in FIGS. 84 and 85, the rod-shaped member 434 is pinched by the pinch portion 432 of the clip 431 while being brought into contact with one wall portion 442 of the container body 441 of the multi-chamber container 404 described later. The rod-shaped member 434 may be secured integrally to one wall portion 442 of the multi-chamber container 404 by adhesive or the like.

Figure 87:
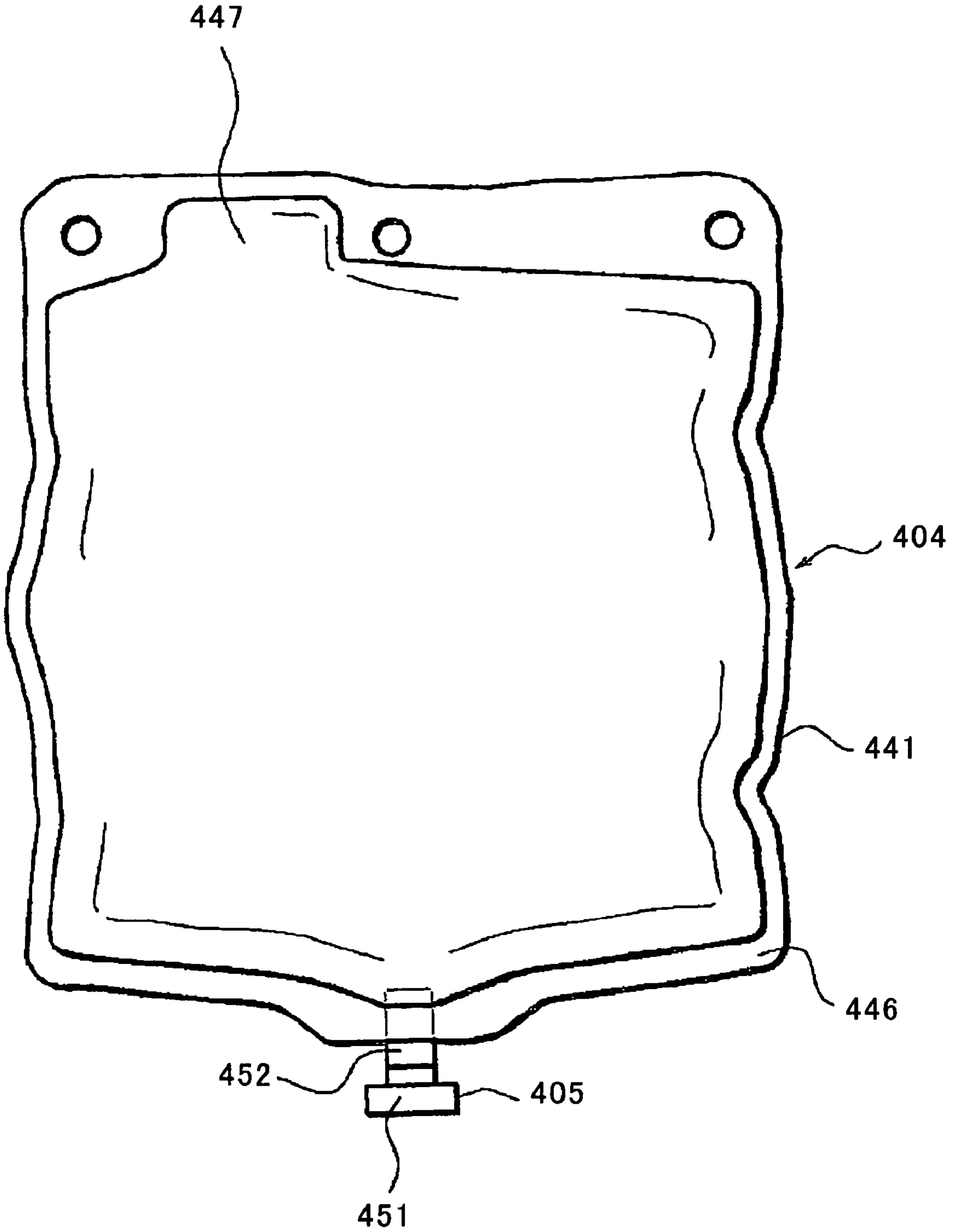
FIG. 87 is a front view showing a multi-chamber container to be stored in the storage member of FIG. 84

As shown in FIG. 87, the multi-chamber container 404 is provided with a seal portion 446 formed on the periphery of the container body 441. The seal portion 446 is formed by heating and fusing the inner surfaces on the peripheries of two film sheets constituting the container body 441 with an ejection tube 451 of a plug 405 held therebetween. The plug 450 is in the shape of a tube, and comprised of the ejection tube 451 and an ejection outlet 452 sealed by a rubber stopper until a hollow needle is inserted.

When the multi-chamber container 404 is stored using the storage member 401 with the above-mentioned configuration, first, the rod-shaped member 432 is brought into contact with one wall portion 422 of the multi-chamber container 404 along the lateral direction in the center of the container body 441 of the multi-chamber container 404. Next, in the contact position of the rod-shaped member 434, the container body 441 is folded in two such that one wall portion 442 is inside. Then, a rectangular film sheet constituting the storage member body 402 is brought into contact with the other wall portion 443 of the multi-chamber container 404 such that the center portion of the film sheet agrees with the folded position of the container body 441. In the position where the rod-shaped member 434 contacts the container, the container body 441 of the multi-chamber container 404 is inserted into the pinch space 433 of the clip 431, and thus pinched by the pinch portion 432 of the clip 431, and the inside of the container body 441 is thereby divided into a first and second filling chambers 444 and 445.

After attaching the dividing means 403 to the multi-chamber container 404 and dividing the inside of the container body 441, an unmixed agent is filled from the ejection outlet 452 of the plug 405 into the first filling chamber 444, and another unmixed agent is filled from a filling inlet 447 formed at an end portion on the side opposite to the plug 405 into the second filling chamber 445. Then, the ejection outlet 451 is sealed by a rubber stopper material, and the filling inlet 447 is fused and sealed to seal each unmixed agent. Next, by heating and fusing the periphery of the single rectangular film sheet constituting the storage member body 402, the multi-chamber container 404 is sealed in the multi-chamber container storage portion 422 of the storage member body 402.

Figure 88A:
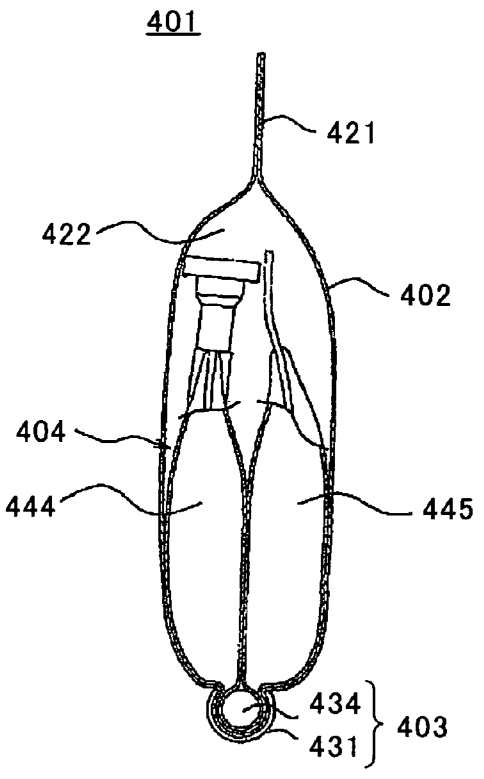
FIG. 88 is a view to explain a state where the dividing means is released from the storage member having the dividing means.
Figure 88B:
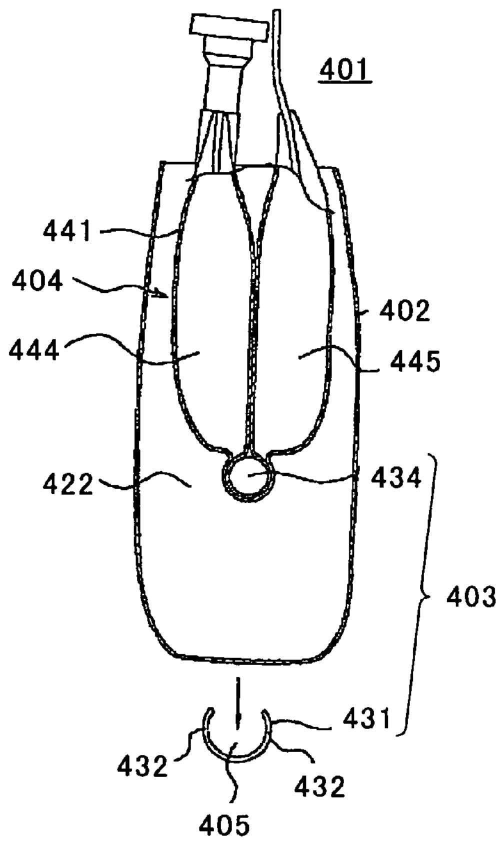
Figure 88C:
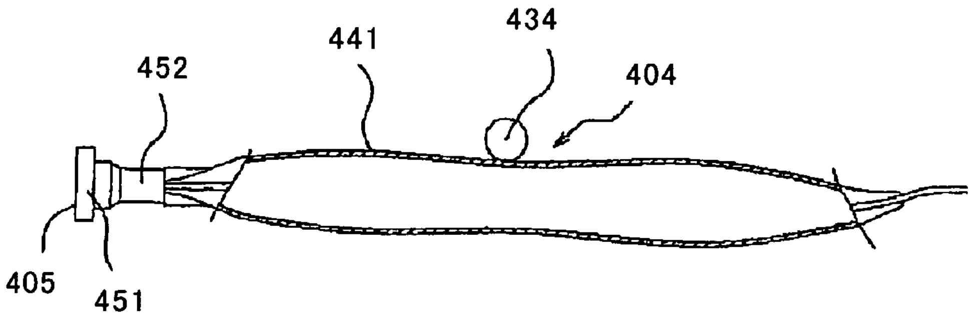

When the multi-chamber container 404 is stored in the storage member 401, as shown in FIG. 88(*a*), the inside of the container body 441 which the rod-shaped member 434 contacts is pinched by the clip 431 and thus clogged, and it is thereby possible to partition the inside of the container body 441 of the multi-chamber container 404 into two portions to completely divide. Further, the storage member 401 is capable of keeping the multi-chamber container 404 folded in two by the storage member body 402, and the multi-chamber container 404 can be identified, from the appearance, as being not allowed to administer agents, without hanging the container 404 on a hook.

In removing the storage member 401 from the multi-chamber container 404, a user cuts the upper portion of the storage member body 402 using the notch 423 to open the multi-chamber container storage portion 422. Then, the user grasps the container body 441 of the multi-chamber container 404 by one hand inserted into the multi-chamber container storage portion 422, while grasping one of the sealing portions 421*b* and 421*c* on the side of the storage member body 402 by the other hand, pulls the multi-chamber container 404 out, thereby releasing the pinching of the clip 431 to drop as shown in FIG. 88(*b*), and is capable of removing the multi-chamber container 404 from the storage member body 402. Since the partition by the dividing means 403 is released, as shown in FIG. 88(*c*), by expanding the container body 441 of the multi-chamber container 404, it is possible to mix unmixed agents. In addition, after peeling off the fused portions of the sealing portions 421*b* and 421*c* on the side of the storage member body 402 and expanding the storage member body 402, the user may grasp the container body 441 of the multi-chamber container 404 by one hand, while grasping opposite ends of the film sheet of the expanded storage member body 402 by the other hand, and pull in opposite directions to release the pinching of the clip 431.

Also in this Embodiment, without performing the specific opening operation, the clip is detached by removing the multi-chamber container from the storage member, the filling chambers are opened in therebetween, and therefore, the agents inside the respective filling chambers are reliably mixed when the user uses the container.

Embodiment 20

Figure 89:
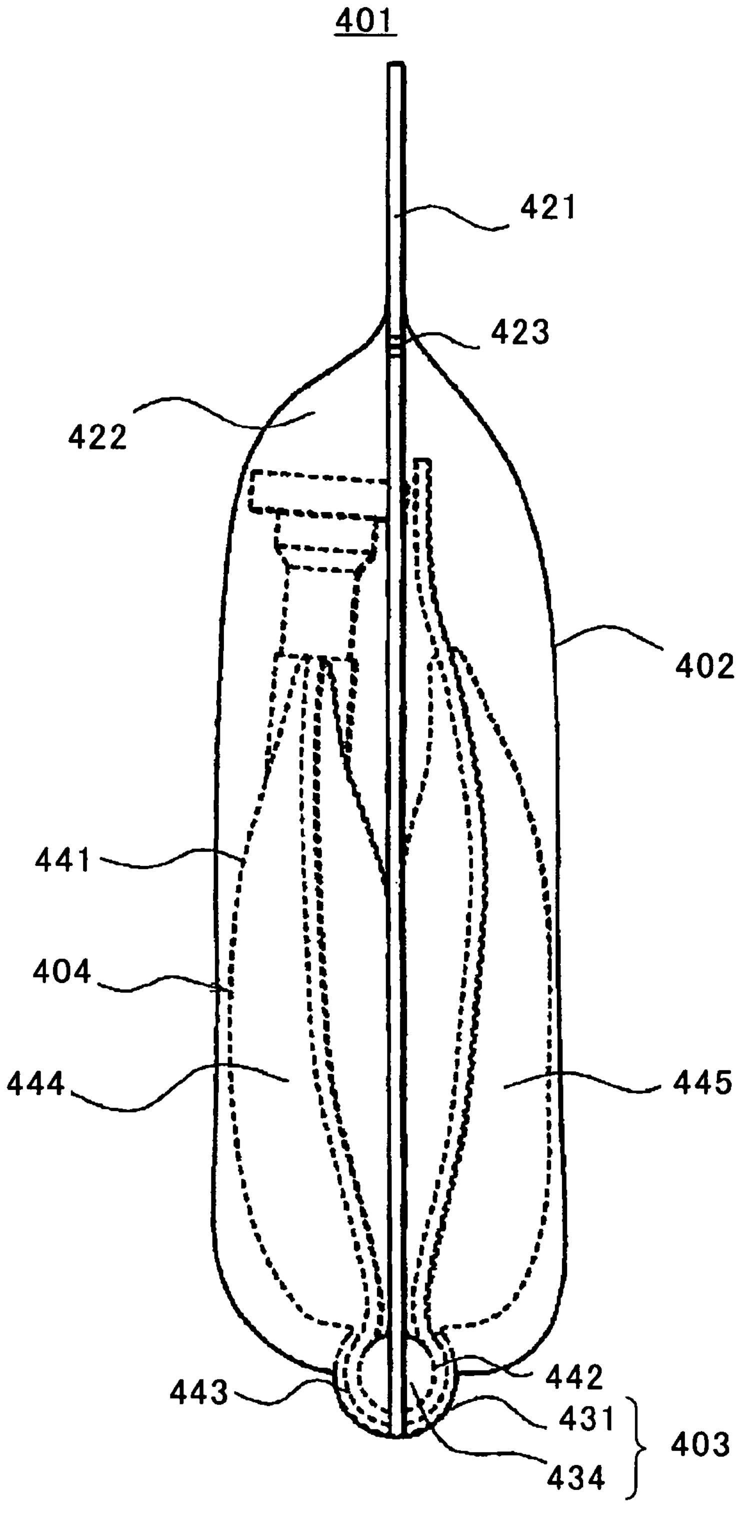
FIG. 89 is a side view showing a storage member according to Embodiment 20 in which a multi-chamber container is stored.
Figure 90:
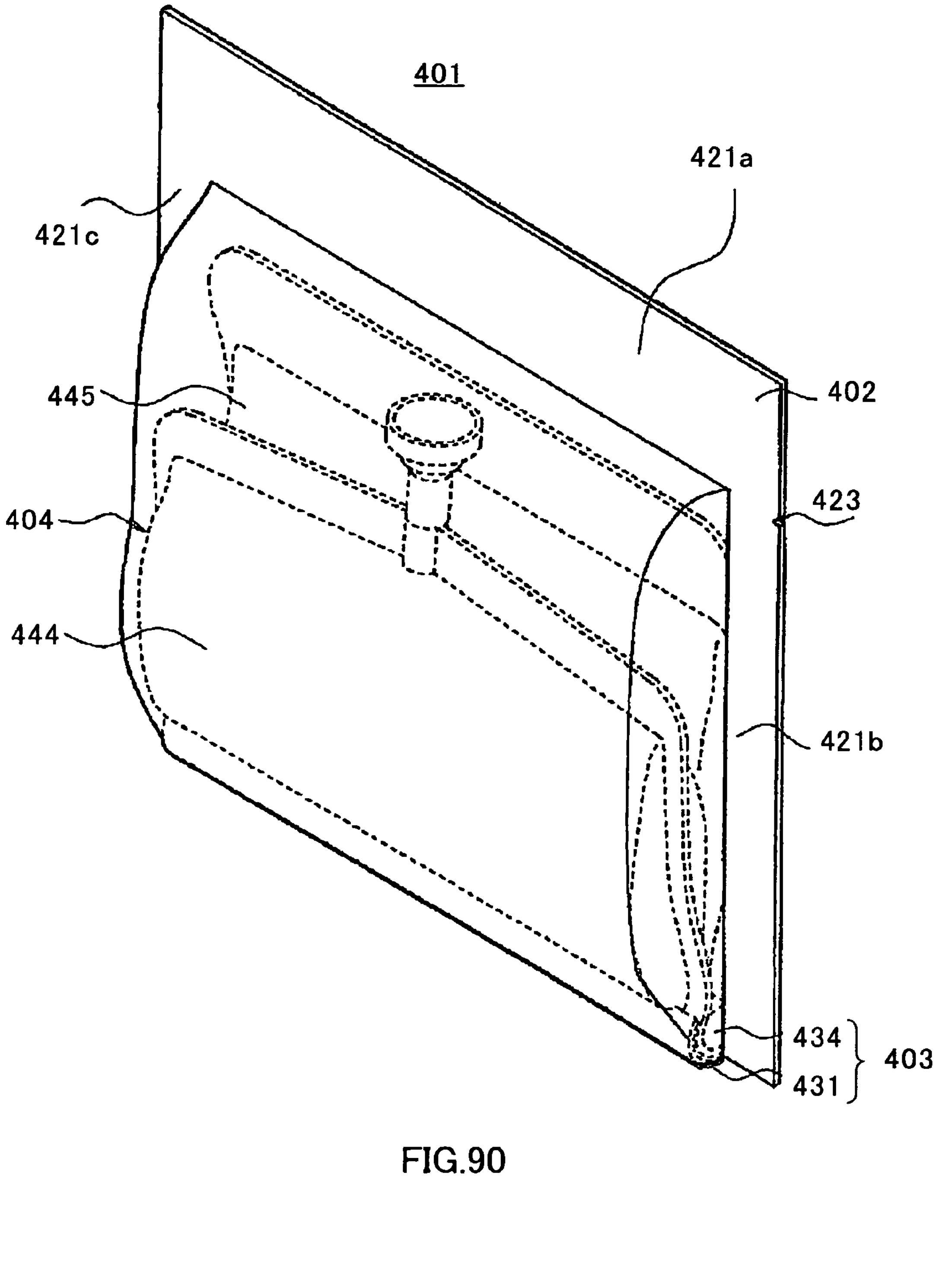
FIG. 90 is a perspective view showing the storage member of FIG. 89.

FIGS. 89 and 90 are views showing a storage member according to Embodiment 20 in which a multi-chamber container is stored. The storage member 401 is comprised of a storage member body 402 and dividing means 403.

As in Embodiment 19, the storage member body 402 is comprised of a sealing portion 421 and multi-chamber container storage portion 442 by heating and fusing the periphery of a single film sheet.

As in Embodiment 19, the dividing means 403 includes a clip 403 and a rod-shape member 434. The clip 431 is formed integrally with the storage member body 402 by heating and fusing the outside of the bottom of the pinch portion 432 and the inner surface of the storage member body 402. As in Embodiment 19, the clip 431 is formed of rigid material having elastic force, pinches the rod-shaped member 434 described later in contact with one wall portion 442 of the multi-chamber container 404 from the other wall portion 443 to clog the inside of the container body 441 of the multi-chamber container 404, and divides the inside of the container body 441 into a first and second filling chambers 444 and 445.

As in Embodiment 19, the rod-shaped member 434 is configured of synthesized resin with the lateral cross section formed in the shape of a circle. As shown in FIGS. 89 and 90, the rod-shaped member 434 is pinched by the pinch portion 432 of the clip 431 while being brought into contact with one wall portion 442 of the multi-chamber container 404.

When the multi-chamber container 404 is stored using the storage member 401 with the above-mentioned configuration, first, the clip 431 is formed integrally into a film sheet by heating and fusing the outside of the bottom of the clip 431 and the inner surface near the center of a single rectangular film sheet constituting the storage member body 402. Then, the rod-shaped member 432 is brought into contact with one wall portion 422 of the multi-chamber container 404 along the lateral direction in the center of the container body 441. Next, in the contact position of the rod-shaped member 434, the container body 441 is folded in two such that one wall portion 442 is inside. Then, the container body 441 of the multi-chamber container 404 is inserted into the pinch space 433 of the clip 431 formed integrally with the single film sheet, and thus pinched by the pinch portion 432 of the clip 431, and the inside of the container body 441 is thereby divided into a first and second filling chambers 444 and 445. Then, in the same method as in Embodiment 19, unmixed agents are filled inside the container body 441 of the multi-chamber container 404 partitioned by the dividing means 403, and by heating and fusing the periphery of the single rectangular film sheet constituting the storage member body 402, the multi-chamber container 404 is sealed in the multi-chamber container storage portion 422 of the storage member body 402.

As in Embodiment 19, when the multi-chamber container 404 is stored in the storage member 401 according to Embodiment 20, the inside of the container body 441 which the rod-shaped member 434 contacts is pinched by the clip 431 and thus clogged, and it is thereby possible to partition the inside of the container body 441 of the multi-chamber container 404 into two portions to completely divide. Further, the storage member 401 is capable of keeping the multi-chamber container 404 folded in two by the storage member body 402, and the multi-chamber container 404 can be identified, from the appearance, as being not allowed to administer agents without hanging the container 404 on a hook.

In removing the storage member 401 from the multi-chamber container 404, a user cuts the upper portion of the storage member body 402 using the notch 423 to open the multi-chamber container storage portion 422. Then, the user grasps the container body 441 of the multi-chamber container 404 by one hand inserted into the multi-chamber container storage portion 422, while grasping one of the sealing portions 421*b* and 421*c* on the side of the storage member body 402 by the other hand, pulls the multi-chamber container 404 out, thereby releasing the pinching of the clip 431, and is capable of removing the multi-chamber container 404 from the storage member body 402. The container body 441 of the multi-chamber container 404 thereby expands, the partition by the dividing means 403 is released, and the unmixed agents can be mixed.

Also in this Embodiment, without performing the specific opening operation, the clip is detached by removing the multi-chamber container from the storage member, the filling chambers are opened in therebetween, and therefore, the agents inside the respective filling chambers are reliably mixed when the user uses the container.

Figure 91C:
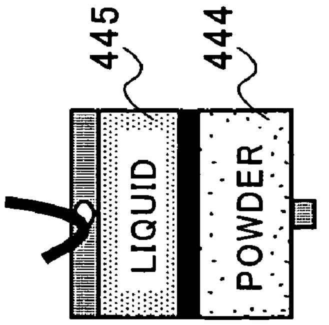
FIG. 91 is a front view showing an example of multi-chamber container to be stored in the storage member.
Figure 91B:
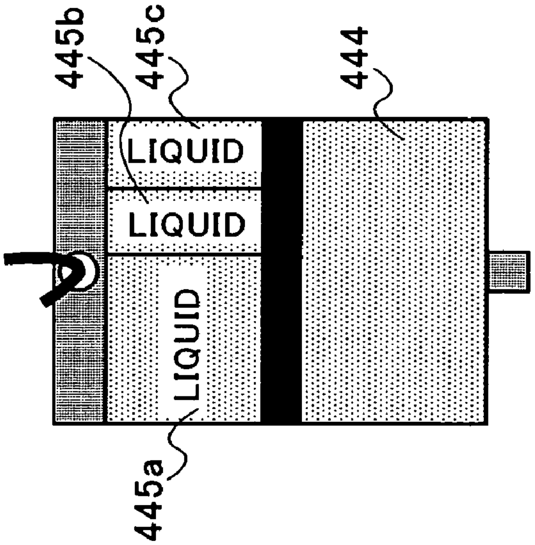
Figure 91A:
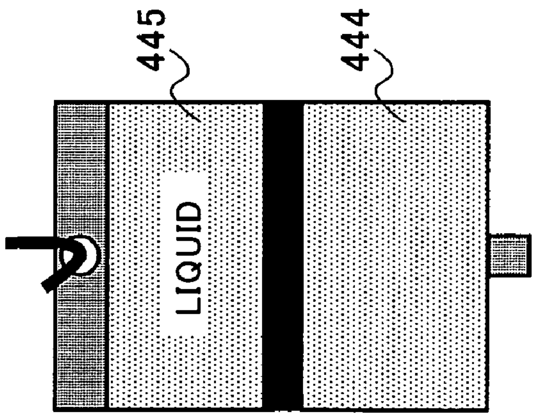

In this Embodiment, the upper filling chamber 445 filled with liquid may be combined with the lower filling chamber 444 filled with liquid as shown in FIG. 91(*a*), a plurality of upper filling chambers 445*a* to 445*c* each filled with liquid may be combined with the lower filling chamber filled with liquid as shown in FIG. 91(*b*), or the upper filling chamber filled with liquid may be combined with the lower filling chamber filled with powder as shown in FIG. 91(*c*). In addition, these combinations are not limited to the foregoing, and are capable of being modified in various manners.

Embodiment 21

Embodiments 21 and 22 described below explain an aspect for cautioning the opening between filling chambers.

Figure 92:
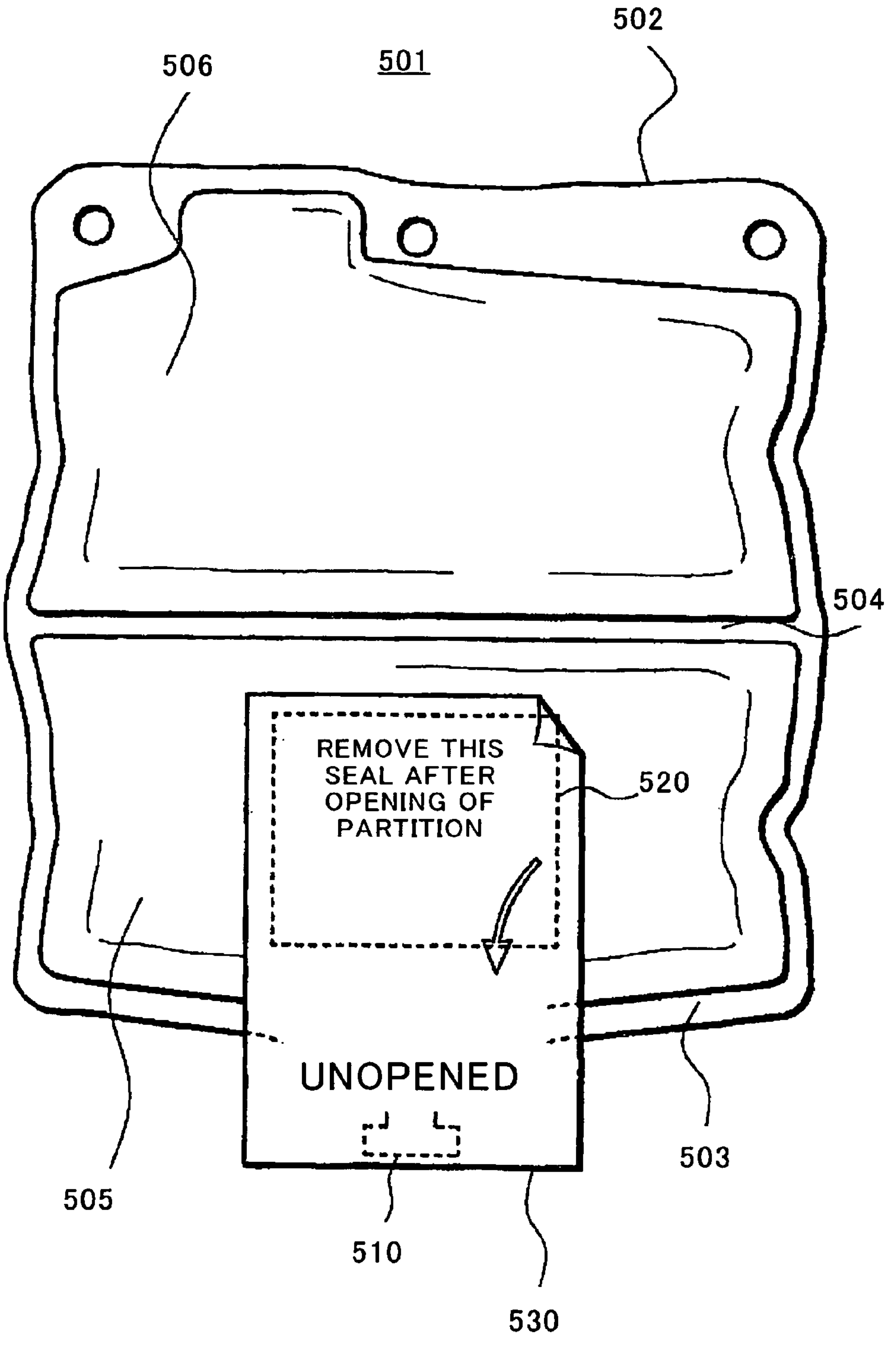
FIG. 92 is a front view showing a multi-chamber container according to Embodiment 21 of the invention.
Figure 96:
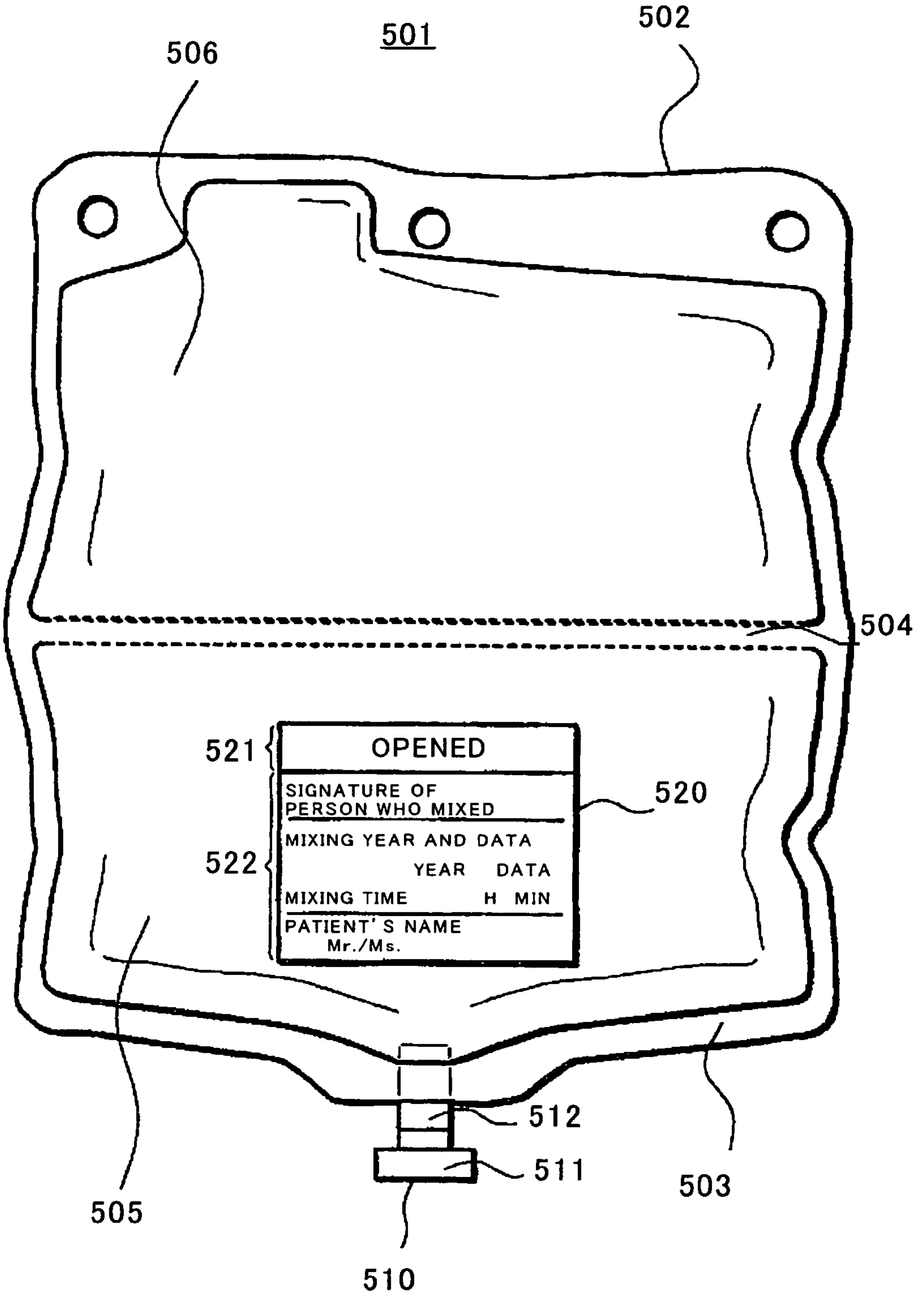
FIG. 96 is a front view showing the multi-chamber container with the caution seal peeled off.

FIG. 92 is a view showing a multi-chamber container according to Embodiment 21 of the invention. As shown in FIG. 96, the multi-chamber container 501 has a container body 502, and an ejection plug 510 attached to an opening of the container body 502.

The container body 502 is comprised of two transparent film sheets and has a seal portion 503. The seal portion 503 is formed by heating and fusing peripheries of the films with an ejection tube 512 of the plug 510 held between inner surfaces of the two transparent film sheets opposite to each other. The seal portion 503 is configured in strength such that the portion cannot peel off by pressing the outer surfaces of first and second filling chambers 505, 506 described later.

The container body 502 has a seal portion 504 and the first and second filling chambers 505, 506□ The seal portion 504 is formed in the lateral direction near the center of the container body 502, by bonding one inner surface and the other opposite inner surface, for example, with mixed resin pieces, or heating and fusing the inner surfaces with mixed resin pieces held therebetween. The seal portion 504 divides the inside of the container body 502 into the first and second filling chambers 505, 506, and is configured in strength that enables the portion 504 to peel off by pressing the outer surfaces of the first and second filling chambers 505, 506.

The plug 510 is in the shape of a tube, and comprised of an ejection outlet 511 sealed with a rubber stopper and an ejection tube 512.

The multi-chamber container 501 has an information checking seal 520. As shown in FIG. 96, the information checking seal 520 is configured in rectangle-shape, and adhered to the outer surface of one filling chamber 505 with an adhesive coated on the entire backside. The information checking seal 520 has an indication portion provided in the upper portion on the surface, and a fill-in form 522 provided under the indication portion 521. As shown in FIG. 96, the indication portion 521 describes white letters of "opened", in green background, indicating that the seal portion 504 has peeled off. As shown in FIG. 96, the fill-in form 522 is provided with a "signature of person who mixed" box, "mixing year and date" box, and "mixing time" box to fill in information on mixing of agents by the peeling of the seal portion 504 and the like, and a "patient's name" box.

Figure 93:
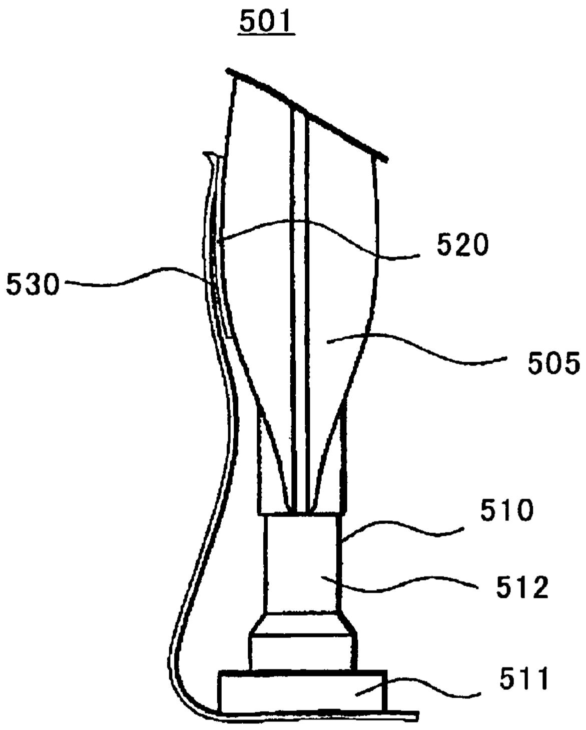
FIG. 93 is a side view showing the multi-chamber container with a caution seal adhered thereto.
Figure 94:
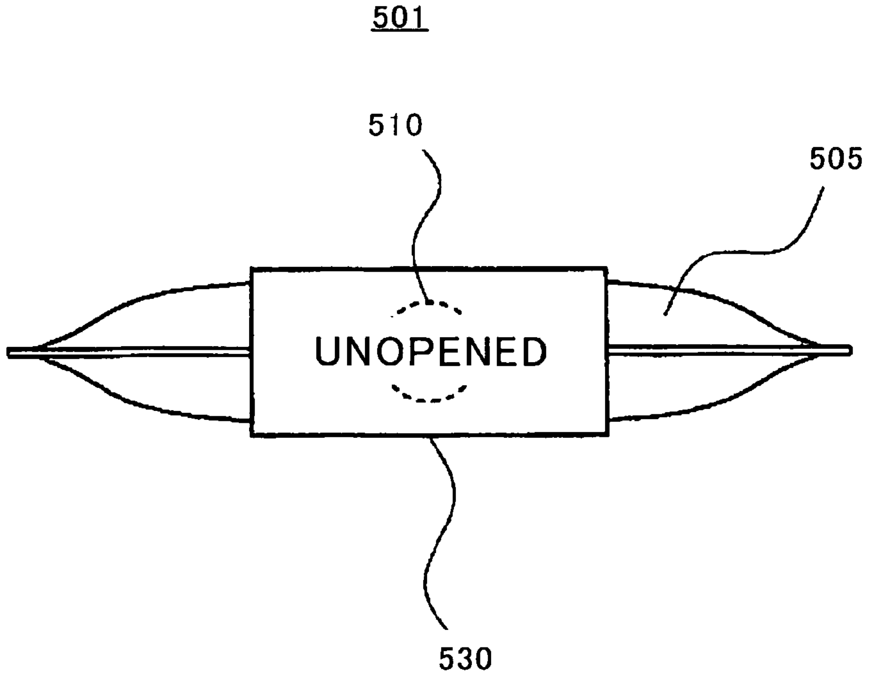
FIG. 94 is a bottom view showing the multi-chamber container of FIG. 92.

The multi-chamber container 501 is further provided with a caution seal 530 that is a cautioning member to check the opening between the filling chambers. As shown in FIGS. 92 to 94, the caution seal 530 is configured in the shape of a rectangle larger than the information checking seal 520, and adhered to the outer surface of one filling chamber 505 and plug 510 with an adhesive coated on opposite upper and lower ends of the backside, while covering the information checking seal 520 and the upper portion of the plug 510. On the surface of the caution seal 530 are described letters of "not opened" indicating that the seal portion 504 is not peeled off, and caution describing that the seal should be peeled off after the seal portion 504 peels off, with white letters in red background. In addition, the caution seal 530 may be adhered with relatively weak adhesion on an over seal provided in the plug 510, or may be directly adhered on the plug 510 instead of the over seal.

When the multi-chamber container 501 of the invention is hung on a hook or placed on a slope with the caution seal 503 adhered, a user is capable of recognizing with ease that a hollow needle should not be inserted into the rubber stopper of the plug 510, and that the user should perform the operation for peeling off the seal portion 504, by the caution seal 530 covering the ejection outlet 511 of the plug 510, and the letters of "not opened" and caution descried on the seal. The user is thus prevented from inserting a hollow needle into the rubber stopper of the plug 510 to administer the unmixed agent to a patient.

Figure 95:
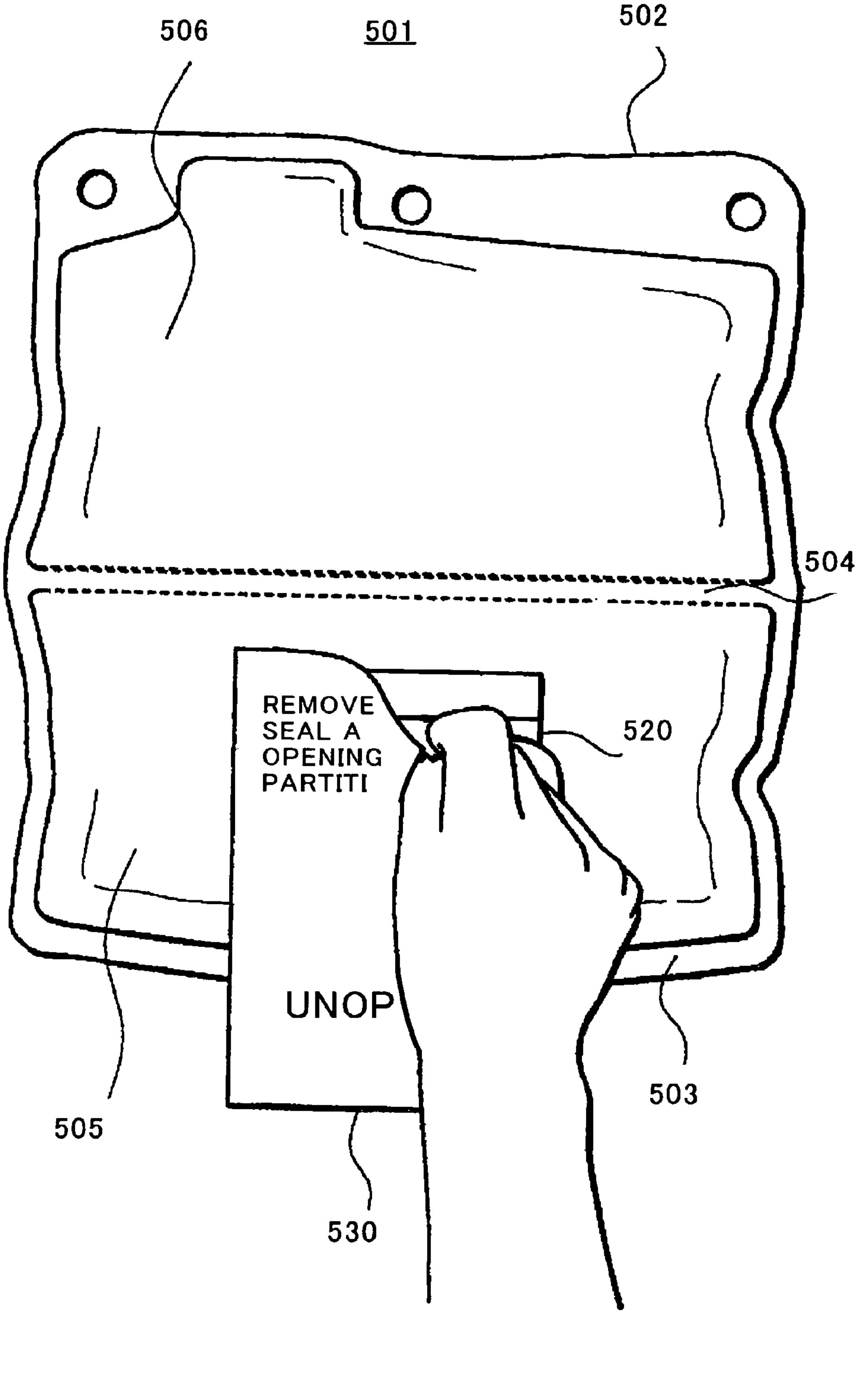
FIG. 95 is a front view showing the multi-chamber container with the caution seal being peeled off.

When a user peels off the seal portion 504 by pressing the outer surface of one of the first and second filling chambers 505, 506 by hand or the like, the user peels off the caution seal 530 as shown in FIG. 95 including the check of the peeling of the peel portion 504, and exposes the information checking seal 520 describing the letters of "opened". Further, to check again that the seal portion 504 has peeled off, the user fills required items on mixing of the agents in the fill-in form 522.

Even if a user neglects to peel off the seal portion 504 and erroneously peels off the caution seal 530, since the items to fill in the fill-in form 522 of the information checking seal 520 are required items for mixing of agents and the like, the user can easily recognize that the operation for peeling off the seal portion is not performed, and is prevented from inserting a hollow needle into the rubber stopper of the plug 510 to administer the unmixed agent to a patient.

In this Embodiment, the step is provided to peel off the caution seal 530 after mixing the agents and fill the opening information in the fill-in form 522. Subsequently, the multi-chamber container is hung and the over seal is peeled off. Therefore, by the step of peeling off the caution seal and filling in the opening information, and the step of hanging the container and peeling off the over seal, the user is capable of checking the opening, and therefore, reliably confirming the opening.

Embodiment 22

Figure 97:
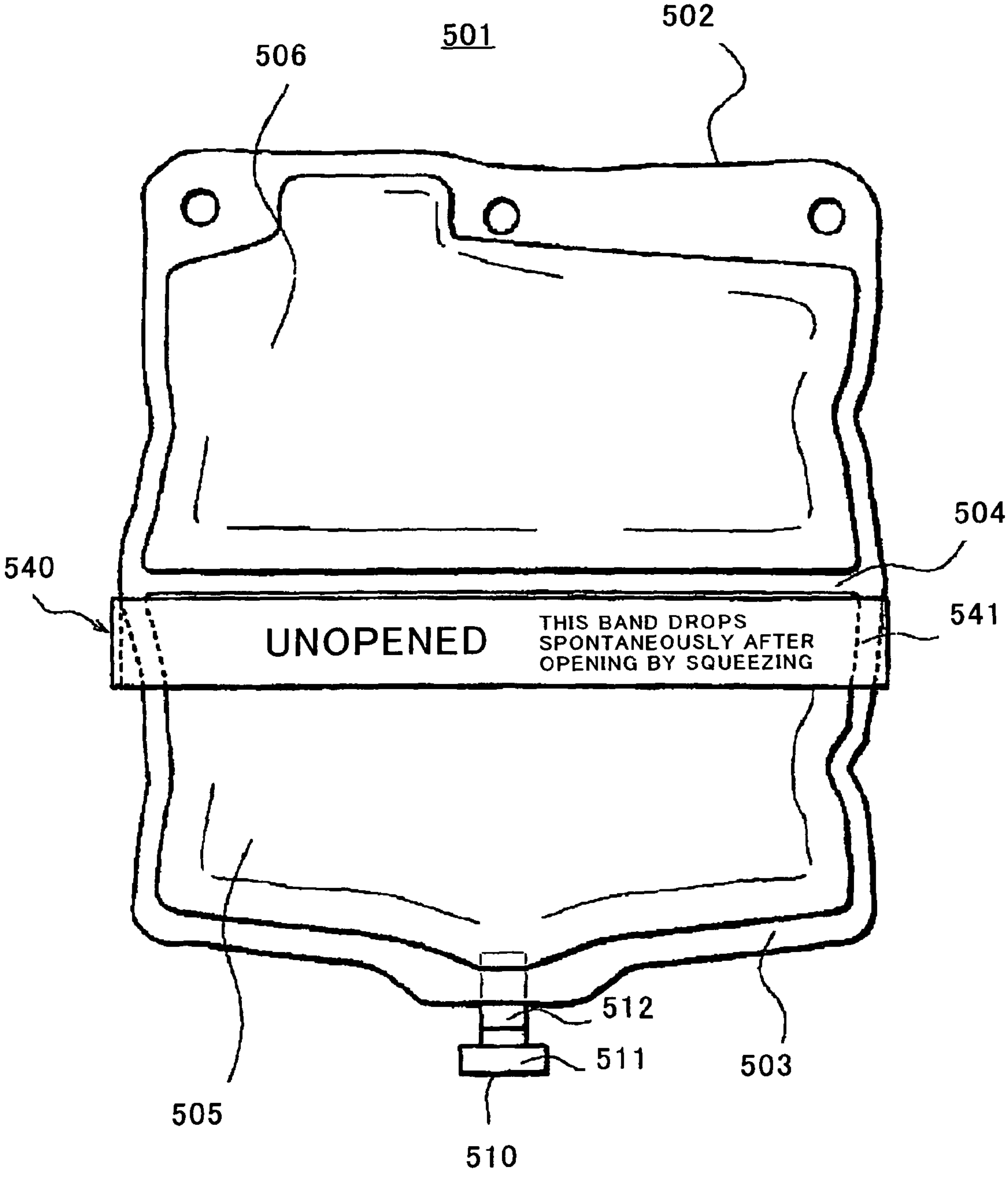
FIG. 97 is a front view showing a multi-chamber container according to Embodiment 22 of the invention.

FIG. 97 is a view showing a multi-chamber container 501 according to Embodiment 22 of the invention. As shown in FIG. 97, the multi-chamber container 501 has a container body 502, and an ejection plug 510 attached to an opening of the container body 502.

The container body 502 is comprised of two transparent film sheets and has a seal portion 503. The seal portion 503 is formed by heating and fusing peripheries of the films with an ejection tube 512 of the plug 510 held between inner surfaces of the two transparent film sheets opposite to each other. The seal portion 503 is configured in strength such that the portion cannot peel off by pressing the outer surfaces of first and second filling chambers 505, 506 described later.

The container body 502 has a seal portion 504 and the first and second filling chambers 505, 506. The seal portion 504 is formed in the lateral direction near the center of the container body 502, by bonding one inner surface and the other opposite inner surface, for example, with mixed resin pieces, or heating and fusing the inner surfaces with mixed resin pieces held therebetween. The seal portion 504 divides the inside of the container body 502 into the first and second filling chambers 505, 506, and is configured in strength that enables the portion 504 to peel off by pressing the outer surface of one of the first and second filling chambers 505, 506.

The plug 510 is in the shape of a tube, and comprised of an ejection outlet 511 sealed with a rubber stopper and an ejection tube 512.

Figure 98:
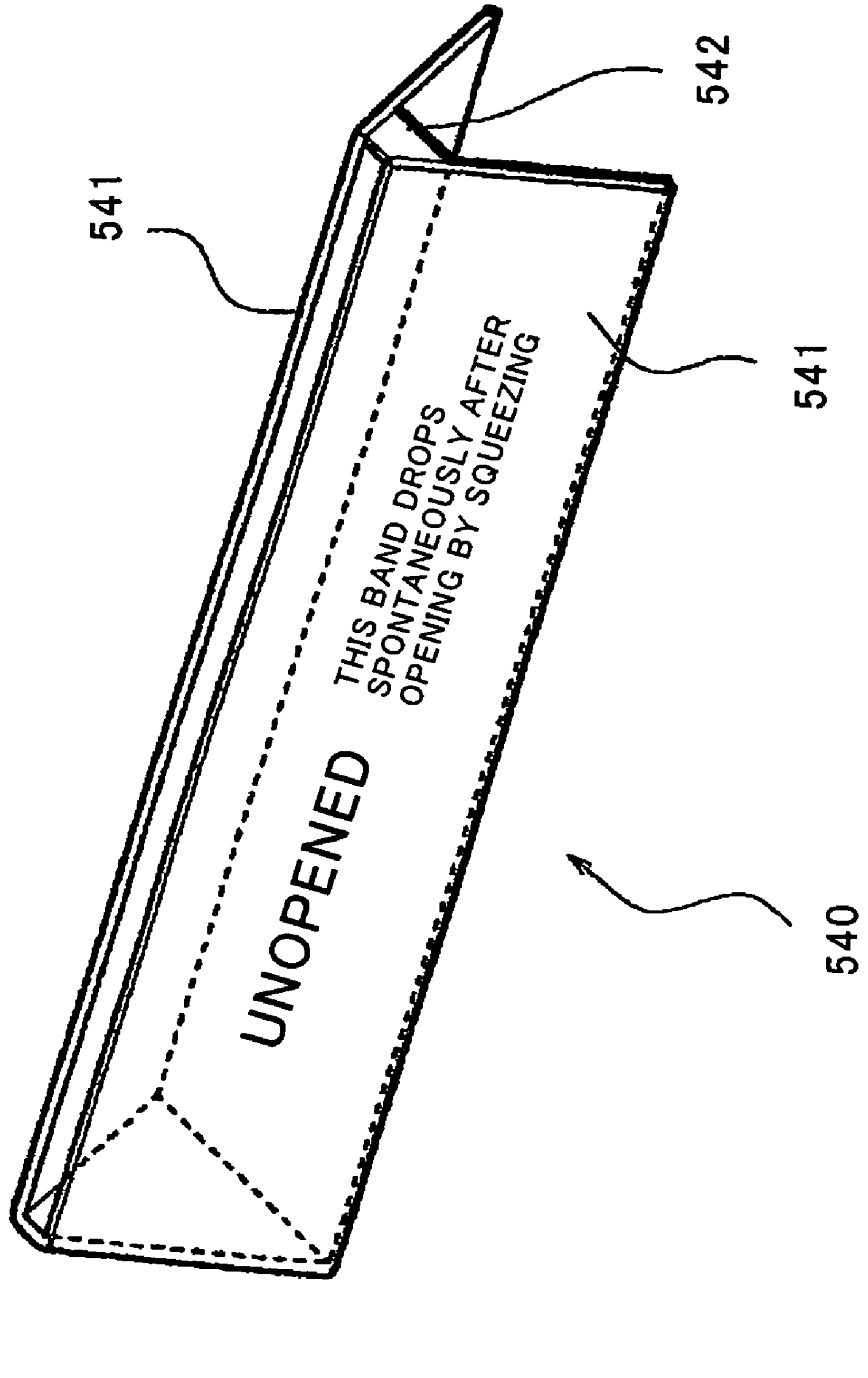
FIG. 98 is a perspective view showing a caution band attached to the multi-chamber container of FIG. 97.

The multi-chamber container 501 has a caution bend 540 that is attached to the container body 502 near the seal portion 504 and that is a caution member to check the opening between the filling chambers. As shown in FIG. 98, the caution band 540 is comprised of a base portion 541 and a weak portion 542 that couples the base portion 541.

The base portion 541 is comprised of long band-shaped thick paper, and bent and formed in the shape of a substantially U. Side surfaces of the front portion and rear portion of the base portion 541 are formed at a predetermined angle. The opposite ends of the base portion 541 are coupled to each other via the weak portion 542 described later. The base portion 541 comes into contact with the chamber along the end portion on the seal portion 504 side of the first filling chamber 505. On the surface of the base portion 541 are described letters of "not opened" indicating that the seal portion 504 is not peeled off, and caution describing that the caution belt drops spontaneously after the seal portion 504 peels off, with white letters in red background.

The weak portion 542 is formed of trapezoidal thin paper. The weak portion 542 couples the opposite ends of the base portion 541 using an adhesive member such as glue, tape and the like. Thus, the caution band 540 is attached to near the seal portion 504 that is a communication portion, and configured to drop by the opening. Further, the caution band 540 may be comprised of a clip to integrate the caution band 540 and the clip, so that the weak portion 542 is broken to drop.

When the multi-chamber container 501 of this Embodiment is hung on a hook or placed on a slope with the caution band 540 attached, a user is capable of recognizing with ease that a hollow needle should not be inserted into the rubber stopper of the plug 510, and that the user should perform the operation for peeling off the seal portion 504, by the caution band 540 and the letters of "not opened" described on the band. The user is thus prevented from inserting a hollow needle into the rubber stopper of the plug 510 while hanging the container on a hook or placing the container on a slope to administer the unmixed agent to a patient.

Figure 99A:
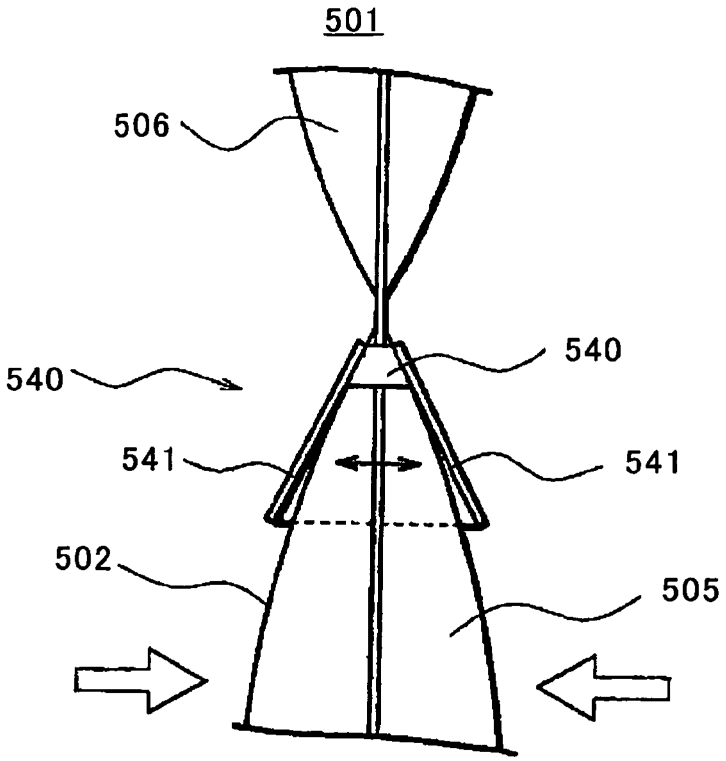
FIG. 99 is a view showing a state where the caution band attached to the multi-chamber container is broken.
Figure 99B:
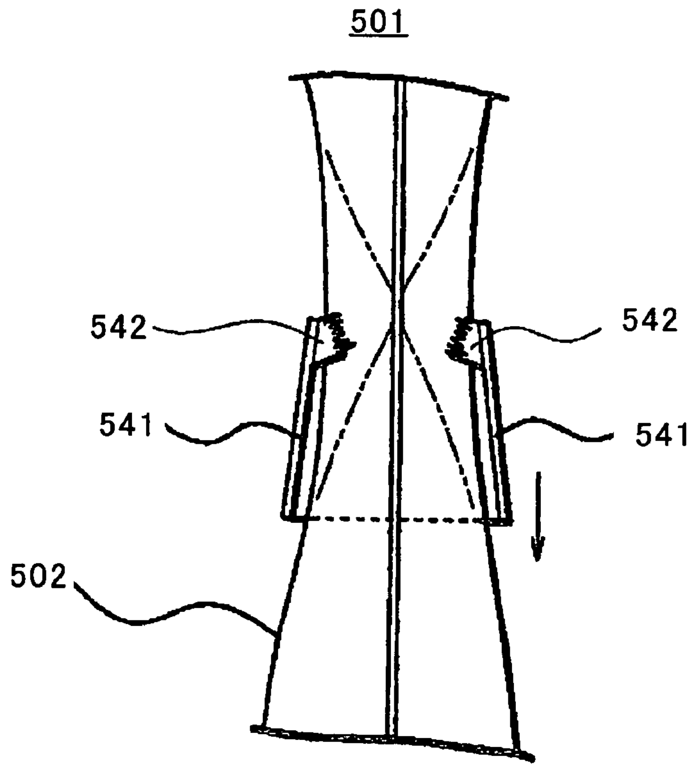

As shown in FIG. 99(*a*), when a user peels off the seal portion 504 by pressing the outer surface of one of the first and second filling chambers 505, 506 by hand or the like, as shown in FIG. 99(*b*), the weak portion 542 ruptures by expansion of the container body 502 due to the peeling of the seal portion 504. Then, when the user lifts the multi-chamber container 501, the base portion 541 expands outward, the caution band 540 drops spontaneously, and therefore, the user is capable of recognizing that the seal portion 504 has peeled off from the appearance of the multi-chamber container 501, and using the container 501 by hanging on a hook or placing on a slope.

Figure 100A:
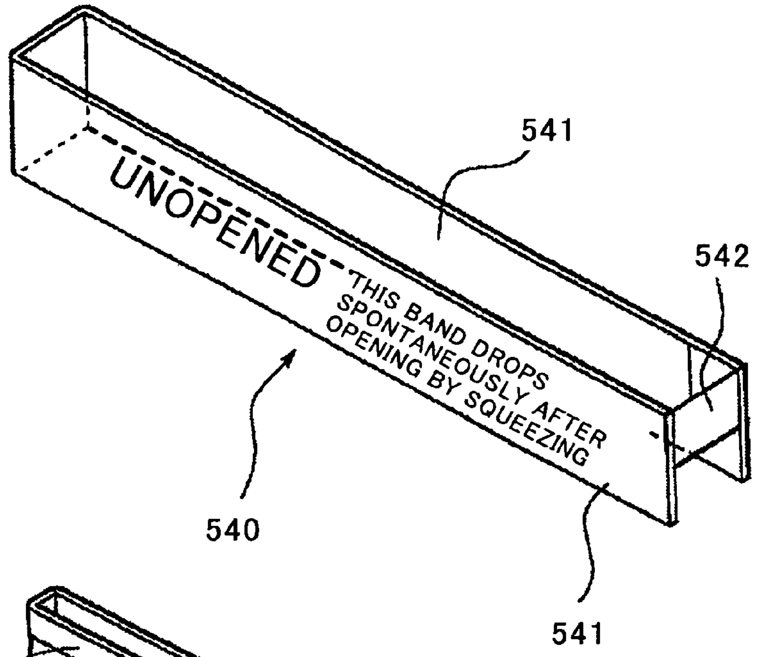
FIG. 100 is a perspective view showing another example of the caution band of FIG. 98.
Figure 100B:
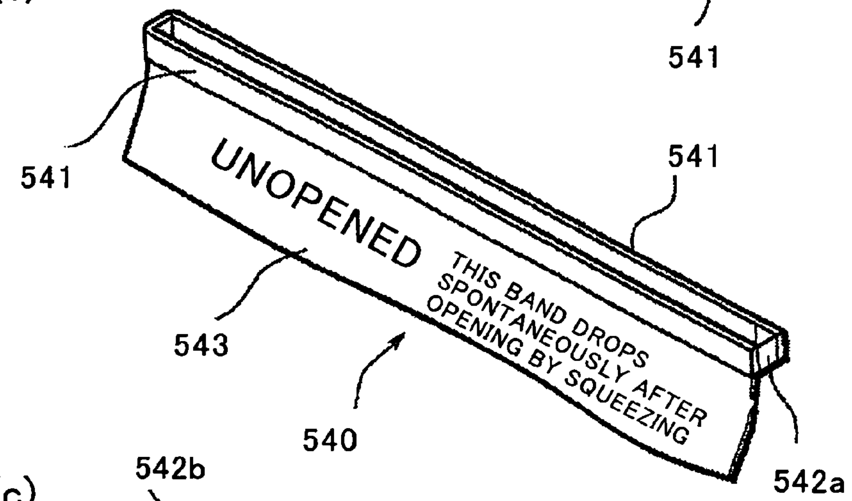
Figure 100C:
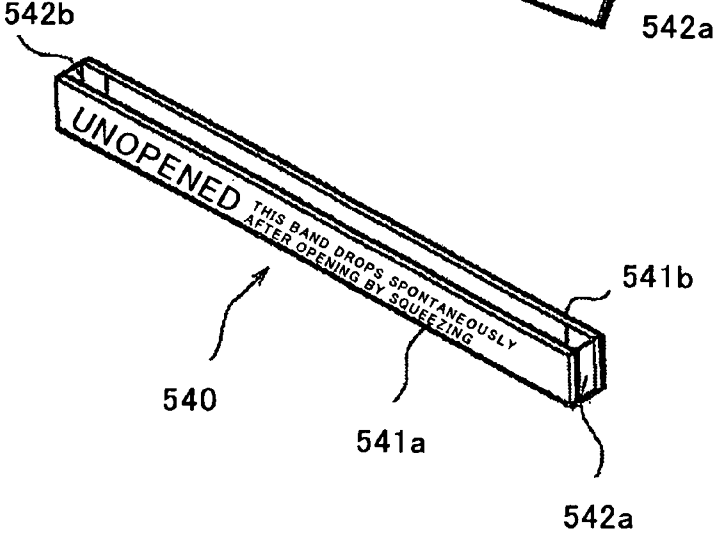

In addition, the side surfaces of the front portion and rear portion of the base portion 541 do not need to have a predetermined angle as in the caution band 540 shown in FIG. 97, and may be formed in parallel as shown in FIGS. 100(*a*) and 100(*b*). Further, the letters of "not opened" and caution do not need to be described on the surface of the base portion as in the caution band 540 shown in FIG. 97. As shown in FIG. 100(*b*), a caution sheet 543 with such letters and caution may be adhered to one of the base portion 541 to constitute the caution band 540. Furthermore, the base portion 541 does not need to be formed in the shape of a substantially U shape, and as shown in FIG. 100(*c*), a pair of base portions 541*a* and 541*b* may be configured with thin paper formed in plate-shape such that opposite right and left ends are coupled by weak portions 542*a* and 542*b* comprised of two sheets of thin paper.

The present invention is not limited to the above-mentioned Embodiments 1 to 22, and is capable of being carried into practice with various modifications thereof. For example, the materials, dimensions, shapes and the like in the above-mentioned Embodiments are examples, and are not limited to the foregoing. Further, the above-mentioned Embodiments 1 to 22 are capable of being carried into practice in a combination thereof as appropriate. Furthermore, it would be apparent to those skilled in the art that the present invention is capable of being carried into practice with various modifications thereof without departing from the scope of the present invention.

The present application is based on Japanese Patent Applications No. 2003-403363 filed on Dec. 2, 2003, No. 2003-433415 filed on Dec. 26, 2003, No. 2004-104771 filed on Mar. 31, 2004, No. 2004-222084 filed on Jul. 29, 2004, No. 2004-222090 filed on Jul. 29, 2004, No. 2004-222095 filed on Jul. 29, 2004, No. 2004-227992 filed on Aug. 4, 2004 and No. 2004-248361 filed on Aug. 27, 2004, entire contents of which are expressly incorporated by reference herein.

The invention claimed is:

1. A multi-chamber container that accommodates a plurality of agents, comprising:

an outer container body formed by at least one flexible sheet of material, the outer container body comprising an inner surface and an outer surface, the inner surface forming a cavity;

an inner container body disposed in the cavity of the outer body, the inner container body formed by at least one flexible sheet of material, wherein the inner container body includes at least a first filling chamber and a second filling chamber to fill agents;

a shape retaining member attached to a portion of the inner surface of the outer container body, the shape retaining portion having a front end portion positioned adjacent the inner container body;

a first communication portion provided to the first filling chamber and a second communication portion provided to the second filling chamber such that the first communication portion of the first filling chamber is separate and independent from the second communication portion of the second filling chamber, the first communication portion and the second communication portion being at least one hole that permits communication with the outer container body; and an opening preventing portion provided on the front end portion of the shape retaining member such that the opening preventing portion closes the first communication portion and the second communication portion in a carrying mode of the multi-chamber container, the opening preventing portion is a seal adapted to peel off by expanding the folded multi-chamber container to a use mode of the multi-chamber container.

2. The multi-chamber container according to claim 1, further comprising:

a caution member to check opening between the filling chambers.

3. The multi-chamber container according to claim 2, wherein the caution member is attached near the communication portion so that the caution member drops by expanding the folded multi-chamber container in the use mode of the multi-chamber container.

4. The multi-chamber container according to claim 1, wherein the seal is positioned over the at least one hole to close the at least one hole until the multi-chamber container is expanded.

* * * * *